US012357681B2

(12) United States Patent
Che et al.

(10) Patent No.: US 12,357,681 B2
(45) Date of Patent: Jul. 15, 2025

(54) *E. coli* FimH MUTANTS AND USES THEREOF

(71) Applicant: Pfizer Inc., New York, NY (US)

(72) Inventors: Ye Che, Niantic, CT (US); Laurent Oliver Chorro, New York, NY (US); Robert George Konrad Donald, South Orange, NJ (US); Matthew Curtis Griffor, North Stonington, CT (US); Natalie Clare Silmon de Monerri, New York, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/554,424

(22) Filed: Dec. 17, 2021

(65) Prior Publication Data

US 2022/0202923 A1 Jun. 30, 2022

Related U.S. Application Data

(60) Provisional application No. 63/282,244, filed on Nov. 23, 2021, provisional application No. 63/185,425, filed on May 7, 2021, provisional application No. 63/130,153, filed on Dec. 23, 2020.

(51) Int. Cl.
*A61K 39/108* (2006.01)
*A61K 39/00* (2006.01)
*C07K 14/245* (2006.01)
*C07K 16/12* (2006.01)

(52) U.S. Cl.
CPC ...... *A61K 39/0258* (2013.01); *A61K 39/0266* (2013.01); *C07K 14/245* (2013.01); *C07K 16/1232* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 4,709,017 A | 11/1987 | Collier et al. |
| 4,950,740 A | 8/1990 | Greenfield et al. |
| 5,340,740 A | 8/1994 | Petitte et al. |
| 5,370,872 A | 12/1994 | Cryz et al. |
| 5,614,382 A | 3/1997 | Metcalf |
| 5,656,479 A | 8/1997 | Petitte et al. |
| 5,830,510 A | 11/1998 | Petitte et al. |
| 5,843,711 A | 12/1998 | Collier et al. |
| 5,917,017 A | 6/1999 | Collier et al. |
| 6,114,168 A | 9/2000 | Samarut et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,455,673 B1 | 9/2002 | Collier |
| 6,500,668 B2 | 12/2002 | Samarut et al. |
| 6,749,831 B1 | 6/2004 | Bennett-Guerrero et al. |
| 7,247,307 B2 | 7/2007 | Szu et al. |
| 8,871,214 B2 | 10/2014 | Serino et al. |
| 9,060,965 B2 | 6/2015 | Costantino et al. |
| 9,492,559 B2 | 11/2016 | Emini et al. |
| 9,517,274 B2 | 12/2016 | Gu et al. |
| 9,585,950 B2 | 3/2017 | Wacker et al. |
| 9,700,612 B2 | 7/2017 | Kowarik et al. |
| 9,849,169 B2 | 12/2017 | Nagy et al. |
| 11,260,119 B2 | 3/2022 | Donald et al. |
| 2003/0199071 A1 | 10/2003 | Langermann et al. |
| 2006/0228380 A1 | 10/2006 | Hausdorff et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2007/0231876 A1 | 10/2007 | Biemans et al. |
| 2007/0253984 A1 | 11/2007 | Kandke et al. |
| 2012/0276137 A1 | 11/2012 | Freese et al. |
| 2013/0122033 A1 | 5/2013 | De Santis et al. |
| 2015/0216996 A1 | 8/2015 | Gu et al. |
| 2015/0328328 A1 | 11/2015 | Han et al. |
| 2016/0015797 A1 | 1/2016 | Bouzari |
| 2016/0106826 A1 | 4/2016 | Ghunaim et al. |
| 2016/0158333 A1 | 6/2016 | White et al. |
| 2016/0193330 A1 | 7/2016 | Eldridge et al. |
| 2016/0220666 A1 | 8/2016 | Eldridge et al. |
| 2016/0324950 A1 | 11/2016 | Anderson et al. |
| 2017/0260240 A1 | 9/2017 | Simon et al. |
| 2019/0275134 A1 | 9/2019 | Poolman |
| 2019/0275135 A1 | 9/2019 | Poolman |
| 2020/0002727 A1 | 1/2020 | Feary et al. |
| 2020/0061177 A1 | 2/2020 | Donald et al. |
| 2021/0221856 A1* | 7/2021 | Grijpstra ............ A61K 39/0258 |

(Continued)

FOREIGN PATENT DOCUMENTS

CA 2004810 6/1990
EP 0 372 501 A2 12/1989

(Continued)

OTHER PUBLICATIONS

Sarshar et al. Antibiotics 9: 397: pp. 1 of 16-16 of 16, 2009.*
Greenspan et al. Nature Biotechnology 17: 936-937, 1999.*
Lazar et al. Mol. Cellular Biol. 8: 1247-1252, 1988.*
Saha et al. J. Gen. Virol. 93: 1548-1555, 2012.*
Hannan et al, "Early Severe Inflammatory Responses to Uropathogenic *E. coli* Predispose to Chronic and Recurrent Urinary Tract Infection", PLoS Pathogens 6(8):e1001042 (2010).
Hannan T., and Hunstad Da, "A Murine Model for *Escherichia coli* Urinary Tract Infection" Methods Mol Biol 1333:159-175 (2016).
Haraoka M., et al. "Neutrophil recruitment and resistance to urinary tract infection", J Infect Dis 180:1220-1229 (1999).

(Continued)

*Primary Examiner* — S. Devi
(74) *Attorney, Agent, or Firm* — Rebecca Wright

(57) ABSTRACT

This disclosure relates to the design of *E. coli* mutated FimH polypeptides that result in improved biochemical properties and immunogenicity, compositions comprising such polypeptides, and uses thereof.

20 Claims, 16 Drawing Sheets

Specification includes a Sequence Listing.

(56) References Cited

U.S. PATENT DOCUMENTS

| | | |
|---|---|---|
| 2021/0268095 A1 | 9/2021 | Donald et al. |
| 2022/0152181 A1 | 5/2022 | Anderson et al. |
| 2022/0168410 A1 | 6/2022 | Donald et al. |
| 2023/0000966 A1 | 1/2023 | Anderson et al. |

FOREIGN PATENT DOCUMENTS

| | | |
|---|---|---|
| EP | 0 413 378 B1 | 2/1991 |
| EP | 0 378 881 B1 | 6/1993 |
| EP | 0 427 347 B1 | 2/1995 |
| EP | 0 471 177 B1 | 10/1995 |
| EP | 0 689 454 B1 | 9/1997 |
| EP | 0 594 610 B1 | 9/1998 |
| EP | 0 735 898 B1 | 3/1999 |
| EP | 0 761 231 B1 | 1/2000 |
| GB | 2 220 211 A | 1/1990 |
| WO | 90/03184 A1 | 4/1990 |
| WO | 91/01146 A1 | 2/1991 |
| WO | 93/003765 A1 | 3/1993 |
| WO | 93/17712 A2 | 9/1993 |
| WO | 94/03208 A1 | 2/1994 |
| WO | 95/20657 A1 | 8/1995 |
| WO | 96/11711 A1 | 4/1996 |
| WO | 97/01640 A2 | 1/1997 |
| WO | 98/36772 A1 | 8/1998 |
| WO | 98/57659 A1 | 12/1998 |
| WO | 98/58668 A2 | 12/1998 |
| WO | 99/11241 A1 | 3/1999 |
| WO | 99/44636 A2 | 9/1999 |
| WO | 99/52549 A1 | 10/1999 |
| WO | 00/004922 A1 | 2/2000 |
| WO | 00/07621 A2 | 2/2000 |
| WO | 00/23105 A2 | 4/2000 |
| WO | 00/37105 A2 | 6/2000 |
| WO | 00/39299 A2 | 7/2000 |
| WO | 00/41720 A1 | 7/2000 |
| WO | 00/48630 A1 | 8/2000 |
| WO | 00/56358 A2 | 9/2000 |
| WO | 00/61761 A2 | 10/2000 |
| WO | 00/62800 A2 | 10/2000 |
| WO | 01/04148 A2 | 1/2001 |
| WO | 01/21152 A1 | 3/2001 |
| WO | 01/21207 A2 | 3/2001 |
| WO | 01/72337 A1 | 10/2001 |
| WO | 01/98334 A2 | 12/2001 |
| WO | 02/04496 A2 | 1/2002 |
| WO | 02/053181 A1 | 7/2002 |
| WO | 02/091998 A2 | 11/2002 |
| WO | 03/054007 A2 | 7/2003 |
| WO | 2004/081515 A2 | 9/2004 |
| WO | 2004/083251 A2 | 9/2004 |
| WO | 2006/032499 A1 | 3/2006 |
| WO | 2006/110381 A1 | 10/2006 |
| WO | 2006/134423 A2 | 12/2006 |
| WO | 2007/026190 A2 | 3/2007 |
| WO | 2008/079653 A1 | 7/2008 |
| WO | 2008/142034 A2 | 11/2008 |
| WO | 2008/143709 A2 | 11/2008 |
| WO | 2009/000826 A1 | 12/2008 |
| WO | 2010/125480 A1 | 11/2010 |
| WO | 2013/164334 A1 | 11/2013 |
| WO | 2013/188539 A2 | 12/2013 |
| WO | 2014/013375 A1 | 1/2014 |
| WO | 2014/027302 A1 | 2/2014 |
| WO | 2014/057109 A1 | 4/2014 |
| WO | 2014/072405 A1 | 5/2014 |
| WO | 2015/052344 A1 | 4/2015 |
| WO | 2015/124769 A1 | 8/2015 |
| WO | 2016/012587 A1 | 1/2016 |
| WO | 2016/115328 A1 | 7/2016 |
| WO | 2016/168324 A1 | 10/2016 |
| WO | 2016/183501 A1 | 11/2016 |
| WO | 2017/035181 A1 | 3/2017 |
| WO | 2017/085586 A1 | 5/2017 |
| WO | 2019/016187 A1 | 1/2019 |
| WO | 2019/175147 A1 | 9/2019 |
| WO | 2020/039359 A2 | 2/2020 |
| WO | 2021/084429 A1 | 5/2021 |
| WO | 2021/144369 A1 | 7/2021 |
| WO | 2021/165928 A2 | 8/2021 |
| WO | 2022/090893 A2 | 5/2022 |

OTHER PUBLICATIONS

Hefzy, E. and Hassuna, N., "Fluoroquinolone-Resistant Sequence Type 131 Subgroups O25b and O16 Among Extraintestinal *Escherichia coli* Isolates from Community-Acquired Urinary Tract Infections", Microb Drug Resist 23:224-229 (2017).

Heinrichs, D., et al., "The Assembly System for the Lipopolysaccharide R2 Core-Type of *Escherichia coli* is a hybrid of those found in *Escherichia coli* K-12 and *Salmonella enterica* Structure and function of the R2 WaaL and WaaL homologs", J Biol Chem. 273(15): 8849-59 (1998).

Hong, Y. and Reeves P., "Model for the Controlled Synthesis of O-Antigen Repeat Units Involving the Waal Ligase" mSphere 1 E00074-15 (2016).

Hull et al, "Construction and Expression of Recombinant Plasmids Encoding Type 1 or D-Mannose-Resistant Pili from a Urinary Tract Infection *Escherichia coli* Isolate", Infection and Immunity 33(3):933-938 (1981).

Huttner, A., et al., "Safety, Immunogenicity, and Preliminary Clinical Efficacy of a Vaccine Against Extraintestinal Pathogenic *Escherichia coli* in Women with a History of Recurrent Urinary Tract Infection: a Randomised, Single-Blind, Placebo-Controlled Phase 1b Trial", Lancet Infect Dis, doi: 10.1016/s1473-3099(17)30108-1 (2017).

Huttner, A., et al., "The Development and Early Clinical Testing of the ExPEC4V Conjugate Vaccine Against Uropathogenic *Escherichia coli*", Clin Microbiol Infect. 24(10):1046-1050 (2018).

Iebba et al., "Microevolution in fimH Gene of Mucosa-Associated *Escherichia coli* Strains Isolated from Pediatric Patients with Inflammatory Bowel Disease", Infection and Immunity 80(4): 1408-1417 (2012).

Iguchi, A., et al., "A Complete View of the Genetic Diversity of the *Escherichia coli* O-antigen Biosynthesis Gene Cluster", DNA Res. 22(1):101-107 (2015).

Inoue, M., et al., "Safety, Tolerability and Immunogenicity of the ExPEC4V (JNJ-63871860) Vaccine for Prevention of Invasive Extraintestinal Pathogenic *Escherichia coli* Disease: A phase 1, Randomized, Double-Blind, Placebo-Controlled Study in Healthy Japanese Participants", Hum Vaccin & Immunother. 14(9):2150-2157 (2018).

Iredell et al, "Antibiotic resistance in Enterobacteriaceae: mechanisms and clinical implications", BMJ 352:h6420 (2016).

Jiang, L., et al., "Structure and Gene Cluster of the O-antigen of *Escherichia coli* O68", Carbohydrate Research 397:27-30 (2014).

Joensen et al, "Rapid and Easy In Silico Serotyping of *Escherichia coli* Isolates by Use of Whole-Genome Sequencing Data", Journal of Clinical Microbiology 53(8):2410-2426 (2015).

Johnson S., et al., "Correlation of opsonophagocytosis and passive protection assays using human anticapsular antibodies in an infant mouse model of bacteremia for *Streptococcus pneumoniae*", J Infect Dis, 180:133-140 (1999).

Jolley et al, "Open-access bacterial population genomics: BIGSdb software, the PubMLST.org website and their applications", Wellcome Open Research 3:124 (2018).

Jonsson, K., et al., "Structural Determination of the O-antigenic Polysaccharide from *Escherichia coli* O74", Carbohydrade Research 344:1592-1595 (2009).

Kalynych, S., et al., "Structure-Guided Investigation of Lipopolysaccharide O-Antigen Chain Length Regulators Reveals Regions Critical for Modal Length Control", J Bacteriol. 193(15): 3710-3721 (2011).

Kalynych, S., et al., "Progress in Understanding the Assembly Process of Bacterial O-antigen", FEMS Microbiol Rev., 38(5):1048-1065 (2014).

Ktnik-Prastowska et al., "Glycosylation of uroplakins. Implications for bladder physiopathology", Glycoconjugate Journal 31:623-636 (2014).

(56) References Cited

OTHER PUBLICATIONS

Khatun et al, "Immunology of carbohydrate-based vaccines", Advanced Drug Delivery Reviews 165-166:117-126 (2020).
Kido et al, "A Single Amino Acid Substitution in a Mannosyltransferase, WbdA, Converts the Escherichia coli O9 Polysaccharide into O9a: Generation of a New O-Serotype Group", Journal of Bacteriology 182(9):2567-2573 (2000).
King et al, "Lipopolysaccharide O antigen size distribution is determined by a chain extension complex of variable stoichiometry in Escherichia coli O9a", Proc. Natl. Acad. Sci. USA 111(17):6407-6412 (2014).
Kisiela et al, "Conformational inactivation induces immunogenicity of the receptor-binding pocket of a bacterial adhesin", PNAS 110(47):19089-19094 (2013).
Kisiela et al, "Conformational inactivation induces immunogenicity of the receptor-binding pocket of a bacterial adhesin—Supporting Information", 10.1073/pnas.1314395110 (2013).
Kisiela et al, "Inhibition and Reversal of Microbial Attachment by an Antibody with Parasteric Activity against the FimH Adhesin of Uropathogenic E. coli", PLoS Pathogens 11(5):e1004857 (2015).
Knirel, "Structure of O-Antigens", Bacterial Lipopolysaccharides, Y.A. Knirel and M.A. Valvano (eds.), Springer-Verlag/Wien 2011, Chapter 3, pp. 41-115.
Konadu, E., et al., Preparation, Characterization, and Immunological Properties in Mice of Escherichia coli O157 O-Specific Polysaccharide-Protein Conjugat Vaccines, Infection and Immunity, 62(11):5048-5054 (1994).
Kuo et al, "Characterization of a Recombinant Pneumolysin and Its Use as a Protein Carrier for Pneumococcal Type 18C Conjugate Vaccines", Infection and Immunity 63(7):2706-2713 (1995).
Lane, M., et al., "Expression of flagella is coincident with uropathogenic Escherichia coli ascension to the upper urinary tract", Proceedings of the National Academy of Sciences, 104:16669-16674 (2007).
Langermann et al, "Prevention of Mucosal Escherichia coli Infection by FimH-Adhesin-Based Systemic Vaccination", Science 276:607-611 (1997).
Larzabal, M., et al, "Human and Veterinary Vaccines against Pathogenic Escherichia coli", IntechOpen, 21 pages (2018).
Lerouge and Vanderleyden, "O-antigen structural variation: mechanisms and possible roles in animal/plant-microbe interactions", FEMS Microbiology Reviews 26(1):17-47 (2001).
Le Trong et al, "Donor strand exchange and conformational changes during E. coli fimbrial formation", Journal of Structural Biology 172(3):380-388 (2010).
Letrong, I., et al., "Structural Basis for Mechanical Force Regulation of the Adhesin FimH via Finger Trap-like b Sheet Twisting", Cell, 141:645-655 (2010).
Liu et al, "Identification of FimH derivatives as adjuvant vaccinated with Pac that enhance protection against Streptococcus mutans colonization", Molecular and Cellular Probes 45:19-25 (2019).
Ma, Z., et al., "Glycoconjugate Vaccine Containing Escherichia coli O157:H7 O-Antigen Linked with Maltose-Binding Protein Elicits Humoral and Cellular Responses", PLOS ONE, 9(8): 1-10 (2014).
Magala et al, "RMSD analysis of structures of the bacterial protein FimH identifies five conformations of its lectin domain", Proteins 88(4):593-603 (2019).
Marder et al, "Multistate Outbreak of Escherichia coli O157:H7 Associated with Bagged Salad", Foodborne Pathogens and Disease 11(8):593-595 (2014).
Mather, "Establishment and Characterization of Two Distinct Mouse Testicular Epithelial Cell Lines", Biology of Reproduction 23:243-252 (1980).
Mather et al, "Culture of Testicular Cells in Hormone-Supplemented Serum-Free Medium", Annals N.Y. Acad. Sci. 383:44-68 (1982).
Meiland, R., et al., "Fimch antiserum inhibits the adherence of Escherichia coli to cells collected by voided urine specimens of diabetic women" J Urol 171:1589-1593 (2004).

Mellata, M., et al, "Novel vaccine antigen combinations elicit protective immune responses against Escherichia coli sepsis", Vaccine, 34(5):656-662 (2016).
Meloni, E., et al., "Simplified low-cost production of O-antigen from Salmonella typhimurium Generalized Modules for Membrane Antigens (GMMA)", Journal of Biotechnology 198:46-52 (2015).
Micoli, F., et al., "A Scalable Method for O-antigen Purification Applied to Various Salmonella serovars", Anal Biochem, 434(1):136-145 (2013).
Milstein et al, "Hybrid hybridomas and their use in immunohistochemistry", Nature 305(5934):537-540 (1983).
Mobley H. and Alteri C., "Development of a Vaccine against Escherichia coli Urinary Tract Infections", Pathogens 5 (2016).
Morales-Barroso, I., et al., "Bacteraemia due to non-ESBL-producing Escherichia coli O25b:H4 sequence type 131: insights into risk factors, clinical features and outcomes", Int J Antimicrob Agents doi:10.1016/j.ijantimicag (2016).
Moriel, D., et al., "Identification of Protective and Broadly Conserved Vaccine Antigens from the Genome of Extraintestinal Pathogenic Escherichia coli", Proc Natl Acad Sci, 107(20):9072-9077 (2010).
Motley, M. & Fries, B., "A New Take on an Old Remedy: Generating Antibodies against Multidrug-Resistant Gram-Negative Bacteria in a Postantibiotic World", mSphere, 2(5) e00397-17 (2017).
Mulford, C. and Osborn M., "An intermediate step in translocation of lipopolysaccharide to the outer membrane of Salmonella typhimurium", Proc Natl Acad Sci U S A 80:1159-1163 (1983).
Muller-Leonnies, S., et al., "Neutralizing and Cross-Reactive Antibodies Against Enterobacterial Lipopolysaccharide", Int J Med Microbiol., 297(5):321-40 (2007).
Munera et al, "Recognition of the N-terminal lectin domain of FimH adhesin by the usher FimD is required for type 1 bilus biogenesis", Molecular Microbiology 64(2):333-346 (2007).
Munera et al, "Specific residues in the N-terminal domain of FimH stimulate type 1 fimbriae assembly in Escherichia coli following the initial binding of the adhesin to FimD usher", Molecular Microbiology 69(4):911-925 (2008).
Murray, G., et al., "Regulation of Salmonella typhimurium lipopolysaccharide O antigen chain length is required for virulence; identification of FepE as a second Wzz", Mol Microbiol, 47:1395-1406 (2003).
Naumenko, O., "Structure and Gene Cluster of the O-antigen of Escherichia coli O54", Carbohydrate Research, 462:34-38 (2018).
Naumenko, O., et al., "Structural Studies on the O-polysaccharide of Escherichia coli O57", Carbohydrate Research 465:1-3 (2018).
Needleman et al, "A General Method Applicable to the Search for Similarities in the Amino Acid Sequence of Two Proteins", J. Mol. Biol. 48(3):443-453 (1970).
Nicolas-Chanoine et al, "Escherichia coli ST131, an Intriguing Clonal Group", Clinical Microbiology Reviews 27(3):543-574 (2014).
O'Brien, V., et al, "Drug and Vaccine Development for the Treatment and Prevention of Urinary Tract Infections", Microbiol Spectrum 4(1): 1-42 (2016).
Osawa, K., et al., "Modulation of O-antigen chain length by the wzz gene in Escherichia coli O157 influences its sensitivities to serum complement", Microbiol Immunol 57:616-623 (2013).
PCT International Search Report and Written Opinion for International Application No. PCT/IB2019/057025 issued on Feb. 17, 2020.
PCT International Search Report and Written Opinion for International Application No. PCT/IB2021/051457 issued on Aug. 16, 2021.
PCT International Search Report and Written Opinion for International Application No. PCT/IB2020/060081 issued on Dec. 21, 2020.
PCT International Search Report and Written Opinion for International Application No. PCT/IB2021/062022 mailed on Jun. 3, 2022.
Pearson et al, "Improved tools for biological sequence comparison", PNAS 85:2444-2448 (1988).
Perepelov, A., et al., "Structure and Gene Cluster of the O-antigen of Escherichia coli O76", Carbohydrate Research, 377:14-14 (2013).
Perepelov, A., et al., "Structure and Gene Cluster of the O-antigen of Escherichia coli O36", Carbohydrate Research, 390:46-49 (2014).

(56) References Cited

OTHER PUBLICATIONS

Perepelov, A., et al., "Structure and Gene Cluster of the O-antigen of *Escherichia coli* O140", Carbohydrate Research 411:33-36 (2015).
Phalipon, A., et al., "A Synthetic Carbohydrate-Protein Conjugate Vaccine Candidate Against Shigella Flexneri 2a Infection", J Immunol., 182(4):2241-7 (2009).
Phan, M., et al., "The Serum Resistome of a Globally Disseminated Multidrug Resistant Uropathogenic *Escherichia coli* Clone", PLoS Genetics 9:e1003834 (2013).
Podschun et al, "*Klebsiella* spp. As Nosocomial Pathogens: Epidemiology, Taxonomy, Typing Methods, and Pathogenicity Factors", Clinical Microbiology Reviews 11(4):589-603 (1998).
Poolman et al, "Extraintestinal Pathogenic *Escherichi coli*, a Common Human Pathogen: Challenges for Vaccine Development and Progress in the Field", The Journal of Infectious Diseases 213:6-13 (2016).
Rabbani, S., et al, "Conformational switch of the bacterial adhesin FimH in the absence of the regulatory domain: Engineering a minimalistic allosteric system", J. Biol. Chem., 293(5): 1835-1849 (2018).
Reyes E., et al., Mechanisms of O-Antigen Structural Variation of Bacterial Lipopolysaccharide (LPS). Chapter 3, The Complex World of Polysaccharides. IntechOpen (2012).
Rodriguez et al, "Allosteric Coupling in the Bacterial Adhesive Protein FimH", The Journal of Biological Chemistry 288(33):24128-24139 (2013).
Rogers et al, "*Escherichia coli* O25b-ST131: a pandemic, multiresistant, community-associated strain", Journal of Antimicrobial Chemotherapy 66:1-14 (2011).
Ronald, L., et al., "Adaptive mutations in the signal peptide of the type 1 fimbrial adhesin of uropathogenic *Escherichia coli*" PNAS, 105(31): 10937-10942 (2008).
Ruiz-Argüello et al., "Thermostability of the human respiratory syncytial virus fusion protein before and after activation: implications for the membrane-fusion mechanism", Journal of General Virology 85(12):3677-3687 (2004).
Russo et al., "Medical and economic impact of extraintestinal infections due to *Escherichia coli*: focus on an increasingly important endemic problem", Microbes and Infection 5:449-456 (2003).
Sarkar et al, "Role of Capsule and O Antigen in the Virulence of Uropathogenic *Escherichia coli*", PLoS One 9(4):e94786 (2014).
Sato, T., et al. , "Tigecycline Nonsusceptibility Occurs Exclusively in Fluoroquinolone-Resistant *Escherichia coli* Clinical Isolates, Including the Major Multidrug-Resistant Lineages", Antimicrob Agents Chemother, O25b:H4-ST131-H30R and O1-ST648. 61 (2017).
Sauer, M., et al, "Catch-bond mechanism of the bacterial adhesin FimH", Nat. Commun. 7:10738 doi: 10.1038/ncomms 10738 (2016).
Schembri M, et al, "Expression and purification of the mannose recognition domain of the FimH adhesin", FEMS Microbiology Letters 188:147-151 (2000).
Schrag et al, "Epidemiology of Invasive Early-Onset Neonatal Sepsis, 2005 to 2014", Pediatrics 138(6):e20162013 (2016).
Schwartz et al, "Population Dynamics and Niche Distribution of Uropathogenic *Escherichia coli* during Acute and Chronic Urinary Tract Infection", Infection and Immunity 79(10):4250-4259 (2011).
Schwartz et al, "Positively selected FimH residues enhance virulence during urinary tract infection by altering FimH conformation", PNAS 110(39):15530-15537 (2013).
Shang, W., et al., "Chemical Synthesis of the Outer Core Oligosaccharide of *Escherichia coli* R3 and Immunological Evaluation" Org Biomol Chem., 13(14):4321-4330 (2015).
Sheikh, A., et al., "Highly conserved type 1 pili promote enterotoxigenic *E. coli* pathogen-host interactions", PLOS Negl Trop Dis 11(5): e0005586 (2017).
Sihra, N., et al., "Nonantibiotic prevention and management of recurrent urinary tract infection", Nat Rev Urol 15: 750-776 (2018).
Sjölander et al., "ISCOMs: an adjuvant with multiple functions", Journal of Leukocyte Biology 64:713-723 (1998).
Smith, SN, "Dissemination and systemic colonization of uropathogenic *Escherichia coli* in a murine model of bacteremia" MBio 1 (2010).

Starks et al, "Optimization and qualification of an assay that demonstrates that a FimH vaccine induces functional antibody responses in women with histories of urinary tract infections", Human Vaccines & Immunotherapeutics 17(1):283-292 (2021).
Stenutz, R., et al., The Structures of *Escherichia coli* O-polysaccharide Antigens, FEMS Microbiol Rev., 30(3):382-403 (2006).
Stoll et al, "Early Onset Neonatal Sepsis: The Burden of Group B Streptococcal and *E. coli* Disease Continues", Pediatrics 127(5):817-826 (2011).
Summers et al, A Manual of Methods for Baculovirus Vectors and Insect Cell Culture Procedures; Texas Agricultural Experiment Station Bulletin No. 1555 (1987).
Szijarto, V., et al., "Diagnostic Potential of Monoclonal Antibodies Specific to the Unique O-Antigen of Multidrug-Resistant Epidemic *Escherichia coli* Clone ST131-025b:H4", Clin Vaccine Immunol., 21(7):930-939 (2014).
Szijarto, V., et al., "Bactericidal monoclonal antibodies specific to the lipopolysaccharide O antigen from multidrug-resistant *Escherichia coli* clone ST131-O25b:H4 elicit protection in mice", Antimicrob Agents Chemother 59:3109-3116 (2015).
Taylor, C., et al., Mutations in the waaR Gene of *Escherichia coli* Which Disrupt Lipopolysaccharide Outer Core Biosynthesis Affect Cell Surface Retention of Group 2 Capsular Polysaccharides, J Bacteriol. 88(3): 1165-1168 (2006).
Tchesnokova, V., et al, "Type 1 Fimbrial Adhesin FimH Elicits an Immune Response That Enhances Cell Adhesion of *Escherichia coli*", Infection and Immunity, 79(10): 3895-3904 (2011).
Thelwall et al, "Annual Epidemiological Commentary: Mandatory MRSA, MSSSA and *E. coli* bacteraemia and *C. difficile* infection data 2015/16", Jul. 7, 2016, Public Health England.
Thumbikat et al, "Bacteria-Induced Uroplakin Signaling Mediates Bladder Response to Infection", PLoS Pathogens 5(5):e1000415 (2009).
Tocilj, A., et al., "Bacterial polysaccharide co-polymerases share a common framework for control of polymer length" Nat Struct Mol Biol 15:130-138 (2008).
Uchida et al., "Mutation in the Structural Gene for Diphtheria Toxin Carried by Temperate Phage Beta", Nature New Biology 233:8-11 (1971).
Uchida et al., "Diphtheria toxin and related proteins. I. Isolation and properties of mutant proteins serologically related to diphtheria toxin", J Biol Chem 248(11):3838-3844 (1973).
Urlaub et al., "Isolation of Chinese hamster cell mutants deficient in dihydrofolate reductase activity", Proc. Natl. Acad. Sci. USA 77(7):4216-4220 (1980).
Van den Dobbelsteen et al., "Immunogenicity and safety of a tetravalent *E. coli* O-antigen bioconjugate vaccine in animal models", Vaccine 34:4152-4160 (2016).
Vetsch et al., "Chaperone-independent Folding of Type 1 Pilus Domains", J. Mol. Biol. 322(4):827-840 (2002).
Vimont, S., et al., "The CTX-M-15-producing *Escherichia coli* clone O25b: H4-ST131 has high intestine colonization and urinary tract infection abilities" PLoS One 7:e46547 (2012).
Vinogradov et al, "Structures of Lipopolysaccharides from Klebsiella pneumoniae: Elucidation of the Structure of the Linkage Region Between Core and Polysaccharide O Chain and Identification of the Residues at the Non-Reducing Termini of the O Chains", The Journal of Biological Chemistry 277(28):25070-25081 (2002).
Weissman et al, "Clonal analysis reveals high rate of structural mutations in fimbrial adhesins of extraintestinal pathogenic *Escherichia coli*", Mol Microbiol. 59(3):975-988 (2006).
Whitfield, C., et al, Molecular Insights Into the Assembly and Diversity of the Outer Core Oligosaccharide in Lipopolysaccharides from *Escherichia coli* and *Salmonella*, J Endotoxin Res., 9(4):244-249 (2003).
Wick et al, "Kaptive Web: User-Friendly Capsule and Lipopolysaccharide Serotype Prediction for Klebsiella Genomes", Journal of Clinical Microbiology 56(6):e00197-18 (2018).
Wirth et al, "Sex and virulence in *Escherichia coli*: an evolutionary perspective", Molecular Microbiology 60(5):1136-1151 (2006).
Wizemann, T., et al., "Adhesins as Targets for Vaccine Development", Emerg Infect Dis, 5(3): 395-403 (1999).

(56) References Cited

OTHER PUBLICATIONS

Wolf, M., Occurrence, Distribution, and Associations of O and H serogroups, Colonization Factor Antigens, and Toxins of Enterotoxigenic *Escherichia coli*, Clin Microbiol Rev., 10(4):569-84 (1997).
Woodward, R., et al., "In vitro bacterial polysaccharide biosynthesis: defining the functions of Wzy and Wzz." Nat Chem Biol., 6(6):418-23 (2010).
Yinnon et al., "Klebsiella bacteraemia: community versus nosocomial infection", Q J Med 89(12):933-941 (1996).
Zhou, G., et al., "Uroplakin la is the urothelial receptor for uropathogenic *Escherichia coli*: evidence from in vitro FimH binding", J Cell Sci 114:4095-4103 (2001).
Zowawi et al, "The emerging threat of multidrug-resistant Gram-negative bacteria in urology", Nature Reviews Urology 12:570-584 (2015).
Abbanat, D., et al., "Development and Qualification of an Opsonophagocytic Killing Assay To Assess Immunogenicity of a Bioconjugated *Escherichia coli* Vaccine", Clin Vaccine Immunol 24(12):e00123-17 (2017).
Al-Hasan et al, "Antimicrobial resistance trends of *Escherichia coli* bloodstream isolates: a population-based study, 1998-2007", Journal of Antimicrobial Chemotherapy 64(1):169-174 (2009).
Alonso-Caballero, A., et al., "Mechanical architecture and folding of *E. coli* type 1 pilus domains", Nat Commun 9, 2758 (2018).
Amor, K., et al., "Distribution of core oligosaccharide types in lipopolysaccharides from *Escherichia coli*", Infect Immun 68:1116-1124 (2000).
Anderson et al, "Bloodstream Infections in Community Hospitals in the 21st Century: A Multicenter Cohort Study", PLoS ONE 9(3):e91713 (2014).
Appelmelk, B., et al., "Frequencies of lipopolysaccharide core types in *Escherichia coli* strains from bacteraemic patients", Microbiology 140:1119-24 (1994).
Aprikian, P., et al., "The Bacterial Fimbrial Tip Acts as a Mechanical Force Sensor", PLoS Biol 9(5):e1000617 (2011).
Baliban, S., et al., "Development of a glycoconjugate vaccine to prevent invasive *Salmonella typhimurium* infections In sub-Saharan Africa", PLoS Negl Trop Dis. 11(4): e0005493 (2017).
Bameri, Z., et al., "High Yield Expression and Modified Purification of Novel Recombinant Truncated Protein FimH. MrpH against Urinary Tract Infections by *Escherichia coli* and *Proteus mirabilis*", Journal of Clinical and Diagnostic Research 12(1): KC06-KC09 (2018).
Baraldo et al, "N19 Polyepitope as a Carrier for Enhanced Immunogenicity and Protective Efficacy of Meningococcal Conjugate Vaccines", Infection and Immunity 72(8):4884-4887 (2004).
Barnhart et al, "PapD-like chaperones provide the missing information for folding of pilin proteins", PNAS 97 (14):7709-7714 (2000).
Barnhart et al, "Chaperone-Subunit-Usher Interactions Required for Donor Strand Exchange during Bacterial Pilus Assembly", Journal of Bacteriology 185(9):2723-2730 (2003).
Bauchart et al, "Pathogenomic comparison of human extraintestinal and avian pathogenic *Escherichia coli*—Search for factors involved in host specificity or zoonotic potential", Microbial Pathogenesis 49(3):105-115 (2010).
Behrens, R., et al., "Efficacy and safety of a patch vaccine containing heat-labile toxin from *Escherichia coli* against travellers' diarrhoea: a phase 3, randomised, double-blind, placebo-controlled field trial in travellers from Europe to Mexico and Guatemala", Lancet Infect Dis. 14(3):197-204 (2014).
Bennett-Guerrero, E., et al., "Preparation and Preclinical Evaluation of a Novel Liposomal Complete-Core Lipopolysaccharide Vaccine", Infect Immun. 68(11):6202-6208 (2000).
Bouckaert et al, "Receptor binding studies disclose a novel class of high-affinity inhibitors of the *Escherichia coli* FimH adhesin", Molecular Microbiology 55(2):441-455 (2005).
Bourgeois, A., et al., "Status of vaccine research and development for enterotoxigenic *Escherichia coli*", Vaccine 34(26):2880-2886 (2016).

Brown et al, "Structure of the streptococcal cell wall C5a peptidase", Proc. Natl. Acad. Sci. USA 102 (51):18391-18396 (2005).
Brumbaugh, A., et al., Preventing urinary tract infection: progress toward an effective *Escherichia coli* vaccine. Expert Rev Vaccines. 11(6):663-76 (2012).
Buckles et al, "Role of the K2 Capsule in *Escherichia coli* Urinary Tract Infection and Serum Resistance", The Journal of Infectious Diseases 199(11):1689-1697 (2009).
Burns et al, "Loss of Resistance to Ingestion and Phagocytic Killing by O- and K- Mutants of a Uropathogenic *Escherichia coli* O75:K5 Strain", Infection and Immunity 67(8):3757-3762 (1999).
Céspedes et al, "Genetic Diversity and Virulence Determinants of *Escherichia coli* Strains Isolated from Patients with Crohn's Disease in Spain and Chile", Frontiers in Microbiology 8:Article 639 (2017).
Chakraborty, S., Human Experimental Challenge With Enterotoxigenic *Escherichia coli* Elicits Immune Responses to Canonical and Novel Antigens Relevant to Vaccine Development, The Journal of Infectious Diseases 218(9):1436-1446 (2018).
Chen, S., et al., "Positive selection identifies an in vivo role for FimH during urinary tract infection in addition to mannose binding", PNAS 106(52): 22439-22444 (2009).
Chen et al, "Carbapenemase-producing Klebsiella pneumoniae: molecular and genetic decoding", Trends in Microbiology 22(12):686-696 (2014).
Chmielewski, M., et al., "FimH-based display of functional eukaryotic proteins on bacteria surfaces", Scientific Reports 9:8410 s41598-019-44883 (2019).
Clarke et al, "Coordination of Polymerization, Chain Termination, and Export in Assembly of the *Escherichia coli* Lipopolysaccharide 09a Antigen in an ATP-binding Cassette Transporter-dependent Pathway", The Journal of Biological Chemistry 284(44):30662-30672 (2009).
Clermont, O., et al., Determination of *Escherichia coli* O Types by Allele-Specific Polymerase Chain Reaction: Application to the O types Involved in Human Septicemia, Diagn Microbiol Infect Dis. 57(2):129-36 (2007).
Cryz, S.J., "Synthesis and Characterization of a Polyvalent *Escherichia coli* O-polysaccharide-toxin A Conjugate Vaccine", Vaccine 13(5):449-453 (1995).
Cusumano et al, "Treatment and Prevention of Urinary Tract Infection with Orally Active FimH Inhibitors", Science Translational Medicine 3(109):109ra115 (2011).
Debroy, C., et al., Comparison of O-Antigen Gene Clusters of All O-Serogroups of *Escherichia coli* and Proposal for Adopting a New Nomenclature for O-Typing. PLoS One 11(1):e0147434 (2016).
Diancourt et al, "Multilocus Sequence Typing of Klebsiella pneumoniae Nosocomial Isolates", Journal of Clinical Microbiology 43(8):4178-4182 (2005).
Douglas et al, "Exotoxin A of Pseudomonas aeruginosa: Substitution of Glutamic Acid 553 with Aspartic Acid Drastically Reduces Toxicity and Enzymatic Activity", Journal of Bacteriology 169(11):4967-4971).
Dreux et al, "Point Mutations in FimH Adhesin of Crohn's Disease-Associated Adherent-Invasive *Escherichia coli* Enhance Intestinal Inflammatory Response", PLoS Pathogens 9(1):e1003141 (2013).
Durant, L., et al., "Identification of candidates for a subunit vaccine against extraintestinal pathogenic *Escherichia coli*", Infect Immun 75:1916-1925 (2007).
Falugi et al, "Rationally designed strings of promiscuous CD4+ T cell epitopes provide help to Haemophilus Influenzae type b oligosaccharide: a model for new conjugate vaccines", Eur. J. Immunol. 31:3816-3824 (2001).
Feenstra et al, "Adhesion of *Escherichia coli* under flow conditions reveals potential novel effects of FimH mutations", Eur J Clin Microbiol Infect Dis 36:467-478 (2017).
Feldman, M., et al., "Engineering N-linked protein glycosylation with diverse O antigen lipopolysaccharide structures in *Escherichia coli*", Proceedings of the National Academy of Sciences of the United States of America 102:3016-3021 (2005).
Follador et al, "The diversity of Klebsiella pneumoniae surface polysaccharides", Microbial Genomics 2:e000073 (2016).

(56) References Cited

OTHER PUBLICATIONS

Forde, B., et al., "The complete genome sequence of *Escherichia coli* EC958: a high quality reference sequence for the globally disseminated multidrug resistant *E. coli* O25b:H4-ST131 clone", PLoS One, 9:e104400 (2014).

Franco, A., et al., "A Wzz (Cld) Protein Determines the Chain Length of K Lipoploysaccharide in *Escherichia coli* O8 and O9 Strains", Journal of Bacteriology 178(7):1903-1907 (1996).

Ghosh et al, "Incidence of multidrug resistance, pathogenicity island markers, and pathoadaptive FimH mutations in uropathogenic *Escherichia coli* isolated from asymptomatic hospitalized patients", Folia Microbiologica 64(4):587-600 (2019).

Giedraitiene, A., et al., "Prevalence of O25b-ST131 clone among *Escherichia coli* strains producing CTX-M-15, CTX-M-14 and CTX-M-92 beta-lactamases", Infect Dis (Lond) 49:106-112 (2017).

Graham et al, "Characteristics of a Human Cell Line Transformed by DNA from Human Adenovirus Type 5", J. Gen. Virol. 36(1):59-74 (1977).

Green, S., et al., "Murine model of chemotherapy-induced extraintestinal pathogenic *Escherichia coli* translocation", Infect Immun 83:3243-3256 (2015).

Greenfield et al, "Biosynthesis of the Polymannose Lipopolysaccharide O-antigens from *Escherichia coli* Serotypes O8 and O9a Requires a Unique Combination of Single- and Multiple-active Site Mannosyltransferases", The Journal of Biological Chemistry 287(42):35078-35091 (2012).

Guachalla et al, "Discovery of monoclonal antibodies cross-reactive to novel subserotypes of K. pneumoniae O3", Scientific Reports 7:6635 (2017).

Jagan E. and Mobley H., "Uropathogenic *Escherichia coli* outer membrane antigens expressed during urinary tract infection", Infect Immun 75:3941-3949 (2007).

Han D., et al., "Regulation of the O-antigen polysaccharide chain length by Wzz—a review", Acta Microbiologica Sinica 54(9):971-976 (2014).

Franco et al, "The Wzz (Cld) Protein in *Escherichia coli*: Amino Acid Sequence Variation Determines O-Antigen Chain Length Specificity", Journal of Bacteriology 180(10):2670-2675 (1998).

Frenck, R., et al., Long-term Immunogenicity and Safety of ExPEC4V Vaccine Against Extraintestinal Pathogenic *Escherichia coli* Disease in Healthy Participants. Presented at the American Society for Microbiology, June 7-11, Atlanta, GA. (2018).

Kurupati et al, "Identification of vaccine candidate antigens of an ESBL producing Klebsiella pneumoniae clinical strain by immunoproteome analysis", Proteomics 6:836-844 (2006).

Yakovenko et al., "Inactive conformation enhances binding function in physiological conditions", PNAS 112 (32):9884-9889 (2015).

Singaravelu, M., et al., "Molecular dynamics simulations of lectin domain of FimH and immunoinformatics for the design of potential vaccine candidates", Computational Biology and Chemistry, 2014, 52:18-24.

\* cited by examiner

E. coli FimH MUTANTS AND USES THEREOF

RELATED APPLICATIONS

This application claims priority to U.S. Provisional Application No. 63/130,153 filed Dec. 23, 2020, U.S. Provisional Application No. 63/185,425 filed May 7, 2021 and U.S. Provisional Application No. 63/282,244 filed Nov. 23, 2021. The entire content of each of the foregoing applications is herein incorporated by reference in its entirety.

REFERENCE TO SEQUENCE LISTING

This application is being filed electronically via EFS-Web and includes an electronically submitted sequence listing in .txt format. The .txt file contains a sequence listing entitled "PC072713_ST25_17Nov2021.txt" created on Nov. 17, 2021 and having a size of 220 KB. The sequence listing contained in this .txt file is part of the specification and is incorporated herein by reference in its entirety.

TECHNICAL FIELD OF THE INVENTION

The present disclosure relates to mutated *Escherichia coli* FimH polypeptides and methods of their use.

BACKGROUND OF THE INVENTION

Urinary tract infections (UTI) affect 1 in 5 women at least once during their lifetime and are responsible for significant mobidity and mortality, resulting in a substantial burden on healthcare systems. While several different bacteria can cause UTI, the most common cause (90-95% of cases) is the Gram-negative bacteria *Escherichia coli* (*E. coli*). Most *E. coli* UTI are caused by uropathogenic *E. coli* (UPEC) that colonise the gastrointestinal tract and migrate from the faecal flora to the urogenital tract, where they adhere to host uroepithelial cells, thus establishing a reservoir for ascending infections of the urinary tract. Adhesion is facilitated by fimbrial adhesins including type 1 fimbriae, which bind to mannosylated glycoproteins in the epithelial layer or secreted into the urine. Type 1 fimbriae are highly conserved among clinical UPEC isolates and are encoded by a cluster of genes called fim, which encode accessory proteins (FimC, FimD), various structural subunits (FimE, FimF, FimG) and an adhesin called FimH. FimH is essential for all characteristics of UTI infection in mouse models that mimic aspects of human bladder infection (Hannan et al. PLoS Pathog. 2010 Aug. 12; 6(8):e1001042; doi: 10.1371/journal.ppat.1001042; Schwartz et al. Infect Immun. 2011 October:79(144250-9. doi: 10.1128/IA1.05339-11). Small molecule inhibitors that target FimH by mimicking mannosylated receptors further validate the role of FimH in UTI, and are showing promise as therapeutics in animal models (Cusumano C K, et al. *Sci Transl Med.* 2011; 3(109):109ra115. doi:10.1126/scitranslmed.3003021). In addition, FimH is under positive selection in *E. coli* human cystitis isolates (Chen S L, et al. Proc Natl Acad Sci USA. 2009 Dec. 29; 106(52):22439-44. doi: 10.1073/pnas.0902179106) and positively selected residues may influence virulence in mouse models of cystitis (Schwartz, D. J. et al. Proc Natl Acad Sci USA 110, 15530-15537, doi:10.1073/pnas.1315203110 (2013)).

FimH is composed of two domains, the lectin binding domain (FimH$_{LD}$) responsible for binding to mannosylated glycoproteins, and the pilin domain. The pilin domain serves to link FimH to other structural subunits of the pilus such as FimG, via a mechanism called donor strand exchange (Le Trong, I et al., *J. Struct Biol.* 2010 December; 172(3):380-8. doi: 10.1016/j.jsb.2010.06.002). The FimH pilin domain forms an incomplete immunoglobulin fold, resulting in a groove that provides a binding site for the N-terminal β-strand of FimG, forming a strong intermolecular linkage between FimH and FimG. While FimH$_{LD}$ can be expressed in a soluble, stable form, full length FimH is unstable alone (Vetsch, M., et al. *J. Mol. Biol.* 322:827-840 (2002); Barnhart M M, et al., *Proc Natl Acad Sci USA.* (2000) July 5; 97(14):7709-14) unless in a complex with the chaperone FimC or complemented with the donor strand peptide of FimG in peptide form or as a fusion protein (Barnhart M M, et al., *Proc Natl Acad Sci USA.* (2000) July 5; 97(14):7709-14; Sauer M M, et al. *Nat Commun.* (2016) March 7; 7:10738; Barnhart M M, et al. *J Bacterial.* 2003 May; 185(9):2723-30). The design and expression of a full length FimH molecule by linking the FimG donor peptide to full length FimH via a glycine-serine linker has been previously described (PCT Intl. Publication No. WO2021/084429, published May 6, 2021), and is designated FimH-DSG.

FimH$_{LD}$ is thought to be a poor immunogen in terms of its ability to stimulate functional immunogenicity. Some studies suggest that although binding antibody titers can be elicited with FimH$_{LD}$ with and without adjuvant, functional neutralizing titers were only observed in the presence of adjuvant (PCT Intl. Publication No. WO2021/084429, published May 6, 2021). Studies suggest that locking FimH in an open conformation, with reduced affinity for mannoside ligands, improves functional immunogenicity (Kisiela, D. I. et al., *Proc Natl Acad Sci USA* 110, 19089-19094 (2013). Accordingly, there is a need in the art for novel FimH mutants with reduced affinity for mannoside ligands and improved biochemical properties that result in improved functional immunogenicity relative to wild type FimH.

SUMMARY OF THE INVENTION

The present disclosure relates to the design of *E. coli* FimH mutated polypeptides that result in improved biochemical properties and immunogenicity, compositions comprising such polypeptides, and uses thereof. For example, in one aspect the present disclosure provides a mutated FimH polypeptide, which comprises at least one amino acid mutation relative to the amino acid sequence of the wild-type FimH polypeptide, wherein the mutation position is selected from the group consisting of: F1, P12, G14, G15, G16, A18, P26, V27, V28, Q32, N33, L34, V35, R60, S62, Y64, G65, L68, F71, T86, L107, Y108, L109, V112, S113, A115, G116, V118, A119, A127, L129, Q133, F144, V154, V155, V156, P157, T158, V163, and V185, wherein the amino acid positions are numbered according to SEQ ID NO:59.

In a further aspect is a mutated FimH polypeptide comprising at least one mutation selected from the group consisting of: F1I; F1L; F1V; F1M; F1Y; F1W; P12C; G14C; G15A; G15P; G16A; G16P; A18C; P26C; V27A; V27C; V28C; Q32C; N33C; L34C; L34N; L34S; L34T; L34D; L34E; L34K; L34R; V35C; R60P; S62C; Y64C; G65A; L68C; F71C; T86C; L107C; Y108C; L109C; V112C; S113C; A115V; G116C; V118C; A119C; A119N; A119S; A119T; A119D; A119E; A119K; A119R; A127C; L129C; Q133K; F144C; V154C; V156C; P157C; T158C; V163I; and V185I, or any combination thereof. For example, a mutated FimH polypeptide comprising the mutations G15A and G16A. Further, for example, a mutated FimH polypeptide comprising the mutations P12C and A18C. Further for example, a mutated FimH polypeptide comprising the mutations G14C and F144C. Further for example, a mutated FimH polypeptide comprising the mutations P26C and V35C. Further for example, a mutated FimH polypeptide comprising the mutations P26C and V154C. Further for example, a mutated FimH polypeptide comprising the mutations P26C and V156C. Further for example, a mutated FimH polypeptide comprising the mutations V27C and L34C. Further for example, a mutated FimH polypeptide comprising the mutations V28C and N33C. Further for example, a mutated FimH polypeptide comprising the mutations V28C and P157C. Further for example, a mutated FimH polypeptide comprising the mutations Q32C and Y108C. Further for example, a mutated FimH polypeptide comprising the mutations N33C and L109C. Further for example, a mutated FimH polypeptide comprising the mutations N33C and P157C. Further for example, a mutated FimH polypeptide comprising the mutations V35C and L107C. Further for example, a mutated FimH polypeptide comprising the mutations V35C and L109C. Further for example, a mutated FimH polypeptide comprising the mutations S62C and T86C. Further for example, a mutated FimH polypeptide comprising the mutations S62C and L129C. Further for example a mutated FimH polypeptide comprising the mutations Y64C and L68C. Further for example a mutated FimH polypeptide comprising the mutations Y64C and A127C. Further for example a mutated FimH polypeptide comprising the mutations L68C and F71C. Further for example a mutated FimH polypeptide comprising the mutations V112C and T158C. Further for example a mutated FimH polypeptide comprising the mutations S113C and G116C. Further for example a mutated FimH polypeptide comprising the mutations S113C and T158C. Further for example a mutated FimH polypeptide comprising the mutations V118C and V156C. Further for example a mutated FimH polypeptide comprising the mutations A119C and V155C. Further for example a mutated FimH polypeptide comprising the mutations L34N and V27A. Further for example a mutated FimH polypeptide comprising the mutations L345 and V27A. Further for example a mutated FimH polypeptide comprising the mutations L34T and V27A. Further for example, a mutated FimH polypeptide comprising the mutations L34D and V27A. Further for example, a mutated FimH polypeptide comprising the mutations L34E and V27A. Further for example, a mutated FimH polypeptide comprising the mutations L34K and V27A. Further for example, a mutated FimH polypeptide comprising the mutations L34R and V27A. Further for example a mutated FimH polypeptide comprising the mutations A119N and V27A. Further for example a mutated FimH polypeptide comprising the mutations A119S and V27A. Further for example a mutated FimH polypeptide comprising the mutations A119T and V27A. Further for example, a mutated FimH polypeptide comprising the mutations A119D and V27A. Further for example, a mutated FimH polypeptide comprising the mutations A119E and V27A. Further for example, a mutated FimH polypeptide comprising the mutations A119K and V27A. Further for example, a mutated FimH polypeptide comprising the mutations A119R and V27A. Further for example a mutated FimH polypeptide comprising the mutations G15A and V27A. Further for example a mutated FimH polypeptide comprising the mutations G16A and V27A. Further for example a mutated FimH polypeptide comprising the mutations G15P and V27A. Further for example a mutated FimH polypeptide comprising the mutations G16P and V27A. Further for example a mutated FimH polypeptide comprising the mutations G15A, G16A, and V27A. Further for example a mutated FimH polypeptide comprising the mutations G65A and V27A. Further for example a mutated FimH polypeptide comprising the mutations V27A and Q133K. Further for example a mutated FimH polypeptide comprising the mutations G15A, G16A, V27A, and Q133K. Further for example a mutated FimH polypeptide comprising the sequence of any one of SEQ ID NOs: 2-58, and 60-64. Further for example a mutated FimH polypeptide disclosed herein, wherein the polypeptide is isolated.

In a further example, the present disclosure provides a pharmaceutical composition comprising (i) a mutated FimH polypeptide as disclosed herein and (ii) a pharmaceutically acceptable carrier.

In a further example, the present disclosure provides an immunogenic composition comprising a mutated FimH polypeptide as disclosed herein. For example, the immunogenic composition further comprises at least one additional antigen, such as a polysaccharide, or a glycoconjugate, or a protein. Further for example, the immunogenic composition further comprises at least one adjuvant.

In a further example, the present disclosure provides a nucleic acid molecule comprising a nucleotide sequence that encodes an amino acid sequence of a mutated FimH polypeptide as disclosed herein.

In a further example, the present disclosure provides a mutated FimH polypeptide as disclosed herein, wherein the polypeptide is immunogenic.

The present disclosure further provides a recombinant mammalian cell, comprising a polynucleotide encoding a mutated FimH polypeptide as disclosed herein.

The present disclosure further provides a culture comprising the recombinant cell as disclosed herein, wherein said culture is at least 5 liters, at least 10 liters, at least 20 liters, at least 50 liters, at least 100 liters, at least 200 liters, at least 500 liters, at least 1000 liters, or at least 2000 liters in size.

The present disclosure further provides a method for producing a mutated FimH polypeptide as disclosed herein, comprising culturing a recombinant mammalian cell as disclosed herein under suitable conditions, thereby expressing the polypeptide; and harvesting the polypeptide.

The present disclosure further provides a method for (i) inducing an immune response in a subject against extra-intestinal pathogenic *E. coli*, or (ii) inducing the production of opsonophagocytic and/or neutralizing antibodies in a subject that are specific to extra-intestinal pathogenic *E. coli*, wherein the method comprises administering to the subject an effective amount of a composition as disclosed herein. In one example, the subject is at risk of developing a urinary tract infection. In a further example, the subject is at risk of developing bacteremia. In a further example, the subject is at risk of developing sepsis. In another example, the subject is at risk of developing Crohn's disease.

The present disclosure further provides a method of eliciting an immune response against *E. coli* in a mammal, comprising administering to the mammal an effective amount of a composition as disclosed herein. In one example, the immune response comprises opsonophagocytic and/or neutralizing antibodies against *E. coli*. In a further example, the immune response protects the mammal from an *E. coli* infection.

The present disclosure further provides a method of preventing, treating or ameliorating a bacterial infection, disease or condition in a subject, comprising administering to the subject an immunologically effective amount of a composition as disclosed herein.

BRIEF DESCRIPTION OF THE DRAWINGS

FIG. 1A shows circular dichroism spectra in the near-UV and FIG. 1B shows circular dichroism spectra in the far-UV regions.

FIG. 5A is the elution profile of FimH-DSG WT on SP-SEPHAROSE column, and FIG. 5B is the SDS-PAGE analysis of eluted fractions.

FIG. 6A shows the elution profile of the FimH-DSG G15A G16A V27A mutant on SP-SP-SEPHAROSE column, and FIG. 6B shows the SDS-PAGE analysis of eluted fractions.

FIG. 11A shows the results from a Direct Luminex FimH IgG assay, and FIG. 11B shows the results from an E. coli binding inhibition assay. As used herein, the term "4plex" has the same meaning, and is interchangeable with, the term "4-valent".

FIG. 13A shows the quantification of MPO in urine, FIG. 13B shows the quantification of IL-8 in urine, and FIG. 13C shows the percentage of animals that had increased PMN in urine sediments. Legend: Placebo (circle); FimH-DSG G15A G16A V27A (square); FimH-DSG G15A G16A V27A+4-valent O-Antigen (triangle).

SEQUENCE IDENTIFIERS

Figure 1A:
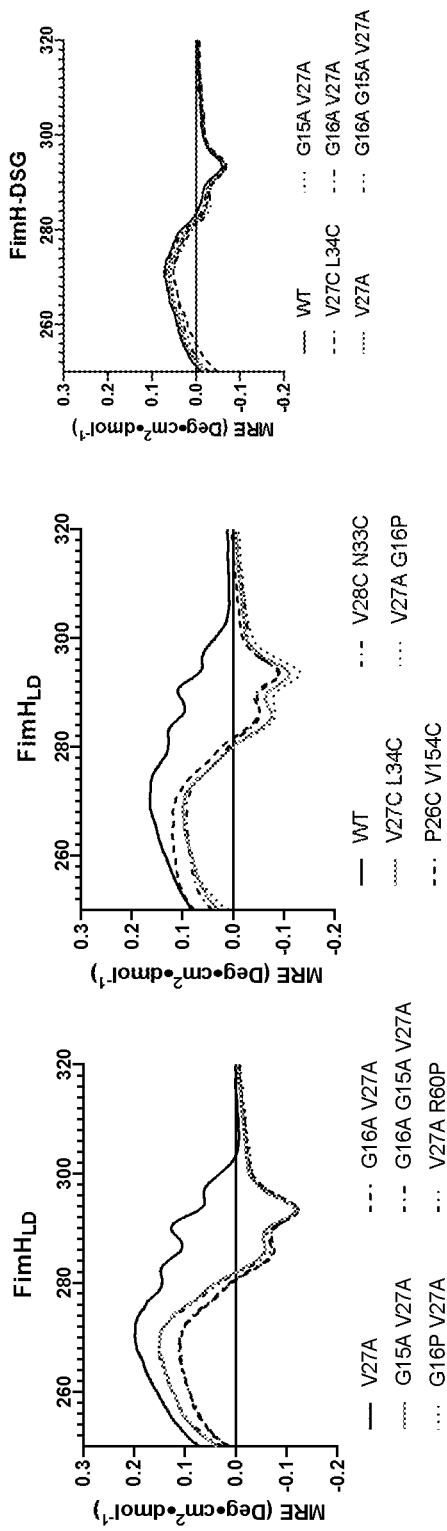
FIG. 1A-1B show circular dichroism spectra of $FimH_{LD}$ and FimH-DSG mutants.

SEQ ID NO: 1 sets forth an amino acid sequence for wild type E. coli $FimH_{LD}$ (FimHLD_WT).

SEQ ID NO: 2 sets forth an amino acid sequence for the mutant E. coli FimHLD_G65A_V27A.

SEQ ID NO: 3 sets forth an amino acid sequence for the mutant E. coli FimHLD_F1I.

SEQ ID NO: 4 sets forth an amino acid sequence for the mutant E. coli FimHLD_F1L.

SEQ ID NO: 5 sets forth an amino acid sequence for the mutant E. coli FimHLD_F1V.

SEQ ID NO: 6 sets forth an amino acid sequence for the mutant E. coli FimHLD_F1M.

SEQ ID NO: 7 sets forth an amino acid sequence for the mutant E. coli FimHLD_F1Y.

SEQ ID NO: 8 sets forth an amino acid sequence for the mutant E. coli FimHLD_F1W.

SEQ ID NO: 9 sets forth an amino acid sequence for the mutant E. coli FimHLD_Q133K.

SEQ ID NO: 10 sets forth an amino acid sequence for the mutant E. coli FimHLD_G15A.

SEQ ID NO: 11 sets forth an amino acid sequence for the mutant E. coli FimHLD_G15P.

SEQ ID NO: 12 sets forth an amino acid sequence for the mutant E. coli FimHLD_G16A.

SEQ ID NO: 13 sets forth an amino acid sequence for the mutant E. coli FimHLD_G16P.

SEQ ID NO: 14 sets forth an amino acid sequence for the mutant E. coli FimHLD_G15A_G16A.

SEQ ID NO: 15 sets forth an amino acid sequence for the mutant E. coli FimHLD_R60P.

SEQ ID NO: 16 sets forth an amino acid sequence for the mutant E. coli FimHLD_G65A.

SEQ ID NO: 17 sets forth an amino acid sequence for the mutant E. coli FimHLD_P12C_A18C.

SEQ ID NO: 18 sets forth an amino acid sequence for the mutant E. coli FimHLD_G14C_F144C.

SEQ ID NO: 19 sets forth an amino acid sequence for the mutant E. coli FimHLD_P26C_V35C.

SEQ ID NO: 20 sets forth an amino acid sequence for the mutant E. coli FimHLD_P26C_V154C.

SEQ ID NO: 21 sets forth an amino acid sequence for the mutant E. coli FimHLD_P26C_V156C.

SEQ ID NO: 22 sets forth an amino acid sequence for the mutant E. coli FimHLD_V27C_L34C.

SEQ ID NO: 23 sets forth an amino acid sequence for the mutant E. coli FimHLD_V28C_N33C.

SEQ ID NO: 24 sets forth an amino acid sequence for the mutant E. coli FimHLD_V28C_P157C.

SEQ ID NO: 25 sets forth an amino acid sequence for the mutant E. coli FimHLD_Q32C_Y108C.

SEQ ID NO: 26 sets forth an amino acid sequence for the mutant E. coli FimHLD_N33C_L109C.

SEQ ID NO: 27 sets forth an amino acid sequence for the mutant E. coli FimHLD_N33C_P157C.

SEQ ID NO: 28 sets forth an amino acid sequence for the mutant E. coli FimHLD_V35C_L107C.

SEQ ID NO: 29 sets forth an amino acid sequence for the mutant E. coli FimHLD_V35C_L109C.

SEQ ID NO: 30 sets forth an amino acid sequence for the mutant E. coli FimHLD_S62C_T86C.

SEQ ID NO: 31 sets forth an amino acid sequence for the mutant E. coli FimHLD_S62C_L129C.

SEQ ID NO: 32 sets forth an amino acid sequence for the mutant E. coli FimHLD_Y64C_L68C.

SEQ ID NO: 33 sets forth an amino acid sequence for the mutant E. coli FimHLD_Y64C_A127C.

SEQ ID NO: 34 sets forth an amino acid sequence for the mutant E. coli FimHLD_L68C_F71C.

SEQ ID NO: 35 sets forth an amino acid sequence for the mutant *E. coli* FimHLD_V112C_T158C.

SEQ ID NO: 36 sets forth an amino acid sequence for the mutant *E. coli* FimHLD_S113C_G116C.

SEQ ID NO: 37 sets forth an amino acid sequence for the mutant *E. coli* FimHLD_S113C_T158C.

SEQ ID NO: 38 sets forth an amino acid sequence for the mutant *E. coli* FimHLD_V118C_V156C.

SEQ ID NO: 39 sets forth an amino acid sequence for the mutant *E. coli* FimHLD_A119C_V155C.

SEQ ID NO: 40 sets forth an amino acid sequence for the mutant *E. coli* FimHLD_L34N_V27A.

SEQ ID NO: 41 sets forth an amino acid sequence for the mutant *E. coli* FimHLD_L34S_V27A.

SEQ ID NO: 42 sets forth an amino acid sequence for the mutant *E. coli* FimHLD_L34T_V27A.

SEQ ID NO: 43 sets forth an amino acid sequence for the mutant *E. coli* FimHLD_A119N_V27A.

SEQ ID NO: 44 sets forth an amino acid sequence for the mutant *E. coli* FimHLD_A119S_V27A.

SEQ ID NO: 45 sets forth an amino acid sequence for the mutant *E. coli* FimHLD_A119T_V27A.

SEQ ID NO: 46 sets forth an amino acid sequence for the mutant *E. coli* FimH-DSG_A115V.

SEQ ID NO: 47 sets forth an amino acid sequence for the mutant *E. coli* FimH-DSG_V163I.

SEQ ID NO: 48 sets forth an amino acid sequence for the mutant *E. coli* FimH-DSG_V185I.

SEQ ID NO: 49 sets forth an amino acid sequence for the mutant *E. coli* FimH-DSG_DSG_V3I.

SEQ ID NO: 50 sets forth an amino acid sequence for the mutant *E. coli* FimHLD_G15A_V27A.

SEQ ID NO: 51 sets forth an amino acid sequence for the mutant *E. coli* FimHLD_G16A_V27A.

SEQ ID NO: 52 sets forth an amino acid sequence for the mutant *E. coli* FimHLD_G15P_V27A.

SEQ ID NO: 53 sets forth an amino acid sequence for the mutant *E. coli* FimHLD_G16P_V27A.

SEQ ID NO: 54 sets forth an amino acid sequence for the mutant *E. coli* FimHLD_G15A_G16A_V27A.

SEQ ID NO: 55 sets forth an amino acid sequence for the mutant *E. coli* FimHLD_V27A_R60P.

SEQ ID NO: 56 sets forth an amino acid sequence for the mutant *E. coli* FimHLD_G65A_V27A.

SEQ ID NO: 57 sets forth an amino acid sequence for the mutant *E. coli* FimHLD_V27A_Q133K.

SEQ ID NO: 58 sets forth an amino acid sequence for the mutant *E. coli* FimHLD_G15A_G16A_V27A_Q133K.

SEQ ID NO: 59 sets forth an amino acid sequence for wild type *E. coli* full-length FimH, including the donor strand FimG peptide connected through a linker (FimH-DSG_WT).

SEQ ID NO: 60 sets forth an amino acid sequence for the mutant *E. coli* FimH-DSG_V27A.

SEQ ID NO: 61 sets forth an amino acid sequence for the mutant *E. coli* FimH-DSG_G15A_V27A.

SEQ ID NO: 62 sets forth an amino acid sequence for the mutant *E. coli* FimH DSG_G15A_G16A_V27A.

SEQ ID NO: 63 sets forth an amino acid sequence for the mutant *E. coli* FimH DSG_V27A_Q133K.

SEQ ID NO: 64 sets forth an amino acid sequence for the mutant *E. coli* FimH DSG_G15A_G16A_V27A_Q133K.

SEQ ID NO: 65 sets forth an amino acid sequence for the mouse Ig Kappa signal peptide sequence.

SEQ ID NOs: 66-108 set forth amino acid and nucleic acid sequences for a nanostructure-related polypeptide or fragment thereof.

SEQ ID NO: 109-primer for PCR.

SEQ ID NO: 110-primer for PCR.

SEQ ID NO: 111-probe for PCR.

SEQ ID NO: 112 sets forth a O25b 2401 WzzB amino acid sequence.

SEQ ID NO: 113 sets forth a O25a:K5:H1 WzzB amino acid sequence.

SEQ ID NO: 114 sets forth a O25a ETEC ATCC WzzB amino acid sequence.

SEQ ID NO: 115 sets forth a K12 W3110 WzzB amino acid sequence.

SEQ ID NO: 116 sets forth a *Salmonella* LT2 WzzB amino acid sequence.

SEQ ID NO: 117 sets forth a O25b 2401 FepE amino acid sequence.

SEQ ID NO: 118 sets forth a O25a:K5:H1 FepE amino acid sequence.

SEQ ID NO: 119 sets forth a O25a ETEC ATCC FepE amino acid sequence.

SEQ ID NO: 120 sets forth a O157 FepE amino acid sequence.

SEQ ID NO: 121 sets forth a *Salmonella* LT2 FepE amino acid sequence.

SEQ ID NO: 122 sets forth a primer sequence for LT2wzzB_S.

SEQ ID NO: 123 sets forth a primer sequence for LT2wzzB_AS.

SEQ ID NO: 124 sets forth a primer sequence for O25bFepE_S.

SEQ ID NO: 125 sets forth a primer sequence for O25bFepE_A.

SEQ ID NO: 126 sets forth a primer sequence for wzzB P1_S.

SEQ ID NO: 127 sets forth a primer sequence for wzzB P2_AS.

SEQ ID NO: 128 sets forth a primer sequence for wzzB P3_S.

SEQ ID NO: 129 sets forth a primer sequence for wzzB P4_AS.

SEQ ID NO: 130 sets forth a primer sequence for O157 FepE_S.

SEQ ID NO: 131 sets forth a primer sequence for O157 FepE_AS.

SEQ ID NO: 132 sets forth a primer sequence for pBAD33_adaptor_S.

SEQ ID NO: 133 sets forth a primer sequence for pBAD33_adaptor_AS.

SEQ ID NO: 134 sets forth a primer sequence for JUMP-START_r.

SEQ ID NO: 135 sets forth a primer sequence for gnd_f.

SEQ ID NO: 136 sets forth an amino acid sequence for a human IgG receptor FcRn large subunit p51 signal peptide.

SEQ ID NO: 137 sets forth an amino acid sequence for a human IL10 protein signal peptide.

SEQ ID NO: 138 sets forth an amino acid sequence for a human respiratory syncytial virus A (strain A2) fusion glycoprotein F0 signal peptide.

SEQ ID NO: 139 sets forth an amino acid sequence for an influenza A hemagglutinin signal peptide.

SEQ ID NOs: 140-147 set forth SignalP 4.1 (DTU Bioinformatics) sequences from various species used for signal peptide predictions.

DETAILED DESCRIPTION

The present disclosure relates to *E. coli* FimH mutated polypeptides (mutants), compositions comprising the FimH mutants, methods for producing and purifying the FimH mutants, nucleic acids that encode the FimH mutants, host cells that comprise such nucleic acids, and methods of using compositions that comprise the FimH mutants.

Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to further illustrate the disclosure and does not pose a limitation on the scope of the claims. No language in the specification should be construed as indicating any non-claimed element essential to the practice of the disclosure.

Several documents are cited throughout the text of this disclosure. Each of the documents cited herein (including all patents, patent applications, scientific publications, manufacturers specifications, instructions, etc.), whether supra or infra, are hereby incorporated by reference in their entirety. Nothing herein is to be construed as an admission that the present disclosure was not entitled to antedate such disclosure.

Definitions

As used herein the term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

As used herein, the term "wild type" or "WT" or "native" refers to an amino acid sequence that is found in nature, including allelic variations. A wild type amino acid sequence, peptide or protein has an amino acid sequence that has not been intentionally modified.

As used herein, "variants" of an amino acid sequence (peptide, protein or polypeptide), or "mutants", or reference to a "mutated" polypeptide, comprise amino acid insertion variants/mutants, amino acid addition variants/mutants, amino acid deletion variants/mutants and/or amino acid substitution variants/mutants. The term "variant" or "mutant" includes all mutants, splice variants, posttranslationally modified variants, conformations, isoforms, allelic variants, species variants, and species homologs, in particular those which are naturally occurring. The term "variant" or "mutant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

As used herein, "sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, -2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues. The amino acid sequence variants/mutants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one aspect, a fragment or variant/mutant of an amino acid sequence (peptide or protein) is preferably a "functional fragment" or "functional variant". The term "functional fragment" or "functional variant/mutant" of an amino acid sequence relates to any fragment or variant/mutant exhibiting one or more functional properties identical or similar to those of the amino acid sequence from which it is derived, i.e., it is functionally equivalent. With respect to antigens or antigenic sequences, one particular function is one or more immunogenic activities displayed by the amino acid sequence from which the fragment or variant is derived. The term "functional fragment" or "functional variant/mutant", as used herein, in particular refers to a variant/mutant molecule or sequence that comprises an amino acid sequence that is altered by one or more amino acids compared to the amino acid sequence of the parent molecule or sequence and that is still capable of fulfilling one or more of the functions of the parent molecule or sequence, e.g., inducing an immune response. In one aspect, the modifications in the amino acid sequence of the parent molecule or sequence do not significantly affect or alter the characteristics of the molecule or sequence. In different embodiments, the function of the functional fragment or functional variant may be reduced but still significantly present, e.g., immunogenicity of the functional variant may be at least 50%, at least 60%, at least 70%, at least 80%, or at least 90% of the parent molecule or sequence. However, in other embodiments, immunogenicity of the functional fragment or functional variant may be enhanced compared to the parent molecule or sequence.

As used herein, "isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

I. *E. coli* FimH Polypeptides

Fimbrial adhesins, including type 1 fimbriae, bind to mannosylated glycoproteins in the epithelial layer or secreted into the urine. Type 1 fimbriae are highly conserved among clinical UPEC isolates and are encoded by a cluster of genes called fim, which encode accessory proteins (FimC, FimD), various structural subunits (FimE, FimF, FimG) and an adhesin called FimH. FimH is composed of two domains, the lectin binding domain (FimH$_{LD}$) responsible for binding to mannosylated glycoproteins, and the pilin domain. The pilin domain serves to link FimH to other structural subunits of the pilus such as FimG, via a mechanism called donor strand exchange. The FimH pilin domain forms an incomplete immunoglobulin fold, resulting in a groove that provides a binding site for the N-terminal β-strand of FimG, forming a strong intermolecular linkage between FimH and FimG. While FimH$_{LD}$ can be expressed in a soluble, stable form, full length FimH is unstable alone unless in a complex with the chaperone FimC or complemented with the donor strand peptide of FimG in peptide form or as a fusion protein. Accordingly, the expression of a full length FimH molecule that is stable is possible by linking the FimG donor peptide to the C-terminus of full length FimH via a glycine-serine linker, and is designated FimH-DSG.

In one aspect, the present disclosure provides mutated FimH polypeptides, such as those shown in Table 1. Such mutants provide mutations in the amino acid sequence relative to the amino acid sequence of the corresponding wild-type (WT) FimH polypeptide. In some aspects, such mutants are immunogenic against the wild-type FimH protein or against a bacteria expressing the wild-type FimH polypeptide. In certain aspects, the FimH mutants possess certain beneficial characteristics, such as increased immunogenic properties as compared to the corresponding wild-type FimH polypeptide.

As used herein, the term "FimH polypeptide" refers to any domain of the full-length wild type E. coli FimH polypeptide, any combination of domains of the full-length wild type E. coli FimH polypeptide, or to the full-length E. coli FimH polypeptide, or any fragment thereof. For example, in one embodiment the present disclosure provides a mutated FimH polypeptide that is a mutated FimH$_{LD}$ polypeptide, or a FimH-DSG polypeptide. The present disclosure relates to novel FimH$_{LD}$ and FimH-DSG mutants with reduced affinity for mannoside ligands (verified by biochemical and biophysical analyses), which improves functional immunogenicity and describes the evaluation of neutralizing responses of these mutants relative to wild type FimH$_{LD}$.

The introduced amino acid mutations in the FimH mutant polypeptides can include amino acid substitutions, deletions, or additions. In some aspects, the only mutations in the amino acid sequence of the FimH polypeptide mutants are amino acid substitutions relative to a wild-type FimH protein.

TABLE 1

| FimH wild type and mutant sequences |
|---|
| SEQ ID NO: 1 >FimHLD_WT<br>FACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 2 >FimHLD_G65A_V27A<br>FACKTASGTAIPIGGGSANVYVNLAPAVNVGQNLVVDLSTQIFCHNDY<br>PETITDYVTLQRGSAYAGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 3 >FimHLD_F1I<br>IACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 4 >FimHLD_F1L<br>LACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |

TABLE 1-continued

| FimH wild type and mutant sequences |
|---|
| SEQ ID NO: 5 >FimHLD_F1V<br>VACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 6 >FimHLD_F1M<br>MACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 7 >FimHLD_F1Y<br>YACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPIGG |
| SEQ ID NO: 8 >FimHLD_F1W<br>WACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 9 >FimHLD_Q133K<br>FACKTASGTAIPIGGGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRKTNNYNSDDFQF<br>VWNIYANNDVVVPTGG |
| SEQ ID NO: 10 >FimHLD_G15A<br>FACKTASGTAIPIGAGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 11 >FimHLD_G15P<br>FACKTASGTAIPIGPGSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPIGG |
| SEQ ID NO: 12 >FimHLD_G16A<br>FACKTASGTAIPIGGASANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 13 >FimHLD_G16P<br>FACKTASGTAIPIGGPSANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 14 >FimHLD_G15A_G16A<br>FACKTASGTAIPIGAASANVYVNLAPVVNVGQNLVVDLSTQIFCHNDY<br>PETITDYVTLQRGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 15 >FimHLD_R60P<br>FACKTASGTAIPIGGGSANVYVNLAPVVNVGQNLVVDLSTQIFCHNDY<br>PETITDYVTLQPGSAYGGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 16 >FimHLD_G65A<br>FACKTASGTAIPIGGGSANVYVNLAPVVNVGQNLVVDLSTQIFCHNDY<br>PETITDYVTLQRGSAYAGVLSSFSGTVKYSGSSYPFPTTSETPRVVYN<br>SRTDKPWPVALYLTPVSSAGGVAIKAGSLIAVLILRQTNNYNSDDFQF<br>VWNIYANNDVVVPTGG |
| SEQ ID NO: 17 >FimHLD_P12C_A18C<br>FACKTASGTAICIGGGSCNVYVNLAPVVNVGQNLVVDLSTQIFCHNDY<br>PETITDYVTLQRGSAYGGVLSSFSGTVKYSGSSYPFPTTSETPRVVYN |

TABLE 1-continued

FimH wild type and mutant sequences

SRTDKPWPVALYLTPVSSAGGVAIKAGSLIAVLILRQTNNYNSDDFQF
VWNIYANNDVVVPTGG

SEQ ID NO: 18 >FimHLD_G14C_F144C
FACKTASGTAIPICGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQC
VWNIYANNDVVVPIGG

SEQ ID NO: 19 >FimHLD_P26C_V35C
FACKTASGTAIPIGGGSANVYVNLACVVNVGQNLCVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 20 >FimHLD_P26C_V154C
FACKTASGTAIPIGGGSANVYVNLACVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDCVVPTGG

SEQ ID NO: 21 >FimHLD_P26C_V156C
FACKTASGTAIPIGGGSANVYVNLACVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVCPTGG

SEQ ID NO: 22 >FimHLD_V27C_L34C
FACKTASGTAIPIGGGSANVYVNLAPCVNVGQNCVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 23 >FimHLD_V28C_N33C
FACKTASGTAIPIGGGSANVYVNLAPVCNVGQCLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 24 >FimHLD_V28C_P157C
FACKTASGTAIPIGGGSANVYVNLAPVCNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVCTGG

SEQ ID NO: 25 >FimHLD_Q32C_Y108C
FACKTASGTAIPIGGGSANVYVNLAPVVNVGQCNLVVDLSTQIFCHNDY
PETITDYVTLQRGSAYGGVLSSFSGTVKYSGSSYPFPTTSETPRVVYN
SRTDKPWPVALCLTPVSSAGGVAIKAGSLIAVLILRQTNNYNSDDFQF
VWNIYANNDVVVPTGG

SEQ ID NO: 26 >FimHLD_N33C_L109C
FACKTASGTAIPIGGGSANVYVNLAPVVNVGQCLVVDLSTQIFCHNDY
PETITDYVTLQRGSAYGGVLSSFSGTVKYSGSSYPFPTTSETPRVVYN
SRTDKPWPVALYCIPVSSAGGVAIKAGSLIAVLILRQTNNYNSDDFQF
VWNIYANNDVVVPTGG

SEQ ID NO: 27 >FimHLD_N33C_P157C
FACKTASGTAIPIGGGSANVYVNLAPVVNVGQCLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVCTGG

SEQ ID NO: 28 >FimHLD_V35C_L107C
FACKTASGTAIPIGGGSANVYVNLAPVVNVGQNLCVDLSTQIFCHNDY
PETITDYVTLQRGSAYGGVLSSFSGTVKYSGSSYPFPTTSETPRVVYN
SRTDKPWPVACYLTPVSSAGGVAIKAGSLIAVLILRQTNNYNSDDFQF
VWNIYANNDVVVPTGG

SEQ ID NO: 29 >FimHLD_V35C_L109C
FACKTASGTAIPIGGGSANVYVNLAPVVNVGQNLCVDLSTQIFCHNDY
PETITDYVTLQRGSAYGGVLSSFSGTVKYSGSSYPFPTTSETPRVVYN
SRTDKPWPVALYCIPVSSAGGVAIKAGSLIAVLILRQTNNYNSDDFQF
VWNIYANNDVVVPTGG

SEQ ID NO: 30 >FimHLD_S62C_T86C
FACKTASGTAIPIGGGSANVYVNLAPVVNVGQNLVVDLSTQIFCHNDY
PETITDYVTLQRGCAYGGVLSSFSGTVKYSGSSYPFPCTSETPRVVYN

SRTDKPWPVALYLTPVSSAGGVAIKAGSLIAVLILRQTNNYNSDDFQF
VWNIYANNDVVVPIGG

SEQ ID NO: 31 >FimHLD_S62C_L129C
FACKTASGTAIPIGGGSANVYVNLAPVVNVGQNLVVDLSTQIFCHNDY
PETITDYVTLQRGCAYGGVLSSFSGTVKYSGSSYPFPTTSETPRVVYN
SRTDKPWPVALYLTPVSSAGGVAIKAGSLIAVCILRQTNNYNSDDFQF
VWNIYANNDVVVPTGG

SEQ ID NO: 32 >FimHLD_Y64C_L68C
FACKTASGTAIPIGGGSANVYVNLAPVVNVGQNLVVDLSTQIFCHNDY
PETITDYVTLQRGSACGGVCSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 33 >FimHLD_Y64C_A127C
FACKTASGTAIPIGGGSANVYVNLAPVVNVGQNLVVDLSTQIFCHNDY
PETITDYVTLQRGSACGGVLSSFSGTVKYSGSSYPFPTTSETPRVVYN
SRTDKPWPVALYLTPVSSAGGVAIKAGSLICVLILRQTNNYNSDDFQF
VWNIYANNDVVVPTGG

SEQ ID NO: 34 >FimHLD_L68C_F71C
FACKTASGTAIPIGGGSANVYVNLAPVVNVGQNLVVDLSTQIFCHNDY
PETITDYVTLQRGSAYGGVCSSCSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 35 >FimHLD_V112C_T158C
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPCSSAGGVAIKAGSLIAVLILRQTNNYNSDDFQF
VWNIYANNDVVPCGG

SEQ ID NO: 36 >FimHLD_S113C_G116C
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVCSACGVAIKAGSLIAVLILRQTNNYNSDDFQF
VWNIYANNDVVVPTGG

SEQ ID NO: 37 >FimHLD_S113C_T158C
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVCSAGGVAIKAGSLIAVLILRQTNNYNSDDFQF
VWNIYANNDVVPCGG

SEQ ID NO: 38 >FimHLD_V118C_V156C
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGCAIKAGSLIAVLILRQTNNYNSDDFQF
VWNIYANNDVVCPTGG

SEQ ID NO: 39 >FimHLD_A119C_V155C
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVCIKAGSLIAVLILRQTNNYNSDDFQF
VWNIYANNDVCVPTGG

SEQ ID NO: 40 >FimHLD_L34N_V27A
FACKTASGTAIPIGGGSANVYVNLAPAVNVGQNNVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 41 >FimHLD_L34S_V27A
FACKTASGTAIPIGGGSANVYVNLAPAVNVGQNSVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 42 >FimHLD_L34T_V27A
FACKTASGTAIPIGGGSANVYVNLAPAVNVGQNTVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 43 >FimHLD_A119N_V27A
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN

TABLE 1-continued

FimH wild type and mutant sequences

SRTDKPWPVALYTPVSSAGGVNIKAGSLIAVLILRQTNNYNSDDFQF
VWNIYANNDVVVPTGG

SEQ ID NO: 44 >FimHLD_A119S_V27A
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVSIKAGSLIAVLILRQTNNYNSDDFQF
VWNIYANNDVVVPTGG

SEQ ID NO: 45 >FimHLD_A119T_V27A
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVTIKAGSLIAVLILRQTNNYNSDDFQF
VWNIYANNDVVVPTGG

SEQ ID NO: 46 >FimH-DSG_A115V
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSVGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 47 >FimH-DSG_V163I
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDISARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 48 >FimH-DSG_V185I
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTIYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 49 >FimH-DSG_DSG_V3I
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
ITITVNGKVVAK

SEQ ID NO: 50 >FimHLD_G15A_V27A
FACKTASGTAIPIGAGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 51 >FimHLD_G16A_V27A
FACKTASGTAIPIGGASANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 52 >FimHLD_G15P_V27A
FACKTASGTAIPIGPGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 53 >FimHLD_G16P_V27A
FACKTASGTAIPIGGPSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 54 >FimHLD_G15A_G16A_V27A
FACKTASGTAIPIGAASANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 55 >FimHLD_V27A_R60P
FACKTASGTAIPIGGGSANVYVNLAPAVNVGQNLVVDLSTQIFCHNDY
PETITDYVTLQPGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 56 >FimHLD_G65A_V27A
FACKTASGTAIPIGGGSANVYVNLAPAVNVGQNLVVDLSTQIFCHNDY
PETITDYVTLQRGSAYAGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGG

SEQ ID NO: 57 >FimHLD_V27A_Q133K
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRKTNNYNSDDFQF
VWNIYANNDVVVPTGG

SEQ ID NO: 58 >FimHLD_G15A_G16A_V27A_Q133K
FACKTASGTAIPIGAASANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRKTNNYNSDDFQF
VWNIYANNDVVVPTGG

SEQ ID NO: 59 >FimH-DSG_WT
FACKTASGTAIPIGGGSANVYVNLAPVVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 60 >FimH-DSG_V27A
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 61 >FimH-DSG_G15A_V27A
FACKTASGTAIPIGAGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 62 >FimH-DSG_G15A_G16A_V27A
FACKTASGTAIPIGAASANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRQTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 63 >FimH-DSG_V27A_Q133K
FACKTASGTAIPIGGGSANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRKTNNYNSDDFQF
VWNIYANNDVVVPIGGCDVSARDVIVTLPDYPGSVPIPLIVYCAKSQN
LGYYLSGTTADAGNSIFTNTASFSPAQGVGVQLTRQGTIIPANNTVSL
GAVGTSAVSLGLTANYARTGGQVTAGNVQSIIGVTFVYQGGSSGGGAD
VTITVNGKVVAK

SEQ ID NO: 64 >FimH-DSG_G15A_G16A_V27A_Q133K
FACKTASGTAIPIGAASANVYVNLAPAVNVGQNLVVDLSTQIFCHNDY
PETITDYVTLQRGSAYGGVLSSFSGTVKYSGSSYPFPTTSETPRVVYN
SRTDKPWPVALYLTPVSSAGGVAIKAGSLIAVLILRKTNNYNSDDFQF
VWNIYANNDVVVPTGGCDVSARDVTVTLPDYPGSVPIPLTVYCAKSQN
LGYYLSGTTADAGNSIFTNTASFSPAQGVGVQLTRQGTIIPANNTVSL

TABLE 1-continued

FimH wild type and mutant sequences

GAVGTSAVSLGLTANYARTGGQVTAGNVQSIIGVTFVYQGGSSGGGAD
VTITVNGKVVAK

SEQ ID NO: 65 >mouse Ig Kappa signal peptide
ETDTLLLWVLLLWVPGSTG

The amino acid sequence, of the wild type FimH polypeptide is well known in the art. For example, the amino acid sequence of the FimH$_{LD}$ domain is provided herein as SEQ ID NO:1. The full-length wild type FimH polypeptide, including the FimG donor peptide linked to the C-terminus of full length FimH via a glycine-serine linker, is provided herein as SEQ ID NO:59. Nucleic acid sequences encoding such amino acid sequences are also well known in the art.

In one aspect of the disclosure, certain mutated FimH polypeptides result in a locked, open confirmation that results in reduced affinity for mannoside ligands, and leads to improved functional immunogenicity. Accordingly, such FimH mutants can be useful as antigens in an immunogenic composition, such as a vaccine, against E. coli infection. Since wild-type FimH$_{LD}$ is considered to be a poor immunogen in terms of its ability to stimulate functional immunogenicity, such FimH mutants can provide improved antigens to be used in such immunogenic compositions.

In one aspect, as described in Example 1, the FimH mutants were designed in an attempt to lock the FimH lectin domain in an open confirmation in order to reduce the affinity for mannoside ligands. Such mutants can include at least 1, 2, 3, 4, 5, or more mutations. Mutations can include: naturally occurring amino acid substitions that are common among urinary tract infection isolates (such as V27A); substitutions in the ligand binding side of FimH$_{LD}$ (such as at positions F1, and Q133); glycine switch mutations in Fim$_{LD}$ (such as at positions G15, G16, and G65); introducing cysteine pairs for disulfide bond stabilization in FimH$_{LD}$ (such as at position pairs P12-A18; G14-F144; P26-V35; P26-V154; P26-V156; V27-L34; V28-N33; V28-P157; Q32-Y108; N33-L109; N33-P157; V35-L107; V35-L109; S62-T86; S62-L129; Y64-A127; L68-F71; V112-T158; S113-T158; V118-V156; and/or A119-V155); nonpolar-to-polar mutations in FimH$_{LD}$ (such as at positions V27, L34, A119, or any combination thereof); cavity filling mutations at the pilin-lectin interface of FimH-DSG (such as at positions A115, V163, V185, or V3 within the DSG sequence); or any combination of the types of mutations and at the amino acid positions noted above. In another aspect, the present disclosure provides FimH mutants as provided in SEQ ID NOs: 2-58, and 60-64, or to any combination of the mutants noted in any of such sequences. In another aspect, the present disclosure provides a FimH mutant according to any of SEQ ID NOs: 23, 50, 51, 52, 53, 54, 60, and 62. In a further aspect, the present disclosure provides a FimH mutant according to SEQ ID NO: 62.

In a further aspect, the present disclosure provides any of the FimH mutants as provided in SEQ ID NOs: 2-58, and 60-64, wherein said mutants are isolated. For example, in one aspect the present disclosure provides a FimH mutant according to any of SEQ ID NOs: 23, 50, 51, 52, 53, 54, 60, and 62 wherein said FimH mutant is isolated. In a further aspect, the present disclosure provides a FimH mutant according to SEQ ID NO: 62, wherein said FimH mutant is isolated.

Accordingly, in some specific aspects, the present disclosure provides a FimH mutant comprising a combination of introduced mutations, wherein the mutant comprises a combination of mutations set forth in any of the mutants provided in Table 1 (i.e. in SEQ ID NOs: 2-58 and 60-64). Any combination of the amino acid substitutions provided in each of the mutants in Table 1 can be made to a wild-type FimH polypeptide sequence to arrive at different FimH mutants. FimH mutants that are based on a native FimH polypeptide sequence of any other subtype or strain and comprise any of the combination of mutations described herein are also within the scope of the present disclosure.

A further aspect of the present disclosure is a polypeptide that is at least 90%, at least 91%, at least 92%, at least 93%, at least 94%, at least 95%, at least 96%, at least 97%, at least 98%, or at least 99% identical to any of SEQ ID NOs: 1-64. In a preferred aspect, the polypeptide is at least 90%, at least 91%, at least 92%, at least 93%, at least 94%, at least 95%, at least 96%, at least 97%, at least 98%, or at least 99% identical to SEQ ID NO: 62. In another aspect of the present invention is a polypeptide that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identical to any of SEQ ID NOs: 1-64. In a preferred aspect, the polypeptide is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identical to SEQ ID NO: 62.

The FimH mutants provided by the present disclosure can be prepared by routine methods known in the art, such as by expression in a recombinant host system using a suitable vector. Suitable recombinant host cells include, for example, insect cells, mammalian cells, avian cells, bacteria, and yeast cells. Examples of suitable insect cells include, for example, Sf9 cells, Sf21 cells, Tn5 cells, Schneider S2 cells, and High Five cells (a clonal isolate derived from the parental Trichoplusia ni BTI-TN-5B1-4 cell line (Invitrogen)). Examples of suitable mammalian cells include Chinese hamster ovary (CHO) cells, human embryonic kidney cells (HEK293 or Expi 293 cells, typically transformed by sheared adenovirus type 5 DNA), NIH-3T3 cells, 293-T cells, Vero cells, and HeLa cells. Suitable avian cells include, for example, chicken embryonic stem cells (e.g., EBx® cells), chicken embryonic fibroblasts, chicken embryonic germ cells, quail fibroblasts (e.g. ELL-O), and duck cells. Suitable insect cell expression systems, such as baculovirus-vectored systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668. Similarly, bacterial and mammalian cell expression systems are also known in the art and described in, e.g., Yeast Genetic Engineering (Barr et al., eds., 1989) Butterworths, London.

A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

The FimH mutant polypeptides can be isolated using any suitable methods. For example, methods for purifying FimH protein mutant polypeptides by immunoaffinity chromatography are known in the art. Ruiz-Arguello et al., J. Gen. Virol., 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the FimH mutant polypeptides can include a "tag" that facilitates purification, such as an epitope tag or a histidine (His) tag. Such tagged polypeptides can conveniently be isolated, for example from conditioned media, by chelating chromatography or affinity chromatography.

The term "antigen" as used herein refers to a molecule that can be recognized by an antibody. Examples of antigens include polypeptides, peptides, lipids, polysaccharides, and nucleic acids containing antigenic determinants, such as those recognized by an immune cell.

II. Nucleic Acids Encoding FimH Mutants

In another aspect, the present disclosure provides nucleic acid molecules that encode a FimH mutant as disclosed herein. Such nucleic acid molecules include DNA, cDNA, and RNA sequences. In one embodiment, the nucleic acid molecule can be incorporated into a vector, such as an expression vector.

In one aspect, nucleic acids encoding the *E. coli* FimH mutated polpeptides, or any fragment thereof, are disclosed. One or more nucleic acid constructs encoding the FimH mutant polypeptides, or a fragment thereof, may be used for genomic integration and subsequent expression of the polypeptide. For example, a single nucleic acid construct encoding the FimH mutant polypeptide, or fragment thereof, may be introduced into a host cell. Alternatively, the coding sequences for the polypeptide may be carried by two or more nucleic acid constructs, which are then introduced into a host cell simultaneously or sequentially.

For example, in one exemplary embodiment, a single nucleic acid construct encodes the lectin domain and pilin domain of an *E. coli* FimH. In another exemplary embodiment, one nucleic acid construct encodes the lectin domain and a second nucleic acid construct encodes the pilin domain of an *E. coli* FimH. In some aspects, genomic integration is achieved.

The nucleic acid construct may comprise genomic DNA that comprises one or more introns, or cDNA. Some genes are expressed more efficiently when introns are present. In some aspects, the nucleic acid sequence is suitable for the expression of exogenous polypeptides in said mammalian cell.

In some aspects, the nucleic acid encoding the polypeptide or fragment thereof is codon optimized to increase the level of expression in any particular cell.

In some aspects, the nucleic acid construct includes a signal sequence that encodes a peptide that directs secretion of the polypeptide derived from *E. coli* or a fragment thereof. In some aspects, the nucleic acid includes the native signal sequence of the polypeptide derived from *E. coli* FimH. In some aspects where the polypeptide derived from *E. coli* or a fragment thereof includes an endogenous signal sequence, the nucleic acid sequence encoding the signal sequence may be codon optimized to increase the level of expression of the protein in a host cell.

In some aspects, the signal sequence is any one of the following lengths: 15, 16, 17, 18, 19, 20, 21, 22, 23, 24, 25, 26, 27, 28, 29, and 30 amino acids long. In some aspects, the signal sequence is 20 amino acids long. In some aspects, the signal sequence is 21 amino acids long.

In some aspects, where the polypeptide or fragment thereof includes a signal sequence, the endogenous signal sequence naturally associated with the polypeptide may be replaced with a signal sequence not associated with the wild type polypeptide to improve the level of expression of the polypeptide or fragment thereof in cultured cells. Accordingly, in some aspects, the nucleic acid does not include the native signal sequence of the polypeptide derived from *E. coli* or a fragment thereof. In some aspects, the nucleic acid does not include the native signal sequence of the polypeptide derived from *E. coli* FimH. In some aspects, the polypeptide derived from *E. coli* or a fragment thereof may be expressed with a heterologous peptide, which is preferably a signal sequence or other peptide having a specific cleavage site at the N-terminus of the mature protein or polypeptide derived from *E. coli* or a fragment thereof. For example, the polypeptide derived from *E. coli* FimH or a fragment thereof may be expressed with a heterologous peptide (e.g., IgK signal sequence), which is preferably a signal sequence or other peptide having a specific cleavage site at the N-terminus of the mature *E. coli* FimH protein. In preferred aspects, the specific cleavage site at the N-terminus of the mature protein *E. coli* FimH occurs immediately before the initial phenylalanine residue of the mature *E. coli* FimH protein. The heterologous sequence selected is preferably one that is recognized and processed (i.e., cleaved by signal peptidase) by the host cell.

In preferred aspects, the signal sequence is an IgK signal sequence. In some aspects, the nucleic acid encodes a polypeptide having the amino acid sequence set forth in any of SEQ ID NOs: 1-64. In some aspects, the nucleic acid encodes the amino acid sequence SEQ ID NO: 23, 50, 51, 52, 53, 54, 60, 61, or 62. In some aspects, the nucleic acid encodes a polypeptide having the amino acid sequence set forth in SEQ ID NO: 62. In preferred aspects, the signal sequence is a mouse IgK signal sequence.

Suitable mammalian expression vectors for producing the FimH mutant polypeptides, or fragments thereof, are known in the art and may be commercially available, such as pSecTag2 expression vector from Invitrogen™. An exemplary mouse Ig Kappa signal peptide sequence includes the sequence ETDTLLLWVLLLWVPGSTG (SEQ ID NO: 65). In some aspects, the vector includes pBudCE4.1 mammalian expression vector from Thermo Fisher. Additional exemplary and suitable vectors include the pcDNA™3.1 mammalian expression vector (Thermo Fisher).

In some aspects, the signal sequence does not include a hemagglutinin signal sequence.

In some aspects, the nucleic acid includes the native signal sequence of the FimH polypeptide, or a fragment thereof. In some aspects, the signal sequence is not an IgK signal sequence. In some aspects, the signal sequence includes a hemagglutinin signal sequence.

In one aspect, disclosed herein are vectors that include the coding sequences for the FimH mutant polypeptide, or a fragment thereof. Exemplary vectors include plasmids that are able to replicate autonomously or to be replicated in a mammalian cell. Typical expression vectors contain suitable promoters, enhancers, and terminators that are useful for regulation of the expression of the coding sequence(s) in the expression construct. The vectors may also include selection markers to provide a phenotypic trait for selection of transformed host cells (such as conferring resistance to antibiotics such as ampicillin or neomycin).

Suitable promoters are known in the art. Exemplary promoters include, e.g., CMV promoter, adenovirus, EF1 a, GAPDH metallothionine promoter, SV-40 early promoter, SV-40 later promoter, murine mammary tumor virus promoter, Rous sarcoma virus promoter, polyhedrin promoter, etc. Promoters may be constitutive or inducible. One or more vectors may be used (e.g., one vector encoding all subunits or domains or fragments thereof, or multiple vectors together encoding the subunits or domains or fragments thereof).

Internal ribosome entry site (IRES) and 2A peptide sequences may also be used. IRES and 2A peptide provides alternative approaches for co-expression of multiple sequences. IRES is a nucleotide sequence that allows for translation initiation in the middle of a messenger RNA (mRNA) sequence as part of the greater process of protein synthesis. Usually, in eukaryotes, translation may be initiated only at the 5' end of the mRNA molecule. IRES elements allow expression of multiple genes in one transcript. IRES-based polycistronic vectors, which express multiple proteins from one transcript, may reduce the escape of non-expressing clones from selection. The 2A peptide allows translation of multiple proteins in a single open reading frame into a polyprotein that is subsequently cleaved into individual proteins through a ribosome-skipping mechanism. 2A peptide may provide more balanced expression of multiple protein products. Exemplary IRES sequences include, e.g., EV71 IRES, EMCV IRES, HCV IRES. For genomic integration, the integration may be site-specific or random. Site-specific recombination may be achieved by introducing homologous sequence(s) into the nucleic acid constructs described herein. Such homologous sequence substantially matches the endogenous sequence at a specific target site in the host genome. Alternatively, random integration may be used. Sometimes, the expression level of a protein may vary depending upon the integration site. Therefore, it may be desirable to select a number of clones according to recombinant protein expression level to identify a clone that achieves the desired level of expression.

Exemplary nucleic acid constructs are further described in the figures, e.g. FIG. 2A-2T, of PCT Intl. Publication No. WO2021/084429, published May 6, 2021, which is incorporated herein by reference.

In one aspect, the nucleic acid sequence encodes the amino acid sequence having at least 90%, at least 91%, at least 92%, at least 93%, at least 94%, at least 95%, at least 96%, at least 97%, at least 98%, at least 99%, identity to any one of any of SEQ ID NOs: 1-64. In a preferred aspect, the nucleic acid sequence encodes the amino acid sequence having at least 90%, at least 91%, at least 92%, at least 93%, at least 94%, at least 95%, at least 96%, at least 97%, at least 98%, or at least 99% identical to SEQ ID NO: 62. In another aspect of the present invention the nucleic acid sequence encodes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identical to any of SEQ ID NOs: 1-64. In a preferred aspect, the nucleic acid sequence encodes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identical to SEQ ID NO: 62.

In certain aspects of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides. In one aspect, the RNA described herein may have modified nucleosides. In some aspects, the RNA comprises a modified nucleoside in place of at least one (e.g., every) uridine.

In some embodiments, compositions or medical preparations described herein comprise RNA encoding an amino acid sequence comprising a FimH mutant polypeptide. Likewise, methods described herein comprise administration of such RNA. One possible platform for use herein is based on an antigen-coding RNA vaccine to induce robust neutralizing antibodies and accompanying/concomitant T cell response to achieve protective immunization with preferably minimal vaccine doses. The RNA administered is preferably in-vitro transcribed RNA. Three different RNA platforms are particularly preferred, namely non-modified uridine containing mRNA (uRNA), nucleoside modified mRNA (modRNA) and self-amplifying RNA (saRNA). In one particularly preferred aspect, the RNA is in vitro transcribed RNA.

III. Host Cells

In one aspect, the disclosure relates to cells in which the sequences encoding the FimH mutant polypeptide, or a fragment thereof are expressed in a mammalian host cell. In one embodiment, the polypeptide is transiently expressed in the host cell. In another embodiment, the polypeptide is stably integrated into the genome of the host cells, and, when cultured under a suitable condition, expresses the polypeptide or a fragment thereof. In a preferred embodiment, the polynucleotide sequence is expressed with high efficiency and genomic stability.

Suitable mammalian host cells are known in the art. Preferably, the host cell is suitable for producing protein at industrial manufacturing scale. Exemplary mammalian host cells include any one of the following and derivatives thereof: Chinese Hamster Ovary (CHO) cells, COS cells (a cell line derived from monkey kidney (African green monkey), Vero cells, Hela cells, baby hamster kidney (BHK) cells, Human Embryonic Kidney (HEK) cells, NSO cells (Murine myeloma cell line), and C127 cells (nontumorigenic mouse cell line). Further exemplary mammalian host cells include mouse Sertoli (TM4), buffalo rat liver (BRL 3A), mouse mammary tumor (MMT), rat hepatoma (HTC), mouse myeloma (NSO), murine hybridoma (Sp2/0), mouse thymoma (EL4), Chinese Hamster Ovary (CHO) and CHO cell derivatives, murine embryonic (NIH/3T3, 3T3 Li), rat myocardial (H9c2), mouse myoblast (C2C12), and mouse kidney (miMCD-3). Further examples of mammalian cell lines include NS0/1, Sp2/0, Hep G2, PER.C6, COS-7, TM4, CV1, VERO-76, MDCK, BRL 3A, W138, MMT 060562, TR1, MRC5, and FS4.

Any cell susceptible to cell culture may be utilized in accordance with the present invention. In some aspects, the cell is a mammalian cell. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59,1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse 28yophil cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred aspects, the cells are GS-cells.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some aspects, a hybridoma is a trioma cell line, which results when progeny of heterohybrid myeloma fusions, which are the product of a fusion between human cells and a murine myeloma cell line, are subsequently fused with a plasma cell. In some aspects, a hybridoma is any immortalized hybrid cell line that produces antibodies such as, for example, quadromas (See, e.g., Milstein et al., Nature 537:3053 (1983)). One skilled in the art will appreciate that hybridoma cell lines might have different nutrition requirements and/or might require different culture conditions for optimal growth, and will be able to modify conditions as needed.

In some aspects, the cell comprises a first gene of interest, wherein the first gene of interest is chromosomally-integrated. In some aspects, the first gene of interest comprises a reporter gene, a selection gene, a gene of interest (e.g., encoding a polypeptide derived from E. coli or a fragment thereof), an ancillary gene, or a combination thereof. In some aspects, the gene of therapeutic interest comprises a gene encoding a difficult to express (DtE) protein.

In some aspects, the first gene of interest is located between two of the distinct recombination target sites (RTS) in a site-specific integration (SSI) mammalian cell, wherein two RTS are chromosomally-integrated within the NL1 locus or the NL2 locus. See, for example, United States Patent Application Publication No. 20200002727, for a description of the NL1 locus, the NL2 locus, the NL3 locus, the NL4 locus, the NL5 locus, and the NL6 locus. In some aspects, the first gene of interest is located within the NL1 locus. In some aspects, the cell comprises a second gene of interest, wherein the second gene of interest is chromosomally-integrated. In some aspects, the second gene of interest comprises a reporter gene, a selection gene, a gene of therapeutic interest (such as a FimH mutant polypeptide, or a fragment thereof), an ancillary gene, or a combination thereof. In some aspects, the gene of therapeutic interest comprises a gene encoding a DtE protein. In some aspects, the second gene of interest is located between two of the RTS. In some aspects, the second gene of interest is located within the NL1 locus or the NL2 locus. In some aspects, the first gene of interest is located within the NL1 locus, and the second gene of interest is located within the NL2 locus. In some aspects, the cell comprises a third gene of interest, wherein the third gene of interest is chromosomally-integrated. In some aspects, the third gene of interest comprises a reporter gene, a selection gene, a gene of therapeutic interest (such as a polypeptide derived from E. coli or a fragment thereof), an ancillary gene, or a combination thereof. In some aspects, the gene of therapeutic interest comprises a gene encoding a DtE protein. In some aspects, the third gene of interest is located between two of the RTS. In some aspects, the third gene of interest is located within the NL1 locus or the NL2 locus. In some aspects, the third gene of interest is located within a locus distinct from the NL1 locus and the NL2 locus. In some aspects, the first gene of interest, the second gene of interest, and the third gene of interest are within three separate loci. In some aspects, at least one of the first genes of interest, the second gene of interest, and the third gene of interest is within the NL1 locus, and at least one of the first gene of interest, the second gene of interest, and the third gene of interest is within the NL2 locus. In some aspects, the cell comprises a site-specific recombinase gene. In some aspects, the site-specific recombinase gene is chromosomally-integrated.

In another aspect, the present disclosure provides a mammalian cell comprising at least four distinct RTS, wherein the cell comprises (a) at least two distinct RTS are chromosomally-integrated within the NL1 locus or NL2 locus; (b) a first gene of interest is integrated between the at least two RTS of (a), wherein the first gene of interest comprises a reporter gene, a gene encoding a DtE protein, an ancillary gene or a combination thereof; (c) and a second gene of interest is integrated within a second chromosomal locus distinct from the locus of (a), wherein the second gene of interest comprises a reporter gene, a gene encoding a DtE protein (such as a polypeptide derived from E. coli or a fragment thereof), an ancillary gene or a combination thereof. In some aspects, the present disclosure provides a mammalian cell comprising at least four distinct RTS, wherein the cell comprises (a) at least two distinct RTS are chromosomally-integrated within the Fer1L4 locus; (b) at least two distinct RTS are chromosomally-integrated within the NL1 locus or the NL2 locus; (c) a first gene of interest is chromosomally-integrated within the Fer1L4 locus, wherein the first gene of interest comprises a reporter gene, a gene encoding a DtE protein, an ancillary gene or a combination thereof; and (d) a second gene of interest is chromosomally-integrated within the within the NL1 locus or NL2 locus of (b), wherein the second gene of interest comprises a reporter gene, a gene encoding a DtE protein (such as a polypeptide derived from E. coli or a fragment thereof), an ancillary gene or a combination thereof.

In some aspects, the present disclosure provides a mammalian cell comprising at least six distinct RTS, wherein the cell comprises (a) at least two distinct RTS and a first gene of interest are chromosomally-integrated within the Fer1L4 locus; (b) at least two distinct RTS and a second gene of interest are chromosomally-integrated within the NL1 locus; and (c) at least two distinct RTS and a third gene of interest are chromosomally-integrated within the NL2 locus.

As referred to herein, the terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. In some aspects, a gene of interest is operably linked to a promoter, wherein the gene of interest is chromosomally-integrated into the host cell. In some aspects, the gene of interest is operably linked to a heterologous promoter; where in the gene of interest is chromosomally-integrated into the host cell. In some aspects, an ancillary gene is operably linked to a promoter, wherein the ancillary gene is chromosomally-integrated into the host cell genome. In some aspects, the ancillary gene is operably linked to a heterologous promoter; where in the ancillary gene is chromosomally-integrated into the host cell genome. In some aspects, a gene encoding a DtE protein is operably linked to a promoter, wherein the gene encoding a DtE protein is chromosomally-integrated into the host cell genome. In some aspects, the gene encoding a DtE protein is operably linked to a heterologous promoter, where in the gene encoding a DtE protein is chromosomally-integrated into the host cell genome. In some aspects, a recombinase gene is operably linked to a promoter, wherein the recombinase gene is chromosomally-integrated into the host cell. In some aspects, the recombinase gene is operably linked to a promoter, where in the recombinase gene is not integrated into the host cell genome. In some aspects, a recombinase gene is operably linked to a heterologous promoter, wherein the recombinase gene is not chromosomally-integrated into the host cell genome. In some aspects, the recombinase gene is operably linked to a heterologous promoter, wherein the recombinase gene is not chromosomally-integrated into the host cell genome.

As referred to herein, the term "chromosomally-integrated" or "chromosomal integration" refers to the stable incorporation of a nucleic acid sequence into the chromosome of a host cell, e.g. a mammalian cell. i.e., a nucleic acid sequence that is chromosomally-integrated into the genomic DNA (gDNA) of a host cell, e.g. a mammalian cell. In some aspects, a nucleic acid sequence that is chromosomally-integrated is stable. In some aspects, a nucleic acid sequence that is chromosomally-integrated is not located on a plasmid or a vector. In some aspects, a nucleic acid sequence that is chromosomally-integrated is not excised. In some aspects, chromosomal integration is mediated by the clustered regularly interspaced short palindromic repeats (CRISPR) and CRISPR associated protein (Cas) gene editing system (CRISPR/CAS).

IV. Compositions and Formulations

In one aspect, the present disclosure includes a composition that comprises at least one FimH mutant polypeptide or fragment thereof as described herein. In some aspects, the composition elicits an immune response, including antibodies, that may confer immunity to pathogenic species of *E. coli*.

In some aspects, the composition comprises a FimH mutant polypeptide as the only antigen. In some aspects, the composition does not include a conjugate.

In some aspects, the composition comprises a FimH mutant polypeptide and at least one additional antigen. In some aspects, the composition comprises a FimH mutant polypeptide and an additional *E. coli* antigen. In some aspects, the composition comprises a FimH mutant polypeptide and a glycoconjugate from *E. coli*.

In some aspects, the composition comprises a FimH mutant polypeptide and a polypeptide derived from *E. coli* FimC or a fragment thereof.

In one embodiment, the disclosure includes a composition comprising a FimH mutant polypeptide, and a saccharide comprising a structure selected from any one of the saccharide structures disclosed in PCT Intl. Publication Nos. WO2021/084429, published May 6, 2021, and WO2020/039359, published Feb. 27, 2020, and US Publication No. US2020/0061177, published Feb. 27, 2020, which are each incorporated herein by reference in their entireties. In one aspect, the disclosure includes a composition comprising a FimH mutant polypeptide; and a saccharide comprising a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100, preferably from 31 to 90.

In some embodiments, the composition includes any one of the saccharides disclosed herein. In preferred embodiments, the composition includes any one of the conjugates disclosed herein.

In some embodiments, the composition includes at least one glycoconjugate from *E. coli* serotype O25, preferably serotype O25b. In one embodiment, the composition includes at least one glycoconjugate from *E. coli* serotype O1, preferably serotype O1a. In one embodiment, the composition includes at least one glycoconjugate from *E. coli* serotype O2. In one embodiment, the composition includes at least one glycoconjugate from *E. coli* serotype O6.

In one embodiment, the composition comprises at least one glycoconjugate selected from any one of the following *E. coli* serotypes O25, O1, O2, and O6, preferably O25b, O1a, O2, and O6. In one embodiment, the composition comprises at least two glycoconjugates selected from any one of the following *E. coli* serotypes O25, O1, O2, and O6, preferably O25b, O1a, O2, and O6. In another embodiment, the composition comprises at least three glycoconjugates selected from any one of the following *E. coli* serotypes O25, O1, O2, and O6, preferably O25b, O1a, O2, and O6. In a further embodiment, the composition comprises a glycoconjugate from each of the following *E. coli* serotypes O25, O1, O2, and O6, preferably O25b, O1a, O2, and O6.

In a preferred embodiment, the glycoconjugate of any of the above compositions is individually conjugated to $CRM_{197}$. In another preferred embodiment, the glycoconjugate of any of the above compositions is individually conjugated to SCP.

Accordingly, in some embodiments, the composition includes a FimH mutant polypeptide, and an O-antigen from at least one *E. coli* serotype. In a preferred embodiment, the composition includes a FimH mutant polypeptide, and an O-antigen from more than 1 *E. coli* serotype. For example, the composition may include an O-antigen from two different *E. coli* serotypes (or "v", valences) to 12 different serotypes (12v). In one embodiment, the composition includes a FimH mutant polypeptide, and an O-antigen from 3 different serotypes. In one embodiment, the composition includes a FimH mutant polypeptide, and an O-antigen from 4 different *E. coli* serotypes. In one embodiment, the composition includes a FimH mutant polypeptide, and an O-antigen from 5 different *E. coli* serotypes. In one embodiment, the composition includes a FimH mutant polypeptide, and an O-antigen from 6 different *E. coli* serotypes. In one embodiment, the composition includes a FimH mutant polypeptide, and an O-antigen from 7 different *E. coli* serotypes. In one embodiment, the composition includes a FimH mutant polypeptide, and an O-antigen from 8 different *E. coli* serotypes. In one embodiment, the composition includes a FimH mutant polypeptide, and an O-antigen from 9 different *E. coli* serotypes. In one embodiment, the composition includes a FimH mutant polypeptide, and an O-antigen from 10 different *E. coli* serotypes. In one embodiment, the composition includes a FimH mutant polypeptide, and an O-antigen from 11 different *E. coli* serotypes. In one embodiment, the composition includes a FimH mutant polypeptide, and an O-antigen from 12 different serotypes. In one embodiment, the composition includes a FimH mutant polypeptide, and an O-antigen from 13 different serotypes. In one embodiment, the composition includes a FimH mutant polypeptide, and an O-antigen from 14 different serotypes. In one embodiment, the composition includes a FimH mutant polypeptide, and an O-antigen from 15 different serotypes. In one embodiment, the composition includes a FimH mutant polypeptide, and an O-antigen from 16 different serotypes. In one embodiment, the composition includes a FimH mutant polypeptide, and an O-antigen from 17 different serotypes. In one embodiment, the composition includes a FimH mutant polypeptide, and an O-antigen from 18 different serotypes. In one embodiment, the composition includes a FimH mutant polypeptide, and an O-antigen from 19 different serotypes. In one embodiment, the composition includes a FimH mutant polypeptide, and an O-antigen from 20 different serotypes.

Preferably, the number of *E. coli* saccharides can range from 1 serotype (or "v", valences) to 26 different serotypes (26v). In one embodiment there is one serotype. In one embodiment there are 2 different serotypes. In one embodiment there are 3 different serotypes. In one embodiment there are 4 different serotypes. In one embodiment there are 5 different serotypes. In one embodiment there are 6 different serotypes. In one embodiment there are 7 different serotypes. In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In one embodiment there are 17 different serotypes. In one embodiment there are 18 different serotypes. In one embodiment there are 19 different serotypes. In one embodiment there are 20 different serotypes. In one embodiment there are 21 different serotypes. In one embodiment there are 22 different serotypes. In one embodiment there are 23 different serotypes. In one embodiment there are 24 different serotypes. In an embodiment there are 25 different serotypes. In one embodiment there are 26 different serotypes. The saccharides are conjugated to a carrier protein to form glycoconjugates as described herein.

In one aspect, the composition includes a FimH mutant polypeptide; and a glycoconjugate that includes an O-antigen from at least one *E. coli* serogroup, wherein the O-antigen is conjugated to a carrier protein. In one embodiment, the composition includes a FimH mutant polypeptide; and an O-antigen from more than 1 *E. coli* serotype, wherein each O-antigen is conjugated to a carrier protein. In one embodiment, the composition includes a FimH mutant polypeptide, and an O-antigen from 2 different *E. coli* serotypes, wherein each O-antigen is conjugated to a carrier protein. In one embodiment, the composition includes a FimH mutant polypeptide, and an O-antigen from 3 different *E. coli* serotypes, wherein each O-antigen is conjugated to a carrier protein. In one embodiment, the composition includes a FimH mutant polypeptide, and an O-antigen from 4 different *E. coli* serotypes, wherein each O-antigen is conjugated to a carrier protein. In one embodiment, the composition includes a FimH mutant polypeptide, and an O-antigen from 5 different *E. coli* serotypes, wherein each O-antigen is conjugated to a carrier protein. In one embodiment, the composition includes a FimH mutant polypeptide, and an O-antigen from 6 different *E. coli* serotypes, wherein each O-antigen is conjugated to a carrier protein. In one embodiment, the composition includes a FimH mutant polypeptide, and an O-antigen from 7 different *E. coli* serotypes, wherein each O-antigen is conjugated to a carrier protein. In one embodiment, the composition includes a FimH mutant polypeptide, and an O-antigen from 8 different *E. coli* serotypes, wherein each O-antigen is conjugated to a carrier protein. In one embodiment, the composition includes a FimH mutant polypeptide, and an O-antigen from 9 different *E. coli* serotypes, wherein each O-antigen is conjugated to a carrier protein. In one embodiment, the composition includes an O-antigen from a FimH mutant polypeptide, and 10 different *E. coli* serotypes, wherein each O-antigen is conjugated to a carrier protein. In one embodiment, the composition includes an O-antigen from a FimH mutant polypeptide, and 11 different *E. coli* serotypes, wherein each O-antigen is conjugated to a carrier protein. In one embodiment, the composition includes a FimH mutant polypeptide, and an O-antigen from 12 different serotypes, wherein each O-antigen is conjugated to a carrier protein. In one embodiment, the composition includes a FimH mutant polypeptide, and an O-antigen from 13 different serotypes, wherein each O-antigen is conjugated to a carrier protein. In one embodiment, the composition includes a FimH mutant polypeptide, and an O-antigen from 14 different serotypes, wherein each O-antigen is conjugated to a carrier protein. In one embodiment, the composition includes a FimH mutant polypeptide, and an O-antigen from 15 different serotypes, wherein each O-antigen is conjugated to a carrier protein. In one embodiment, the composition includes a FimH mutant polypeptide, and an O-antigen from 16 different serotypes, wherein each O-antigen is conjugated to a carrier protein. In one embodiment, the composition includes a FimH mutant polypeptide, and an O-antigen from 17 different serotypes, wherein each O-antigen is conjugated to a carrier protein. In one embodiment, the composition includes a FimH mutant polypeptide, and an O-antigen from 18 different serotypes, wherein each O-antigen is conjugated to a carrier protein. In one embodiment, the composition includes a FimH mutant polypeptide, and an O-antigen from 19 different serotypes, wherein each O-antigen is conjugated to a carrier protein. In one embodiment, the composition includes a FimH mutant polypeptide, and an O-antigen from 20 different serotypes, wherein each O-antigen is conjugated to a carrier protein.

In another aspect, the composition includes an O-polysaccharide from at least one *E. coli* serotype. In a preferred embodiment, the composition includes an O-polysaccharide from more than 1 *E. coli* serotype. For example, the composition may include an O-polysaccharide from two different *E. coli* serotypes to 12 different *E. coli* serotypes. In one embodiment, the composition includes an O-polysaccharide from 3 different *E. coli* serotypes. In one embodiment, the composition includes an O-polysaccharide from 4 different *E. coli* serotypes. In one embodiment, the composition includes an O-polysaccharide from 5 different *E. coli* serotypes. In one embodiment, the composition includes an O-polysaccharide from 6 different *E. coli* serotypes. In one embodiment, the composition includes an O-polysaccharide from 7 different *E. coli* serotypes. In one embodiment, the composition includes an O-polysaccharide from 8 different *E. coli* serotypes. In one embodiment, the composition includes an O-polysaccharide from 9 different *E. coli* serotypes. In one embodiment, the composition includes an O-polysaccharide from 10 different *E. coli* serotypes. In one embodiment, the composition includes an O-polysaccharide from 11 different *E. coli* serotypes. In one embodiment, the composition includes an O-polysaccharide from 12 different serotypes. In one embodiment, the composition includes an O-polysaccharide from 13 different serotypes. In one embodiment, the composition includes an O-polysaccharide from 14 different serotypes. In one embodiment, the composition includes an O-polysaccharide from 15 different serotypes. In one embodiment, the composition includes an O-polysaccharide from 16 different serotypes. In one embodiment, the composition includes an O-polysaccharide from 17 different serotypes. In one embodiment, the composition includes an O-polysaccharide from 18 different serotypes. In one embodiment, the composition includes an O-polysaccharide from 19 different serotypes. In one embodiment, the composition includes an O-polysaccharide from 20 different serotypes.

In a preferred embodiment, the composition includes an O-polysaccharide from at least one *E. coli* serotype, wherein the O-polysaccharide is conjugated to a carrier protein. In a preferred embodiment, the composition includes an O-polysaccharide from more than 1 *E. coli* serotype, wherein each O-polysaccharide is conjugated to a carrier protein. For example, the composition may include an O-polysaccharide from two different *E. coli* serotypes to 12 different *E. coli* serotypes, wherein each O-polysaccharide is conjugated to a carrier protein. In one embodiment, the composition includes an O-polysaccharide from 3 different *E. coli* serotypes, wherein each O-polysaccharide is conjugated to a carrier protein. In one embodiment, the composition includes an O-polysaccharide from 4 different *E. coli* serotypes, wherein each O-polysaccharide is conjugated to a carrier protein. In one embodiment, the composition includes an O-polysaccharide from 5 different *E. coli* serotypes, wherein each O-polysaccharide is conjugated to a carrier protein. In one embodiment, the composition includes an O-polysaccharide from 6 different *E. coli* serotypes, wherein each O-polysaccharide is conjugated to a carrier protein. In one embodiment, the composition includes an O-polysaccharide from 7 different *E. coli* serotypes, wherein each O-polysaccharide is conjugated to a carrier protein. In one embodiment, the composition includes an O-polysaccharide from 8 different *E. coli* serotypes, wherein each O-polysaccharide is conjugated to a carrier protein. In one embodiment, the composition includes an O-polysaccharide from 9 different *E. coli* serotypes, wherein each O-polysaccharide is conjugated to a carrier protein. In one embodiment, the composition includes an O-polysaccharide from 10 different *E. coli* serotypes, wherein each O-polysaccharide is conjugated to a carrier protein. In one embodiment, the composition includes an O-polysaccharide from 11 different *E. coli* serotypes, wherein each O-polysaccharide is conjugated to a carrier protein. In one embodiment, the composition includes an O-polysaccharide from 12 different serotypes, wherein each O-polysaccharide is conjugated to a carrier protein. In one embodiment, the composition includes an O-polysaccharide from 13 different serotypes, wherein each O-polysaccharide is conjugated to a carrier protein. In one embodiment, the composition includes an O-polysaccharide from 14 different serotypes, wherein each O-polysaccharide is conjugated to a carrier protein. In one embodiment, the composition includes an O-polysaccharide from 15 different serotypes, wherein each O-polysaccharide is conjugated to a carrier protein. In one embodiment, the composition includes an O-polysaccharide from 16 different serotypes, wherein each O-polysaccharide is conjugated to a carrier protein. In one embodiment, the composition includes an O-polysaccharide from 17 different serotypes, wherein each O-polysaccharide is conjugated to a carrier protein. In one embodiment, the composition includes an O-polysaccharide from 18 different serotypes, wherein each O-polysaccharide is conjugated to a carrier protein. In one embodiment, the composition includes an O-polysaccharide from 19 different serotypes, wherein each O-polysaccharide is conjugated to a carrier protein. In one embodiment, the composition includes an O-polysaccharide from 20 different serotypes, wherein each O-polysaccharide is conjugated to a carrier protein.

In a most preferred embodiment, the composition includes an O-polysaccharide from at least one *E. coli* serotype, wherein the O-polysaccharide is conjugated to a carrier protein, and wherein the O-polysaccharide includes the O-antigen and core saccharide. In a preferred embodiment, the composition includes an O-polysaccharide from more than 1 *E. coli* serotype, wherein each O-polysaccharide is conjugated to a carrier protein, and wherein the O-polysaccharide includes the O-antigen and core saccharide. For example, the composition may include an O-polysaccharide from two different *E. coli* serotypes to 12 different *E. coli* serotypes, wherein each O-polysaccharide is conjugated to a carrier protein, and wherein the O-polysaccharide includes the O-antigen and core saccharide. In one embodiment, the composition includes an O-polysaccharide from 3 different *E. coli* serotypes, wherein each O-polysaccharide is conjugated to a carrier protein, and wherein the O-polysaccharide includes the O-antigen and core saccharide. In one embodiment, the composition includes an O-polysaccharide from 4 different *E. coli* serotypes, wherein each O-polysaccharide is conjugated to a carrier protein, and wherein the O-polysaccharide includes the O-antigen and core saccharide. In one embodiment, the composition includes an O-polysaccharide from 5 different *E. coli* serotypes, wherein each O-polysaccharide is conjugated to a carrier protein, and wherein the O-polysaccharide includes the O-antigen and core saccharide. In one embodiment, the composition includes an O-polysaccharide from 6 different *E. coli* serotypes, wherein each O-polysaccharide is conjugated to a carrier protein, and wherein the O-polysaccharide includes the O-antigen and core saccharide. In one embodiment, the composition includes an O-polysaccharide from 7 different *E. coli* serotypes, wherein each O-polysaccharide is conjugated to a carrier protein, and wherein the O-polysaccharide includes the O-antigen and core saccharide. In one embodiment, the composition includes an O-polysaccharide from 8 different *E. coli* serotypes, wherein each O-polysaccharide is conjugated to a carrier protein, and wherein the O-polysaccharide includes the O-antigen and core saccharide. In one embodiment, the composition includes an O-polysaccharide from 9 different *E. coli* serotypes, wherein each O-polysaccharide is conjugated to a carrier protein, and wherein the O-polysaccharide includes the O-antigen and core saccharide. In one embodiment, the composition includes an O-polysaccharide from 10 different *E. coli* serotypes, wherein each O-polysaccharide is conjugated to a carrier protein, and wherein the O-polysaccharide includes the O-antigen and core saccharide. In one embodiment, the composition includes an O-polysaccharide from 11 different *E. coli* serotypes, wherein each O-polysaccharide is conjugated to a carrier protein, and wherein the O-polysaccharide includes the O-antigen and core saccharide. In one embodiment, the composition includes an O-polysaccharide from 12 different serotypes, wherein each O-polysaccharide is conjugated to a carrier protein, and wherein the O-polysaccharide includes the O-antigen and core saccharide. In one embodiment, the composition includes an O-polysaccharide from 13 different serotypes, wherein each O-polysaccharide is conjugated to a carrier protein, and wherein the O-polysaccharide includes the O-antigen and core saccharide. In one embodiment, the composition includes an O-polysaccharide from 14 different serotypes, wherein each O-polysaccharide is conjugated to a carrier protein, and wherein the O-polysaccharide includes the O-antigen and core saccharide. In one embodiment, the composition includes an O-polysaccharide from 15 different serotypes, wherein each O-polysaccharide is conjugated to a carrier protein, and wherein the O-polysaccharide includes the O-antigen and core saccharide. In one embodiment, the composition includes an O-polysaccharide from 16 different serotypes, wherein each O-polysaccharide is conjugated to a carrier protein, and wherein the O-polysaccharide includes the O-antigen and core saccharide. In one embodiment, the composition includes an O-polysaccharide from 17 different serotypes, wherein each O-polysaccharide is conjugated to a carrier protein, and wherein the O-polysaccharide includes the O-antigen and core saccharide. In one embodiment, the composition includes an O-polysaccharide from 18 different serotypes, wherein each O-polysaccharide is conjugated to a carrier protein, and wherein the O-polysaccharide includes the O-antigen and core saccharide. In one embodiment, the composition includes an O-polysaccharide from 19 different serotypes, wherein each O-polysaccharide is conjugated to a carrier protein, and wherein the O-polysaccharide includes the O-antigen and core saccharide. In one embodiment, the composition includes an O-polysaccharide from 20 different serotypes, wherein each O-polysaccharide is conjugated to a carrier protein, and wherein the O-polysaccharide includes the O-antigen and core saccharide. In a preferred embodiment, the carrier protein is $CRM_{197}$.

In another preferred embodiment, the composition includes a FimH mutant polypeptide, and an O-polysaccharide conjugated to $CRM_{197}$, wherein the O-polysaccharide includes Formula O25a, wherein n is at least 30, and the core saccharide. In a preferred embodiment, the composition further includes an O-polysaccharide conjugated to $CRM_{197}$, wherein the O-polysaccharide includes Formula O25b, wherein n is at least 40, and the core saccharide. In another embodiment, the composition further includes an O-polysaccharide conjugated to $CRM_{197}$, wherein the O-polysaccharide includes Formula O1a, wherein n is at least 30, and the core saccharide. In another embodiment, the composition further includes an O-polysaccharide conjugated to $CRM_{197}$, wherein the O-polysaccharide includes Formula O2, wherein n is at least 30, and the core saccharide. In another embodiment, the composition further includes an O-polysaccharide conjugated to $CRM_{197}$, wherein the O-polysaccharide includes Formula O6, wherein n is at least 30, and the core saccharide.

In another embodiment, the composition further includes an O-polysaccharide conjugated to $CRM_{197}$, wherein the O-polysaccharide includes Formula O17, wherein n is at least 30, and the core saccharide. In another embodiment, the composition further includes an O-polysaccharide conjugated to $CRM_{197}$, wherein the O-polysaccharide includes Formula O15, wherein n is at least 30, and the core saccharide. In another embodiment, the composition further includes an O-polysaccharide conjugated to $CRM_{197}$, wherein the O-polysaccharide includes Formula O18A, wherein n is at least 30, and the core saccharide. In another embodiment, the composition further includes an O-polysaccharide conjugated to $CRM_{197}$, wherein the O-polysaccharide includes Formula O75, wherein n is at least 30, and the core saccharide. In another embodiment, the composition further includes an O-polysaccharide conjugated to $CRM_{197}$, wherein the O-polysaccharide includes Formula O4, wherein n is at least 30, and the core saccharide. In another embodiment, the composition further includes an O-polysaccharide conjugated to $CRM_{197}$, wherein the O-polysaccharide includes Formula O16, wherein n is at least 30, and the core saccharide. In another embodiment, the composition further includes an O-polysaccharide conjugated to $CRM_{197}$, wherein the O-polysaccharide includes Formula O13, wherein n is at least 30, and the core saccharide. In another embodiment, the composition further includes an O-polysaccharide conjugated to $CRM_{197}$, wherein the O-polysaccharide includes Formula O7, wherein n is at least 30, and the core saccharide.

In another embodiment, the composition further includes an O-polysaccharide conjugated to $CRM_{197}$, wherein the O-polysaccharide includes Formula O8, wherein n is at least 30, and the core saccharide. In another embodiment, the O-polysaccharide includes Formula O8, wherein n is 1-20, preferably 2-5, more preferably 3. In another embodiment, the composition further includes an O-polysaccharide conjugated to $CRM_{197}$, wherein the O-polysaccharide includes Formula O9, wherein n is at least 30, and the core saccharide. In another embodiment, the O-polysaccharide includes Formula O9, wherein n is 1-20, preferably 4-8, more preferably 5. In another embodiment, the O-polysaccharide includes Formula O9a, wherein n is 1-20, preferably 4-8, more preferably 5.

In some embodiments, the O-polysaccharide is selected from any one of Formula O20ab, Formula O20ac, Formula O52, Formula O97, and Formula O101, wherein n is 1-20, preferably 4-8, more preferably 5.

As described above, the composition may include a FimH mutant polypeptide, and any combination of conjugated O-polysaccharides (antigens). In one exemplary embodiment, the composition includes a polysaccharide that includes Formula O25b, a polysaccharide that includes Formula O1a, a polysaccharide that includes Formula O2, and a polysaccharide that includes Formula O6. More specifically, such as a composition that includes: (i) an O-polysaccharide conjugated to CRM197, wherein the O-polysaccharide includes Formula O25b, wherein n is at least 30, and the core saccharide; (ii) an O-polysaccharide conjugated to $CRM_{197}$, wherein the O-polysaccharide includes Formula O1a, wherein n is at least 30, and the core saccharide; (iii) an O-polysaccharide conjugated to $CRM_{197}$, wherein the O-polysaccharide includes Formula O2, wherein n is at least 30, and the core saccharide; and (iv) an O-polysaccharide conjugated to $CRM_{197}$, wherein the O-polysaccharide includes Formula O6, wherein n is at least 30, and the core saccharide.

In one embodiment, the composition includes a FimH mutant polypeptide, and at least one O-polysaccharide derived from any *E. coli* serotype, wherein the serotype is not O25a. For example, in one embodiment, the composition does not include a saccharide that includes the Formula O25a. Such a composition may include, for example, an O-polysaccharide that includes Formula O25b, an O-polysaccharide that includes Formula O1a, an O-polysaccharide that includes Formula O2, and an O-polysaccharide that includes Formula O6.

In one embodiment, the composition includes a FimH mutant polypeptide, and an O-polysaccharide from 2 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 3 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 4 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 5 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 6 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 7 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 8 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 9 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 10 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 11 different *E. coli* serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 12 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 13 different serotypes, wherein each O-polysaccharide is conjugated to $CRM_{197}$ and wherein the O-polysaccharide includes the O-antigen and core saccharide. In one embodiment, the composition includes a FimH mutant polypeptide, and an O-polysaccharide from 14 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 15 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 16 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 17 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 18 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 19 different serotypes, wherein each O-polysaccharide is conjugated to $CRM_{197}$, and wherein the O-polysaccharide includes the O-antigen and core saccharide. In one embodiment, the composition includes a FimH mutant polypeptide, and an O-polysaccharide from 20 different serotypes, wherein each O-polysaccharide is conjugated to $CRM_{197}$, and wherein the O-polysaccharide includes the O-antigen and core saccharide.

In one aspect, the invention provides a composition that comprises a FimH mutant polypeptide, and a conjugate including a saccharide covalently bound to a carrier protein, wherein the saccharide includes Formula O25b, wherein n is 15±2. In one aspect, the invention relates to a composition that includes a FimH mutant polypeptide, and a conjugate including a saccharide covalently bound to a carrier protein, wherein the saccharide includes Formula O25b, wherein n is 17±2. In one aspect, the invention relates to a composition that includes a FimH mutant polypeptide, and a conjugate including a saccharide covalently bound a carrier protein, wherein the saccharide includes Formula O25b, wherein n is 55±2. In another aspect, the invention relates to a composition that includes a FimH mutant polypeptide, and a conjugate including a saccharide covalently bound a carrier protein, wherein the saccharide includes Formula O25b, wherein n is 51±2. In another aspect, the invention relates to a composition that includes a FimH mutant polypeptide, and a conjugate including a saccharide covalently bound a carrier protein, wherein the saccharide includes Formula O25b, wherein n is an integer greater than 30, preferably n is an integer from 31 to 100. In one embodiment, the saccharide further includes the E. coli R1 core saccharide moiety. In another embodiment, the saccharide further includes the E. coli K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one aspect, the immunogenic composition elicits IgG antibodies in humans, said antibodies being capable of binding an E. coli serotype O25b polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O25b to assess the potential increase of responders. In one embodiment, the immunogenic composition elicits IgG antibodies in humans, said antibodies being capable of killing E. coli serotype O25b as determined by in vitro opsonophagocytic assay. In one embodiment, the immunogenic composition elicits functional antibodies in humans, said antibodies being capable of killing E. coli serotype O25b as determined by in vitro opsonophagocytic assay. In one embodiment, the immunogenic composition of the invention increases the proportion of responders against E. coli serotype O25b (i.e., individual with a serum having a titer of at least 1:8 as determined by in vitro OPA) as compared to the pre-immunized population. In one embodiment, the immunogenic composition elicits a titer of at least 1:8 against E. coli serotype O25b in at least 50% of the subjects as determined by in vitro opsonophagocytic killing assay. In one embodiment, the immunogenic composition of the invention elicits a titer of at least 1:8 against E. coli serotype O25b in at least 60%, 70%, 80%, or at least 90% of the subjects as determined by in vitro opsonophagocytic killing assay. In one embodiment, the immunogenic composition of the invention significantly increases the proportion of responders against E. coli serotypes O25b (i.e., individual with a serum having a titer of at least 1:8 as determined by in vitro OPA) as compared to the pre-immunized population. In one embodiment, the immunogenic composition of the invention significantly increases the OPA titers of human subjects against E. coli serotype O25b as compared to the pre-immunized population.

In one aspect, the invention relates to a composition that includes a FimH mutant polypeptide, and a conjugate including a saccharide covalently bound to a carrier protein, wherein the saccharide includes Formula O1a, wherein n is an integer greater than 30, preferably n is an integer from 31 to 100. In another aspect, the invention relates to a composition that includes a FimH mutant polypeptide, and a conjugate including a saccharide covalently bound a carrier protein, wherein the saccharide includes Formula O1a, wherein n is 39 ±2. In another aspect, the invention relates to a composition that includes a FimH polypeptide, and a conjugate including a saccharide covalently bound a carrier protein, wherein the saccharide includes Formula O1a, wherein n is 13±2. In one embodiment, the saccharide further includes the E. coli R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an E. coli serotype O1a polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O1a to assess the potential increase of responders. In one embodiment, the immunogenic composition elicits IgG antibodies in humans, said antibodies being capable of killing E. coli serotype O1a as determined by in vitro opsonophagocytic assay. In one embodiment, the immunogenic composition elicits functional antibodies in humans, said antibodies being capable of killing E. coli serotype O1a as determined by in vitro opsonophagocytic assay. In one embodiment, the immunogenic composition of the invention increases the proportion of responders against E. coli serotype O1 a (i.e., individual with a serum having a titer of at least 1:8 as determined by in vitro OPA) as compared to the pre-immunized population. In one embodiment, the immunogenic composition elicits a titer of at least 1:8 against E. coli serotype O1a in at least 50% of the subjects as determined by in vitro opsonophagocytic killing assay. In one embodiment, the immunogenic composition of the invention elicits a titer of at least 1:8 against E. coli serotype O1a in at least 60%, 70%, 80%, or at least 90% of the subjects as determined by in vitro opsonophagocytic killing assay. In one embodiment, the immunogenic composition of the invention significantly increases the proportion of responders against E. coli serotypes O1a (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O1a as compared to the pre-immunized population.

In one aspect, the invention relates to a composition that includes a FimH mutant polypeptide, and a conjugate including a saccharide covalently bound to a carrier protein, wherein the saccharide includes Formula O2, wherein wherein n is an integer greater than 30, preferably n is an integer from 31 to 100. In another aspect, the invention relates to a composition that includes a FimH mutant polypeptide, and a conjugate including a saccharide covalently bound to a carrier protein, wherein the saccharide includes Formula O2, wherein n is 43±2. In another aspect, the invention relates to a composition that includes a FimH mutant polypeptide, and a conjugate including a saccharide covalently bound to a carrier protein, wherein the saccharide includes Formula O2, wherein n is 47±2. In another aspect, the invention relates to a composition that includes FimH mutant polypeptide, and a conjugate including a saccharide covalently bound a carrier protein, wherein the saccharide includes Formula O2, wherein n is 17±2. In another aspect, the invention relates to a composition that includes FimH mutant polypeptide, and a conjugate including a saccharide covalently bound to a carrier protein, wherein the saccharide includes Formula O2, wherein n is 18±2. In one embodiment, the saccharide further includes the *E. coli* R1 core saccharide moiety. In another embodiment, the saccharide further includes the *E. coli* R4 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio) ethyl)carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O2 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O2 to assess the potential increase of responders. In one embodiment, the immunogenic composition elicits IgG antibodies in humans, said antibodies being capable of killing *E. coli* serotype O2 as determined by in vitro opsonophagocytic assay. In one embodiment, the immunogenic composition elicits functional antibodies in humans, said antibodies being capable of killing *E. coli* serotype O2 as determined by in vitro opsonophagocytic assay. In one embodiment, the immunogenic composition of the invention increases the proportion of responders against *E. coli* serotype O2 (i.e., individual with a serum having a titer of at least 1:8 as determined by in vitro OPA) as compared to the pre-immunized population. In one embodiment, the immunogenic composition elicits a titer of at least 1:8 against *E. coli* serotype O2 in at least 50% of the subjects as determined by in vitro opsonophagocytic killing assay. In one embodiment, the immunogenic composition of the invention elicits a titer of at least 1:8 against *E. coli* serotype O2 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O2 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O2 as compared to the pre-immunized population.

In one aspect, the invention relates to a composition that includes a FimH mutant polypeptide, and a conjugate including a saccharide covalently bound to a carrier protein, wherein the saccharide includes Formula O6, wherein n is an integer greater than 30, preferably n is an integer from 31 to 100. In one aspect, the invention relates to a composition that includes a FimH mutant polypeptide, and a conjugate including a saccharide covalently bound to a carrier protein, wherein the saccharide includes Formula O6, wherein n is 42±2. In another aspect, the invention relates to a composition that includes a FimH mutant polypeptide, and a conjugate including a saccharide covalently bound to a carrier protein, wherein the saccharide includes Formula O6, wherein n is 50±2. In another aspect, the invention relates to a composition that includes a FimH mutant polypeptide, and a conjugate including a saccharide covalently bound to a carrier protein, wherein the saccharide includes Formula O6, wherein n is 17±2. In another aspect, the invention relates to a composition that includes a FimH mutant polypeptide, and a conjugate including a saccharide covalently bound to a carrier protein, wherein the saccharide includes Formula O6, wherein n is 18±2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O6 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O6 to assess the potential increase of responders. In one embodiment, the immunogenic composition elicits IgG antibodies in humans, said antibodies being capable of killing *E. coli* serotype O6 as determined by in vitro opsonophagocytic assay. In one embodiment, the immunogenic composition elicits functional antibodies in humans, said antibodies being capable of killing *E. coli* serotype O6 as determined by in vitro opsonophagocytic assay. In one embodiment, the immunogenic composition of the invention increases the proportion of responders against *E. coli* serotype O6 (i.e., individual with a serum having a titer of at least 1:8 as determined by in vitro OPA) as compared to the pre-immunized population. In one embodiment, the immunogenic composition elicits a titer of at least 1:8 against *E. coli* serotype O6 in at least 50% of the subjects as determined by in vitro opsonophagocytic killing assay. In one embodiment, the immunogenic composition of the invention elicits a titer of at least 1:8 against *E. coli* serotype O6 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O6 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O6 as compared to the pre-immunized population.

In one aspect, the composition includes a FimH mutant polypeptide, and a conjugate including a saccharide covalently bound to a carrier protein, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100, preferably from 31 to 90. In one embodiment, the saccharide further includes the *E. coli* R1 core saccharide moiety. In one embodiment, the saccharide further includes the *E. coli* R2 core saccharide moiety. In one embodiment, the saccharide further includes the *E. coli* R3 core saccharide moiety. In another embodiment, the saccharide further includes the *E. coli* R4 core saccharide moiety. In one embodiment, the saccharide further includes the *E. coli* K12 core saccharide moiety. In another embodiment, the saccharide further includes the KDO moiety. Preferably, the carrier protein is CRM$_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl)carbamate (eTEC) spacer. Preferably, the composition further includes a pharmaceutically acceptable diluent. In one embodiment, the composition further includes at least 1, 2, 3, 4, 5, 6, 7, 8, 9, 10, 11, 12, 13, 14, 15, 16, 17, 18, 19, 20, 21, 22, 23, 24, 25, 26, 27, 28, or 29 additional conjugates to at most 30 additional conjugates, each conjugate including a saccharide covalently bound to a carrier protein, wherein the saccharide includes a structure selected from any one of said Formulas.

A. Saccharides

1. Saccharides and O-polysaccharides

In one embodiment, the saccharide is produced by expression (not necessarily overexpression) of different Wzz proteins (e.g., WzzB) to control of the size of the saccharide.

As used herein, the term "saccharide" refers to a single sugar moiety or monosaccharide unit as well as combinations of two or more single sugar moieties or monosaccharide units covalently linked to form disaccharides, oligosaccharides, and polysaccharides. The saccharide may be linear or branched.

In one embodiment, the saccharide is produced in a recombinant Gram-negative bacterium. In one embodiment, the saccharide is produced in a recombinant *E. coli* cell. In one embodiment, the saccharide is produced in a recombinant *Salmonella* cell. Exemplary bacteria include *E. coli* O25K5H1, *E. coli* BD559, *E. coli* GAR2831, *E. coli* GAR865, *E. coli* GAR868, *E. coli* GAR869, *E. coli* GAR872, *E. coli* GAR878, *E. coli* GAR896, *E. coli* GAR1902, *E. coli* O25a ETC NR-5, *E. coli* O157:H7:K-, *Salmonella enterica* serovar Typhimurium strain LT2, *E. coli* GAR2401, *Salmonella enterica* serotype Enteritidis CVD 1943, *Salmonella enterica* serotype Typhimurium CVD 1925, *Salmonella enterica* serotype Paratyphi A CVD 1902, and *Shigella flexneri* CVD 1208S. In one embodiment, the bacterium is not *E. coli* GAR2401. This genetic approach towards saccharide production allows for efficient production of O-polysaccharides and O-antigen molecules as vaccine components.

The term "wzz protein," as used herein, refers to a chain length determinant polypeptide, such as, for example, wzzB, wzz, wzz$_{SF}$, wzz$_{ST}$, fepE, wzz$_{fepE}$, wzzI and wzz2. The GenBank accession numbers for the exemplary wzz gene sequences are AF011910 for E4991/76, AF011911 for F186, AF011912 for M70/1-1, AF011913 for 79/311, AF011914 for Bi7509-41, AF011915 for C664-1992, AF011916 for C258-94, AF011917 for C722-89, and AF011919 for EDL933. The GenBank accession numbers for the G7 and Bi316-41 wzz genes sequences are U39305 and U39306, respectively. Further GenBank accession numbers for exemplary wzz gene sequences are NP_459581 for *Salmonella enterica* subsp. Enterica serovar Typhimurium str. LT2 FepE; AIG66859 for *E. coli* O157:H7 Strain EDL933 FepE;

NP_461024 for *Salmonella enterica* subsp. Enterica serovar Typhimurium str. LT2 WzzB. NP_416531 for *E. coli* K-12 substr. MG1655 WzzB, NP_415119 for *E. coli* K-12 substr. MG1655 FepE. In preferred aspects, the wzz family protein is any one of wzzB, wzz, wzz$_{SF}$, wzz$_{ST}$, fepE, wzz$_{fepE}$, wzz1 and wzz2, most preferably wzzB, more preferably fepE.

Exemplary wzzB sequences include sequences set forth in SEQ ID Nos: 112-116. Exemplary FepE sequences include sequences set forth in SEQ ID Nos: 117-121.

In some aspects, a modified saccharide (modified as compared to the corresponding wild-type saccharide) may be produced by expressing (not necessarily overexpressing) a wzz family protein (e.g., fepE) from a Gram-negative bacterium in a Gram-negative bacterium and/or by switching off (i.e., repressing, deleting, removing) a second wzz gene (e.g., wzzB) to generate high molecular weight saccharides, such as lipopolysaccharides, containing intermediate or long O-antigen chains, which have an increased number of repeating units as compared to the corresponding wild-type O-polysaccharide. For example, the modified saccharides may be produced by expressing (not necessarily overexpressing) wzz2 and switching off wzzI. Or, in the alternative, the modified saccharides may be produced by expressing (not necessarily overexpressing) wzz/fepE and switching off wzzB. In another embodiment, the modified saccharides may be produced by expressing (not necessarily overexpressing) wzzB but switching off wzz/fepE. In another embodiment, the modified saccharides may be produced by expressing fepE. Preferably, the wzz family protein is derived from a strain that is heterologous to the host cell. Methods of determining the length of saccharides are known in the art. Such methods include, but are not limited to, nuclear magnetic resonance, mass spectroscopy, and size exclusion chromatography. Methods for producing the high molecular weight saccharides described herein, such as lipopolysaccharides, containing intermediate or long O-antigen chains, are described in PCT Intl. Publication No. WO2020/039359 and corresponding US Publication No. US2020/0061177, which are each incorporated herein by reference in their entireties.

In some embodiments, the saccharide is produced by expressing a wzz family protein having an amino acid sequence that is at least 30%, 50%, 70%, 75%, 80%, 85%, 90%, 95%, 98%, 99% or 100% sequence identity to any one of SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121. In one embodiment, the wzz family protein includes a sequence selected from any one of SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121. Preferably, the wzz family protein has at least 30%, 50%, 70%, 75%, 80%, 85%, 90%, 95%, 98%, 99% or 100% sequence identity to SEQ ID NO: 112, SEQ ID NO: 113, SEQ ID NO: 114, SEQ ID NO: 115, SEQ ID NO: 116. In some embodiments, the saccharide is produced by expressing a protein having an amino acid sequence that is at least 30%, 50%, 70%, 75%, 80%, 85%, 90%, 95%, 98%, 99% or 100% sequence identity to an fepE protein.

In one aspect, the invention relates to saccharides produced by expressing a wzz family protein, preferably fepE, in a Gram-negative bacterium to generate high molecular weight saccharides containing intermediate or long O-antigen chains, which have an increase of at least 1, 2, 3, 4, or 5 repeating units, as compared to the corresponding wild-type O-polysaccharide. In one aspect, the invention relates to saccharides produced by a Gram-negative bacterium in culture that expresses (not necessarily overexpresses) a wzz family protein (e.g., wzzB) from a Gram-negative bacterium to generate high molecular weight saccharides containing intermediate or long O-antigen chains, which have an increase of at least 1, 2, 3, 4, or 5 repeating units, as compared to the corresponding wild-type O-antigen. See description of O-polysaccharides and O-antigens below for additional exemplary saccharides having increased number of repeat units, as compared to the corresponding wild-type saccharides. A desired chain length is the one which produces improved or maximal immunogenicity in the context of a given vaccine construct.

In another embodiment, the saccharide includes any one Formula selected from Table A, wherein the number of repeat units n in the saccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. Methods of determining the length of saccharides are known in the art. Such methods include nuclear magnetic resonance, mass spectroscopy, and size exclusion chromatography.

In a preferred embodiment, the invention relates to a saccharide produced in a recombinant *E. coli* host cell, wherein the gene for an endogenous wzz O-antigen length regulator (e.g., wzzB) is deleted and is replaced by a (second) wzz gene from a Gram-negative bacterium heterologous to the recombinant *E. coli* host cell (e.g., *Salmonella* fepE) to generate high molecular weight saccharides, such as lipopolysaccharides, containing intermediate or long O-antigen chains. In some embodiments, the recombinant *E. coli* host cell includes a wzz gene from *Salmonella*, preferably from *Salmonella enterica*.

In one embodiment, the host cell includes the heterologous gene for a wzz family protein as a stably maintained plasmid vector. In another embodiment, the host cell includes the heterologous gene for a wzz family protein as an integrated gene in the chromosomal DNA of the host cell. Methods of stably expressing a plasmid vector in an *E. coli* host cell and methods of integrating a heterologous gene into the chromosome of an *E. coli* host cell are known in the art. In one embodiment, the host cell includes the heterologous genes for an O-antigen as a stably maintained plasmid vector. In another embodiment, the host cell includes the heterologous genes for an O-antigen as an integrated gene in the chromosomal DNA of the host cell. Methods of stably expressing a plasmid vector in an *E. coli* host cell and a *Salmonella* host cell are known in the art. Methods of integrating a heterologous gene into the chromosome of an *E. coli* host cell and a *Salmonella* host cell are known in the art.

In one aspect, the recombinant host cell is cultured in a medium that comprises a carbon source. Carbon sources for culturing *E. coli* are known in the art. Exemplary carbon sources include sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate and methylamine. In a preferred embodiment, the medium includes glucose. In some embodiments, the medium includes a polyol or aldol sugar, for example, mannitol, inositol, sorbose, glycerol, sorbitol, lactose and arabinose as the carbon source. All of the carbon sources may be added to the medium before the start of culturing, or it may be added step by step or continuously during culturing.

An exemplary culture medium for the recombinant host cell includes an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4\text{-}7H_2O$, $Na_2MoO_4\text{-}2H_2O$, $H_3BO_3$, $CoCl_2\text{-}6H_2O$, $CuCl_2\text{-}2H_2O$, $MnCl_2\text{-}4H_2O$, $ZnCl_2$ and $CaCl_2\text{-}2H_2O$. Preferably, the medium includes $KH_2PO_4$, $K_2HPO_4$, $(NH_4)_2SO_4$, sodium citrate, $Na_2SO_4$, aspartic acid, glucose, $MgSO_4$, $FeSO_4\text{-}7H_2O$, $Na_2MoO_4\text{-}2H_2O$, $H_3BO_3$, $CoCl_2\text{-}6H_2O$, $CuCl_2\text{-}2H_2O$, $MnCl_2\text{-}4H_2O$, $ZnCl_2$ and $CaCl_2\text{-}2H_2O$.

The medium used herein may be solid or liquid, synthetic (i.e. man-made) or natural, and may include sufficient nutrients for the cultivation of the recombinant host cell. Preferably, the medium is a liquid medium.

In some embodiments, the medium may further include suitable inorganic salts. In some embodiments, the medium may further include trace nutrients. In some embodiments, the medium may further include growth factors. In some embodiments, the medium may further include an additional carbon source. In some embodiments, the medium may further include suitable inorganic salts, trace nutrients, growth factors, and a supplementary carbon source. Inorganic salts, trace nutrients, growth factors, and supplementary carbon sources suitable for culturing E. coli are known in the art.

In some embodiments, the medium may include additional components as appropriate, such as peptone, N-Z Amine, enzymatic soy hydrosylate, additional yeast extract, malt extract, supplemental carbon sources and various vitamins. In some embodiments, the medium does not include such additional components, such as peptone, N-Z Amine, enzymatic soy hydrosylate, additional yeast extract, malt extract, supplemental carbon sources and various vitamins.

Illustrative examples of suitable supplemental carbon sources include, but are not limited to other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

In some embodiments, the medium further includes a nitrogen source. Nitrogen sources suitable for culturing E. coli are known in the art. Illustrative examples of suitable nitrogen sources include, but are not limited to ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

In some embodiments, the medium includes an inorganic salt. Illustrative examples of suitable inorganic salts include, but are not limited to salts of potassium, calcium, sodium, magnesium, manganese, iron, cobalt, zinc, copper, molybdenum, tungsten and other trace elements, and phosphoric acid.

In some embodiments, the medium includes appropriate growth factors. Illustrative examples of appropriate trace nutrients, growth factors, and the like include, but are not limited to coenzyme A, pantothenic acid, pyridoxine-HCl, biotin, thiamine, riboflavin, flavine mononucleotide, flavine adenine dinucleotide, DL-6,8-thioctic acid, folic acid, Vitamin B12, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. The amounts may be determined empirically by one skilled in the art according to methods and techniques known in the art.

In another embodiment, the modified saccharide (as compared to the corresponding wild-type saccharide) described herein is synthetically produced, for example, in vitro. Synthetic production or synthesis of the saccharides may facilitate the avoidance of cost- and time-intensive production processes. In one embodiment, the saccharide is synthetically synthesized, such as, for example, by using sequential glycosylation strategy or a combination of sequential glycosylations and [3+2] block synthetic strategy from suitably protected monosaccharide intermediates. For example, thioglycosides and glycosyl trichloroacetimidate derivatives may be used as glycosyl donors in the glycosylations. In one embodiment, a saccharide that is synthetically synthesized in vitro has the identical structure to a saccharide produced by recombinant means, such as by manipulation of a wzz family protein described above.

The saccharide produced (by recombinant or synthetic means) includes a structure derived from any E. coli serotype including, for example, any one of the following E. coli serotypes: O1 (e.g., O1A, O1B, and O1C), O2, O3, O4 (e.g., O4:K52 and O4:K6), O5 (e.g., O5ab and O5ac (strain 180/C3)), O6 (e.g., O6:K2; K13; K15 and O6:K54), O7, O8, O9, O10, O11, O12, O13, O14, O15, O16, O17, O18 (e.g., O18A, O18ac, O18A1, O18B, and O18B1), O19, O20, O21, O22, O23 (e.g., O23A), O24, O25 (e.g., O25a and O25b), O26, O27, O28, O29, O30, O32, O33, O34, O35, O36, O37, O38, O39, O40, O41, O42, O43, O44, O45 (e.g., O45 and O45rel), O46, O48, O49, O50, O51, O52, O53, O54, O55, O56, O57, O58, O59, O60, O61, O62, 62D1, O63, O64, O65, O66, O68, O69, O70, O71, O73 (e.g., O73 (strain 73-1)), O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

The individual polysaccharides are typically purified (enriched with respect to the amount of polysaccharide-protein conjugate) through methods known in the art, such as, for example, dialysis, concentration operations, diafiltration operations, tangential flow filtration, precipitation, elution, centrifugation, precipitation, ultra-filtration, depth filtration, and/or column chromatography (ion exchange chromatography, multimodal ion exchange chromatography, DEAE, and hydrophobic interaction chromatography). Preferably, the polysaccharides are purified through a method that includes tangential flow filtration.

Purified polysaccharides may be activated (e.g., chemically activated) to make them capable of reacting (e.g., either directly to the carrier protein or via a linker such as an eTEC spacer) and then incorporated into glycoconjugates of the invention, as further described herein.

In one preferred embodiment, the saccharide of the invention is derived from an *E. coli* serotype, wherein the serotype is O25a. In another preferred embodiment, the serotype is O25b. In another preferred embodiment, the serotype is O1A. In another preferred embodiment, the serotype is O2. In another preferred embodiment, the serotype is O6. In another preferred embodiment, the serotype is O17. In another preferred embodiment, the serotype is O15. In another preferred embodiment, the serotype is O18A. In another preferred embodiment, the serotype is O75. In another preferred embodiment, the serotype is O4. In another preferred embodiment, the serotype is O16. In another preferred embodiment, the serotype is O13. In another preferred embodiment, the serotype is O7. In another preferred embodiment, the serotype is O8. In another preferred embodiment, the serotype is O9.

As used herein, reference to any of the serotypes listed above, refers to a serotype that encompasses a repeating unit structure (O-unit, as described below) known in the art and is unique to the corresponding serotype. For example, the term "O25a" serotype (also known in the art as serotype "O25") refers to a serotype that encompasses Formula O25 shown in Table A. As another example, the term "O25b" serotype refers to a serotype that encompasses Formula O25b shown in Table A.

As used herein, the serotypes are referred generically herein unless specified otherwise such that, for example, the term Formula "O18" refers generically to encompass Formula O18A, Formula O18ac, Formula 18A1, Formula O18B, and Formula O18B1. As used herein, the term "O1" refers generically to encompass the species of Formula that include the generic term "O1" in the Formula name according to Table A, such as any one of Formula O1A, Formula O1A1, Formula O1B, and Formula O1C, each of which is shown in Table A. Accordingly, an "O1 serotype" refers generically to a serotype that encompasses any one of Formula O1A, Formula O1A1, Formula O1B, and Formula O1C.

As used herein, the term "O6" refers generically to species of Formula that include the generic term "O6" in the Formula name according to Table A, such as any one of Formula O6:K2; K13; K15; and O6:K54, each of which is shown in Table A. Accordingly, an "O6 serotype" refers generically to a serotype that encompasses any one of Formula O6:K2; K13; K15; and O6:K54. Other examples of terms that refer generically to species of a Formula that include the generic term in the Formula name according to Table A include: "O4", "O5", "O18", and "O45". As used herein, the term "O2" refers to Formula O2 shown in Table A. The term "O2 O-antigen" refers to a saccharide that encompasses Formula O2 shown in Table A.

As used herein, reference to an O-antigen from a serotype listed above refers to a saccharide that encompasses the formula labeled with the corresponding serotype name. For example, the term "O25B O-antigen" refers to a saccharide that encompasses Formula O25B shown in Table A.

As another example, the term "O1 O-antigen" generically refers to a saccharide that encompasses a Formula including the term "O1," such as the Formula O1A, Formula O1A1, Formula O1B, and Formula O1C, each of which are shown in Table A.

As another example, the term "O6 O-antigen" generically refers to a saccharide that encompasses a Formula including the term "O6," such as Formula O6:K2; Formula O6:K13; Formula O6:K15 and Formula O6:K54, each of which are shown in Table A.

As used herein, the term "O-polysaccharide" refers to any structure that includes an O-antigen, provided that the structure does not include a whole cell or Lipid A. For example, in one embodiment, the O-polysaccharide includes a lipopolysaccharide wherein the Lipid A is not bound. The step of removing Lipid A is known in the art and includes, as an example, heat treatment with addition of an acid. An exemplary process includes treatment with 1% acetic acid at 100° C. for 90 minutes. This process is combined with a process of isolating Lipid A as removed. An exemplary process for isolating Lipid A includes ultracentrifugation.

In one embodiment, the O-polysaccharide refers to a structure that consists of the O-antigen, in which case, the O-polysaccharide is synonymous with the term O-antigen. In one preferred embodiment, the O-polysaccharide refers to a structure that includes repeating units of the O-antigen, without the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* K12 core moiety. In another preferred embodiment, the O-polysaccharide refers to a structure that includes an O-antigen and a core saccharide. In another embodiment, the O-polysaccharide refers to a structure that includes an O-antigen, a core saccharide, and a KDO moiety.

Methods of purifying an O-polysaccharide, which includes the core oligosaccharide, from LPS are known in the art. For example, after purification of LPS, purified LPS may be hydrolyzed by heating in 1% (v/v) acetic acid for 90 minutes at 100 degrees Celsius, followed by ultracentrifugation at 142,000×g for 5 hours at 4 degrees Celsius. The supernatant containing the O-polysaccharide is freeze-dried and stored at 4 degrees Celsius. In certain embodiments, deletion of capsule synthesis genes to enable simple purification of O-polysaccharide is described.

The O-polysaccharide can be isolated by methods including, but not limited to mild acid hydrolysis to remove lipid A from LPS. Other embodiments may include use of hydrazine as an agent for O-polysaccharide preparation. Preparation of LPS can be accomplished by known methods in the art.

In certain embodiments, the O-polysaccharides purified from wild-type, modified, or attenuated Gram-negative bacterial strains that express (not necessarily overexpress) a Wzz protein (e.g., wzzB) are provided for use in conjugate vaccines. In preferred embodiments, the O-polysaccharide chain is purified from the Gram-negative bacterial strain expressing (not necessarily overexpressing) wzz protein for use as a vaccine antigen either as a conjugate or complexed vaccine.

In one embodiment, the O-polysaccharide has a molecular weight that is increased by about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 61-fold, 62-fold, 63-fold, 64-fold, 65-fold, 66-fold, 67-fold, 68-fold, 69-fold, 70-fold, 71-fold, 72-fold, 73-fold, 74-fold, 75-fold, 76-fold, 77-fold, 78-fold, 79-fold, 80-fold, 81-fold, 82-fold, 83-fold, 84-fold, 85-fold, 86-fold, 87-fold, 88-fold, 89-fold, 90-fold, 91-fold, 92-fold, 93-fold, 94-fold, 95-fold, 96-fold, 97-fold, 98-fold, 99-fold, 100-fold or more, as compared to the corresponding wild-type O-polysaccharide. In a preferred embodiment, the O-polysaccharide has a molecular weight that is increased by at least 1-fold and at most 5-fold, as compared to the corresponding wild-type O-polysaccharide. In another embodiment, the O-polysaccharide has a molecular weight that is increased by at least 2-fold and at most 4-fold, as compared to the corresponding wild-type O-polysaccharide. An increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein.

In one embodiment, the O-polysaccharide has a molecular weight that is increased by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 kDa or more, as compared to the corresponding wild-type O-polysaccharide. In one embodiment, the O-polysaccharide of the invention has a molecular weight that is increased by at least 1 and at most 200 kDa, as compared to the corresponding wild-type O-polysaccharide. In one embodiment, the molecular weight is increased by at least 5 and at most 200 kDa. In one embodiment, the molecular weight is increased by at least 10 and at most 200 kDa. In one embodiment, the molecular weight is increased by at least 12 and at most 200 kDa. In one embodiment, the molecular weight is increased by at least 15 and at most 200 kDa. In one embodiment, the molecular weight is increased by at least 18 and at most 200 kDa. In one embodiment, the molecular weight is increased by at least 20 and at most 200 kDa. In one embodiment, the molecular weight is increased by at least 21 and at most 200 kDa. In one embodiment, the molecular weight is increased by at least 22 and at most 200 kDa. In one embodiment, the molecular weight is increased by at least 30 and at most 200 kDa. In one embodiment, the molecular weight is increased by at least 1 and at most 100 kDa. In one embodiment, the molecular weight is increased by at least 5 and at most 100 kDa. In one embodiment, the molecular weight is increased by at least 10 and at most 100 kDa. In one embodiment, the molecular weight is increased by at least 12 and at most 100 kDa. In one embodiment, the molecular weight is increased by at least 15 and at most 100 kDa. In one embodiment, the molecular weight is increased by at least 20 and at most 100 kDa. In one embodiment, the molecular weight is increased by at least 1 and at most 75 kDa. In one embodiment, the molecular weight is increased by at least 5 and at most 75 kDa. In one embodiment, the molecular weight is increased by at least 10 and at most 75 kDa. In one embodiment, the molecular weight is increased by at least 12 and at most 75 kDa. In one embodiment, the molecular weight is increased by at least 15 and at most 75 kDa. In one embodiment, the molecular weight is increased by at least 18 and at most 75 kDa. In one embodiment, the molecular weight is increased by at least 20 and at most 75 kDa. In one embodiment, the molecular weight is increased by at least 30 and at most 75 kDa. In one embodiment, the molecular weight is increased by at least 10 and at most 90 kDa. In one embodiment, the molecular weight is increased by at least 12 and at most 85 kDa. In one embodiment, the molecular weight is increased by at least 10 and at most 75 kDa. In one embodiment, the molecular weight is increased by at least 10 and at most 70 kDa. In one embodiment, the molecular weight is increased by at least 10 and at most 60 kDa. In one embodiment, the molecular weight is increased by at least 10 and at most 50 kDa. In one embodiment, the molecular weight is increased by at least 10 and at most 49 kDa. In one embodiment, the molecular weight is increased by at least 10 and at most 48 kDa. In one embodiment, the molecular weight is increased by at least 10 and at most 47 kDa. In one embodiment, the molecular weight is increased by at least 10 and at most 46 kDa. In one embodiment, the molecular weight is increased by at least 20 and at most 45 kDa. In one embodiment, the molecular weight is increased by at least 20 and at most 44 kDa. In one embodiment, the molecular weight is increased by at least 20 and at most 43 kDa. In one embodiment, the molecular weight is increased by at least 20 and at most 42 kDa. In one embodiment, the molecular weight is increased by at least 20 and at most 41 kDa. Such an increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein.

In another embodiment, the O-polysaccharide includes any one Formula selected from Table A, wherein the number of repeat units n in the O-polysaccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide.

2. O-Antigen

The O-antigen is part of the lipopolysaccharide (LPS) in the outer membrane of Gram-negative bacteria. The O-antigen is on the cell surface and is a variable cell constituent. The variability of the O-antigen provides a basis for serotyping of Gram-negative bacteria. The current *E. coli* serotyping scheme includes O-polysaccharides 1 to 181.

The O-antigen includes oligosaccharide repeating units (O-units), the wild type structure of which usually contains two to eight residues from a broad range of sugars. The O-units of exemplary *E. coli* O-antigens are described Table A and in PCT Intl. Publication No. WO2021/084429, published May 6, 2021, which is incorporated herein by reference in its entirety. In some embodiments, the present disclosure includes a composition comprising at least one FimH mutant polypeptide and at least one of the O-antigens as described Table A and in PCT Intl. Publication No. WO2021/084429, published May 6, 2021, which is incorporated herein by reference in its entirety.

In one embodiment, the saccharide of the invention may be one oligosaccharide unit. In one embodiment, the saccharide of the invention is one repeating oligosaccharide unit of the relevant serotype. In such embodiments, the saccharide may include a structure selected from any one of Formula O1a, Formula O2, Formula O6, Formula O8, Formula O9a, Formula O9, Formula O20ab, Formula O20ac, Formula O25b, Formula O52, Formula O97, and Formula O101. In a further embodiment, the saccharide may include a structure selected from any one of Formula O1a, Formula O2, Formula O6, and Formula O25b. In one embodiment, the saccharide of the invention may be oligosaccharides.

Oligosaccharides have a low number of repeat units (typically 5-15 repeat units) and are typically derived synthetically or by hydrolysis of polysaccharides. In such embodiments, the saccharide may include a structure selected from any one of Formula O1a, Formula O2, Formula O6, Formula O8, Formula O9a, Formula O9, Formula O20ab, Formula O20ac, Formula O25b, Formula O52, Formula O97, and Formula O101. In a further embodiment, the saccharide may include a structure selected from any one of Formula O1a, Formula O2, Formula O6, and Formula O25b.

Preferably, all of the saccharides of the present invention and in the immunogenic compositions of the present invention are polysaccharides. High molecular weight polysaccharides may induce certain antibody immune responses due to the epitopes present on the antigenic surface. The isolation and purification of high molecular weight polysaccharides are preferably contemplated for use in the conjugates, compositions and methods of the present invention.

In some embodiments, the number of repeat O units in each individual O-antigen polymer (and therefore the length and molecular weight of the polymer chain) depends on the wzz chain length regulator, an inner membrane protein. Different wzz proteins confer different ranges of modal lengths (4 to >100 repeat units). The term "modal length" refers to the number of repeating O-units. Gram-negative bacteria often have two different Wzz proteins that confer two distinct Oag modal chain lengths, one longer and one shorter. The expression (not necessarily the overexpression) of wzz family proteins (e.g., wzzB) in Gram-negative bacteria may allow for the manipulation of O-antigen length, to shift or to bias bacterial production of O-antigens of certain length ranges, and to enhance production of high-yield large molecular weight lipopolysaccharides. In one embodiment, a "short" modal length as used herein refers to a low number of repeat O-units, e.g., 1-20. In one embodiment, a "long" modal length as used herein refers to a number of repeat O-units greater than 20 and up to a maximum of 40. In one embodiment, a "very long" modal length as used herein refers to greater than 40 repeat O-units.

In one embodiment, the saccharide produced has an increase of at least 10 repeating units, 15 repeating units, 20 repeating units, 25 repeating units, 30 repeating units, 35 repeating units, 40 repeating units, 45 repeating units, 50 repeating units, 55 repeating units, 60 repeating units, 65 repeating units, 70 repeating units, 75 repeating units, 80 repeating units, 85 repeating units, 90 repeating units, 95 repeating units, or 100 repeating units, as compared to the corresponding wild-type O-polysaccharide.

In another embodiment, the saccharide of the invention has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21. Methods of determining the length of saccharides are known in the art. Such methods include nuclear magnetic resonance, mass spectroscopy, and size exclusion chromatography, as described in Example 13.

Methods of determining the number of repeat units in the saccharide are also known in the art. For example, the number of repeat units (or "n" in the Formula) may be calculated by dividing the molecular weight of the polysaccharide (without the molecular weight of the core saccharide or KDO residue) by the molecular weight of the repeat unit (i.e., molecular weight of the structure in the corresponding Formula, shown for example in Table 1, which may be theoretically calculated as the sum of the molecular weight of each monosaccharide within the Formula). The molecular weight of each monosaccharide within the Formula is known in the art. The molecular weight of a repeat unit of Formula O25b, for example, is about 862 Da. The molecular weight of a repeat unit of Formula O1a, for example, is about 845 Da. The molecular weight of a repeat unit of Formula O2, for example, is about 829 Da. The molecular weight of a repeat unit of Formula O6, for example, is about 893 Da. When determining the number of repeat units in a conjugate, the carrier protein molecular weight and the protein:polysaccharide ratio is factored into the calculation. As defined herein, "n" refers to the number of repeating units (represented in brackets in Table 1) in a polysaccharide molecule. As is known in the art, in biological macromolecules, repeating structures may be interspersed with regions of imperfect repeats, such as, for example, missing branches. In addition, it is known in the art that polysaccharides isolated and purified from natural sources such as bacteria may be heterogenous in size and in branching. In such a case, n may represent an average or median value for n for the molecules in a population.

In one embodiment, the O-polysaccharide has an increase of at least one repeat unit of an O-antigen, as compared to the corresponding wild-type O-polysaccharide. The repeat units of O-antigens are shown in Table 1. In one embodiment, the O-polysaccharide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more total repeat units. Preferably, the saccharide has a total of at least 3 to at most 80 repeat units. In another embodiment, the O-polysaccharide has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide.

In one embodiment, the saccharide includes an O-antigen wherein n in any of the O-antigen formulas (such as, for example, the Formulas shown in Table 1 (see also FIG. 9A-9C and FIG. 10A-10B)) is an integer of at least 1, 2, 3, 4, 5, 10, 20, 21, 22, 23, 24, 25, 26, 27, 28, 29, 30, 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80, preferably at most 90. In one preferred embodiment, n is at least 31 to at most 90. In a preferred embodiment, n is 40 to 90, more preferably 60 to 85.

In one embodiment, the saccharide includes an O-antigen wherein n in any one of the O-antigen Formulas is at least 1 and at most 200. In one embodiment, n in any one of the O-antigen Formulas is at least 5 and at most 200. In one embodiment, n in any one of the O-antigen Formulas is at least 10 and at most 200. In one embodiment, n in any one of the O-antigen Formulas is at least 25 and at most 200. In one embodiment, n in any one of the O-antigen Formulas is at least 50 and at most 200. In one embodiment, n in any one of the O-antigen Formulas is at least 75 and at most 200. In one embodiment, n in any one of the O-antigen Formulas is at least 100 and at most 200. In one embodiment, n in any one of the O-antigen Formulas is at least 125 and at most 200. In one embodiment, n in any one of the O-antigen Formulas is at least 150 and at most 200. In one embodiment, n in any one of the O-antigen Formulas is at least 175 and at most 200. In one embodiment, n in any one of the O-antigen Formulas is at least 1 and at most 100. In one embodiment, n in any one of the O-antigen Formulas is at least 5 and at most 100. In one embodiment, n in any one of the O-antigen Formulas is at least 10 and at most 100. In one embodiment, n in any one of the O-antigen Formulas is at least 25 and at most 100. In one embodiment, n in any one of the O-antigen Formulas is at least 50 and at most 100. In one embodiment, n in any one of the O-antigen Formulas is at least 75 and at most 100. In one embodiment, n in any one of the O-antigen Formulas is at least 1 and at most 75. In one embodiment, n in any one of the O-antigen Formulas is at least 5 and at most 75. In one embodiment, n in any one of the O-antigen Formulas is at least 10 and at most 75. In one embodiment, n in any one of the O-antigen Formulas is at least 20 and at most 75. In one embodiment, n in any one of the O-antigen Formulas is at least 25 and at most 75. In one embodiment, n in any one of the O-antigen Formulas is at least 30 and at most 75. In one embodiment, n in any one of the O-antigen Formulas is at least 40 and at most 75. In one embodiment, n in any one of the O-antigen Formulas is at least 50 and at most 75. In one embodiment, n in any one of the O-antigen Formulas is at least 30 and at most 90. In one embodiment, n in any one of the O-antigen Formulas is at least 35 and at most 85. In one embodiment, n in any one of the O-antigen Formulas is at least 35 and at most 75. In one embodiment, n in any one of the O-antigen Formulas is at least 35 and at most 70. In one embodiment, n in any one of the O-antigen Formulas is at least 35 and at most 60. In one embodiment, n in any one of the O-antigen Formulas is at least 35 and at most 50. In one embodiment, n in any one of the O-antigen Formulas is at least 35 and at most 49. In one embodiment, n in any one of the O-antigen Formulas is at least 35 and at most 48. In one embodiment, n in any one of the O-antigen Formulas is at least 35 and at most 47. In one embodiment, n in any one of the O-antigen Formulas is at least 35 and at most 46. In one embodiment, n in any one of the O-antigen Formulas is at least 36 and at most 45. In one embodiment, n in any one of the O-antigen Formulas is at least 37 and at most 44. In one embodiment, n in any one of the O-antigen Formulas is at least 38 and at most 43. In one embodiment, n in any one of the O-antigen Formulas is at least 39 and at most 42. In one embodiment, n in any one of the O-antigen Formulas is at least 39 and at most 41.

For example, in one embodiment, n in the saccharide is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, most preferably 40. In another embodiment, n is at least 35 to at most 60. For example, in one embodiment, n is any one of 35, 36, 37, 38, 39, 40, 41, 42, 43, 44, 45, 46, 47, 48, 49, 50, 51, 52, 53, 54, 55, 56, 57, 58, 59, and 60, preferably 50. In another preferred embodiment, n is at least 55 to at most 75. For example, in one embodiment, n is 55, 56, 57, 58, 59, 60, 61, 62, 63, 64, 65, 66, 67, 68, or 69, most preferably 60.

The saccharide structure may be determined by methods and tools known art, such as, for example, NMR, including 1D, 1H, and/or 13C, 2D TOCSY, DQF-COSY, NOESY, and/or HMQC.

In some embodiments, the purified polysaccharide before conjugation has a molecular weight of between 5 kDa and 400 kDa. In other such embodiments, the saccharide has a molecular weight of between 10 kDa and 400 kDa; between 5 kDa and 400 kDa; between 5 kDa and 300 kDa; between 5 kDa and 200 kDa; between 5 kDa and 150 kDa; between 10 kDa and 100 kDa; between 10 kDa and 75 kDa; between 10 kDa and 60 kDa; between 10 kDa and 40 kDa; between 10 kDa and 100 kDa; 10 kDa and 200 kDa; between 15 kDa and 150 kDa; between 12 kDa and 120 kDa; between 12 kDa and 75 kDa; between 12 kDa and 50 kDa; between 12 and 60 kDa; between 35 kDa and 75 kDa; between 40 kDa and 60 kDa; between 35 kDa and 60 kDa; between 20 kDa and 60 kDa; between 12 kDa and 20 kDa; or between 20 kDa and 50 kDa. In further embodiments, the polysaccharide has a molecular weight of between 7 kDa to 15 kDa; 8 kDa to 16 kDa; 9 kDa to 25 kDa; 10 kDa to 100; 10 kDa to 60 kDa; 10 kDa to 70 kDa; 10 kDa to 160 kDa; 15 kDa to 600 kDa; 20 kDa to 1000 kDa; 20 kDa to 600 kDa; 20 kDa to 400 kDa; 30 kDa to 1,000 Kda; 30 kDa to 60 kDa; 30 kDa to 50 kDa or 5 kDa to 60 kDa. Any whole number integer within any of the above ranges is contemplated as an embodiment of the disclosure.

As used herein, the term "molecular weight" of polysaccharide or of carrier protein-polysaccharide conjugate refers to molecular weight calculated by size exclusion chromatography (SEC) combined with multiangle laser light scattering detector (MALLS).

A polysaccharide can become slightly reduced in size during normal purification procedures. Additionally, as described herein, polysaccharide can be subjected to sizing techniques before conjugation. Mechanical or chemical sizing maybe employed. Chemical hydrolysis may be conducted using acetic acid. Mechanical sizing may be conducted using High Pressure Homogenization Shearing. The molecular weight ranges mentioned above refer to purified polysaccharides before conjugation (e.g., before activation).

TABLE A

_E. coli serogroups/serotypes and O-unit moieties_

| Serogroup/Serotype | Moiety Structure (O-unit) | Moiety structure referred to herein as: |
|---|---|---|
| O1A, O1A1 | [→3)-α-L-Rha-(1→3)-α-L-Rha-(1→3)-β-L-Rha-(1→4)-β-D-GlcNAc-(1→ \| β-D-ManNAc-(1→2) ]$_n$ | Formula O1A |
| O1B | [→3)-α-L-Rha-(1→2)-α-L-Rha-(1→2)-α-D-Gal-(1→3)-β-D-GlcNAc-(1→\|β-D-ManNAc-(1→2) ]$_n$ | Formula O1B |
| O1C | [→3)-α-L-Rha-(1→2)-α-L-Rha-(1→3)-α-D-Gal-(1→3)-β-D-GlcNAc-(1→\|β-D-ManNAc-(1→2) ]$_n$ | Formula O1C |
| O2 | [→3)-α-L-Rha-(1→2)-α-L-Rha-(1→3)-β-L-Rha-(1→4)-β-D-GlcNAc-(1→ \| α-D-ManNAc-(1→2) ]$_n$ | Formula O2 |
| O3 | [β-L-RhaNAc(1→4)α-D-Glc-(1→4)\| \| →3)-β-D-GlcNAc-(1→3)-α-D-Gal-(1→3)-β-D-GlcNAc-(1→ ]$_n$ | Formula O3 |
| O4:K52 | [→2)-α-L-Rha-(1→6)-α-D-Glc-(1→3)-α-L-FucNAc-(1→3)-β-D-GlcNAc(1→ ]$_n$ | Formula O4:K52 |
| O4:K6 | [α-D-Glc-(1→3) \| →2)-α-L-Rha-(1→6)-α-D-Glc-(1→3)-α-L-FucNAc-(1→3)-β-D-GlcNAc(1→ ]$_n$ | Formula O4:K6 |
| O5ab | [→4)-β-D-Qui3Nac-(1→3)-β-D-Ribf-(1→4)-β-D-Gal-(1→3)-α-D-GalNAc-(1→]$_n$ | Formula O5ab |
| O5ac (strain 180/C3) | [→2)-β-D-Qui3Nac-(1→3)-β-D-Ribf-(1→4)-β-D-Gal-(1→3)-α-D-GalNAc-(1→ ]$_n$ | Formula O5ac (strain 180/C3) |
| O6:K2; K13; K15 | [→4)-α-D-GalNAc-(1→3)-β-D-Man-(1→4)-β-D-Man-(1→3)-α-D-GlcNAc-(1→ \| β-D-Glc-(1→2) ]$_n$ | Formula O6:K2; K13; K15 |
| O6:K54 | [→4)-α-D-GalNAc-(1→3)-β-D-Man-(1→4)-β-D-Man-(1→3)-α-D-GlcNAc-(1→\|β-D-GlcNAc-(1→2) ]$_n$ | Formula O6:K54 |
| O7 | [α-L-Rha-(1→3) \| →3)-β-D-Qui4Nac-(1→2)-α-D-Man-(1→4)-β-D-Gal-(1→3)-α-D-GlcNAc-(1→ ]$_n$ | Formula O7 |
| O10 | [→3)-α-L-Rha-(1→3)-α-L-Rha-(1→3)-α-D-Gal-(1→3)-β-D-GlcNAc-(1→ \| α-D-Fuc4Nacyl-(1→2) Acyl = acetyl (60%) or l-3-hydroxybutyryl (40%) ]$_n$ | Formula O10 |
| O16 | [→2)-β-D-Galf-(1→6)-α-D-Glc-(1→3)-α-L-Rha2Ac-(1→3)-α-D-GlcNAc-(1→ ]$_n$ | Formula O16 |
| O17 | [α-D-Glc-(1→6) \| →6)-α-D-Man-(1→2)-α-D-Man-(1→2)-β-D-Man-(1→3)-α-D-GlcNAc(1→ ]$_n$ | Formula O17 |
| O18A, O18ac | [→2)-α-L-Rha-(1→6)-α-D-Glc-(1→4)-α-D-Gal-(1→3)-α-D-GlcNAc-(1→ \| β-D-GlcNAc-(1→3) ]$_n$ | Formula O18A, Formula O18ac |
| O18A1 | [α-D-Glc-(1→6) \| →2)-α-L-Rha-(1→6)-α-D-Glc-(1→4)-α-D-Gal-(1→3)-α-D-GlcNAc-(1→ \| β-D-GlcNAc-(1→3) ]$_n$ | Formula O18A1 |
| O18B | [→3)-α-L-Rha-(1→6)-α-D-Glc-(1→4)-α-D-Gal-(1→3)-α-D-GlcNAc-(1→ \| β-D-Glc-(1→3) ]$_n$ | Formula O18B |
| O18B1 | [α-D-Glc-(1→4) \| →3)-α-L-Rha-(1→6)-α-D-Glc-(1→4)-α-D-Gal-(1→3)-α-D-GlcNAc-(1→ \| β-D-Glc-(1→3) ]$_n$ | Formula O18B1 |
| O21 | [(β-D-Gal-(1→4) \| →3)-β-D-Gal-(1→4)-β-D-Glc-(1→3)-α-D-GalNAc-(1→ \| β-D-GlcNAc-(1→2) ]$_n$ | Formula O21 |
| O23A | [α-D-Glc-(1→6) \| →6)-α-D-Glc-(1→4)-α-D-Gal-(1→3)-α-D-GalNAc-(1→3)-β-D-GlcNAc-(1→ \| β-D-GlcNAc(1→3) ]$_n$ | Formula O23A |
| O24 | [→7)-α-Neu5Ac-(2→3)-β-D-Glc-(1→3)-β-D-GalNAc-(1→ \| α-D-Glc-(1→2) ]$_n$ | Formula O24 |
| O25/O25a | [β-D-Glc-(1→6) \| →4)-α-D-Glc-(1→3)-α-L-FucNAc-(1→3)-β-D-GlcNAc-(1→ \| α-L-Rha-(1→3) ]$_n$ | Formula O25a |
| O25b | β-Glcp-<br>1<br>↓<br>6<br>[α-Rhap-(1→3)-α-Glcp-(1→3)-α-Rhap2Oac-(1→3)–β–GlcpNAc-]$_n$ | Formula O25b |
| O26 | [ →3)-α-L-Rha-(1→4)-α-L-FucNAc-(1→3)-β-D-GlcNAc-(1→ ]$_n$ | Formula O26 |
| O28 | [ →2)-l-Gro-1-P→4)-β-D-GlcNAc-(1→3)-β-D-Galf2Ac-(1→3)-α-D-GlcNAc-(1→ ]$_n$ | Formula O28 |
| O36 | [α-L-Rhap-(1→2)-α-L-Fucp<br>1<br>↓<br>3<br>→4)α-D-Manp-(1→3)-α-L-Fucp-(1→3)-β-D-GlcpNAc-(1→]n | Formula O36 |
| O44 | [ α-D-Glc-(1→4) \| →6)-α-D-Man-(1→2)-α-D-Man-(1→2)-β-D-Man-(1→3)-α-D-GlcNAc(1→ ]$_n$ | Formula O44 |

TABLE A-continued

_E. coli serogroups/serotypes and O-unit moieties_

| Serogroup/Serotype | Moiety Structure (O-unit) | Moiety structure referred to herein as: |
|---|---|---|
| O45 | [ →2)-β-D-Glc-(1→3)-α-L-6dTal2Ac-(1→3)-α-D-FucNAc-(1→ ]$_n$ | Formula O45 |
| O45rel | [ →2)-β-D-Glc-(1→3)-α-L-6dTal2Ac-(1→3)-β-D-GlcNAc-(1→ ]$_n$ | Formula O45rel |
| O54 | [→4)-α-d-GalpA-(1 → 2)-α-l-Rhap-(1 → 2)-β-d-Ribf-(1 → 4)-β-d-Galp-(1 → 3)-β-d-GlapNAc-(1→]n | Formula O54 |
| O55 | [ →6)-β-D-GlcNAc-(1→3)-α-D-Gal-(1→3)-β-D-GalNAc-(1→ \| α-Col-(1→2)-β-D-Gal-(1→3) ]$_n$ | Formula O55 |
| O56 | [ →7)-α-Neu5Ac-(2→3)-β-D-Glc-(1→3)-β-D-GlcNAc-(1→ \| α-D-Gal-(1→2) ]$_n$ | Formula O56 |
| O57 | [→3)-α-D-Galp-(1→3)-α-L-FucpNAc-(1→3)-α-D-GlcpNAc-(1→]n<br><br>$\phantom{xxxxxxx}$2$\phantom{xxxxxxxx}$4<br>$\phantom{xxxxxxx}$↑$\phantom{xxxxxxxx}$↑<br>$\phantom{xxxxxxx}$1$\phantom{xxxxxxxx}$1<br><br>α-D-GalpA2/3Ac$\phantom{xx}$β-D-Glcp | Formula O57 |
| O58 | [ 3-O-[l-1-carboxyethyl]-α-L-Rha -(1→3) \| →4)-α-D-Man-(1→4)-α-D-Man2Ac-(1→3)-β-D-GlcNAc-(1→ ]$_n$ | Formula O58 |
| O64 | [ β-D-Gal-(1→6) \| →3)-α-D-ManNAc-(1→3)-β-D-GlcA-(1→3)-β-D-Gal-(1→3)-β-D-GlcNAc(1→ ]$_n$ | Formula O64 |
| O68 | [α-L-Rhap$\phantom{xxxx}$α-D-Glcp<br>$\phantom{xx}$1$\phantom{xxxxxxxxx}$1<br>$\phantom{xx}$↓$\phantom{xxxxxxxxx}$↓<br>$\phantom{xx}$3$\phantom{xxxxxxxxx}$3<br><br>→6)α-D-Manp-(1→2)-α-D-Manp-(1→2)-α-D-Manp-(1→2)-β-D-Manp-(1→3)-α-D-GlcpNAc-(1→]n | Formula O68 |
| O69 | [ →2)-α-L-Rha-(1→2)-α-L-Rha-(1→2)-α-D-Gal-(1→3)-β-D-GlcNAc-(1→ ]$_n$ | Formula O69 |
| O73 (Strain 73-1) | [ α-D-Glc-(1→3) \| →4)-α-D-Man-(1→2)-α-D-Man-(1→2)-β-D-Man-(1→3)-α-D-GalNAc(1→ ]$_n$ | Formula O73 (Strain 73-1) |
| O74 | →6)-α-D-GlcpNAc-(1→4)-β-D-GalpA-(1→3)-β-D-GlcpNAc-(1→]n<br>$\phantom{xxxxxxxxxxxxxxxxxxx}$\|<br>[β-D-Fucp3Nac-(1→3) | Formula O74 |
| O75 | [ β-D-Man-(1→4) \| 3)-α-D-Gal-(1→4)-α-L-Rha-(1→3)-β-D-GlcNAc-(1→ ]$_n$ | Formula O75 |
| O76 | [→4)-β-D-GlcpA-(1→4)-β-D-GalpNAc3Ac-(1→4)-α-D-GalpNAc-(1→3)-β-D-GalpNAc-(1→]n | Formula O76 |
| O77 | [ →6)-α-D-Man-(1→2)-α-D-Man-(1→2)-α-D-Man-(1→3)-α-D-GlcNAc(1→ ]$_n$ | Formula O77 |
| O78 | [ →4)-β-D-GlcNAc-(→4)-β-D-Man-(1→4)-α-D-Man-(1→3)-β-D-GlcNAc-(1→ ]$_n$ | Formula O78 |
| O86 | [ α-D-Gal-(1→3) \| →4)-α-L-Fuc-(1→2)-β-D-Gal-(1→3)-α-D-GalNAc-(1→3)-β-D-GalNAc-(1→ ]$_n$ | Formula O86 |
| O88 | [ α-L-6dTal-(1→3) \| →4)-α-D-Man-(1→3)-β-D-GlcNAc-(1→ ]$_n$ | Formula O88 |
| O90 | [ →4)-α-L-Fuc2/3Ac-(1→2)-β-D-Gal-(1→3)-α-D-GalNAc-(1→3)-β-D-GalNAc-(1→ ]$_n$ | Formula O90 |
| O98 | [ →3)-α-L-QuiNAc-(1→4)-α-D-GalNAcA-(1→3)-α-L-QuiNAc-(1→3)-β-D-GlcNAc-(1→ ]$_n$ | Formula O98 |
| O104 | [ →4)-α-D-Gal-(1→4)-α-Neu5,7,9Ac$_3$-(2→3)-β-D-Gal-(1→3)-β-D-GalNAc-(1→]$_n$ | Formula O104 |
| O111 | [ α-Col-(1→6) \| →4)-α-D-Glc-(1→4)-α-D-Gal-(1→3)-β-D-GlcNAc-(1→ \| α-Col-(1→3) ]$_n$ | Formula O111 |
| O113 | [ →4)-α-D-GalNAc-(1→4)-α-D-GalA-(1→3)-α-D-Gal-(1→3)-β-D-GlcNAc-(1→ \| β-D-Gal-(1→3) ]$_n$ | Formula O113 |
| O114 | [ →4)-β-D-Qui3N(N-acetyl-L-seryl)-(1→3)-β-D-Ribf-(1→4)-β-D-Gal-(1→3)-α-D-GlcNAc(1→ ]$_n$ | Formula O114 |
| O119 | [ β-D-RhaNAc3Nfo-(1→3) \| →2)-β-D-Man-(1→3)-α-D-Gal-(1→4)-α-L-Rha-(1→3)-α-D-GlcNAc-(1→ ]$_n$ | Formula O119 |

TABLE A-continued

*E. coli* serogroups/serotypes and O-unit moieties

| Serogroup/ Serotype | Moiety Structure (O-unit) | Moiety structure referred to herein as: |
|---|---|---|
| O121 | [ →3)-β-D-Qui4N(N-acetyl-glycyl)-(1→4)-α-D-GalNAc3AcA6N-(1→4)-α-D-GalNAcA-(1→3)-α-D-GlcNAc-(1→ ]$_n$ | Formula O121 |
| O124 | [ 4-O-[l-1-carboxyethyl]-β-D-Glc-(1→6)-α-D-Glc(1→4) ⏐→3)-α-D-Gal-(1→6)-β-D-Galf-(1→3)-β-D-GalNAc-(1→ ]$_n$ | Formula O124 |
| O125 | [ α-D-Glc-(1→3) ⏐ →4)-β-D-GalNAc-(1→2)-α-D-Man-(1→3)-α-L-Fuc-(1→3)-α-D-GalNAc-(1→⏐ β-D-Gal-(1→3) ]$_n$ | Formula O125 |
| O126 | [ →)-β-D-Man-(1→3)-β-D-Gal-(1→3)-αD-GlcNAc-(1→3)-β-D-GlcNAc-(1→ ⏐ α-L-Fuc-(1→2) ]$_n$ | Formula O126 |
| O127 | [ →2)-α-L-Fuc-(1→2)-β-D-Gal-(1→3)-α-D-GalNAc-(1→3)-α-D-GalNAc-(1→ ]$_n$ | Formula O127 |
| O128 | [ α-L-Fuc-(1→2) ⏐ →6)-β-D-Gal-(1→3)-β-D-GalNAc-(1→4)-α-D-Gal-(1→3)-β-D-GalNAc-(1→ ]$_n$ | Formula O128 |
| O136 | [ →4)-β-Pse5Ac7Ac-(2→4)-β-D-Gal-(1→4)-β-D-GlcNAc-(1→β-Pse5Ac7Ac = 5,7-diacetamido-3,5,7,9-tetradeoxy-L-glycero-β-L-manno-nonulosonic acid ]$_n$ | Formula O136 |
| O138 | [ →2)-α-L-Rha-(1→3)-α-L-Rha-(1→4)-α-D-GalNAcA-(1→3)-β-D-GlcNAc-(1→ ]$_n$ | Formula O138 |
| O140 | [α-D-Galf-(1→2)α-L-Rhap<br><br>1<br>↓<br>4<br><br>→3)-β-D-Galp-(1→4)-α-D-Glcp-(1→4)-β-D-GlcpA-(1→3)-β-D-GalpNAc-(1→]n | Formula O140 |
| O141 | [ α-L-Rha-(1→3) ⏐→4)-α-D-Man-(1→3)-α-D-Man6Ac-(1→3)-β-D-GlcNAc-(1→ ⏐ β-D-GlcA-(1→2) ]$_n$ | Formula O141 |
| O142 | [ →2)-α-L-Rha-(1→6)-α-D-GalNAc-(1→4)-α-D-GalNAc-(1→3)-α-D-GalNAc-(1→ ⏐ β-D-GlcNAc-(1→3) ]$_n$ | Formula O142 |
| O143 | [ →2)-β-D-GalA6R3,4Ac-(1→3)-α-D-GalNAc-(1→4)-β-D-GlcA-(1→3)-β-D-GlcNAc-(1→ R = 1,3-dihydroxy-2-propylamino ]$_n$ | Formula O143 |
| O147 | [ →2)-α-L-Rha-(1→2)-α-L-Rha-(1→4)-β-D-GalA-(1→3)-β-D-GalNAc-(1→ ]$_n$ | Formula O147 |
| O149 | [ →3)-β-D-GlcNAc-(S)-4,6Py-(1→3)-β-L-Rha-(1→4)-β-D-GlcNAc-(1→ (S)-4,6Py = 4,6-O-[(S)-1-carboxyethylidene]- ]$_n$ | Formula O149 |
| O152 | [ β-L-Rha-(1→4) ⏐ →3)-α-D-GlcNAc-(1-P→6)-α-D-Glc-(1→2)-β-D-Glc-(1→3)-β-D-GlcNAc-(1→ ]$_n$ | Formula O152 |
| O157 | [ →2)-α-D-Rha4Nac-(1→3)-α-L-Fuc-(1→4)-β-D-Glc-(1→3)-α-D-GalNAc-(1→ ]$_n$ | Formula O157 |
| O158 | [ α-D-Glc-(1→6) ⏐ →4)-α-D-Glc-(1→3)-α-D-GalNAc-(1→3)-β-D-GalNAc-(1→ ⏐ α-L-Rha-(1→3) ]$_n$ | Formula O158 |
| O159 | [ α-L-Fuc-(1→4) ⏐ →3)-β-D-GlcNAc-(1→4)-α-D-GalA-(1→3)-α-L-Fuc-(1→3)-β-D-GlcNAc-(1→ ]$_n$ | Formula O159 |
| O164 | [ β-D-Glc-(1→6)-α-D-Glc(1→4) ⏐ →3)-β-D-Gal-(1→6)-β-D-Galf-(1→3)-β-D-GalNAc-(1→ ]$_n$ | Formula O164 |
| O173 | [ α-L-Fuc-(1→4) ⏐ →3)-α-D-Glc-(1-P→6)-α-D-Glc-(1→2)-β-D-Glc-(1→3)-β-D-GlcNAc-(1→]$_n$ | Formula O173 |
| 62D$_1$ Suggested as *Erwinia herbicola* | [ α-D-Gal(1→6) ⏐ →2)-β-D-Qui3Nac-(1→3)-α-L-Rha-(1→3)-β-D-Gal-(1→3)-α-D-FucNAc-(1→ ]$_n$ | Formula 62D$_1$ |
| O22 | [ →6)-α-D-Glc-(1→4)-β-D-GlcA-(1→4)-β-D-GalNAc3Ac-(1→3)-α-D-Gal-(1→3)-β-D-GalNAc-(1→]$_n$ | Formula O22 |
| O35 | [ →3)-α-L-Rha-(1→2)-α-L-Rha-(1→3)-α-L-Rha-(1→2)-α-L-Rha-(1→3)-β-D-GlcNAc-(1→ ⏐ α-D-GalNAcA6N-(1→2) ]$_n$ | Formula O35 |
| O65 | [ →2)-β-D-Qui3Nac-(1→4)-α-D-GalA6N-(1→4)-α-D-GalNAc-(1→4)-β-D-GalA-(1→3)-α-D-GlcNAc-(1→ ]$_n$ | Formula O65 |
| O66 | [ →2)-β-D-Man-(1→3)-α-D-GlcNAc-(1→2)-β-D-Glc3Ac-(1→3)-α-L-6dTal-(1→3)-α-D-GlcNAc(1→ ]$_n$ | Formula O66 |
| O83 | [ →6)-α-D-Glc-(1→4)-β-D-GlcA-(1→6)-β-D-Gal-(1→4)-β-D-Gal-(1→4)-β-D-GlcNAc-(1→ ]$_n$ | Formula O83 |
| O91 | [ →4)-α-D-Qui3Nacyl-(1→4)-β-D-Gal-(1→4)-β-D-GlcNAc-(1→4)-β-D-GlcA6Ngly-(1→3)-β-D-GlcNAc-(1→ Acyl = l-3-hydroxybutyryl ]$_n$ | Formula O91 |
| O105 | [ β-D-Ribf-(1→3) ⏐ →4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→ ]$_n$ | Formula O105 |
| O116 | [ →2)-β-D-Qui4Nac-(1→6)-α-D-GlcNAc-(1→4)-α-D-GalNAc-(1→4)-α-D-GalA-(1→3)-α-D-GlcNAc-(1→ ]$_n$ | Formula O116 |
| O117 | [ →4)-β-D-GalNAc-(1→3)-α-L-Rha-(1→4)-α-D-Glc-(1→4)-β-D-Gal-(1→3)-α-D-GalNAc-(1→]$_n$ | Formula O117 |

TABLE A-continued

*E. coli* serogroups/serotypes and O-unit moieties

| Serogroup/Serotype | Moiety Structure (O-unit) | Moiety structure referred to herein as: |
|---|---|---|
| O139 | [ β-D-Glc-(1→3) \| →3)-α-L-Rha-(1→4)-α-D-GalA-(1→2)-α-L-Rha-(1→3)-α-L-Rha-(1→2)-α-L-Rha-(1→3)-α-D-GlcNAc-(1→ ]$_n$ | Formula O139 |
| O153 | [ →2)-β-D-Ribf-(1→4)-β-D-Gal-(1→4)-α-D-GlcNAc-(1→4)-β-D-Gal-(1→3)-α-D-GlcNAc-(1→ ]$_n$ | Formula O153 |
| O167 | [ α-D-Galf-(1→4) \| →2)-β-D-GalA6N(L)Ala-(1→3)-α-D-GlcNAc-(1→2)-β-D-Galf-(1→5)-β-D-Galf-(1→3)-β-D-GlcNAc-(1→ ]$_n$ | Formula O167 |
| O172 | [ →3)-α-L-FucNAc-(1→4)-α-D-Glc6Ac-(1-P→4)-α-D-Glc-(1→3)-α-L-FucNAc-(1→3)-α-D-GlcNAc-(1→ ]$_n$ | Formula O172 |
| O8 | [ →2)-α-D-Man-(1→2)-α-D-Man-(1→3)-β-D-Man-(1→ ]$_n$ | Formula O8 |
| O9a | [ →2)-α-D-Man-(1→2)-α-D-Man-(1→3)-α-D-Man-(1→3)-α-D-Man-(1→ ]$_n$ | Formula O9a |
| O9 | [ →2)-[α-D-Man-(1→2)]$_2$-α-D-Man-(1→3)-α-D-Man-(1→3)-α-D-Man-(1→ ]$_n$ | Formula O9 |
| O20ab | [ →2)-β-D-Ribf-(1→4)-α-D-Gal-(1→ ]$_n$ | Formula O20ab |
| O20ac | [ α-D-Gal-(1→3) \| →2)-β-D-Ribf-(1→4)-α-D-Gal-(1→ ]$_n$ | Formula O20ac |
| O52 | [ →3)-β-D-Fucf-(1→3)-β-D-6dmanHep2Ac-(1→ ]$_n$ | Formula O52 |
| O97 | [ →3)-α-L-Rha-(1→3)-β-L-Rha-(1→ \|\| β-D-Xulf-(2→2)β-D-Xulf-(2→2) ]$_n$ | Formula O97 |

† β-D-6dmanHep2Ac is 2-O-acetyl-6-deoxy-β-D-manno-heptopyranosyl.
‡ β-D-Xulf is β-D-threo-pentofuranosyl.

3. Core Oligosaccharide

The core oligosaccharide is positioned between Lipid A and the O-antigen outer region in wild-type *E. coli* LPS. More specifically, the core oligosaccharide is the part of the polysaccharide that includes the bond between the O-antigen and the lipid A in wild type *E. coli*. This bond includes a ketosidic bond between the hemiketal function of the innermost 3-deoxy-d-manno-oct-2-ulosonic acid (KDO)) residue and a hydroxyl-group of a GlcNAc-residue of the lipid A. The core oligosaccharide region shows a high degree of similarity among wild-type *E. coli* strains. It usually includes a limited number of sugars. The core oligosaccharide includes an inner core region and an outer core region.

More specifically, the inner core is composed primarily of L-glycero-D-manno-heptose (heptose) and KDO residues. The inner core is highly conserved. A KDO residue includes the following Formula KDO:

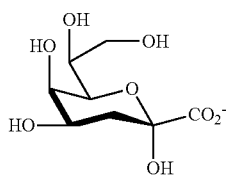

The outer region of the core oligosaccharide displays more variation than the inner core region, and differences in this region distinguish the five chemotypes in *E. coli*: R1, R2, R3, R4, and K-12. The generalized structures of the carbohydrate backbone of the outer core oligosaccharides of the five known chemotypes are well-known in the art. HepII is the last residue of the inner core oligosaccharide. While all of the outer core oligosaccharides share a structural theme, with a (hexose)$_3$ carbohydrate backbone and two side chain residues, the order of hexoses in the backbone and the nature, position, and linkage of the side chain residues can all vary. The structures for the R1 and R4 outer core oligosaccharides are highly similar, differing in only a single β-linked residue.

The core oligosaccharides of wild-type *E. coli* are categorized in the art based on the structures of the distal oligosaccharide, into five different chemotypes: *E. coli* R1, *E. coli* R2, *E. coli* R3, *E. coli* R4, and *E. coli* K12.

In a preferred embodiment, the compositions described herein include glycoconjugates in which the O-polysaccharide includes a core oligosaccharide bound to the O-antigen. In one embodiment, the composition induces an immune response against at least any one of the core *E. coli* chemotypes *E. coli* R1, *E. coli* R2, *E. coli* R3, *E. coli* R4, and *E. coli* K12. In another embodiment, the composition induces an immune response against at least two core *E. coli* chemotypes. In another embodiment, the composition induces an immune response against at least three core *E. coli* chemotypes. In another embodiment, the composition induces an immune response against at least four core *E. coli* chemotypes. In another embodiment, the composition induces an immune response against all five core *E. coli* chemotypes.

In another preferred embodiment, the compositions described herein include glycoconjugates in which the O-polysaccharide does not include a core oligosaccharide bound to the O-antigen. In one embodiment, such a composition induces an immune response against at least any one of the core *E. coli* chemotypes *E. coli* R1, *E. coli* R2, *E. coli* R3, *E. coli* R4, and *E. coli* K12, despite the glycoconjugate having an O-polysaccharide that does not include a core oligosaccharide.

*E. coli* serotypes may be characterized according to one of the five chemotypes. Table B lists exemplary serotypes characterized according to chemotype. The serotypes in bold represent the serotypes that are most commonly associated with the indicated core chemotype. Accordingly, in a preferred embodiment, the composition induces an immune response against at least any one of the core *E. coli* chemotypes *E. coli* R1, *E. coli* R2, *E. coli* R3, *E. coli* R4, and *E. coli* K12, which includes an immune response against any one of the respective corresponding *E. coli* serotypes.

TABLE B

Core Chemotype and associated E. coli Serotype

| Core chemotype | Serotype |
|---|---|
| R1 | O25a, O6, O2, O1, O75, O4, O16, O8, O18, O9, O13, O20, O21, O91, and O163. |
| R2 | O21, O44, O11, O89, O162, O9 |
| R3 | O25b, O15, O153, O21, O17, O11, O159, O22 O86, O93 |
| R4 | O2, O1, O86, O7, O102, O160, O166 |
| K-12 | O25b, O16 |

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O8, Formula O18, Formula O9, Formula O13, Formula O20, Formula O21, Formula O91, and Formula O163, wherein n is 1 to 100. In some embodiments, the saccharide in said composition further includes an E. coli R1 core moiety.

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O18, Formula O13, Formula O20, Formula O21, Formula O91, and Formula O163, wherein n is 1 to 100, preferably 31 to 100, preferably from 31 to 90 more preferably 35 to 90, most preferably 35 to 65. In some embodiments, the saccharide in said composition further includes an E. coli R1 core moiety in the saccharide.

In some embodiments, the composition includes a saccharide that includes a structure derived from a serotype having an R2 chemotype, e.g., selected from a saccharide having Formula O21, Formula O44, Formula O11, Formula O89, Formula O162, and Formula O9, wherein n is 1 to 100, preferably 31 to 100, preferably from 31 to 90, more preferably 35 to 90, most preferably 35 to 65. In some embodiments, the saccharide in said composition further includes an E. coli R2 core moiety.

In some embodiments, the composition includes a saccharide that includes a structure derived from a serotype having an R3 chemotype, e.g., selected from a saccharide having Formula O25b, Formula O15, Formula O153, Formula O21, Formula O17, Formula O11, Formula O159, Formula O22, Formula O86, and Formula O93, wherein n is 1 to 100, preferably 31 to 100, preferably from 31 to 90, more preferably 35 to 90, most preferably 35 to 65. In some embodiments, the saccharide in said composition further includes an E. coli R3 core moiety.

In some embodiments, the composition includes a saccharide that includes a structure derived from a serotype having an R4 chemotype, e.g., selected from a saccharide having Formula O2, Formula O1, Formula O86, Formula O7, Formula O102, Formula O160, and Formula O166, wherein n is 1 to 100, preferably 31 to 100, preferably from 31 to 90, more preferably 35 to 90, most preferably 35 to 65. In some embodiments, the saccharide in said composition further includes an E. coli R4 core moiety.

In some embodiments, the composition includes a saccharide that includes a structure derived from a serotype having an K-12 chemotype (e.g., selected from a saccharide having Formula O25b and a saccharide having Formula O16), wherein n is 1 to 1000, preferably 31 to 100, preferably from 31 to 90, more preferably 35 to 90, most preferably 35 to 65. In some embodiments, the saccharide in said composition further includes an E. coli K-12 core moiety.

In some embodiments, the saccharide includes the core saccharide. Accordingly, in one embodiment, the O-polysaccharide further includes an E. coli R1 core moiety. In another embodiment, the O-polysaccharide further includes an E. coli R2 core moiety. In another embodiment, the O-polysaccharide further includes an E. coli R3 core moiety. In another embodiment, the O-polysaccharide further includes an E. coli R4 core moiety. In another embodiment, the O-polysaccharide further includes an E. coli K12 core moiety.

In some embodiments, the saccharide does not include the core saccharide. Accordingly, in one embodiment, the O-polysaccharide does not include an E. coli R1 core moiety. In another embodiment, the O-polysaccharide does not include an E. coli R2 core moiety. In another embodiment, the O-polysaccharide does not include an E. coli R3 core moiety. In another embodiment, the O-polysaccharide does not include an E. coli R4 core moiety. In another embodiment, the O-polysaccharide does not include an E. coli K12 core moiety.

4. Conjugated O-Antigens

Chemical linkage of O-antigens or preferably O-polysaccharides to protein carriers may improve the immunogenicity of the O-antigens or O-polysaccharides. However, variability in polymer size represents a practical challenge for production. In commercial use, the size of the saccharide can influence the compatibility with different conjugation synthesis strategies, product uniformity, and conjugate immunogenicity. Controlling the expression of a Wzz family protein chain length regulator through manipulation of the O-antigen synthesis pathway allows for production of a desired length of O-antigen chains in a variety of Gram-negative bacterial strains, including E. coli.

In one embodiment, the purified saccharides are chemically activated to produce activated saccharides capable of reacting with the carrier protein. Once activated, each saccharide is separately conjugated to a carrier protein to form a conjugate, namely a glycoconjugate. As used herein, the term "glycoconjugate" refers to a saccharide covalently linked to a carrier protein. In one embodiment a saccharide is linked directly to a carrier protein. In another embodiment, a saccharide is linked to a protein through a spacer/linker. Conjugates may be prepared by schemes that bind the carrier to the O-antigen at one or at multiple sites along the O-antigen, or by schemes that activate at least one residue of the core oligosaccharide.

In one embodiment, each saccharide is conjugated to the same carrier protein. If the protein carrier is the same for 2 or more saccharides in the composition, the saccharides may be conjugated to the same molecule of the carrier protein (e.g., carrier molecules having 2 or more different saccharides conjugated to it).

In a preferred embodiment, the saccharides are each individually conjugated to different molecules of the protein carrier (each molecule of protein carrier only having one type of saccharide conjugated to it). In said embodiment, the saccharides are said to be individually conjugated to the carrier protein.

The chemical activation of the saccharides and subsequent conjugation to the carrier protein can be achieved by the activation and conjugation methods disclosed herein. After conjugation of the polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration. After the individual glycoconjugates are purified, they are compounded to formulate the immunogenic composition of the present invention.

a. Activation. The present invention further relates to activated polysaccharides produced from any of the embodiments described herein wherein the polysaccharide is activated with a chemical reagent to produce reactive groups for conjugation to a linker or carrier protein. In some embodiments, the saccharide of the invention is activated prior to conjugation to the carrier protein. In some embodiments, the degree of activation does not significantly reduce the molecular weight of the polysaccharide. For example, in some embodiments, the degree of activation does not cleave the polysaccharide backbone. In some embodiments, the degree of activation does not significantly impact the degree of conjugation, as measured by the number of lysine residues modified in the carrier protein, such as, $CRM_{197}$ (as determined by amino acid analysis). For example, in some embodiments, the degree of activation does not significantly increase the number of lysine residues modified (as determined by amino acid analysis) in the carrier protein by 3-fold, as compared to the number of lysine residues modified in the carrier protein of a conjugate with a reference polysaccharide at the same degree of activation. In some embodiments, the degree of activation does not increase the level of unconjugated free saccharide. In some embodiments, the degree of activation does not decrease the optimal saccharide/protein ratio.

In some embodiments, the activated saccharide has a percentage of activation wherein moles of thiol per saccharide repeat unit of the activated saccharide is between 1-100%, such as, for example, between 2-80%, between 2-50%, between 3-30%, and between 4-25%. The degree of activation is at least 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, or 90%, or about 100%. Preferably, the degree of activation is at most 50%, more preferably at most 25%. In one embodiment, the degree of activation is at most 20%. Any minimum value and any maximum value may be combined to define a range.

In one embodiment, the polysaccharide is activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$ or tetanus toxoid).

For example, the spacer may be cystamine or cysteamine to give a thiolated polysaccharide which could be coupled to the carrier via a thioether linkage obtained after reaction with a maleimide-activated carrier protein (for example using N-[Y-maleimidobutyrloxy]succinimide ester (GMBS)) or a haloacetylated carrier protein (for example using 76yophilized76e, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA), or succinimidyl 3-[bromoacetamido]proprionate (SBAP)). In one embodiment, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier.

Other suitable techniques for conjugation use carbodiimides, hydrazides, active esters, norborane, p-nitrobenzoic acid, N-hydroxysuccinimide, S-NHS, EDC, TSTU. Conjugation may involve a carbonyl linker which may be formed by reaction of a free hydroxyl group of the saccharide with CDI followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein (CDI chemistry).

b. Molecular weight. In some embodiments, the glycoconjugate comprises a saccharide having a molecular weight of between 10 kDa and 2,000 kDa. In other embodiments, the saccharide has a molecular weight of between 50 kDa and 1,000 kDa. In other embodiments, the saccharide has a molecular weight of between 70 kDa and 900 kDa. In other embodiments, the saccharide has a molecular weight of between 100 kDa and 800 kDa. In other embodiments, the saccharide has a molecular weight of between 200 kDa and 600 kDa. In further embodiments, the saccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In one embodiment, the glycoconjugate having such a molecular weight is produced by single-end conjugation. In another embodiment, the glycoconjugate having such a molecular weight is produced by reductive amination chemistry (RAC) prepared in aqueous buffer. Any whole number integer within any of the above ranges is contemplated as an embodiment of the disclosure.

In some embodiments, the glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the glycoconjugate has a molecular weight of between 500 kDa and 10,000 kDa. In other embodiments, glycoconjugate has a molecular weight of between 1,000 kDa and 8,000 kDa. In still other embodiments, the glycoconjugate has a molecular weight of between 2,000 kDa and 8,000 kDa or between 3,000 kDa and 7,000 kDa. In further embodiments, the glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In one embodiment, the glycoconjugate having such a molecular weight is produced by eTEC conjugation described herein. In another embodiment, the glycoconjugate having such a molecular weight is produced by reductive amination chemistry (RAC). In another embodiment, the glycoconjugate having such a molecular weight is produced by reductive amination chemistry (RAC) prepared in DMSO.

In further embodiments, the glycoconjugate of the invention has a molecular weight of between 1,000 kDa and 20,000 kDa; between 1,000 kDa and 15,000 kDa; between 2,000 kDa and 10,000 kDa; between 2000 kDa and 7,500 kDa; between 2,000 kDa and 5,000 kDa; between 3,000 kDa and 20,000 kDa; between 3,000 kDa and 15,000 kDa; between 3,000 kDa and 12,500 kDa; between 4,000 kDa and 10,000 kDa; between 4,000 kDa and 7,500 kDa; between 4,000 kDa and 6,000 kDa; or between 5,000 kDa and 7,000 kDa. In one embodiment, the glycoconjugate having such a molecular weight is produced by reductive amination chemistry (RAC). In another embodiment, the glycoconjugate having such a molecular weight is produced by reductive amination chemistry (RAC) prepared in DMSO. In another embodiment, the glycoconjugate having such a molecular weight is produced by eTEC conjugation described herein.

In further embodiments, the glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate may be measured by SEC-MALLS. Any whole number integer within any of the above ranges is contemplated as an embodiment of the disclosure. The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of polysaccharide to carrier protein in the conjugate is between 0.9 and 1.1. In some such embodiments, the carrier protein is CRM197.

The glycoconjugates may also be characterized by their molecular size distribution (Kd).

Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of Kd, columns are calibrated to establish the fraction at which molecules are fully excluded (V0), (Kd=0), and the fraction representing the maximum retention (Vi), (Kd=1). The fraction at which a specified sample attribute is reached (Ve), is related to $K_d$ by the expression, Kd=(Ve−Vo)/(Vi−V0).

c. Free saccharide. The glycoconjugates and immunogenic compositions of the invention may include free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate. In a preferred embodiment, the glycoconjugate comprises at most 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises at most about 20% of free polysaccharide compared to the total amount of polysaccharide. In a preferred embodiment the glycoconjugate comprises at most about 15% of free polysaccharide compared to the total amount of polysaccharide. In another preferred embodiment, the glycoconjugate comprises at most about 20%, 19%, 18%, 17%, 16%, 15%, 14%, 13%, 12%, 11%, 10%, 9%, 8%, 7%, 6%, 5%, 4%, 3%, 2%, or 1% of free polysaccharide compared to the total amount of polysaccharide. In a preferred embodiment the glycoconjugate comprises less than about 8% of free polysaccharide compared to the total amount of polysaccharide. In a preferred embodiment the glycoconjugate comprises at most about 6% of free polysaccharide compared to the total amount of polysaccharide. In a preferred embodiment the glycoconjugate comprises at most about 5% of free polysaccharide compared to the total amount of polysaccharide.

d. Covalent linkage. In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 1 1 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is CRM197. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In one embodiment, the carrier protein is CRM197. Any whole number integer within any of the above ranges is contemplated as an embodiment of the disclosure.

e. Lysine residues. Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In one embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is $CRM_{197}$.

The frequency of attachment of the saccharide chain to a lysine on the carrier protein is another parameter for characterizing the glycoconjugates of the invention. For example, in some embodiments, at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

f. O-acetylation. In some embodiments, the saccharides of the invention are O-acetylated. In some embodiments, the glycoconjugate comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is ≥10%, ≥20%, ≥30%, ≥40%, ≥50%, ≥60%, ≥70%, ≥80%, or ≥90%, or about 100%. By % of O-acetylation it is meant the percentage of a given saccharide relative to 100% (where each repeat unit is fully acetylated relative to its acetylated structure).

In some embodiments, the glycoconjugate is prepared by reductive amination. In some embodiments, the glycoconjugate is a single-end-linked conjugated saccharide, wherein the saccharide is covalently bound to a carrier protein directly. In some embodiments, the glycoconjugate is covalently bound to a carrier protein through a (2-((2-oxoethyl)thio)ethyl) carbamate (eTEC) spacer.

g. Reductive Amination. In one embodiment, the saccharide is conjugated to the carrier protein by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709).

Reductive amination includes (1) oxidation of the saccharide, (2) reduction of the activated saccharide and a carrier protein to form a conjugate. Before oxidation, the saccharide is optionally hydrolyzed. Mechanical or chemical hydrolysis may be employed. Chemical hydrolysis may be conducted using acetic acid.

The oxidation step may involve reaction with periodate. The term "periodate" as used herein refers to both periodate and periodic acid. The term also includes both metaperiodate ($IO_4^-$) and orthoperiodate ($IO_6^{5-}$) and the various salts of periodate (e.g., sodium periodate and potassium periodate). In one embodiment the polysaccharide is oxidized in the presence of metaperiodate, preferably in the presence of sodium periodate ($NaIO_4$). In another embodiment the polysaccharide is oxidized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls. In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from any one of N-ChloroSuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

Following the oxidation step of the saccharide, the saccharide is said to be activated and is referred to as "activated" herein below. The activated saccharide and the carrier protein may be 82yophilized (freeze-dried), either independently (discrete lyophilization) or together (co-lyophilized). In one embodiment the activated saccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The next step of the conjugation process is the reduction of the activated saccharide and a carrier protein to form a conjugate (so-called reductive amination), using a reducing agent. Suitable reducing agents include the cyanoborohydrides, such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN—BH3, benzylamine-BH3 or 5-ethyl-2-methylpyridine borane (PEMB), borane-pyridine, or borohydride exchange resin. In one embodiment the reducing agent is sodium cyanoborohydride.

In an embodiment, the reduction reaction is carried out in aqueous solvent (e.g., selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride (NaBH4). Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. The glycoconjugates maybe purified by diafiltration and/or ion exchange chromatography and/or size exclusion chromatography. In an embodiment, the glycoconjugates are purified by diafiltration or ion exchange chromatography or size exclusion chromatography. In one embodiment the glycoconjugates are sterile filtered.

In a preferred embodiment, a glycoconjugate from an *E. coli* serotype is selected from any one of O25b, O1a, O2, and O6 is prepared by reductive amination. In a preferred embodiment, the glycoconjugates from *E. coli* serotypes O25b, O1a, O2, and O6 are prepared by reductive amination.

In one aspect, the invention relates to a conjugate that includes a carrier protein, e.g., CRM197, linked to a saccharide of Formula O25B, presented by

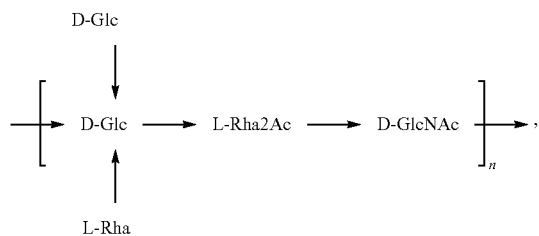

wherein n is any integer greater than or equal to 1. In a preferred embodiment, n is an integer of at least 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80. In one preferred embodiment, n is at least 31 to at most 90, more preferably 40 to 90, most preferably 60 to 85.

In another aspect, the invention relates to a conjugate that includes a carrier protein, e.g., CRM197, linked to a saccharide having any one of the following structures shown in Table A, wherein n is an integer greater than or equal to 1.

Without being bound by theory or mechanism, in some embodiments, a stable conjugate is believed to require a level of saccharide antigen modification that is balanced against preserving the structural integrity of the critical immunogenic epitopes of the antigen.

h. Activation and formation of an Aldehyde. In some embodiments, the saccharide of the invention is activated and results in the formation of an aldehyde. In such embodiments wherein the saccharide is activated, the percentage (%) of activation (or degree of oxidation (DO)) refers to moles of a saccharide repeat unit per moles of aldehyde of the activated polysaccharide. For example, in some embodiments, the saccharide is activated by periodate oxidation of vicinal diols on a repeat unit of the polysaccharide, resulting in the formation of an aldehyde. Varying the molar equivalents (meq) of sodium periodate relative to the saccharide repeat unit and temperature during oxidation results in varying levels of degree of oxidation (DO).

The saccharide and aldehyde concentrations are typically determined by colorimetric assays. An alternative reagent is TEMPO (2,2,6,6-tetramethylpiperidine 1-oxyl radical)-N-chlorosuccinimide (NCS) combination, which results in the formation of aldehydes from primary alcohol groups.

In some embodiments, the activated saccharide has a degree of oxidation wherein the moles of a saccharide repeat unit per moles of aldehyde of the activated saccharide is between 1-100, such as, for example, between 2-80, between 2-50, between 3-30, and between 4-25. The degree of activation is at least 1, 2, 3, 4, 5, 6, 7, 8, 9, 10, 11, 12, 13, 14, 15, 16, 17, 18, 19, 20, 30, 40, 50, 60, 70, 80, or 90, or about 100. Preferably, the degree of oxidation (DO) is at least 5 and at most 50, more preferably at least 10 and at most 25. In one embodiment, the degree of activation is at least 10 and at most 25. Any minimum value and any maximum value may be combined to define a range. A degree of oxidation value may be represented as percentage (%) of activation. For example, in one embodiment, a DO value of 10 refers to one activated saccharide repeat unit out of a total of 10 saccharide repeat units in the activated saccharide, in which case the DO value of 10 may be represented as 10% activation.

In some embodiments, the conjugate prepared by reductive amination chemistry includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100 or 31 to 90, more preferably 35 to 90, most preferably 35 to 65.

i. Single-end Linked Conjugates. In some embodiments, the conjugate is single-end-linked conjugated saccharide, wherein the saccharide is covalently bound at one end of the saccharide to a carrier protein. In some embodiments, the single-end-linked conjugated polysaccharide has a terminal saccharide. For example, a conjugate is single-end linked if one of the ends (a terminal saccharide residue) of the polysaccharide is covalently bound to a carrier protein. In some embodiments, the conjugate is single-end linked if a terminal saccharide residue of the polysaccharide is covalently bound to a carrier protein through a linker. Such linkers may include, for example, a cystamine linker (A1), a 3,3'-dithio bis(propanoic dihydrazide) linker (A4), and a 2,2'-dithio-N,N'-bis(ethane-2,2-diyl)bis(2-(aminooxy)acetamide) linker (A6).

In some embodiments, the saccharide is conjugated to the carrier protein through a 3-deoxy-d-manno-oct-2-ulosonic acid (KDO) residue to form a single-end linked conjugate.

In some embodiments, the conjugate is preferably not a bioconjugate. The term "bioconjugate" refers to a conjugate between a protein (e.g., a carrier protein) and an antigen, e.g., an O antigen (e.g., O25B) prepared in a host cell background, wherein host cell machinery links the antigen to the protein (e.g., N-links). Glycoconjugates include bioconjugates, as well as sugar antigen (e.g., oligo- and polysaccharides)-protein conjugates prepared by means that do not require preparation of the conjugate in a host cell, e.g., conjugation by chemical linkage of the protein and saccharide.

j. Thiol Activated Saccharides. In some embodiments, the saccharide of the invention is thiol activated. In such embodiments wherein the saccharide is thiol activated, the percentage (%) of activation refers to moles of thiol per saccharide repeat unit of the activated polysaccharide. The saccharide and thiol concentrations are typically determined by Ellman's assay for quantitation of sulfhydryls. For example, in some embodiments, the saccharide includes activation of 2-Keto-3-deoxyoctanoic acid (KDO) with a disulfide amine linker. In some embodiments, the saccharide is covalently bound to a carrier protein through a bivalent, heterobifunctional linker (also referred to herein as a "spacer"). The linker preferably provides a thioether bond between the saccharide and the carrier protein, resulting in a glycoconjugate referred to herein as a "thioether glycoconjugate." In some embodiments, the linker further provides carbamate and amide bonds, such as, for example, (2-((2-oxoethyl)thio)ethyl) carbamate (eTEC).

In some embodiments, the single-end linked conjugate includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45re1), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

For example, in one embodiment, the single-end linked conjugate includes a carrier protein and a saccharide having a structure selected from Formula O8, Formula O9a, Formula O9, Formula O20ab, Formula O20ac, Formula O52, Formula O97, and Formula O101, wherein n is an integer from 1 to 10.

5. eTEC Conjugates

In one aspect, the invention relates generally to glycoconjugates comprising a saccharide derived from *E. coli* described above covalently conjugated to a carrier protein through a (2-((2-oxoethyl)thio)ethyl)carbamate (eTEC) spacer (as described, for example, in U.S. Pat. No. 9,517,274 and International Patent Application Publication WO2014027302, incorporated by reference herein in their entireties), including immunogenic compositions comprising such glycoconjugates, and methods for the preparation and use of such glycoconjugates and immunogenic compositions. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC spacer includes seven linear atoms (i.e., —C(O)NH(CH2)2SCH2C(O)—) and provides stable thioether and amide bonds between the saccharide and carrier protein.

The eTEC linked glycoconjugates of the invention may be represented by the general formula (I):

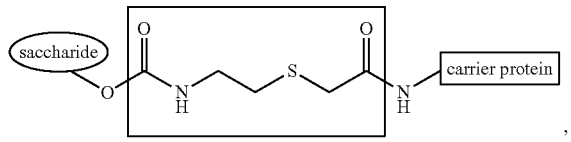

(I)

where the atoms that comprise the eTEC spacer are contained in the central box.

In said glycoconjugates of the invention, the saccharide may be a polysaccharide or an oligosaccharide.

The carrier proteins incorporated into the glycoconjugates of the invention are selected from the group of carrier proteins generally suitable for such purposes, as further described herein or known to those of skill in the art. In particular embodiments, the carrier protein is CRM197.

In another aspect, the invention provides a method of making a glycoconjugate comprising a saccharide described herein conjugated to a carrier protein through an eTEC spacer, comprising the steps of a) reacting a saccharide with a carbonic acid derivative in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an eTEC linked glycoconjugate is produced.

In frequent embodiments, the carbonic acid derivative is 1,1'-carbonyl-di-(1,2,4-triazole) (CDT) or 1,1'-carbonyl-diimidazole (CDI). Preferably, the carbonic acid derivative is CDT and the organic solvent is a polar aprotic solvent, such as dimethylsulfoxide (DMSO). In preferred embodiments, the thiolated saccharide is produced by reaction of the activated saccharide with the bifunctional symmetric thioalkylamine reagent, cystamine or a salt thereof. Alternatively, the thiolated saccharide may be formed by reaction of the activated saccharide with cysteamine or a salt thereof. The eTEC linked glycoconjugates produced by the methods of the invention may be represented by general Formula (I).

In frequent embodiments, the first capping reagent is N-acetyl-L-cysteine, which reacts with unconjugated α-haloacetamide groups on lysine residues of the carrier protein to form an S-carboxymethylcysteine (CMC) residue covalently linked to the activated lysine residue through a thioether linkage.

In other embodiments, the second capping reagent is iodoacetamide (IAA), which reacts with unconjugated free sulfhydryl groups of the activated thiolated saccharide to provide a capped thioacetamide. Frequently, step e) comprises capping with both a first capping reagent and a second capping reagent. In certain embodiments, step e) comprises capping with N-acetyl-L-cysteine as the first capping reagent and IAA as the second capping reagent.

In some embodiments, the capping step e) further comprises reaction with a reducing agent, for example, DTT, TCEP, or mercaptoethanol, after reaction with the first and/or second capping reagent.

The eTEC linked glycoconjugates and immunogenic compositions of the invention may include free sulfhydryl residues. In some instances, the activated thiolated saccharides formed by the methods provided herein will include multiple free sulfhydryl residues, some of which may not undergo covalent conjugation to the carrier protein during the conjugation step. Such residual free sulfhydryl residues are capped by reaction with a athiol-reactive capping reagent, for example, iodoacetamide (IAA), to cap the potentially reactive functionality. Other thiol-reactive capping reagents, e.g., maleimide containing reagents and the like are also contemplated. In addition, the eTEC linked glycoconjugates and immunogenic compositions of the invention may include residual unconjugated carrier protein, which may include activated carrier protein which has undergone modification during the capping process steps.

In some embodiments, step d) further comprises providing an activated carrier protein comprising one or more α-haloacetamide groups prior to reacting the activated thiolated saccharide with the activated carrier protein. In frequent embodiments, the activated carrier protein comprises one or more α-bromoacetamide groups.

In another aspect, the invention provides an eTEC linked glycoconjugate comprising a saccharide described herein conjugated to a carrier protein through an eTEC spacer produced according to any of the methods disclosed herein.

In some embodiments, the carrier protein is CRM197 and the covalent linkage via an eTEC spacer between the CRM197 and the polysaccharide occurs at least once in every 4, 10, 15 or 25 saccharide repeat units of the polysaccharide.

For each of the aspects of the invention, in particular embodiments of the methods and compositions described herein, the eTEC linked glycoconjugate comprises a saccharide described herein, such as, a saccharide derived from E. coli.

In another aspect, the invention provides a method of preventing, treating or ameliorating a bacterial infection, disease or condition in a subject, comprising administering to the subject an immunologically effective amount of an immunogenic composition of the invention, wherein said immunogenic composition comprises an eTEC linked glycoconjugate comprising a saccharide described herein. In some embodiments, the saccharide is derived from E. coli.

In some embodiments, the eTEC linked glycoconjugate comprises a carrier protein and a saccharide, in which said saccharide comprises a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

The number of lysine residues in the carrier protein that become conjugated to the saccharide can be characterized as a range of conjugated lysines. For example, in some embodiments of the immunogenic compositions, the $CRM_{197}$ may comprise 4 to 16 lysine residues out of 39 covalently linked to the saccharide. Another way to express this parameter is that about 10% to about 41% of $CRM_{197}$ lysines are covalently linked to the saccharide. In other embodiments, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide.

In frequent embodiments, the carrier protein is $CRM_{197}$ and the covalent linkage via an eTEC spacer between the $CRM_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

6. Carrier Proteins

A component of the glycoconjugate of the invention is a carrier protein to which the saccharide is conjugated. The terms "protein carrier" or "carrier protein" or "carrier" may be used interchangeably herein. Carrier proteins should be amendable to standard conjugation procedures.

One component of the conjugate is a carrier protein to which the O-polysaccharide is conjugated. In one embodiment, the conjugate includes a carrier protein conjugated to the core oligosaccharide of the O-polysaccharide. In one embodiment, the conjugate includes a carrier protein conjugated to the O-antigen of the O-polysaccharide.

The terms "protein carrier" or "carrier protein" or "carrier" may be used interchangeably herein. Carrier proteins should be amendable to standard conjugation procedures.

In a preferred embodiment, the carrier protein of the conjugates is independently selected from any one of TT, DT, DT mutants (such as CRM197), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of C. Difficile and PsaA. In an embodiment, the carrier protein of the conjugates of the invention is DT (Diphtheria toxoid). In another embodiment, the carrier protein of the conjugates of the invention is TT (tetanus toxoid). In another embodiment, the carrier protein of the conjugates of the invention is PD (*Haemophilus influenzae* protein D—see, e.g., EP 0 594 610 B). In some embodiments, the carrier protein includes poly(L-lysine) (PLL).

In a preferred embodiment, the saccharides are conjugated to CRM197 protein. The CRM197 protein is a non-toxic form of diphtheria toxin but is immunologically indistinguishable from the diphtheria toxin. CRM197 is produced by *C. diphtheriae* infected by the nontoxigenic phage β197tox-created by nitrosoguanidine mutagenesis of the toxigenic corynephage beta. The CRM197 protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM197 protein is a safe and effective T-cell dependent carrier for saccharides.

Accordingly, in some embodiments, the conjugates of the invention include $CRM_{197}$ as the carrier protein, wherein the saccharide is covalently linked to $CRM_{197}$.

In a preferred embodiment, the carrier protein of the glycoconjugates is selected in the group consisting of DT (Diphtheria toxin), TT (tetanus toxoid) or fragment C of TT, CRM197 (a nontoxic but antigenically identical variant of diphtheria toxin), other DT mutants (such as CRM176, CRM228, CRM 45 (Uchida et al J. Biol. Chem. 218; 3838-3844, 1973), CRM9, CRM45, CRM102, CRM103 or CRM107; and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Giy and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711), pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein—usually extracted from *N. meningitidis* serogroup B—EP0372501), PorB (from *N. meningitidis*), PD (*Haemophilus influenzae* protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Uchida Cameron D M, R J Collier. 1987. J. Bacteriol. 169:4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*.

In some embodiments, the carrier protein is selected from any one of, for example, CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), flagellin, detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP). In embodiment, the carrier protein is detoxified *Pseudomonas* exotoxin (EPA). In another embodiment, the carrier protein is not detoxified *Pseudomonas* exotoxin (EPA). In one embodiment, the carrier protein is flagellin. In another embodiment, the carrier protein is not flagellin.

In a preferred embodiment, the carrier protein of the glycoconjugates is independently selected from the group consisting of TT, DT, DT mutants (such as CRM197), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of *C. Difficile* and PsaA. In an embodiment, the carrier protein of the glycoconjugates of the invention is DT (Diphtheria toxoid). In another embodiment, the carrier protein of the glycoconjugates of the invention is TT (tetanus toxoid). In another embodiment, the carrier protein of the glycoconjugates of the invention is PD (*Haemophilus influenzae* protein D—see, e.g., EP 0 594 610 B).

In a preferred embodiment, the capsular saccharides of the invention are conjugated to CRM197 protein. The CRM197 protein is a nontoxic form of diphtheria toxin but is immunologically indistinguishable from the diphtheria toxin. CRM197 is produced by *C. diphtheriae* infected by the nontoxigenic phage β197tox-created by nitrosoguanidine mutagenesis of the toxigenic corynephage beta (Uchida, T. et al. 1971, Nature New Biology 233:8-11). The CRM197 protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM197 protein is a safe and effective T-cell dependent carrier for saccharides. Further details about CRM197 and production thereof can be found e.g. in U.S. Pat. No. 5,614,382

Accordingly, in frequent embodiments, the glycoconjugates of the invention comprise CRM197 as the carrier protein, wherein the capsular polysaccharide is covalently linked to CRM197.

In a further embodiment, the carrier protein of the glycoconjugates is SCP (Streptococcal C5a Peptidase). All human isolates of β-hemolytic streptococci produce a highly conserved cell-wall protein SCP (Streptococcal C5a Peptidase) that specifically inactivates C5a. The scp genes encode a polypeptide containing between 1,134 and 1,181 amino acids (Brown et al., PNAS, 2005, vol. 102, no. 51 pages 18391-18396). The first 31 residues are the export signal presequence and are removed upon passing through the cytoplasmic membrane. The next 68 residues serve as a pro-sequence and must be removed to produce active SCP. The next 10 residues can be removed without loss of protease activity. At the other end, starting with Lys-1034, are four consecutive 17-residue motifs followed by a cell sorting and cell-wall attachment signal. This combined signal is composed of a 20-residue hydrophilic sequence containing an LPTTND sequence, a 17-residue hydrophobic sequence, and a short basic carboxyl terminus.

Figure 1B:
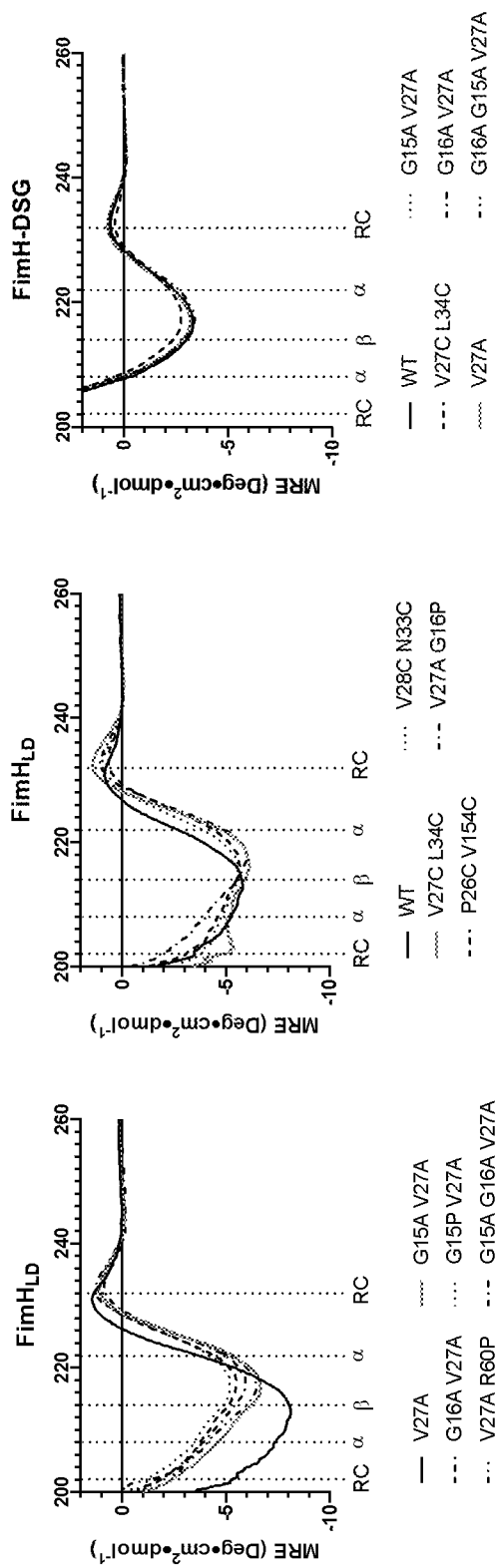

SCP can be divided in domains (see FIG. 1B of Brown et al., PNAS, 2005, vol. 102, no. 51 pages 18391-18396). These domains are the Pre/Pro domain (which comprises the export signal presequence (commonly the first 31 residues) and the pro-sequence (commonly the next 68 residues)), the protease domain (which is split in two part (protease part 1 commonly residues 89-333/334 and protease domain part 2 and commonly residues 467/468-583/584), the protease-associated domain (PA domain) (commonly residues 333/334-467/468), three fibronectin type III (Fn) domains (Fn1, commonly residues 583/584-712/713; Fn2, commonly residues 712/713-928/929/930; commonly Fn3, residues 929/930-1029/1030/1031) and a cell wall anchor domain (commonly residues 1029/1030/1031 to the C-terminus).

In an embodiment, the carrier protein of the glycoconjugates of the invention is an SCP from GBS (SCPB). An example of SCPB is provided at SEQ. ID. NO: 3 of WO97/26008. See also SEQ ID NO: 3 of WO00/34487.

In another embodiment, the carrier protein of the glycoconjugate of the invention is an SCP from GAS (SCPA). Examples of SCPA can be found at SEQ.ID.NO:1 and SEQ.ID.NO:2 of WO97/26008. See also SEQ ID Nos: 1, 2 and 23 of WO00/34487.

In a further embodiment, the carrier protein of the glyconjugate of the invention is an SCP as set forth in SEQ ID NO: 150 or 151 of WO2014/136064.

B. Adjuvants

In some aspects, the immunogenic compositions disclosed herein may further comprise at least one, two or three adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (TWEEN 80), 0.5% w/v sorbitan trioleate (SPAN 85), water-in-oil emulsions such as MONTANIDE, and poly(D,L-lactide-co-glycolide) (PLG) microparticles or nanoparticles.

In one aspect, the immunogenic compositions disclosed herein comprise aluminum salts (alum) as adjuvant (e.g., aluminum phosphate, aluminum sulfate or aluminum hydroxide). In a further aspect, the immunogenic compositions disclosed herein comprise aluminum phosphate or aluminum hydroxide as adjuvant. In one aspect, the immunogenic compositions disclosed herein comprise from 0.1 mg/mL to 1 mg/mL or from 0.2 mg/mL to 0.3 mg/mL of elemental aluminum in the form of aluminum phosphate. In one aspect, the immunogenic compositions disclosed herein comprise about 0.25 mg/mL of elemental aluminum in the form of aluminum phosphate.

Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, AS01, and the like.

Examples of known suitable immune modulatory type adjuvants with both delivery and immune modulatory features that can be used in humans include, but are not limited to, ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-di-palmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion.

Further exemplary adjuvants to enhance effectiveness of the immunogenic compositions disclosed herein include, but are not limited to (1) oil-in-water emulsion formulations (with or without other specific immunostimulating agents such as muramyl peptides (see below) or bacterial cell wall components), such as for example (a) SAF, containing 10% Squalane, 0.4% TWEEN 80, 5% pluronic-blocked polymer L121, and thr-MDP either microfluidized into a submicron emulsion or vortexed to generate a larger particle size emulsion, and (b) RIBI™ RIBI adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), preferably MPL+CWS (DETOX); (2) saponin adjuvants, such as QS21, STIMULON (Cambridge Bioscience, Worcester, Mass.), ABISCO (Isconova, Sweden), or ISCO-MATRIXRISCOMATRIX (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB2220211, EP0689454) (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In another embodiment, the adjuvant is a liposomal Quillaja Saponaria-21 (QS21) formulation comprising 5.1 mg/mL QS-21, 5 mM Succinate, 60 mM NaCl, 0.1% PS80, pH 5.6. In a further embodiment, the adjuvant is a liposomal monophosphoryl Lipid A (MPLA, Synthetic, PHAD®, Avanti) formulation comprising 15 mM phosphate buffer, pH 6.1, 4 mg/mL 1,2-dioleoyl-sn-glycero-3-phosphocholine (DOPC), 1 mg/mL Cholesterol, 0.2 mg/mL MPLA (Lot 00714551-0018-2XLipoMPL), having a liposomal particle size of 71 nm determined by dynamic light scattering. In a still further embodiment, the adjuvant is a liposomal MPLA/QS21 formulation comprising 15 mM phosphate buffer, pH 6.1, 4 mg/mL DOPC, 1 mg/mL Cholesterol, 0.2 mg/mL MPLA, and 0.2 mg/mL QS-21 (Lot 00714551-0018-2XlipoMQ), having a particle size of 75 nm for MPLA-QS21 liposomes determined by dynamic light scattering.

In a further aspect of the present disclosure, the immunogenic compositions as disclosed herein comprise a CpG oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail at page 3, line 22, to page 12, line 36, of WO 2010/125480. Methods of the present disclosure include the use of these different classes of CpG immunostimulatory oligonucleotides.

V. Methods of Purification and Production

In one aspect, the present disclosure relates to methods of producing a FimH mutated polypeptide. Such methods can include, for example, culturing a mammalian cell under a suitable condition, thereby expressing the Fim H mutant polypeptide. The method may further include harvesting the polypeptide from the culture. The process may further include purifying the polypeptide.

In some aspects, the method produces the FimH mutant polypeptide at a yield of about 0.1 g/L to 0.5 g/L. In some aspects, the yield of the FimH mutated polypeptide is at least about 1 mg/L, at least about 2 mg/L, at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 11 mg/L, at least about 12 mg/L, at least about 13 mg/L, at least about 14 mg/L, at least about 15 mg/L, at least about 16 mg/L, at least about 17 mg/L, at least about 18 mg/L, at least about 19 mg/L, at least about 20 mg/L, at least about 25 mg/L, at least about 30 mg/L, at least about 35 mg/L, at least about 40 mg/L, at least about 45 mg/L, at least about 50 mg/L, at least about 55 mg/L, at least about 60 mg/L, at least about 65 mg/L, at least about 70 mg/L, at least about 75 mg/L, at least about 80 mg/L, at least about 85 mg/L, at least about 90 mg/L, at least about 95 mg/L, or at least about 100 mg/L.

In some aspects, a cell culture suitable for the present disclosure is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally isolated. In some aspects, the fed-batch culture comprises a base medium supplemented with feed media.

In some aspects, the cells may be grown in batch or fed-batch cultures, where the culture is terminated after sufficient expression of the polypeptide, after which the expressed polypeptide is harvested and optionally isolated. In some aspects, the cells may be grown in perfusion cultures, where the culture is not terminated and new nutrients and other components are periodically or continuously added to the culture, during which the expressed polypeptide is periodically or continuously harvested.

In some aspects, the expression level or activity of the FimH mutant polypeptide is increased by at least 2-fold, at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to expression of the FimH mutant polypeptide in a bacterial cell, such as, for example, an E. coli host cell.

In some aspects, the cells may be grown in small scale reaction vessels to form a cell culture ranging in volume from a few milliliters to several liters. In some aspects, the cells may be grown in large scale commercial bioreactors to form a cell culture, wherein the cell culture may range in volume from approximately at least 1 liter to 10, 100, 250, 500, 1,000, 2,500, 5,000, 8,000, 10,000, 12,000 liters or more, or any volume in between. In some embodiments, the cell culture size may range from 10 L to 5000 L, from 10 L to 10,000 L, from 10 L to 20,000 L, from 10 L to 50,000 L, from 40 L to 50,000 L, from 100 L to 50,000 L, from 500 L to 50,000 L, from 1000 L to 50,000 L, from 2000 L to 50,000 L, from 3000 L to 50,000 L, from 4000 L to 50,000

L, from 4500 L to 50,000 L, from 1000 L to 10,000 L, from 1000 L to 20,000 L, from 1000 L to 25,000 L, from 1000 L to 30,000 L, from 15 L to 2000 L, from 40 L to 1000 L, from 100 L to 500 L, from 200 L to 400 L, or any integer in between.

The temperature of the cell culture will be selected based primarily on the range of temperatures at which the cell culture remains viable, at which a high level of polypeptide is produced, the temperature at which production or accumulation of metabolic waste products is minimized, and/or any combination of these or other factors deemed important by the practitioner. As one non-limiting example, CHO cells grow well and produce high levels of protein or polypeptide at approximately 37° C. In general, most mammalian cells grow well and/or can produce high levels or protein or polypeptide within a range of about 25° C. to 42° C., although methods taught by the present disclosure are not limited to these temperatures. Certain mammalian cells grow well and/or can produce high levels of protein or polypeptide within the range of about 35° C. to 40° C. In certain aspects, the cell culture is grown at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. at one or more times during the cell culture process.

The terms "culture" and "cell culture" as used herein refer to a cell population that is suspended in a medium under conditions suitable to survival and/or growth of the cell population. As will be clear to those of ordinary skill in the art, in some aspects, these terms as used herein refer to the combination comprising the cell population and the medium in which the population is suspended. In some aspects, the cells of the cell culture comprise mammalian cells.

In some aspects, cells may be grown in one of a variety of chemically defined media, wherein the components of the media are both known and controlled. In some aspects, cells may be grown in a complex medium, in which not all components of the medium are known and/or controlled. Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

Not all components of complex media are well characterized, and so complex media may contain additives such as simple and/or complex carbon sources, simple and/or complex nitrogen sources, and serum, among other things. In some aspects, complex media suitable for the present invention contains additives such as hydrolysates in addition to other components of defined medium as described herein. In some aspects, defined media typically includes roughly fifty chemical entities at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some aspects, supplementary components may be added to the initial cell culture. In some aspects, supplementary components may be added after the beginning of the cell culture. Typically, trace elements refer to a variety of inorganic salts included at micromolar or lower levels. For example, commonly included trace elements are zinc, selenium, copper, and others. In some aspects, iron (ferrous or ferric salts) can be included as a trace element in the initial cell culture medium at micromolar concentrations. Manganese is also frequently included among the trace elements as a divalent cation (MnCl2 or MnSO4) in a range of nanomolar to micromolar concentrations. Numerous less common trace elements are usually added at nanomolar concentrations.

In some aspects, the medium used in the method of the invention is a medium suitable for supporting high cell density, such as for example 1×106 cells/mL, 5×106 cells/mL, 1×107 cells/mL, 5×107 cells/mL, 1×108 cells/mL or 5×108 cells/mL, in a cell culture. In some aspects, the cell culture is a mammalian cell fed-batch culture, preferably a CHO cells fed-batch culture.

In some aspects, the cell culture medium comprises phenylalanine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tyrosine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tryptophan at a concentration below 2 mM, below 1 mM, between 0.1 and 2 mM, between 0.1 to 1 mM, between 0.5 and 1.5 mM or between 0.5 to 1 mM. In some aspects, the cell culture medium comprises methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises leucine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises serine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises threonine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises two of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine and tyrosine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine and tryptophan at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine and methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tyrosine and tryptophan at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tyrosine and methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tryptophan and methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises three of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine, tyrosine and tryptophan at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine, tyrosine and methionine at a concentration below 2 mM, below 1 mM, between 0.1 and 2 mM, between 0.1 to 1 mM, between 0.5 and 1.5 mM or between 0.5 to 1 mM.

In some aspects, the cell culture medium comprises phenylalanine, tryptophan and methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises tyrosine, tryptophan and methionine at a concentration below 2 mM, below 1 mM, between 0.1 and 2 mM, between 0.1 to 1 mM, between 0.5 and 1.5 mM or between 0.5 to 1 mM.

In some aspects, the cell culture medium comprises four of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some aspects, the cell culture medium comprises phenylalanine, tyrosine, tryptophan and methionine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises five of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises six of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises seven of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium comprises phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some aspects, the cell culture medium further comprises at least 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium further comprises at least 5 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium further comprises glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium further comprises at least 1, 2, 3, 4, 5, 6, 7, 8, or 9 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium further comprises at least 5 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium further comprises valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some aspects, the cell culture medium comprises serine at a concentration above 3 mM, 5 mM, 7 mM, 10 mM, 15 mM or 20 mM, preferably 10 mM. In some aspects, the cell culture medium comprises valine at a concentration above 3 mM, 5 mM, 7 mM, 10 mM, 15 mM or 20 mM, preferably 10 mM. In some aspects, the cell culture medium comprises cysteine at a concentration above 3 mM, 5 mM, 7 mM, 10 mM, 15 mM or 20 mM, preferably 10 mM. In some aspects, the cell culture medium comprises isoleucine at a concentration above 3 mM, 5 mM, 7 mM, 10 mM, 15 mM or 20 mM, preferably 10 mM.

In some aspects, the cell culture medium comprises leucine at a concentration above 3 mM, 5 mM, 7 mM, 10 mM, 15 mM or 20 mM, preferably 10 mM. In some aspects, the above cell culture medium is for use in a method as disclosed herein. In some aspects, the above cell culture medium is used in a method as disclosed herein as a base media. In some aspects, the above cell culture medium is used a method as disclosed herein as a feed media.

The methods of the present disclosure may be used with any cell culture method that is amenable to the desired process (e.g., production of a recombinant protein). As a non-limiting example, cells may be grown in batch or fed-batch cultures, where the culture is terminated after sufficient expression of the recombinant protein (e.g., antibody), after which the expressed protein is harvested. Alternatively, as another non-limiting example, cells may be grown in batch-refeed, where the culture is not terminated and new nutrients and other components are periodically or continuously added to the culture, during which the expressed recombinant protein is harvested periodically or continuously. Other suitable methods (e.g., spin-tube cultures) are known in the art and can be used to practice the present invention.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although methods taught by the present disclosure are not limited to these temperatures. Certain mammalian cells grow well and can produce desired products (e.g., recombinant proteins or antibodies) within the range of about 35° C. to 40° C. In certain aspects, a cell culture is grown at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In some embodiment, the cells are grown at 37° C. In some aspects, the cells are grown at 36.5° C.

In some aspects, the cells may be grown during the initial growth phase (or growth phase) for a greater or lesser amount of time, depending on the needs of the practitioner and the requirement of the cells themselves. In some aspects, the cells are grown for a period of time sufficient to achieve a predefined cell density. In some aspects, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some aspects, the cells are grown until the cell density does not increase by more than 15%, 14%, 13%, 12%, 11%, 10%, 9%, 8%, 7%, 6%, 5%, 4%, 3%, 2% or 1% per day of culture. In some aspects, the cells are grown until the cell density does not increase by more than 5% per day of culture.

In some aspects the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

At the end of the initial growth phase, at least one of the culture conditions may be shifted so that a second set of culture conditions is applied and a metabolic shift occurs in the culture. A metabolic shift can be accomplished by, e.g., a change in the temperature, pH, osmolality or chemical inductant level of the cell culture. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. The timing of the culture shift will be determined by the practitioner of the present invention, based on protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some aspects, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In some aspects, the temperature of the culture is shifted. According to this embodiment, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

The term "titer" as used herein refers, for example, to the total amount of recombinantly expressed protein produced by a cell culture in a given amount of medium volume. Titer is typically expressed in units of grams of protein per liter of medium.

In some aspects, cell growth is increased by at least 5%, 10%, 15%, 20% or 25% as compared to the control culture. In some aspects, cell growth is increased by at least 10% as compared to the control culture. In some aspects, cell growth is increased by at least 20% as compared to the control culture.

In some aspects, the productivity is determined by titer and/or volumetric productivity. In some aspects, the productivity is determined by titer. In some aspects, the productivity is increased by at least 5%, 10%, 15%, 20% or 25% as compared to the control culture. In some aspects, the productivity is increased by at least 10% as compared to a control culture. In some aspects, the productivity is increased by at least 20% as compared to a control culture.

Purification

In some aspects, the method for producing a FimH mutant polypeptide includes isolating and/or purifying the polypeptide. In some aspects, the expressed polypeptide is secreted into the medium and thus cells and other solids may be removed by centrifugation and/or filtration. In a preferred embodiment, the polypeptide or a fragment thereof is soluble.

The FimH mutated polypeptide produced in accordance with the methods described herein may be harvested from host cells and isolated using any suitable method, and are generally known in the art (e.g. Ruiz-Arguello et al., J. Gen. Virol., 85:3677-3687 (2004)). Suitable methods for purifying the polypeptide include precipitation and various types of chromatography, such as hydrophobic interaction, ion exchange, affinity, chelation, and size exclusion, all of which are known in the art. Suitable purification schemes may include two or more of these or other suitable methods. In some aspects, one or more of the polypeptides may include a "tag" that facilitates purification or detection. Examples include, e.g., His tag (binds to metal ion, e.g. hexahistidine), an antibody, maltose-binding protein (MBP) (binds to amylose), glutathione-S-transferase (GST) (binds to glutathione), FLAG tag (binds to anti-flag antibody), Strep tag (binds to streptavidin or a derivative thereof). Such tagged polypeptides may conveniently be isolated, for example from conditioned media, by chelating chromatography or affinity chromatography. Optionally, the tag sequence may be cleaved post-purification. In one aspect, the FimH mutant polypeptide does not include a purification tag.

In one aspect, the FimH mutant polypeptides can be isolated by first obtaining the cell culture supernatant, and then subjecting the supernatant to both ultrafiltration and diafiltration methods. Such filtration methods are known to those of skilled in the art. Following ultrafiltration and diafiltration, the resulting cell-free solution is then subjected to a chromatography step, such as Ni-NTA chromatography using, for example, nickel affinity resin. This step can then be followed by dialysis, which can then be followed by cation exchange chromatography, such as with a SP column. Use of acidic pH (e.g. less than about 6.0, less than about 5.5, less than about 5.0, less than about 4.5, about 4.4, about 4.3, about 4.2, about 4.1 or about 4.0 or less) during the purification on SP-SEPHAROSE can be desirable under certain conditions.

While specific strains of E. coli may be referenced herein, it should be understood that the polypeptide derived from E. coli or a fragment thereof are not limited to specific strains unless specified.

VI. Uses of the Compositions

In one aspect, the disclosure provides the use of a FimH mutant polypeptide, nucleic acids encoding such mutant, vectors for expressing such mutant, compositions comprising such mutant or nucleic acids as a medicament, or in the manufacture of a medicament, for eliciting an immune response against E. coli infection or for preventing E. coli infection in a subject.

In other aspects, the present disclosure provides a method of eliciting an immune response against E. coli in a subject, such as a human, comprising administering to the subject an effective amount of a FimH mutant polypeptide, a nucleic acid molecule encoding a FimH mutant polypeptide, or a composition comprising a FimH mutant polypeptide or nucleic acid molecule. The present disclosure also provides a method of preventing E. coli infection in a subject, comprising administering to the subject an effective amount of a pharmaceutical composition, such as a vaccine, comprising a FimH mutant polypeptide, a nucleic acid encoding a FimH mutant polypeptide, or a vector expressing a FimH mutant polypeptide. In some particular aspects, the pharmaceutical composition comprises a FimH mutant polypeptide as disclosed herein. In some aspects of the methods provided herein above, the subject is a human.

In other aspects, the present disclosure provides a method for inducing an immune response in a subject against extra-intestinal pathogenic E. coli, or inducing the production of opsonophagocytic and/or neutralizing antibodies in a subject that are specific to extra-intestinal pathogenic E. coli, wherein the method comprises administering to the subject an effective amount of any of the compositions describe herein, such as those comprising a FimH mutant polypeptide as described herein. In a further aspect of such methods, the subject is at risk of developing a urinary tract infection, and/or at risk of developing bacteremia, and/or at risk of developing sepsis.

In a further aspect, the present disclosure provides a method of eliciting an immune response against E. coli in a mammal, comprising administering to the mammal an effective amount of any of the compositions described herein. For example, in one aspect the immune response comprises opsonophagocytic and/or neutralizing antibodies against E. coli. In a further aspect, the immune response protects the mammal from an E. coli infection.

In a further aspect the present disclosure provides a method of preventing, treating or ameliorating a bacterial infection, disease or condition in a subject, comprising administering to the subject an immunologically effective amount of any of the compositions described herein.

In the methods of the present disclosure, the composition may be administered to the subject with or without administration of an adjuvant. The effective amount administered to the subject is an amount that is sufficient to elicit an immune response against an E. coli antigen, such as a FimH protein, in the subject. Subjects that can be selected for treatment include those that are at risk for developing an E. coli infection, such as those at risk of developing a urinary tract infection, and/or at risk of developing bacteremia, and/or at risk of developing sepsis, because of exposure or the possibility of exposure to E. coli.

"As used herein, "subject" means a mammal, preferably a human. In one embodiment, the subject is at risk of any one of the conditions selected from the group consisting of urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

Administration of the compositions provided by the present disclosure, such as pharmaceutical compositions, can be carried out using standard routes of administration. Non-limiting embodiments include parenteral administration, such as intradermal, intramuscular, subcutaneous, transcutaneous, mucosal, or oral administration.

The total dose of the composition provided to a subject during one administration can be varied as is known to the skilled practitioner.

It is also possible to provide one or more booster administrations of one or more of the immunogenic compositions. If a boosting vaccination is performed, typically, such a boosting vaccination will be administered to the same subject at a moment between one week and 10 years, preferably between two weeks and six months, after administering the composition to the subject for the first time (which is in such cases referred to as "priming vaccination"). In alternative boosting regimens, it is also possible to administer different vectors, e.g., one or more adenovirus, or other vectors such as modified vaccinia virus of Ankara (MVA), or DNA, or protein, to the subject after the priming vaccination. The immunogenic compositions provided by the present disclosure may be used together with one or more other immunogenic compositions.

Dosages of the Compositions

Dosage regimens may be adjusted to provide the optimum desired response. For example, a single dose of a mutated FimH polypeptide may be administered, several divided doses may be administered over time, or the dose may be proportionally reduced or increased as indicated by the exigencies of the situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In some aspects, the amount of the FimH mutant polypeptide in the composition, may range from about 10 μg to about 300 μg of each protein antigen. In some aspects, the amount of the FimH mutant polypeptide in the composition may range from about 20 μg to about 200 μg of each protein antigen.

The amount of glycoconjugate(s) in each dose is selected as an amount which induces an immunoprotective response without significant, adverse side effects in typical vaccines. Such amount will vary depending upon which specific immunogen is employed and how it is presented. The amount of a particular glycoconjugate in an immunogenic composition can be calculated based on total polysaccharide for that conjugate (conjugated and non-conjugated). For example, a glycoconjugate with 20% free polysaccharide will have about 80 g of conjugated polysaccharide and about 20 g of non-conjugated polysaccharide in a 100 g polysaccharide dose. The amount of glycoconjugate can vary depending upon the E. coli serotype. The saccharide concentration can be determined by the uronic acid assay.

The "immunogenic amount" of the different polysaccharide components in the immunogenic composition, may diverge and each may comprise about 1.0 g, about 2.0 g, about 3.0 g, about 4.0 g, about 5.0 g, about 6.0 g, about 7.0 g, about 8.0 g, about 9.0 g, about 10.0 g, about 15.0 g, about 20.0 g, about 30.0 g, about 40.0 pg, about 50.0 pg, about 60.0 pg, about 70.0 pg, about 80.0 pg, about 90.0 pg, or about 100.0 g of any particular polysaccharide antigen. Generally, each dose will comprise 0.1 g to 100 g of polysaccharide for a given serotype, particularly 0.5 g to 20 g, more particularly 1 g to 10 g, and even more particularly 2 g to 5 g. Any whole number integer within any of the above ranges is contemplated as an embodiment of the disclosure. In one embodiment, each dose will comprise 1 g, 2 g, 3 g, 4 g, 5 g, 6 g, 7 g, 8 g, 9 g, 10 g, 15 g or 20 g of polysaccharide for a given serotype.

VII. Combination with a Saccharide and/or Polypeptide or Fragment Thereof Derived from *Klebsiella Pneumoniae*

*Klebsiella pneumoniae* (*K. pneumoniae*) is a Gram-negative pathogen, known to cause urinary tract infections, bacteremia, and sepsis. Multidrug-resistant *K. pneumoniae* infections are an increasing cause of mortality in vulnerable populations at risk. The O-antigen serotypes are highly prevalent among strains causing invasive disease globally and derived O-antigen glycoconjugates are attractive as vaccine antigens.

In one aspect, any of the compositions disclosed herein may further comprise at least one saccharide that is, or is derived from, at least one *K. pneumoniae* serotype selected from O1 (and d-Gal-III variants), O2 (and d-Gal-III variants), O2ac, O3, O4, O5, O7, O8, and O12. In a preferred embodiment, any of the compositions disclosed herein may further comprise a polypeptide derived from *K. pneumoniae* selected from a polypeptide derived from *K. pneumoniae* Type I fimbrial protein or an immunogenic fragment thereof; or a polypeptide derived from *K. pneumoniae* Type III fimbrial protein or an immunogenic fragment thereof; or a combination thereof.

As is known in the art, *K. pneumoniae* O1 and O2 O-antigens and their corresponding v1 and v2 subtypes are polymeric galactans that differ in the structures of their repeat units. *K. pneumoniae* O1 and O2 antigens contain homopolymer galactose units (or galactans). *K. pneumoniae* O1 and O2 antigens each contain D-galactan I units (sometimes referred to as the O2a repeat unit), but O1 antigens differ in that O1 antigens have a D-galactan II cap structure. D-galactan III (d-Gal-III) is a variant of D-galactan I. Structures of the base galactans I and III that define the two distinct serotype O2 subtypes, O2v1 and O2v2; and structures of the derived chimeras resulting from capping by galactan II which yields subtypes O1v1 and O1v2, are shown in Kelly S D, et al. J Biol Chem 2019; 294:10863-76; and Clarke B R, et al. J Biol Chem 2018; 293:4666-79.

In some embodiments, the saccharide derived from *K. pneumoniae* O1 includes a repeat unit of [→3)-β-D-Galf-(1→3)-α-D-Galp-(1→]. In some embodiments, the saccharide derived from *K. pneumoniae* O1 includes a repeat unit of [→3)-α-D-Galp-(1→3)-β-D-Galp-(1→]. In some embodiments, the saccharide derived from *K. pneumoniae* O1 includes a repeat unit of [→3)-β-D-Galf-(1→3)-α-D-Galp-(1→], and a repeat unit of [→3)-α-D-Galp-(1→3)-β-D-Galp-(1→]. In some embodiments, the saccharide derived from *K. pneumoniae* O1 includes a repeat unit of →3)-β-D-Galf-(1→3)-[α-D-Galp-(1→4)]-α-D-Galp-(1→] (referred to as the D-Gal-III repeat unit). (Kol O., et al. (1992) Carbohydr. Res. 236, 339-344; Whitfield C., et al. (1991) J. Bacteriol. 173, 1420-1431).

In some embodiments, the saccharide derived from *K. pneumoniae* O2 includes a repeat unit of [→3)-α-D-Galp-(1→3)-β-D-Galf-(1→] (which may be an element of *K. pneumoniae* serotype O2a antigen). In some embodiments, the saccharide derived from *K. pneumoniae* O2 includes a repeat unit of [→3)-β-D-GlcpNAc-(1→5)-β-D-Galf-(1→] (which may be an element of *K. pneumoniae* serotype O2c antigen). In some embodiments, the saccharide derived from *K. pneumoniae* O2 includes a modification of the O2a repeat unit by side chain addition of (1→4)-linked Galp residues (which may be an element of the *K. pneumoniae* O2afg antigen). In some embodiments, the saccharide derived from *K. pneumoniae* O2 includes a modification of the O2a repeat unit by side chain addition of (1→2)-linked Galp residues (which may be an element of the *K. pneumoniae* O2aeh antigen). (Whitfield C., et al. (1992) J. Bacteriol. 174, 4913-4919).

Without being bound by mechanism or theory, O-antigen polysaccharide structure of *K. pneumoniae* serotypes O3 and O5 are disclosed in the art to be identical to those of *E. coli* serotypes O9a (Formula O9a) and O8 (Formula O8), respectively.

In some embodiments, the saccharide derived from *K. pneumoniae* O4 includes a repeat unit of [→4)-α-D-Galp-(1→2)-β-D-Ribf-(1→)]. In some embodiments, the saccharide derived from *K. pneumoniae* O7 includes a repeat unit of [→2-α-L-Rhap-(1→2)-β-D-Ribf-(1→3)-α-L-Rhap-(1→3)-α-L-Rhap-(1→]. In some embodiments, the saccharide derived from *K. pneumoniae* O8 serotype includes the same repeat-unit structure as *K. pneumoniae* O2a, but is nonstoichiometrically O-acetylated. In some embodiments, the saccharide derived from *K. pneumoniae* O12 serotype includes a repeat unit of [α-Rhap-(1→3)-β-GlcpNAc] disaccharide repeat unit.

In one aspect, the invention includes a composition including a polypeptide derived from *E. coli* FimH or a fragment thereof; and at least one saccharide that is, or derived from, at least one *K. pneumoniae* serotype selected from O1 (and d-Gal-III variants), O2 (and d-Gal-III variants), O2ac, O3, O4, O5, O7, O8, and O12. In some embodiments, the composition includes saccharides from or derived from one or more of serotypes O1, O2, O3, and O5, or a combination thereof. In some embodiments, the composition includes saccharides from or derived from each of serotypes O1, O2, O3, and O5.

In another aspect, the invention includes a composition including at least one saccharide that is, or is derived from, at least one *K. pneumoniae* serotype selected from O1 (and d-Gal-III variants), O2 (and d-Gal-III variants), O2ac, O3, O4, O5, O7, O8, and O12; and a saccharide derived from an *E. coli* O-antigen having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In some embodiments, the composition includes a saccharide from or derived from one or more of *K. pneumoniae* serotypes O1, O2, O3 and O5, or a combination thereof. In some embodiments, the composition includes a saccharide from or derived from each of *K. pneumoniae* serotypes O1, O2, O3 and O5. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In another aspect, the invention relates to a composition including a polypeptide derived from *E. coli* FimH or a fragment thereof; at least one saccharide that is, or derived from, at least one *K. pneumoniae* serotype selected from O1 (and d-Gal-III variants), O2 (and d-Gal-III variants), O2ac, O3, O4, O5, O7, O8, and O12; and a saccharide having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100, preferably from 31 to 90. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In some embodiments, the composition includes at least one saccharide derived from any one *K. pneumoniae* type selected from the group consisting of O1, O2, O3, and O5.

In some embodiments, the composition includes at least one saccharide derived from *K. pneumoniae* type O1. In one aspect of this embodiment, the *K. pneumoniae* O-antigen is selected from subtype v1 (O1v1) or subtype v2 (O1v2). In one aspect of this embodiment, the *K. pneumoniae* O-antigen is selected from subtype v1 (O1v1) and subtype v2 (O1v2). In some embodiments, the composition includes at least one saccharide derived from *K. pneumoniae* type O2. In one aspect of this embodiment, the *K. pneumoniae* O-antigen is selected from subtype b1 (O2v1) or subtype v2 (O2v2). In one aspect of this embodiment, the *K. pneumoniae* O-antigen is selected from subtype v1 (O2v1) and subtype v2 (O2v2). In another aspect, the *K. pneumoniae* O-antigen is selected from the group consisting of: a) serotype O1 subtype v1 (O1v1), b) serotype O1 subtype v2 (O1v2), c) serotype O2 subtype v1 (O2v1), and d) serotype O2 subtype v2 (O2v2). In one aspect of this embodiment, the *K. pneumoniae* O-antigen is subtype v1 (O1v1). In one aspect of this embodiment, the *K. pneumoniae* O-antigen is subtype v2 (O1v2). In one aspect of this embodiment, the *K. pneumoniae* O-antigen is subtype v1 (O2v1). In one aspect of this embodiment, the *K. pneumoniae* O-antigen is subtype v2 (O2v2). In another aspect of this embodiment, the composition comprises one, two, three or four *K. pneumoniae* O-antigen selected from the group consisting of: a) serotype O1 subtype v1 (O1v1), b) serotype O1 subtype v2 (O1v2), c) serotype O2 subtype v1 (O2v1), and d) serotype O2 subtype v2 (O2v2). In some embodiments, the composition includes a combination of saccharides derived from *K. pneumoniae*, wherein a first saccharide is derived from any one of *K. pneumoniae* types selected from the group consisting of O1, O2, O3, and O5; and a second saccharide is derived from a saccharide is derived from any one of *K. pneumoniae* types selected from the group consisting of O1 (and d-Gal-III variants), O2 (and d-Gal-III variants), O2ac, O3, O4, O5, O7, O8, and O12. For example, in some embodiments, the composition includes at least one saccharide derived from *K. pneumoniae* type O1 and at least one saccharide derived from *K. pneumoniae* type O2. In a preferred embodiment, the saccharide derived from *K. pneumoniae* is conjugated to a carrier protein; and the saccharide derived from *E. coli* is conjugated to a carrier protein.

In another aspect, the invention includes a composition including a polypeptide derived from *E. coli* FimH or a fragment thereof; and at least one saccharide derived from any one *K. pneumoniae* type selected from the group consisting of O1, O2, O3, and O5.

In another aspect, the invention includes at least one saccharide derived from any one *K. pneumoniae* type selected from the group consisting of O1, O2, O3, and O5; and at least one saccharide derived from *E. coli* having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In some embodiments, the composition includes at least one saccharide derived from *K. pneumoniae* type O1; and at least one saccharide derived from *E. coli* having a structure selected from the group consisting of Formula O8 and Formula O9. In another embodiment, the composition includes at least one saccharide derived from *K. pneumoniae* type O2; and at least one saccharide derived from *E. coli* having a structure selected from the group consisting of Formula O8 and Formula O9. In another embodiment, the composition includes at least one saccharide derived from *K. pneumoniae* type O1; at least one saccharide derived from *K. pneumoniae* type O2; and at least one saccharide derived from *E. coli* having a structure selected from the group consisting of Formula O8 and Formula O9.

In one embodiment, the invention provides a method of inducing an immune response to *K. pneumoniae* in a subject comprising administering to the subject an immunologically effective amount of an immunogenic composition comprising at least one glycoconjugate from *E. coli* serotype O8 or O9, wherein said immunogenic composition does not comprise glycoconjugates from *K. pneumoniae* serotype O5 or O3. In one aspect, the composition includes a saccharide derived from an *E. coli* O-antigen having Formula O8 and does not include a saccharide derived from *K. pneumoniae* serotype O5. In another aspect, the composition includes a saccharide derived from an *E. coli* O-antigen having Formula O9 and does not include a saccharide derived from *K. pneumoniae* serotype O3.

In another embodiment, the invention provides a method of inducing an immune response to *E. coli* in a subject comprising administering to the subject an immunologically effective amount of an immunogenic composition comprising at least one glycoconjugate from *K. pneumoniae* serotype O5 or O3, or a variant thereof, wherein said immunogenic composition does not comprise glycoconjugates from *E. coli* serotype O8 or O9. In one aspect, the composition includes a saccharide derived from *K. pneumoniae* serotype O5 and does not include a saccharide derived from an *E. coli* O-antigen having Formula O8. In another aspect, the composition includes a saccharide derived from *K. pneumoniae* serotype O3 and does not include a saccharide derived from an *E. coli* O-antigen having Formula O9.

In some embodiments, the composition includes at least one saccharide that is, or is derived from, at least one *K. pneumoniae* serotype selected from O1 (and d-Gal-III variants), O2 (and d-Gal-III variants), O2ac, O3, O4, O5, O7, O8, and O12; at least one saccharide derived from *E. coli* having a structure selected from the group consisting of Formula O8 and Formula O9. In some embodiments, the composition includes at least one saccharide that is, or derived from, at least one *K. pneumoniae* serotype selected from O1 (and d-Gal-III variants), O2 (and d-Gal-III variants), O2ac, O3, O4, O5, O7, O8, and O12; at least one saccharide derived from *E. coli* having a structure selected from the group consisting of Formula O1A, Formula O1B, Formula O2, Formula O6, and Formula O25B.

In some embodiments, the composition further includes a polypeptide derived from *K. pneumoniae* selected from a polypeptide derived from *K. pneumoniae* Type I fimbrial protein or an immunogenic fragment thereof; or a polypeptide derived from *K. pneumoniae* Type III fimbrial protein or an immunogenic fragment thereof, or a combination thereof. The sequences of said polypeptides are known in the art.

VIII. Nanoparticles

In another aspect, disclosed herein is an immunogenic complex that includes 1) a nanostructure; and 2) at least one fimbrial polypeptide antigen or fragment thereof. Preferably, the fimbrial polypeptide or fragment thereof is derived from *E. coli* fimbrial H (fimH). In a preferred embodiment, the fimbrial polypeptide is selected from any one of the fimbrial polypeptides described above. For example, the fimbrial polypeptide may comprise any one amino acid sequence selected from SEQ ID NOs:1-65.

In some embodiments, the antigen is fused or conjugated to the nanostructure exterior to stimulate development of adaptive immune responses to the displayed epitopes. In some embodiments, the immunogenic complex further includes an adjuvant or other immunomodulatory compounds attached to the exterior and/or encapsulated in the cage interior to help tailor the type of immune response generated for each pathogen. In some embodiments, the nanostructure includes a single assembly including a plurality of identical first nanostructure-related polypeptides.

In alternative embodiments, the the nanostructure includes a plurality assembly, including a plurality of identical first nanostructure-related polypeptides and a plurality of second assemblies, each second assembly comprising a plurality of identical second nanostructure-related polypeptides.

Various nanostructure platforms can be employed in generating the immunogenic compositions described herein. In some embodiments, the nanostructures employed are formed by multiple copies of a single subunit. In some embodiments, the nanostructures employed are formed by multiple copies of multiple different subunits.

The nanostructures are typically ball-like shaped, and/or have rotational symmetry (e.g., with 3-fold and 5-fold axis), e.g., with an icosahedral structure exemplified herein.

In some embodiments, the antigen is presented on self-assembling nanoparticles such as self-assembling nanostructures derived from ferritin (FR), E2p, Qβ, and I3-01. E2p is a redesigned variant of dihydrolipoyl acyltransferase from *Bacillus stearothermophilus*. I3-01 is an engineered protein that may self-assemble into hyperstable nanoparticles. Sequences of the subunits of these proteins are known in the art. In a first aspect, disclosed herein is a nanostructure-related polypeptide comprising an amino acid sequence that is at least 75% identical over its length, and identical at least at one identified interface position, to the amino acid sequence of a nanostructure-related polypeptide selected from the group consisting of SEQ ID NOS: 66-105. The nanostructure-related polypeptides can be used, for example, to prepare the nanostructures. The nanostructure-related polypeptides were designed for their ability to self-assemble in pairs to form nanostructures, such as icosahedral nanostructures.

In some embodiments, the nanostructure includes (a) a plurality of first assemblies, each first assembly comprising a plurality of identical first nanostructure-related polypeptides, wherein the first nanostructure-related polypeptides comprise the amino acid sequence of a nanostructure-related polypeptide selected from the group consisting of SEQ ID NOS: 66-105; and (b) a plurality of second assemblies, each second assembly comprising a plurality of identical second nanostructure-related polypeptides, wherein the second nanostructure-related polypeptides comprise the amino acid sequence of a nanostructure-related polypeptide selected from the group consisting of SEQ ID NOS: 66-105, and wherein the second nanostructure-related polypeptide differs from the first nanostructure-related polypeptide; wherein the plurality of first assemblies non-covalently interact with the plurality of second assemblies to form a nanostructure;

The nanostructures include symmetrically repeated, non-natural, non-covalent polypeptide-polypeptide interfaces that orient a first assembly and a second assembly into a nanostructure, such as one with an icosahedral symmetry.

SEQ ID NOS: 66-105 provide the amino acid sequence of exemplary nanostructure-related polypeptides. The number of interface residues for the exemplary nanostructure-related polypeptides of SEQ ID NO:66-105 range from 4-13 residues. In various embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given nanostructure-related polypeptide), to the amino acid sequence of a nanostructure-related polypeptide selected from the group consisting of SEQ ID NOS: 66-105. In other embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a nanostructure-related polypeptide selected from the group consisting of SEQ ID NOS: 66-105. In further embodiments, the nanostructure-related polypeptides include a nanostructure-related polypeptide having the amino acid sequence of a nanostructure-related polypeptide selected from the group consisting of SEQ ID NOS: 66-105.

In one non-limiting embodiment, the nanostructure-related polypeptides can be modified to facilitate covalent linkage to a "cargo" of interest. In one non-limiting example, the nanostructure-related polypeptides can be modified, such as by introduction of various cysteine residues at defined positions to facilitate linkage to one or more antigens of interest, such that a nanostructure of the nanostructure-related polypeptides would provide a scaffold to provide a large number of antigens for delivery as a vaccine to generate an improved immune response.

In some embodiments, some or all native cysteine residues that are present in the nanostructure-related polypeptides but not intended to be used for conjugation may be mutated to other amino acids to facilitate conjugation at defined positions. In another non-limiting embodiment, the nanostructure-related polypeptides may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the nanostructure-related polypeptides can be modified, for example, by introducing cysteine residues that will allow chemical conjugation of such a lipid or organic polymer to the monomer or resulting assembly surface. In another non-limiting example, the nanostructure-related polypeptides can be modified, for example, by introducing cysteine residues that will allow chemical conjugation of fluorophores or other imaging agents that allow visualization of the nanostructures in vitro or in vivo.

Surface amino acid residues on the nanostructure-related polypeptides can be mutated in order to improve the stability or solubility of the protein subunits or the assembled nanostructures. As will be known to one of skill in the art, if the nanostructure-related polypeptide has significant sequence homology to an existing protein family, a multiple sequence alignment of other proteins from that family can be used to guide the selection of amino acid mutations at non-conserved positions that can increase protein stability and/or solubility, a process referred to as consensus protein design (9).

Surface amino acid residues on the nanostructure-related polypeptides can be mutated to positively charged (Arg, Lys) or negatively charged (Asp, Glu) amino acids in order to endow the protein surface with an overall positive or overall negative charge. In one non-limiting embodiment, surface amino acid residues on the nanostructure-related polypeptides can be mutated to endow the interior surface of the self-assembling nanostructure with a high net charge. Such a nanostructure can then be used to package or encapsulate a cargo molecule with the opposite net charge due to the electrostatic interaction between the nanostructure interior surface and the cargo molecule. In one non-limiting embodiment, surface amino acid residues on the nanostructure-related polypeptides can be mutated primarily to Arginine or Lysine residues in order to endow the interior surface of the self-assembling nanostructure with a net positive charge. Solutions containing the nanostructure-related polypeptides can then be mixed in the presence of a nucleic acid cargo molecule such as a dsDNA, ssDNA, dsRNA, ssRNA, cDNA, miRNA., siRNA, shRNA, piRNA, or other nucleic acid in order to encapsulate the nucleic acid inside the self-assembling nanostructure. Such a nanostructure could be used, for example, to protect, deliver, or concentrate nucleic acids.

In one embodiment, the nanostructure has icosahedral symmetry. In this embodiment, the nanostructure may comprise 60 copies of the first nanostructure-related polypeptide and 60 copies of the second nanostructure-related polypeptide. In one such embodiment, the number of identical first nanostructure-related polypeptides in each first assembly is different than the number of identical second nanostructure-related polypeptides in each second assembly. For example, in one embodiment, the nanostructure comprises twelve first assemblies and twenty second assemblies; in this embodiment, each first assembly may; for example, comprise five copies of the identical first nanostructure-related polypeptide, and each second assembly may, for example, comprise three copies of the identical second nanostructure-related polypeptide. In another embodiment, the nanostructure comprises twelve first assemblies and thirty second assemblies; in this embodiment, each first assembly may, for example, comprise five copies of the identical first nanostructure-related polypeptide, and each second assembly may, for example, comprise two copies of the identical second nanostructure-related polypeptide. In a further embodiment, the nanostructure comprises twenty first assemblies and thirty second assemblies; in this embodiment, each first assembly may, for example, comprise three copies of the identical first nanostructure-related polypeptide, and each second assembly may, for example, comprise two copies of the identical second nanostructure-related polypeptide. All of these embodiments are capable of forming synthetic nanomaterials with regular icosahedral symmetry.

EXAMPLES

In order that the disclosure may be better understood, the following examples are set forth. These examples are for purposes of illustration only and are not to be construed as limiting the scope of the disclosure in any manner.

Example 1: Antigen Design

Mutations in $FimH_{LD}$ or FimH-DSG were designed to lock the FimH lectin domain in an open conformation with the goal of improving functional immunogenicity. Mutations were of different classes, described in the Tables 2-9 below. The amino acid sequences for the various mutated FimH polypeptides are shown in Table 1.

TABLE 2

Wild type FimHLD constructs including introduction of naturally occurring amino acid substitution commong among UTI clinical isolates

| SEQ ID NO: | Protein ID | Substitutions |
|---|---|---|
| 1 | FimHLD_WT | WT |
| | FimHLD_V27A | V27A |

TABLE 3

Substitutions in the ligand binding site of $FimH_{LD}$

| SEQ ID NO: | Protein ID | Substitutions |
|---|---|---|
| 3 | FimHLD_F1I | F1I |
| 4 | FimHLD_F1L | F1L |
| 5 | FimHLD_F1V | F1V |
| 6 | FimHLD_F1M | F1M |
| 7 | FimHLD_F1Y | F1Y |
| 8 | FimHLD_F1W | F1W |
| 9 | FimHLD_Q133K | Q133K |

TABLE 4

Glycine switch mutations in the $FimH_{LD}$

| SEQ ID NO: | Protein ID | Substitutions |
|---|---|---|
| 10 | FimHLD_G15A | G15A |
| 11 | FimHLD_G15P | G15P |
| 12 | FimHLD_G16A | G16A |

TABLE 4-continued

Glycine switch mutations in the $FimH_{LD}$

| SEQ ID NO: | Protein ID | Substitutions |
|---|---|---|
| 13 | FimHLD_G16P | G16P |
| 14 | FimHLD_G15A_G16A | G15A G16A |
| 15 | FimHLD_R60P | R60P |
| 16 | FimHLD_G65A | G65A |

TABLE 5

Cysteine pairs for disulfide bond stabilization in the $FimH_{LD}$

| SEQ ID NO: | Protein ID | Substitutions |
|---|---|---|
| 17 | FimHLD_P12C_A18C | P12C A18C |
| 18 | FimHLD_G14C_F144C | G14C F144C |
| 19 | FimHLD_P26C_V35C | P26C V35C |
| 20 | FimHLD_P26C_V154C | P26C V154C |
| 21 | FimHLD_P26C_V156C | P26C V156C |
| 22 | FimHLD_V27C_L34C | V27C L34C |
| 23 | FimHLD_V28C_N33C | V28C N33C |
| 24 | FimHLD_V28C_P157C | V28C P157C |
| 25 | FimHLD_Q32C_Y108C | Q32C Y108C |
| 26 | FimHLD_N33C_L109C | N33C L109C |
| 27 | FimHLD_N33C_P157C | N33C P157C |
| 28 | FimHLD_V35C_L107C | V35C L107C |
| 29 | FimHLD_V35C_L109C | V35C L109C |
| 30 | FimHLD_S62C_T86C | S62C T86C |
| 31 | FimHLD_S62C_L129C | S62C L129C |
| 32 | FimHLD_Y64C_L68C | Y64C L68C |
| 33 | FimHLD_Y64C_A127C | Y64C A127C |
| 34 | FimHLD_L68C_F71C | L68C F71C |
| 35 | FimHLD_V112C_T158C | V112C T158C |
| 36 | FimHLD_S113C_G116C | S113C G116C |
| 37 | FimHLD_S113C_T158C | S113C T158C |
| 38 | FimHLD_V118C_V156C | V118C V156C |
| 39 | FimHLD_A119C_V155C | A119C V155C |

TABLE 6

Nonpolar-to-polar mutations in $FimH_{LD}$

| SEQ ID NO: | Protein ID | Substitutions |
|---|---|---|
| 40 | FimHLD_L34N_V27A | V27A L34N |
| 41 | FimHLD_L34S_V27A | V27A L34S |
| 42 | FimHLD_L34T_V27A | V27A L34T |
| 43 | FimHLD_A119N_V27A | V27A A119N |
| 44 | FimHLD_A119S_V27A | V27A A119S |
| 45 | FimHLD_A119T_V27A | V27A A119T |
| | FimHLD_L34D_V27A | V27A L34D |
| | FimHLD_L34E_V27A | V27A L34E |
| | FimHLD_L34K_V27A | V27A L34K |
| | FimHLD_L34R_V27A | V27A L34R |
| | FimHLD_A119D_V27A | V27A A119D |
| | FimHLD_A119E_V27A | V27A A119E |
| | FimHLD_A119K_V27A | V27A A119K |
| | FimHLD_A119R_V27A | V27A A119R |

TABLE 7

Cavity-filling mutations at the Pilin-Lectin interface of FimH-DSG

| SEQ ID NO: | Protein ID | Substitutions |
|---|---|---|
| 46 | FimH-DSG_A115V | A115V |
| 47 | FimH-DSG_V163I | V163I |
| 48 | FimH-DSG_V185I | V185I |
| 49 | FimH-DSG_DSG_V3I | DSG V3I |

TABLE 8

Combination of representative mutations in FimH$_{LD}$

| SEQ ID NO: | Protein ID | Substitutions |
|---|---|---|
| 50 | FimHLD_G15A_V27A | G15A V27A |
| 51 | FimHLD_G16A_V27A | G16A V27A |
| 52 | FimHLD_G15P_V27A | G15P V27A |
| 53 | FimHLD_G16P_V27A | G16P V27A |
| 54 | FimHLD_G15A_G16A_V27A | G15A G16A V27A |
| 55 | FimHLD_V27A_R60P | V27A R60P |
| 56 | FimHLD_V27A_G65A | V27A G65A |
| 57 | FimHLD_V27A_Q133K | V27A Q133K |
| 58 | FimHLD_G15A_G16A_V27A_Q133K | G15A G16A V27A Q133K |

TABLE 9

Combination of representative mutations in FimH-DSG

| SEQ ID NO: | Protein ID | Substitutions |
|---|---|---|
| 59 | FimH-DSG_WT | WT/none |
| 60 | FimH-DSG_V27A | V27A |
| 61 | FimH-DSG_G15A_V27A | G15A V27A |
| 62 | FimH-DSG_G15A_G16A_V27A | G15A G16A V27A |
| 63 | FimH-DSG_V27A_Q133K | V27A Q133K |
| 64 | FimH-DSG_G15A_G16A_V27A_Q133K | G15A G16A V27A Q133K |

Example 2: Antigen Expression and Purification

DNA encoding FimH$_{LD}$ and FimH-DSG mutants was cloned into pcDNA3.1 containing a mouse IgK signal peptide and expressed in Expi293™ cells as previously described (PCT Intl. Publication No. WO2021/084429, published May 6, 2021). For protein characterization and immunogenicity studies, proteins were isolated using nickel affinity resin and size exclusion chromatography as described in PCT Intl. Publication No. WO2021/084429, published May 6, 2021.

Example 3: Fluorescence Polarization Assay

To determine dissociation constants of FimH mutants for mannoside ligands, a fluorescence polarization assay was developed based on methods described by Rabbani et al. (*J. Biol. Chem.* 293:1835-1849 (2018)) using fluorescein conjugated to mannoside ligands with a high affinity for FimH. FimH proteins were diluted in 20 mM HEPES pH 7.4, 150 mM NaCl, 0.05 mg/mL plus BSA 0.05% in an 11-point threefold titration in a black flat bottom 96-well polypropylene plate (Greiner) with a final volume of 50 µL. 50 µL of fluorescein octylbiphenylmannopyranoside ligand at 0.7 nM in same buffer was added to each well. Plates were incubated overnight at room temperature, shaking at 100 rpm. After 20-24 hr, plates were read in a ClarioStar Plus plate reader with fluorescein excitation at 488 nm and emission at 530 nm.

Example 4: Thermal Stability Assay (ThermoFluor Assay)

A 384-well thermal stability assay using SYPRO orange was developed to determine the melting temperatures of isolated proteins in APO (unbound) form and in the presence of ligand. Mannoside compounds (methyl α-D-mannopyranoside (Sigma M6882) mimicking the natural ligand of FimH (mannose) were used to analyze association to the protein. FimH protein stock solutions were prepared by diluting proteins in 40 mM Tris pH 8, 400 mM NaCl (Assay Buffer) to 4 µM; SYPRO orange dye (Invitrogen S6650) was diluted 1:10 in Assay Buffer. 4 µM FimH mutants (5 µL) were mixed with 1:10 SYPRO orange dye (0.1 µL) and either Assay Buffer or ligand diluted in Assay Buffer (5 µL) for 10 µL final reaction volume in a MicroAmp EndurePlate Optical 384-well plate (Applied Biosystems 4483285). The plate was subjected to melt curve analysis in a QuantStudio 5 Real-time PCR system (ThermoFisher) using a dissociation protocol from 20° C. to 98° C., at 0.05° C./second. TAMRA was specified as the target and reporter, ROX as a passive reference (not used for any analysis however). Data was plotted as a Maxwell-Boltzmann distribution, with Temperature (from 20° C. to 98° C.) on the X-axis, and fluorescence from the TAMRA channel charted on the Y-axis (each temperature point read during the melt curve being assigned a specific fluorescence excitation value for the TAMRA reporter). A normalization algorithm was established to equalize fluorescence intensity between wells and samples, so the Y-axis of fluorescence could be compared from plate to plate, on a scale from 0 (no fluorescence) to 1 (highest recorded fluorescence). This equation is shown below. Using a search function in Microsoft Excel (also below), a relative fluorescence (after normalization) value of 0.5 (indicating approximately half of the protein has disassociated) was recorded, correlating to a specific temperature. This temperature, the taken melting temperature ($T_m$) of the protein was thus calculated. The shift in melting temperature ($\Delta T_m$) was calculated by subtracting the $T_m$ of the protein+ ligand from the apo condition. Pivot tables in Microsoft Excel were used to organize $T_m$ from plate layout.

Equation to normalize TAMRA fluorescence signal $$\text{Normalization value (between 0 \& 1)} = \frac{\text{raw fluorescence value} - \text{minimum fluorescence value from entire well (from 20° C. to 98° C.)}}{\text{Maximum fluorescence value from entire well} - \text{minimum fluorescence value from entire well}}$$

Excel search function to Identify $T_m$ (0.5 normalized fluorescence, or 50% protein melting):
=LOOKUP (0.5, beginning of normalized fluorescence values:end of values, $ beginning of temperature values:$ end of values)

Example 5: Confirmation of Conformational State of FimH Mutants with FimH-Specific Neutralizing Monoclonal Antibodies Neutralizing monoclonal antibodies 299-3, 304-1 and 440-2 (developed in-house) were used to confirm the conformational state of FimH mutants; 229-3 and 304-1 bind to similar epitopes as Mab 475 and 926 (Kisiela, D. I. et al. *Proc Natl Acad Sci USA* 110, 19089-19094 (2013)) while 440-2 recognizes a different epitope and appears to preferentially bind FimH$_{LD}$ in an open conformational state. Variants maintaining structural integrity similar to wildtype are expected to bind all antibodies. Octet HTX from ForteBio was used for all the kinetic real-time biomolecular interaction experiments to measure antibody reactivity with each mutant. Experiments were carried out at 30° C. with 1000 rpm agitation in 96-well black plates containing 240 µL per well. Ni-NTA biosensors were equilibrated in buffer containing 1×PBS buffer containing 0.5% BSA and 0.05% TWEEN 20 (PBT) before allowing them to load His-tagged FimH mutant proteins at 5 µg/mL for 5 minutes. FimH loaded biosensors were allowed to reestablish baseline in PBT for 3 minutes before allowing them to associate with antibodies from different bins at 5 µg/mL for 5 minutes. Octet data analysis software was used for kinetic analysis of association step and obtain response in nm shift (tabulated).

Example 6: Circular Dichroism Spectroscopy

Far-UV (320-250 nm) and near-UV (260-200 nm) circular dichroism spectra were recorded for $FimH_{LD}$ and FimH-DSG mutants using JASCO J-810 Spectropolarometer (Jasco), equipped with JASCO PTC-424S/15 (Jasco) temperature control and Isotemp water bath (Fisher Scientific) units. For far-UV, a 1 mm cell was used, and for near-UV a 10 mm cell was used. Proteins were diluted to 0.3 mg/mL in PBS and spectra were recorded at 20° C. using a cell with 1 mm (far-UV) or 10 mm (near-UV) path length. Scans were performed at 100 nm/min, DIT was set to 1 s, bandwidth to 3 s, and data pitch to 0.1 nm. Sensitivity was set to standard. Ten spectra were accumulated and averaged for near-UV and five for far-UV measurements respectively. Spectra were corrected to background manually using CD spectra arising from blank PBS runs and were converted to mean residue ellipticity using EQ. 1. Where ΘMRE is the calculated mean residue ellipticity, ΘEXP is experimentally measured CD signal, MW is protein molecular weight, N is the number of amino acid residues, C is protein concentration in mg/mL, I is the optical path length in cm.

$$\Theta_{MRE} = (\Theta_{EXP} \cdot MW)/(10 \cdot N \cdot C \cdot 1) \qquad \text{EQ. 1}$$

Example 7: Animal Immunogenicity Study EC-1678

6-8 week old CD-1 mice were obtained from Charles River Laboratories. For each group, 20 animals were immunized subcutaneously 0, 4 and 8 weeks with 10 µg FimH protein mixed with 20 µg Quillaja Saponaria-21 (QS-21) from a 5.1 mg/mL QS-21 stock solution containing 5 mM Succinate, 60 mM NaCl, 0.1% PS80, pH 5.6.

Example 8: FimH Whole Cell Neutralization Assays

To evaluate the ability of serum from vaccinated animals to inhibit binding of fimbriated *E. coli* to mannosylated substrates, a whole cell neutralization assay using yeast mannan was employed as described in PCT Intl. Publication No. WO2021/084429, published May 6, 2021.

Example 9: Purification of FimH-DSG WT and FimH-DSG G15A G16A V27A Mutant from CHO Cells Proteins were expressed in CHO cells as secreted proteins with C-terminal His tags. Cell culture supernatant was harvested and 1 M Tris pH 7.4 and 5 M NaCl were added to final concentrations of 20 mM and 150 mM final concentrations respectively. A 5 kDa TFF cassette buffer was rinsed and equilibrated in 20 mM Tris pH 7.5 with 500 mM NaCl and 40 mM imidazole. Supernatant was concentrated 2-fold and diafiltered against 6 volumes of 20 mM Tris pH 7.5 500 mM NaCl 40 mM imidazole. Retentate was collected and rinsed with 50-100 ml of 20 mM Tris pH 7.5 500 mM NaCl 40 mM imidazole. Retentate was filtered and rinsed with a 0.2 µm bottletop filter. An XK26/20 column was packed with Ni-SEPHAROSE 6 Fast Flow resin (Cytiva Life Sciences) and equilibrated with 5 column volumes of 20 mM Tris pH 7.5 500 mM NaCl 40 mM imidazole. Retentate was applied at half flow rate and washed until a stable baseline was reached (approximately 55 column volumes). Bound protein was eluted with 20 mM Tris, 500 mM NaCl, 500 mM imidazole, pH 7.5. Fractions containing the protein of interest were pooled and dialyzed in a 2 kDa dialysis cassette against 20 mM sodium acetate, pH 4.3 at 4° C. with two buffer changes. Protein was applied to a SP-SEPHAROSE cation exchange column (Cytiva Life Sciences) that had been equilibrated with the same buffer. Material bound to the cation-exchange resin was eluted with a linear gradient of NaCl using 20 mM sodium acetate, pH 4.3, 1 M NaCl buffer. Fractions were pooled, and dialyzed against TBS, pH 7.4.

Example 10: Analytical Size Exclusion Chromatography (SEC) on FimH-DSG WT and FimH-DSG G15A G16A V27A Mutant Analytical SEC was conducted using Waters X bridge Protein BEH SEC 125 Å 2.5 µm, 4.6×300 mm column in TBS, pH 7.4 buffer containing 10 mM EDTA at 25° C. The injection volume was 10 µl and the flow rate 0.5 mL/min.

Example 11: Monosaccharide Analysis by High pH Anion Exchange Chromatography using Pulsed Amperometric Detection (HPAEC-PAD)

Aqueous samples of FimH-DSG wild type and FimH-DSG triple mutant (G15A, G16A, V27A) were digested for 2 hr at 120° C. in 2N Trifluoroacetic acid. After this time samples were evaporated to dryness under vacuum at 45° C. for 6 hrs. Samples were re-constituted in Milli-Q $H_2O$ and were evaluated by HPAEC-PAD on a DIONEX ICS 3000 ion chromatography system. A Dionex CarboPac PA1 column (4×250 mm) was used with an isocratic elution using a mixture of $H_2O$ and 200 mM NaOH. Monosaccharide composition was confirmed by comparing retention times of peaks detected in FimH samples with solutions of known monosaccharide standards.

Example 12: Detection of O-Antigen Sugar Moiety Binding to FimH-DSG WT and FimH-DSG G15A G16A V27A Mutant Octet HTX from ForteBio was used for all the kinetic real-time biomolecular interaction experiments to measure possible O-antigen interactions with FimH-DSG WT and FimH-DSG G15A G16A V27A mutant. Experiments were carried out at 30° C. with 1000 rpm agitation in 96-well black plates containing 240 µl per well. Ni-NTA biosensors were equilibrated in buffer containing 1×PBS buffer with 0.5% BSA and 0.05% Tween 20 (PBT) before allowing them to load His-tagged FimH-DSG WT or FimH-DSG G15A G16A V27A mutant at 5 µg/ml for 5 min. FimH-DSG WT or FimH-DSG G15A G16A V27A-loaded biosensors were allowed to reestablish baseline in PBT for 3 min before allowing them to load with 2-fold titrations (200-3.125 pg/ml) of O-antigen polysaccharide CRM conjugates, O9 or O25b or O1a or O2. An antigen loaded biosensor without any polysaccharide was used as reference. FimH and O-antigen titration loaded biosensors were immersed in PBT for 3 min for new baseline to be established. Detection of O-antigen binding to the mutant was tested in an association step with 5 μg/mL O-antigen specific mAb for 5 min (MAb 601 for O9, MAb ECO-80-11 for O25b, MAb ECO-48-2 for O1a and MAb ECO-172-13 for O2). Octet data analysis software was used for kinetic analysis of reference subtracted association step and obtain response in nm shift (tabulated).

Example 13: Protein Expression and Purification

FimH$_{LD}$ and FimH-DSG mutants were expressed in Expi293 cells and isolated from supernatants by nickel affinity capture followed by size exclusion chromatography. Note, some mutants had poor expression levels and were not progressed to biochemical or biophysical evaluation (e.g. FimH$_{LD}$ P26C V35C, N33C P157C, N33C L109C, V35C L107C, V35C L109C, S113C T158C). Mutants for which sufficient yields could be obtained were evaluated in thermal stability and ligand binding assays.

Example 14: Identification of FimH$_{LD}$ and FimH-DSG Mutants with Improved Thermal Stability and Reduced Shift in Melting Temperature in the Presence of Mannoside Ligand Melting temperatures of FimH mutant proteins were determined using a SYPRO orange thermal shift-based differential scanning fluorimetry assay, wherein T$_m$ designates the temperature at which 50% of the protein is unfolded. Non-covalent ligands often stabilize protein targets upon specific binding, resulting in an increase in protein melting temperature. Melting temperatures were therefore determined in the presence of methyl alpha-D-mannopyranoside, which is a derivative of alpha-D-mannose and has a micromolar affinity for FimH (Bouckaert, J. et al. *Mol Microbiol.* 55, 441-455 (2005)) and the difference in melting temperature (ΔT$_m$) of protein in the presence of ligand relative to apo form was calculated.

Wild type (WT) FimH-DSG proteins exhibited significantly higher melting temperatures compared to FimH$_{LD}$ WT and had lower ΔT, in the presence of ligand (Table 10, Table 11). FimH-DSG WT had a melting temperature of 71.66° C. while the melting temperature of FimH$_{LD}$ WT was significantly lower (61.54° C.). In the presence of methyl alpha-D-mannopyranoside, the melting temperature of FimH$_{LD}$ WT shifted by 10.99° C., while the temperature for FimH-DSG in the presence of ligand shifted only by 2.13° C. This suggests that FimH$_{LD}$ is more efficiently stabilized by the ligand compared to FimH-DSG which may reflect reduced ligand binding by FimH-DSG.

Mutations impacted the melting temperature of FimH proteins in the apo state and in the presence of ligand. The FimH$_{LD}$ lock mutant V27C L34C described previously (Kisiela, D. I. et al. *Proc Natl Acad Sci USA* 110, 19089-19094 (2013); Rodriguez, V. B. et al. *J Biol Chem* 288, 24128-24139 (2013)) exhibited a lower melting temperature (51.42° C.) compared to wild type FimH$_{LD}$ (61.54° C.), consistent with published data (Kisiela, D. I. et al. *Proc Natl Acad Sci USA* 110, 19089-19094 (2013); Rodriguez, V. B. et al. *J Biol Chem* 288, 24128-24139 (2013)). Incubation of FimH$_{LD}$ V27C L34C with methyl alpha-D-mannopyranoside increased the melting temperature by 7.27° C. compared to the apo form, suggesting that this mutant is partly stabilized by the ligand and may have residual ligand binding efficiency. In the context of FimH-DSG, the V27C L34C mutant was less thermostable compared to WT (T$_m$=63.29° C.) and the temperature shift in the presence of ligand was slightly reduced in the V27C L34C mutant compared to WT (ΔT$_m$=1.29° C.). Five of the six Phe1 FimH$_{LD}$ mutants had decreased melting temperatures compared to WT FimH$_{LD}$, except F1L which had a similar melting temperature. In the presence of ligand, four of six FimH$_{LD}$ Phe1 mutants showed a small ΔTm, suggesting poor stabilization by the ligand. In contrast, the most conservative amino acid substitutions F1W and F1Y, exhibited intermediate and comparable ΔTm values respectively, versus the Phe1 wildtype FimH$_{LD}$. With regard to overall thermal stability, the R60P reference mutation (described previously—Rabbani et al. *J. Biol. Chem.* 293:1835-1849 (2018); Rodriguez, V. B. et al. *J Biol Chem* 288, 24128-24139 (2013)) and several novel mutations designed in-house had significantly increased melting temperatures relative to V27C L34C. Interestingly, FimH$_{LD}$ V28C N33C (both sites shifted just one residue away from the reference FimH$_{LD}$ V27C L34C) had the highest melting temperature of any FimH$_{LD}$ mutant (T$_m$=65.77° C.) and had a ΔT$_m$ of 2.81° C. in the presence of methyl alpha-D-mannopyranoside, suggesting reduced affinity for ligand. Mutations in the glycine loop region (G15A, G16A) in FimH$_{LD}$ significantly increased thermal stability relative to V27C L34C and a very low shift in melting temperature was observed in the presence of ligand. The glycine loop mutations also slightly increased the thermal stability of FimH-DSG and no temperature shift was observed with ligand, together suggesting that FimH$_{LD}$ and FimH-DSG mutants are not stabilized by the ligand and therefore may have reduced binding efficiency relative to wild type.

The sequence of FimH$_{LD}$ WT is derived from *E. coli* UTI isolate J96 (Hull, R. A. et al., *Infect Immun* 33, 933-938 (1981)). V27A is a natural variant that is associated with virulent UTI isolates and isolates associated with Crohn's Disease (Schwartz, D. J. et al., *Proc Natl Acad Sci USA* 110, 15530-15537 (2013); Cespedes et al., *Front Microbiol* 8:639 (2017)). Incorporation of V27A into FimH$_{LD}$ slightly reduced the melting temperature of FimH$_{LD}$ WT and a smaller shift was observed with the V27A in the presence of methyl alpha-D-mannopyranoside compared to WT. On the other hand, V27A appeared to have a stabilizing effect in the context of glycine loop mutants G15A, G16A, G15P, G16P in FimH$_{LD}$, which all had a higher melting temperature with V27A compared to without, and had a ΔT$_m$ of <2° C. in the presence of V27A compared to up to 6.05° C. (G16P) without this mutation. In addition, FimH-DSG mutants containing V27A had slightly increased thermal stability and there was no detectable temperature shift in the presence of ligand. Together, this suggests that V27A has a stabilizing effect on the melting temperature of FimH and reduces ligand binding efficiency.

Several FimH$_{LD}$ disulfide and nonpolar to polar residue mutants were expressed at low levels and were either poorly thermostable or exhibited significant temperature shifts in the presence of mannoside compound suggesting that they retained ligand binding efficiency (Table 12). These were tested in single replicates and were excluded from further analysis. Similarly, the thermal stability of several other FimH-DSG mutants was analyzed, two of which had improved thermal stability and reduced shift with ligand (FimH-DSG V27A Q133K and FimH-DSG G15A G16A V27A Q133K) (Table 13). The Q133K mutation is a mutation in the binding pocket of FimH that eliminates ligand binding, which was described previously (Schwartz et al., *Proc Natl Acad Sci USA* 110:15530-15537 (2013)). These mutants were not analyzed further.

TABLE 10

Melting temperature of FimH$_{LD}$ mutants in apo state and in the presence of methyl alpha-D-mannopyranoside

| FimH variant | Repli-cates | Tm (Average)/ °C. | St. Dev. (Tm)/ °C. | ΔTm (Average)/ °C. | St. Dev. (ΔTm)/ °C. |
|---|---|---|---|---|---|
| FimH$_{LD}$ WT | 11 | 61.54 | 0.81 | 10.99 | 0.84 |
| FimH$_{LD}$ V27C L34C | 7 | 51.42 | 0.81 | 7.27 | 0.57 |
| FimH$_{LD}$ V27A | 6 | 59.87 | 0.88 | 9.95 | 0.57 |
| FimH$_{LD}$ G15A | 3 | 56.16 | 0.13 | 3.81 | 0.39 |
| FimH$_{LD}$ G15P | 2 | 55.99 | 1.05 | 2.86 | 0.06 |
| FimH$_{LD}$ G16A | 2 | 54.59 | 0.25 | 6.05 | 0.33 |
| FimH$_{LD}$ G16P | 2 | 55.34 | 0.62 | 1.53 | 0.25 |
| FimH$_{LD}$ G15A V27A | 4 | 57.77 | 0.54 | 1.45 | 0.51 |
| FimH$_{LD}$ G15P V27A | 2 | 58.2 | 0.56 | 1.26 | 0.55 |
| FimH$_{LD}$ G16A V27A | 6 | 57.65 | 0.45 | 1.84 | 0.97 |
| FimH$_{LD}$ G16P V27A | 5 | 58.19 | 0.52 | 0.81 | 0.76 |
| FimH$_{LD}$ R60P | 2 | 56.25 | 0.21 | 8.4 | 1.7 |
| FimH$_{LD}$ V27A R60P | 3 | 60.1 | 0.44 | 3.12 | 0.45 |
| FimH$_{LD}$ G15A G16A V27A | 3 | 59.14 | 0.43 | 0.42 | 0.5 |
| FimH$_{LD}$ V28C N33C | 5 | 65.77 | 1.13 | 2.81 | 0.21 |
| FimH$_{LD}$ P26C V154C | 4 | 60.41 | 1.79 | 5.74 | 1.05 |
| FimH$_{LD}$ F1I | 2 | 55.18 | 0.04 | 0.34 | 1.16 |
| FimH$_{LD}$ F1L | 2 | 60.07 | 0.23 | 0.78 | 0.54 |
| FimH$_{LD}$ F1M | 3 | 52.68 | 1.52 | 1.1 | 1.63 |
| FimH$_{LD}$ F1V | 3 | 52.4 | 0.05 | 0.74 | 0.93 |
| FimH$_{LD}$ F1W | 3 | 52.82 | 0.6 | 4.51 | 0.64 |
| FimH$_{LD}$ F1Y | 3 | 54.17 | 0.18 | 10.09 | 0.32 |

TABLE 11

Melting temperature of FimH-DSG mutants in apo state and in the presence of methyl alpha-D-mannopyranoside

| FimH variant | Repli-cates | $T_m$ (average)/ °C. | St. Dev. $(T_m)$/ °C. | $\Delta T_m$/ °C. | St. Dev. $(\Delta T_m)$/ °C. |
|---|---|---|---|---|---|
| FimH-DSG WT | 11 | 71.66 | 0.48 | 2.13 | 0.17 |
| FimH-DSG V27C L34C | 6 | 63.29 | 1.24 | 1.29 | 0.49 |
| FimH-DSG V27A | 5 | 72.56 | 0.55 | -0.35 | 0.22 |
| FimH-DSG G15A V27A | 5 | 73.02 | 0.64 | -0.14 | 0.29 |
| FimH-DSG G16A V27A | 5 | 72.27 | 0.48 | -0.04 | 0.06 |
| FimH-DSG G15A G16A V27A | 10 | 73.42 | 0.52 | 0.04 | 0.12 |

TABLE 12

Melting temperature of FimH$_{LD}$ mutants in apo state and in the presence of methyl alpha-D-mannopyranoside, single replicates

| FimH variant | $T_m$/° C. | $\Delta T_m$/° C. |
|---|---|---|
| FimH$_{LD}$ P26C V156C | 58.86 | 5.42 |
| FimH$_{LD}$ Q32C Y108C | 61.09 | 9.77 |
| FimH$_{LD}$ P26C V154C | 62.51 | 4.65 |
| FimH$_{LD}$ V28C P157C | 59.61 | 7.16 |
| FimH$_{LD}$ S62C T86C | 58.28 | 11.71 |
| FimH$_{LD}$ S62C L129C | 57.12 | 12.77 |
| FimH$_{LD}$ Y64C A127C | 60.22 | 12.87 |
| FimH$_{LD}$ V112C T158C | 59.64 | 15.2 |
| FimH$_{LD}$ V118C V156C | 56.7 | 12.89 |
| FimH$_{LD}$ P12C A18C | 54.47 | 5.23 |
| FimH$_{LD}$ G14C F144C | 49.24 | -0.1 |
| FimH$_{LD}$ L68C F71C | 49.92 | 12.2 |
| FimH$_{LD}$ S113C G116C | 59.8 | 9.29 |

TABLE 12-continued

Melting temperature of FimH$_{LD}$ mutants in apo state and in the presence of methyl alpha-D-mannopyranoside, single replicates

| FimH variant | $T_m$/° C. | $\Delta T_m$/° C. |
|---|---|---|
| FimH$_{LD}$ A119C V155C | 59.12 | 14.52 |
| FimH$_{LD}$ L34S V27A | 48.86 | 12.78 |
| FimH$_{LD}$ L34T V27A | 53.22 | 10.46 |
| FimH$_{LD}$ L34N V27A | 47.31 | 13.07 |
| FimH$_{LD}$ A119S V27A | 59.8 | 8.52 |
| FimH$_{LD}$ A119T V27A | 59.51 | 9.19 |
| FimH$_{LD}$ A119N V27A | 57.87 | 7.55 |
| FimH$_{LD}$ V27A G65A | 59.8 | 10.85 |

TABLE 13

Melting temperature of FimH-DSG mutants in apo state and in the presence of methyl alpha-D-mannopyranoside, limited replicates

| FimH variant | Repli-cates | $T_m$ (average)/ °C. | St. Dev. $(T_m)$/ °C. | $\Delta T_m$/ °C. | St. Dev. $(\Delta T_m)$/ °C. |
|---|---|---|---|---|---|
| FimH-DSG A115I | 2 | 68.51 | 0 | 4.07 | 0 |
| FimH-DSG V185I | 2 | 71.37 | 0.48 | 2.51 | 0.41 |
| FimH-DSG DSG V3I | 1 | 70.74 | N/A | 3.09 | N/A |
| FimH-DSG V163I | 1 | 70.36 | N/A | 3.48 | N/A |
| FimH-DSG Q133K | 1 | 71.61 | N/A | 1.74 | N/A |
| FimH-DSG V27A Q133K | 1 | 75.1 | N/A | 0.1 | N/A |
| FimH-DSG G15A G16A V27A Q133K | 1 | 73.93 | N/A | 1.27 | N/A |

Example 15: Identification of FimH Mutants with Reduced Affinity for Mannoside Ligand Dissociation constants ($K_d$) of FimH mutants for mannoside ligand were determined using a direct binding fluorescence polarization assay with a fluorescein-conjugated octylbiphenylmannopyranoside (BPMP) ligand. The $K_d$ values of FimH$_{LD}$ mutants relative to WT are shown in Table 14. FimH$_{LD}$ WT and V27A showed similar high affinities for BPMP. The reference lock mutant FimH$_{LD}$ V27C L34C (Kisiela, D. I. et al., *Proc Natl Acad Sci USA* 110, 19089-19094 (2013); Rodriguez, V. V. et al., *J Biol Chem* 288: 24128-24139 (2013)) had a 91-fold lower affinity for the ligand relative to FimH$_{LD}$ WT, while FimH$_{LD}$ R60P V27A (Rabbani et al., *J Biol Chem* 293:1835-1849 (2018)) had a 179-fold lower affinity. The mutants disclosed herein were compared to reference lock mutants. No binding was detected for Glycine loop mutants FimH$_{LD}$ G15A V27A, G15P V27A, G16P V27A and G16A G16A V27A, while G16A V27A had a 156-fold increase in $K_d$ relative to WT. Glycine loop mutations combined with V27A all exhibited a significantly higher $K_d$ than the Glycine loop mutants alone, suggesting that V27A has an indeterminate stabilizing effect, though it had little impact on the $K_d$ of FimH$_{LD}$ WT. Inclusion of V27A also further decreased the binding affinity of FimH$_{LD}$ R60P.

Three novel disulfide lock mutants were tested in this assay, all of which had a modest reduction in ligand binding affinity relative to FimH$_{LD}$ WT (33 to 43-fold lower affinity). FimH$_{LD}$ mutants containing nonpolar to polar mutations (A119T V27A, A119N V27A, L34T V27A, L34N V27A) had a high affinity for BPMP, similar to that of FimH$_{LD}$ WT. FimH$_{LD}$ F1 mutants exhibited poor binding, except F1Y, which had a similar binding affinity to FimH$_{LD}$ WT.

Ligand binding affinities of FimH-DSG constructs are shown in Table 15. The $K_d$ of FimH-DSG WT was more than 100-fold higher than that of FimH$_{LD}$ WT, likely reflecting the different conformational states of the two forms of FimH. FimH-DSG V27A also had a lower affinity relative to FimH-DSG WT. This is consistent with previous data showing that full length FimH with A27 in complex with FimC and FimG has a reduced binding affinity for mannoside relative to FimH V27 (Schwartz et al., Proc Natl Acad Sci USA 110:15530-15537 (2013)). Introduction of lock mutation V27C L34C into FimH-DSG reduced the affinity for BPMP 2.5-fold, while the Glycine loop mutant FimH-DSG G15A G16A V27A had a 28-fold lower affinity relative to FimH-DSG WT. $K_d$ could not be calculated for FimH-DSG G15A V27A and FimH-DSG G16A V27A suggesting that these mutants cannot bind BPMP. Mutations designed to stabilize FimH-DSG in an open conformation via alteration of the pilin-lectin domain interface (A115I, V185I) improved binding affinity relative to FimH-DSG WT, as suggested from thermal stability data (Example 14).

In summary, Glycine loop mutations in either the FimH$_{LD}$ or FimH-DSG protein were identified that had very low binding affinities for BPMP. Based on these and thermal stability data, Glycine mutants were selected for evaluation in functional immunogenicity studies in mice.

TABLE 14

Binding $K_d$ of FimH$_{LD}$ mutants to octylbiphenylmannopyranoside ligand

| FimH variant | Replicates | Average $K_d$/nM | StdDev/nM |
|---|---|---|---|
| FimH$_{LD}$ WT | 10 | 0.193 | 0.041 |
| FimH$_{LD}$ V27A | 3 | 0.213 | 0.034 |
| FimH$_{LD}$ V27C L34C | 7 | 17.706 | 3.052 |
| FimH$_{LD}$ G15P | 1 | >2000 | N/A |
| FimH$_{LD}$ G15P V27A | 4 | >2000 | N/A |
| FimH$_{LD}$ G15A | 1 | 46.74 | N/A |
| FimH$_{LD}$ G15A V27A | 4 | >2000 | N/A |
| FimH$_{LD}$ G16P | 1 | >2000 | N/A |
| FimH$_{LD}$ G16P V27A | 4 | >2000 | N/A |
| FimH$_{LD}$ G16A | 1 | 9.588 | N/A |
| FimH$_{LD}$ G16A V27A | 3 | 30.177 | 0.8 |
| FimH$_{LD}$ R60P | 1 | 4.46 | N/A |
| FimH$_{LD}$ V27A R60P | 6 | 34.555 | 8.232 |
| FimH$_{LD}$ G15A G16A V27A | 2 | >2000 | N/A |
| FimH$_{LD}$ V27A G65A | 1 | 4.6 | N/A |
| FimH$_{LD}$ V28C N33C | 2 | 6.465 | 2.128 |
| FimH$_{LD}$ V28C P157C | 1 | 7.68 | N/A |
| FimH$_{LD}$ P26C V154C | 1 | 8.4 | N/A |
| FimH$_{LD}$ L34T V27A | 1 | 0.4 | N/A |
| FimH$_{LD}$ L34N V27A | 1 | 1.7 | N/A |
| FimH$_{LD}$ A119T V27A | 1 | 0.4 | N/A |
| FimH$_{LD}$ A119N V27A | 1 | 1 | N/A |
| FimH$_{LD}$ F1Y | 2 | 0.317 | N/A |
| FimH$_{LD}$ F1W | 1 | 48.4 | N/A |
| FimH$_{LD}$ F1M | 1 | >2000 | N/A |
| FimH$_{LD}$ F1L | 1 | 534 | N/A |
| FimH$_{LD}$ F1I | 1 | >2000 | N/A |
| FimH$_{LD}$ F1V | 1 | 472 | N/A |

TABLE 15

Binding $K_d$ of FimH-DSG mutants to octylbiphenylmannopyranoside ligand

| FimH variant | Replicates | Average $K_d$/nM | StdDev/nM |
|---|---|---|---|
| FimH-DSG WT | 10 | 23.384 | 8.197 |
| FimH-DSG V27A | 2 | 53.545 | 8.973 |
| FimH-DSG V27C L34C | 3 | 59.927 | 28.187 |

TABLE 15-continued

Binding $K_d$ of FimH-DSG mutants to octylbiphenylmannopyranoside ligand

| FimH variant | Replicates | Average $K_d$/nM | StdDev/nM |
|---|---|---|---|
| FimH-DSG G15A V27A | 2 | >2000 | N/A |
| FimH-DSG G16A V27A | 2 | >2000 | N/A |
| FimH-DSG G15A G16A V27A | 1 | 667.9 | N/A |
| FimH-DSG A115I | 1 | 9.8 | N/A |
| FimH-DSG V185I | 1 | 21 | N/A |

Example 16: Confirmation of Conformational State of FimH Mutants by Circular Dichroism Spectroscopy FimH$_{LD}$ and FimH-DSG mutants that exhibited improved thermal stability and reduced binding affinity for mannoside ligand (Examples 14 and 15) were subjected to secondary and tertiary structure analysis by circular dichroism (CD). Wild type and conformationally locked FimH$_{LD}$ mutants have distinct tertiary CD profiles (Rabbani et al., J Biol Chem 293:1835-1849 (2018)). The secondary and tertiary structures of selected FimH$_{LD}$ and FimH-DSG wild type and mutant proteins were examined by far-UV CD (secondary structure) and near-UV CD (tertiary structure) (see FIG. 1). The far-UV CD spectrum of FimH$_{LD}$ is consistent with previously published data (Rabbani et al. J Biol Chem 293:1835-1849 (2018)) and the far-UV spectrum of both FimH$_{LD}$ and FimH-DSG is characteristic of a protein with high beta-sheet content. FimH$_{LD}$ V27C L34C had a slightly different far-UV spectrum compared to wild type FimH$_{LD}$, as observed by others (Rabbani et al. J Biol Chem 293:1835-1849 (2018)) reflecting an open conformational state. The secondary structure profile of the naturally occurring FimH$_{LD}$ V27A mutant also varied somewhat. Overall, the secondary structures of the FimH$_{LD}$ or FimH-DSG mutants are highly similar to wild type proteins (FIG. 1), suggesting that the overall secondary structure is not altered in these mutants. The tertiary structure profiles of FimH$_{LD}$ mutants closely resemble in-house and published CD spectra of FimH$_{LD}$ V27 L34C and V27A R60P, which are stabilized in an open conformational state (Rabbani et al. J Biol Chem 293:1835-1849 (2018)). The profiles of the mutants described here also differ significantly compared to wild type FimH$_{LD}$ or FimH$_{LD}$ V27A. Together, these data suggest that the mutations that were introduced shift the conformation of FimH$_{LD}$ to an open conformation, while FimH-DSG tertiary structure remains largely unchanged upon introduction of conformation stabilizing mutations assessed herein.

Example 17: Characterization of FimH Mutants using Neutralizing Monoclonal Antibodies The conformations of several selected FimH antigens were characterized by biolayer interferometry assay using lectin domain-specific monoclonal antibodies 299-3, 304-1 and 440-2. Competition experiments (not shown) demonstrated that antibodies 229-3 and 304-1 bind to similar ligand binding site epitopes as MAb 475 and 926 (Kisiela et al., Proc Natl Acad Sci USA 110:19089-19094 (2013)). Monoclonal antibody 440-2 binds to a different epitope and appears to preferentially bind to FimH$_{LD}$ in the open conformation. Antibodies 229-3 and 304-1 were able to recognize all FimH$_{LD}$ (Table 16) and FimH-DSG (Table 17) variants, though binding was reduced for FimH$_{LD}$ V27A. In contrast, responses to antibody 440-2 were higher in all of the FimH$_{LD}$ or FimH-DSG mutants relative to WT or V27A. This is consistent with CD spectroscopy profiles shown in FIG. 1, suggesting that FimH$_{LD}$ mutants are in an open conformation. The response with 440-2 was also increased in FimH-DSG WT, which combined with the overlapping CD spectroscopy profiles of FimH-DSG mutants and WT (Example 16) suggests that this protein is in an open conformational state regardless of the presence or absence of stabilizing mutations.

TABLE 16

MAb binding to FimH$_{LD}$ variants

| FimH variant | Response (nm) Monoclonal antibody | | |
|---|---|---|---|
| | 299-3 | 304-1 | 440-2 |
| FimH$_{LD}$ WT | 3.1034 | 3.0195 | 0.0427 |
| FimH$_{LD}$ V27A | 0.4378 | 0.5354 | 0.0595 |
| FimH$_{LD}$ V27A R60P | 3.1921 | 3.0254 | 0.8483 |
| FimH$_{LD}$ V27A G15A | 3.3127 | 3.0286 | 0.7799 |
| FimH$_{LD}$ V27A G15P | 3.0686 | 2.9482 | 0.6242 |
| FimH$_{LD}$ V27A G16A | 3.438 | 3.1974 | 0.7486 |
| FimH$_{LD}$ V27A G16P | 3.255 | 3.1626 | 0.8816 |
| FimH$_{LD}$ G15A G16A V27A | 3.3359 | 3.0596 | 0.7854 |
| FimH$_{LD}$ V27C L34C | 3.107 | 2.7702 | 0.8063 |
| FimH$_{LD}$ V28C N33C | 3.0536 | 2.7444 | 0.7231 |
| FimH$_{LD}$ P26C V154C | 3.1056 | 2.8871 | 0.8254 |

TABLE 17

MAb binding to FimH-DSG variants

| FimH variant | Response (nm) Monoclonal antibody | | |
|---|---|---|---|
| | 299-3 | 304-1 | 440-2 |
| FimH-DSG WT | 2.4379 | 2.2184 | 0.3763 |
| FimH-DSG V27A | 2.4802 | 2.1687 | 0.3516 |
| FimH-DSG V27C L34C | 2.3477 | 2.2249 | 0.3329 |
| FimH-DSG V27A G15A | 2.5204 | 2.2999 | 0.3707 |
| FimH-DSG V27A G16A | 2.6876 | 2.4157 | 0.4183 |
| FimH-DSG G15A G16A V27A | 2.6765 | 2.3015 | 0.4926 |

Example 18: FimH Mutant Neutralization Data

Figure 2:
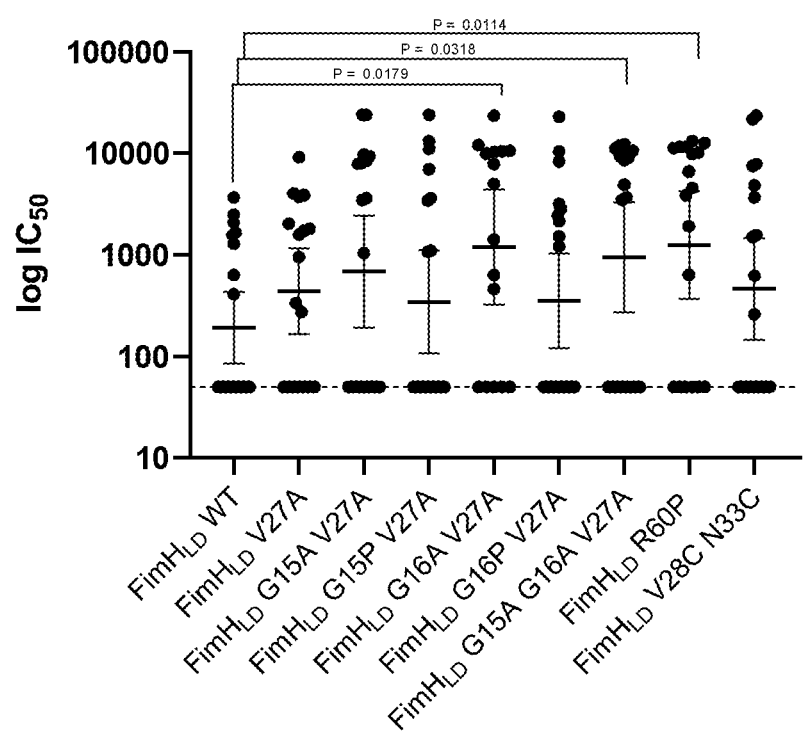
FIG. 2 shows the relative immunogenicity of $FimH_{LD}$ mutants in yeast mannan neutralization assay at PD3.
Figure 3A:
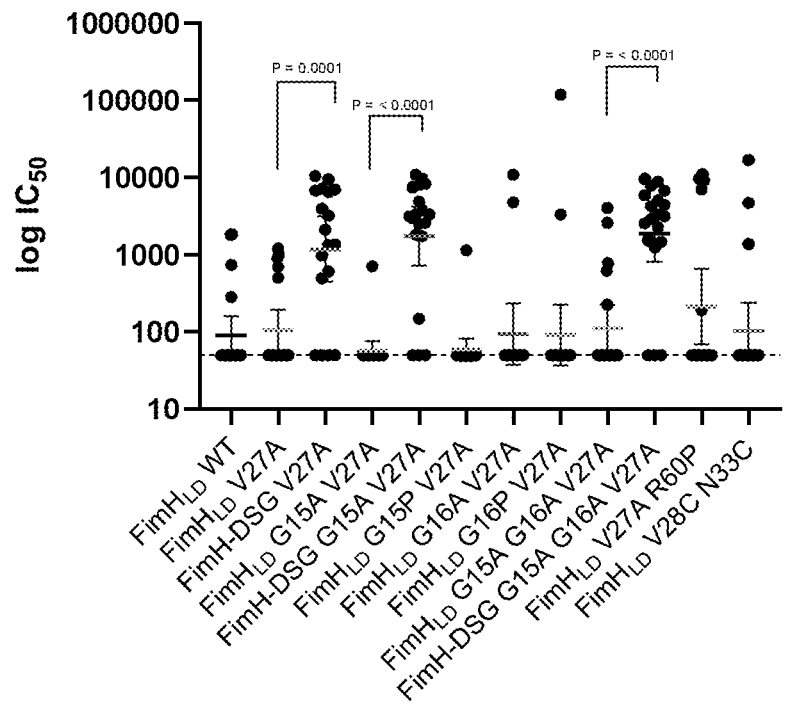
FIG. 3A-3B show the immunogenicity of $FimH_{LD}$ and FimH-DSG mutants in yeast mannan neutralization assay at PD2 (FIG. 3A) and PD3 (FIG. 3B).
Figure 3B:
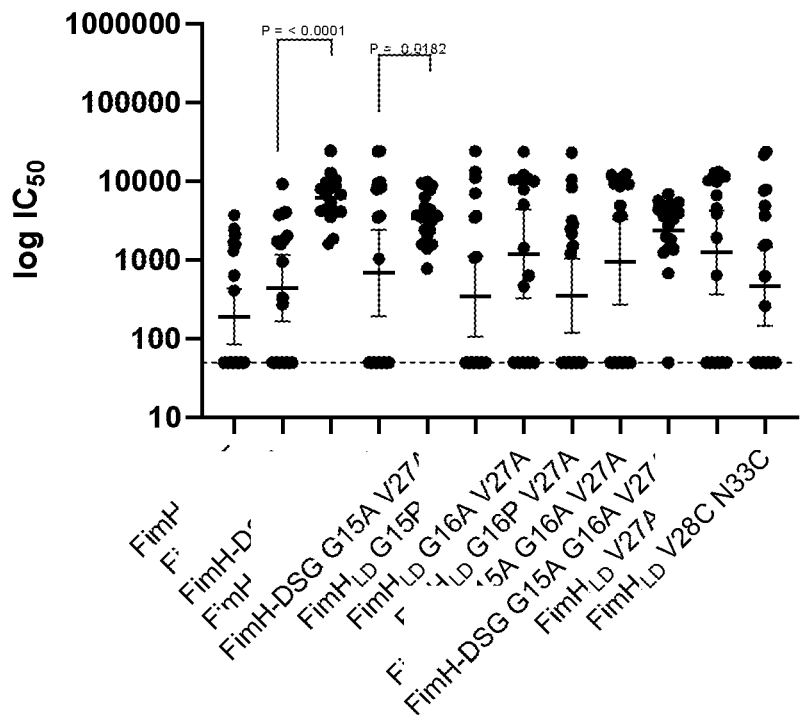

To evaluate the relative immunogenicity of selected mutants, mice were vaccinated with FimH mutants. The potency of FimH mutants to elicit functional antibody titers was quantified using a whole cell yeast mannan neutralization assay described above and previously (PCT Intl. Publication No. WO2021/084429, published May 6, 2021). Briefly, fimbriated $E.$ $coli$ were incubated with serum and allowed to bind to a yeast mannan coated microtiter plate. The plate was washed and the number of viable $E.$ $coli$ bound to the plate was detected using a luminescent probe. Serum neutralization titers that inhibit binding of fimbriated bacteria to yeast mannan were determined from an eight-point two-fold dilution series of sera from vaccinated mice. Titers represent the reciprocal of the dilution of serum at which 50% of bacteria remain bound to the plate. A summary of mean titers and responses is shown in Table 18. Plots of individual mouse IC$_{50}$ responses at post dose 2 and 3 are shown in FIG. 2 and FIG. 3.

TABLE 18

VAC-2020-PRL-EC-1678 FimH$_{LD}$ and FimH-DSG mutant yeast mannan binding neutralization assay responder rates and GMTs

| Protein | IC$_{50}$ GMTs | | Responder rate (%) | | Responders (n) | | Mice (n) | |
|---|---|---|---|---|---|---|---|---|
| | PD2 | PD3 | PD2 | PD3 | PD2 | PD3 | PD2 | PD3 |
| FimH$_{LD}$ WT | 89 | 191 | 20 | 40 | 4 | 8 | 20 | 20 |
| FimH$_{LD}$ V27A | 104 | 439 | 26 | 61 | 5 | 11 | 19 | 18 |
| FimH-DSG V27A | 1175 | 6102 | 78 | 100 | 14 | 18 | 18 | 18 |
| FimH$_{LD}$ G15A V27A | 57 | 683 | 5 | 53 | 1 | 10 | 20 | 19 |
| FimH-DSG G15A V27A | 1740 | 3400 | 84 | 100 | 16 | 19 | 19 | 19 |
| FimH$_{LD}$ G15P V27A | 58 | 346 | 5 | 42 | 1 | 8 | 20 | 19 |
| FimH$_{LD}$ G16A V27A | 93 | 1193 | 13 | 69 | 2 | 11 | 16 | 16 |
| FimH$_{LD}$ G16P V27A | 91 | 352 | 10 | 45 | 2 | 9 | 20 | 20 |
| FimH$_{LD}$ G15A G16A V27A | 111 | 1307 | 26 | 63 | 5 | 12 | 19 | 19 |
| FimH-DSG G15A G16A V27A | 1869 | 2386 | 84 | 95 | 16 | 18 | 19 | 19 |
| FimH$_{LD}$ V27A R60P | 212 | 1056 | 32 | 63 | 6 | 12 | 19 | 19 |
| FimH$_{LD}$ V280 N33C | 103 | 461 | 16 | 53 | 3 | 10 | 19 | 19 |

Previous work (PCT Intl. Publication No. WO2021/084429, published May 6, 2021) showed that the previously described disulfide lock mutant FimH$_{LD}$ V27C L34C (Kisiela et al., $Proc$ $Natl$ $Acad$ $Sci$ $USA$ 110:19089-19094 (2013)) did not improve functional immunogenicity relative to FimH$_{LD}$ WT. The functional immunogenicity of novel FimH$_{LD}$ mutants and another previously described conformationally constrained mutant FimH$_{LD}$ V27A R60P (Rabbani et al., $J$ $Biol$ $Chem$ 293:1835-1849 (2018) are directly compared in FIG. 2. Mutants FimH$_{LD}$ G16A V27A, FimH$_{LD}$ G15A G16A V27A and FimH$_{LD}$ V27A R60P yielded higher numbers of responders and higher titers (p value<0.05) than FimH$_{LD}$ WT. Other mutations (G15A V27A, G16P V27A, V28C N33C) did not significantly enhance functional immunogenicity, although high titers were observed for mice that did respond, the number of responders in these groups was similar to that of the FimH$_{LD}$ WT group. Thus, several mutants designed to enhance functional immunogenicity of FimH$_{LD}$ by locking FimH$_{LD}$ in an open conformation improved functional immunogenicity relative to FimH$_{LD}$ WT. Following vaccination with 2 doses of FimH$_{LD}$ and FimH-DSG mutants, significantly more animals yielded neutralizing titers in the groups vaccinated with FimH-DSG compared to FimH$_{LD}$ (FIG. 3). This trend was sustained at post dose 3, where 95%-100% of mice responded in groups vaccinated with FimH-DSG V27A, FimH-DSG G15A V27A and FimH-DSG G15A G16A V27A. IC$_{50}$ Geometric mean titers (GMT) were also significantly higher in all groups vaccinated with FimH-DSG mutants at post dose 3. Analogous FimH-DSG mutants (V27A, G15A V27A, G15A G16A V27A) generated higher GMTs relative to FimH$_{LD}$ mutants (p value of <0.05).

Figure 4:
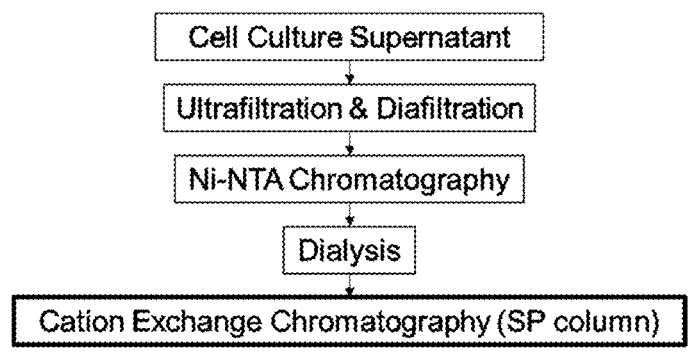
FIG. 4 is a diagram showing the major purification steps utilized for isolation of the wild type and mutated forms of His-tagged FimH-DsG.

Example 19: FimH-DSG G15A G16A V27A Does Not Bind Host Glycans and Can Be Isolated to Homogeneity FimH-DSG WT and FimH-DSG G15A G16A V27A mutant proteins were expressed in CHO cells as secreted proteins containing C-terminal His tags. Purification of recombinant His-tagged forms of FimH-DSG was performed as shown in FIG. 4.

Figure 5A:
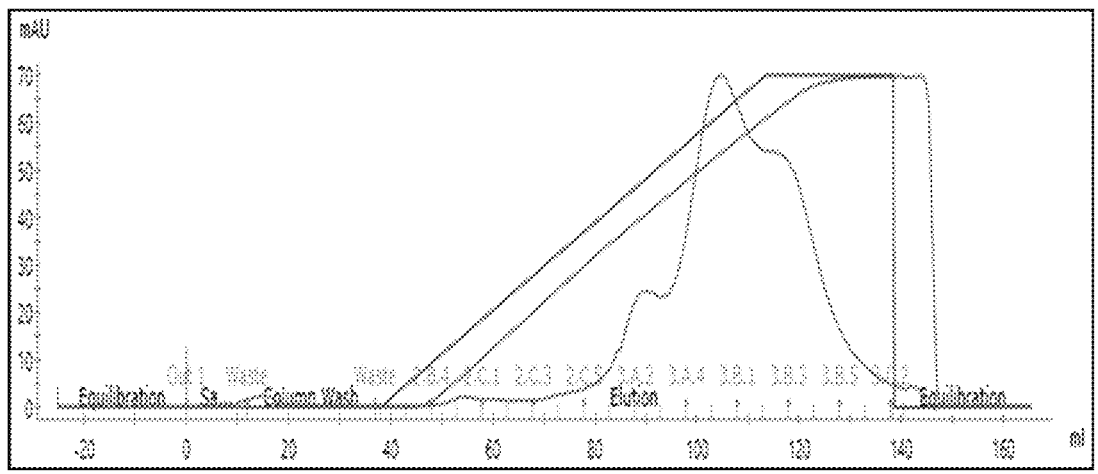
FIG. 5A-5B show a purification profile of FimH-DSG WT.
Figure 5B:
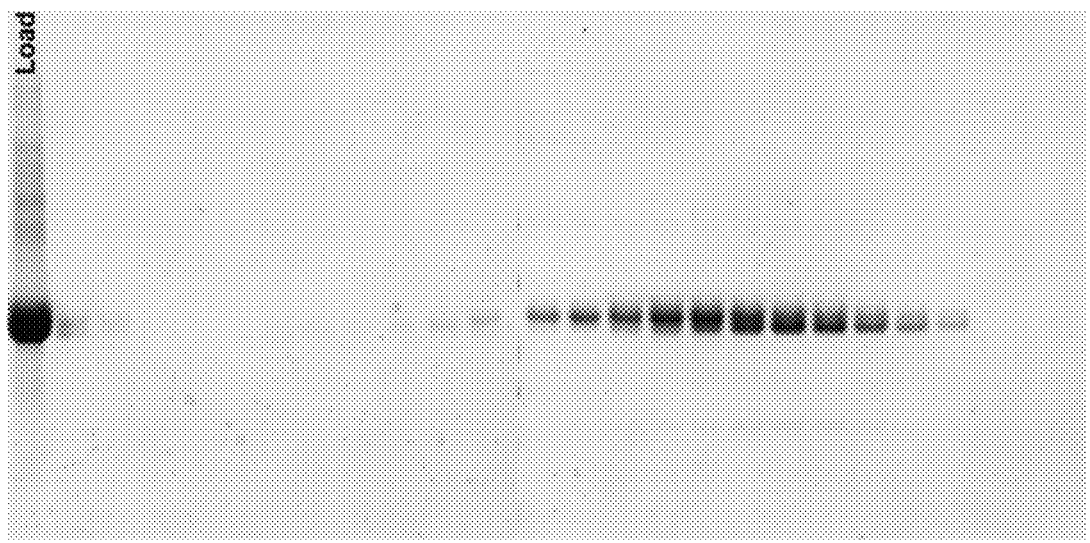

Following ultrafiltration and diafiltration, cell-free culture media containing FimH-DSG WT was isolated on nickel affinity resin and subjected to cation exchange chromatography. The eluted peak was rather broad and exhibited several distinctive shoulders suggesting possible heterogeneity of the FimH-DSG WT species (FIG. 5). Interestingly, when eluted fractions were analyzed by SDS-PAGE only single bands corresponding to the FimH-DSG WT were detected in each fraction.

During the purification process, FimH-DSG exhibited properties suggesting that it has poor solubility. Particularly, FimH-DSG WT Ni-SEPHAROSE eluates always appeared hazy by visual inspection. Shift to acidic pH (4.3) for subsequent purification on SP-SEPHAROSE resulted in clarification of the protein solution. However, poor solubility of FimH-DSG WT preparations and the tendency for aggregation was observed again after the transfer (dialysis) of isolated protein into TBS, pH 7.4. This resulted in progressive loss of the protein due to aggregation and precipitation. Removal of precipitates by centrifugation did not terminate or slow down the aggregation process, even though the protein concentration at this point would be typically reduced down to 0.2-0.4 mg/mL. Loss of protein due to aggregation could be controlled in the presence of 10% glycerol incorporated into the storage (TBS, pH 7.4) buffer. However, the presence of glycerol did not prevent the formation of HMW soluble aggregates that were detected spectrophotometrically by monitoring light scattering at 350 nm.

Figure 6A:
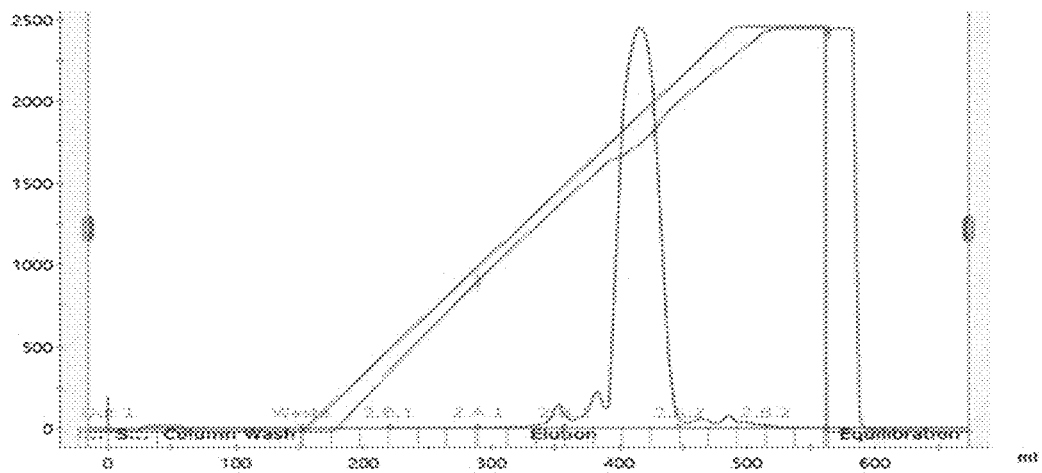
FIG. 6A-6B show a purification profile of the FimH-DSG G15A G16A V27A mutant.
Figure 6B:
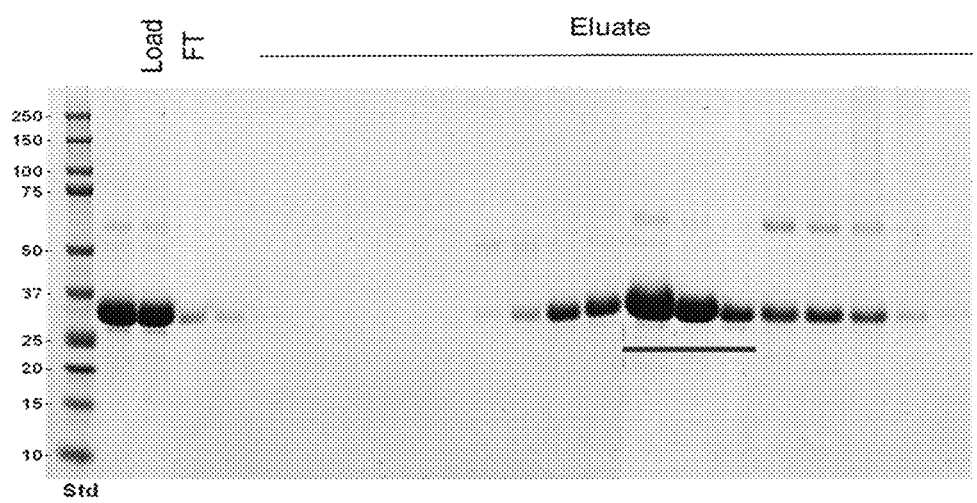

When the same process was utilized for isolation of FimH-DSG G15A G16A V27A mutant, several differences were observed. Firstly, these include the lack of any signs of haziness upon elution of the protein from the Ni-SEPHAROSE column. Secondly, the profile of eluted from SP-SEPHAROSE column peak was not as broad as the one observed with the WT FimH-DSG FIG. 6. And finally, FimH-DSG G15A G16A V27A mutant remained fully soluble after transfer into physiological pH buffer (TBS pH 7.4). At concentrations up to 5-6 mg/mL, FimH-DSG G15A G16A V27A mutant did not show any signs of aggregation or precipitation.

Figure 7A:
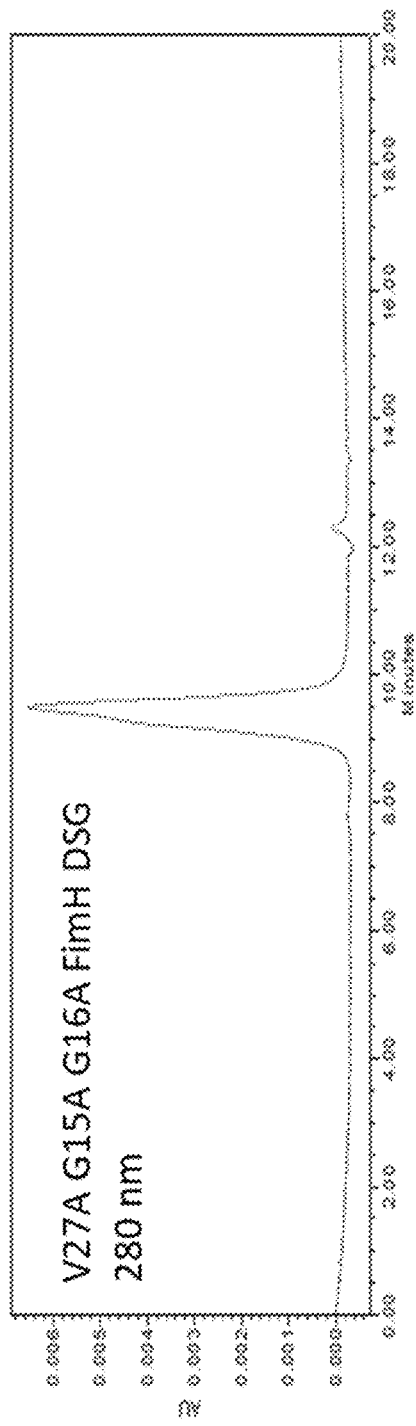
FIG. 7A-7B show the analytical SEC of FimH-DSG proteins. The analytical SEC of FimH-DSG G15A G16A V27A is shown in FIG. 7A, and that of wild type FimH-DSG WT is shown in FIG. 7B.
Figure 7B:
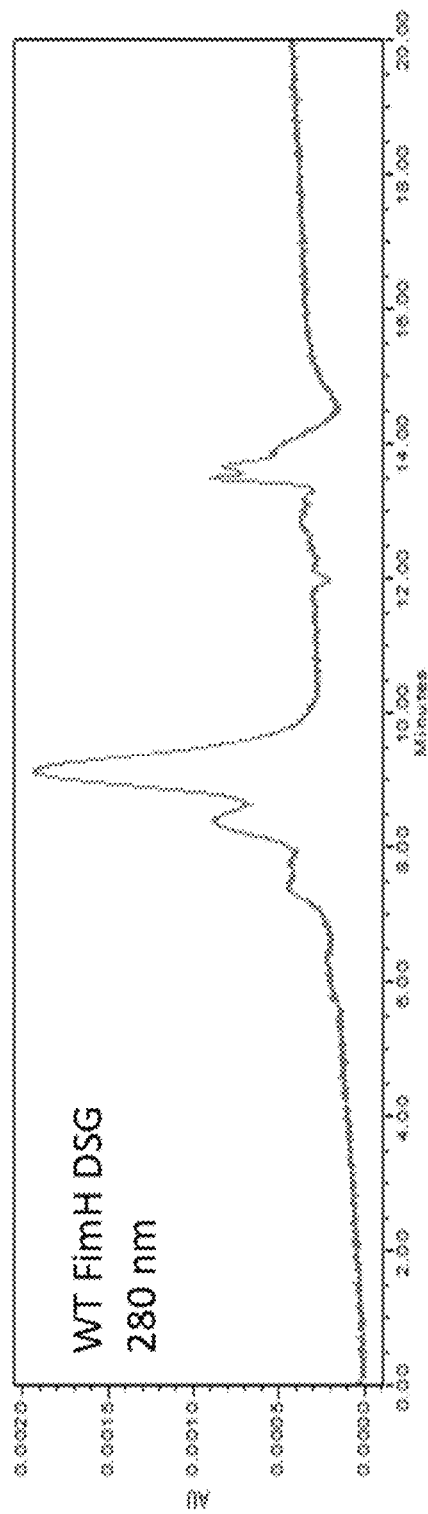
Figure 8:
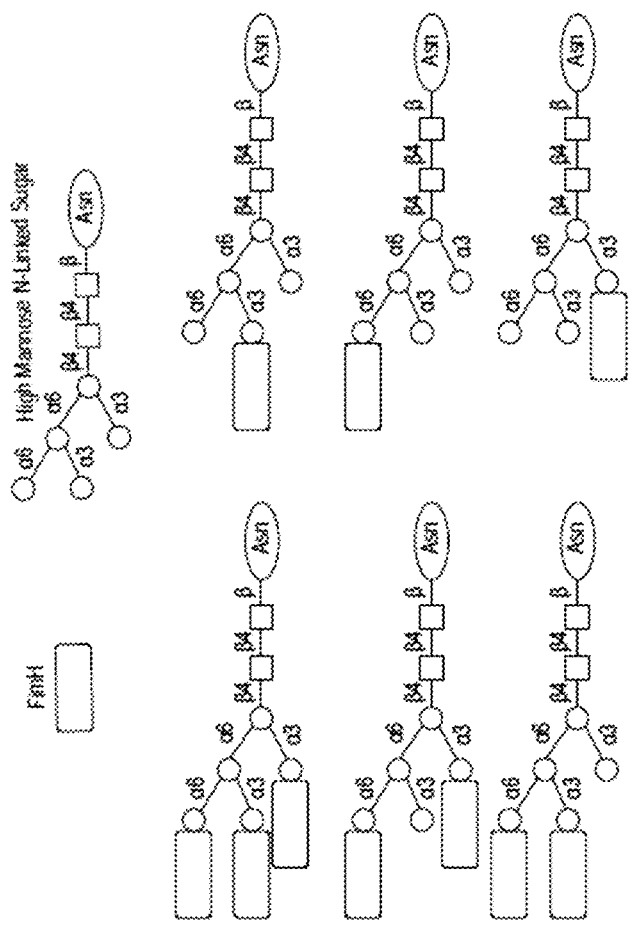
FIG. 8 shows a schematic representation of the mechanism of FimH HMW complex formation.

Analysis of isolated FimH-DSG WT and the FimH-DSG G15A G16A V27A mutant further revealed distinctive differences between these two variants of FimH-DSG. Analytical size exclusion chromatography (SEC) demonstrated that FimH-DSG G15A G16A V27A mutant eluted as a single peak with a retention time consistent with its molecular weight. In contrast, the elution profile of the wild type FimH-DSG was composed of several peaks where the retention time of the major peak was less than that of the mutant shown in FIG. 7. These data clearly demonstrate that the FimH-DSG WT forms high molecular mass complexes detectable by SEC. The presence of HMW complexes formed by the FimH-DSG WT and the tendency to aggregate could be linked to the functional activity of its N-terminal lectin-binding domain. We hypothesized that during CHO fermentation and upon secretion into the culture media the FimH-DSG WT binds glycan molecule(s) released from the surface of the host CHO cells. Due to the branched nature of the glycans, more than one copy of the FimH-DSG molecule could be accommodated by each glycan. Continuous "decoration" of the glycan by increasing numbers of FimH-DSG would result in formation of the various HMW complexes and eventually lead to the loss of solubility and precipitation (see FIG. 8). To test this hypothesis, isolated wild type and mutant FimH-DSG (and $FimH_{LD}$) species were subjected to High pH Anion-Exchange Chromatography with Pulsed Amperometric (electrochemical) Detection (HPAEC-PAD) analysis. This method allows the identification of oligosaccharides or glycans in a protein sample as well as providing information on the composition of these oligosaccharides. Briefly, acid hydrolysis is performed to release monosaccharides, followed by analysis of peaks relative to a monosaccharide standard. The results of HPAEC-PAD analysis revealed that isolated FimH-DSG WT (glycosylated) and $FimH_{LD}$ (not glycosylated, data not shown) preparations contain significant amounts of monosaccharides. The summary of identified monosaccharides in the FimH-DSG WT and FimH-DSG G15A G16A V27A mutant is shown in Table 19. The content of monosaccharides in FimH-DSG G15A G16A V27A mutant was significantly less than that of FimH-DSG WT. Furthermore, it is entirely possible that the low monosaccharide content that was detected represents sugar moieties of the N-glycan predicted to modify N235.

TABLE 19

Normalized amounts of monosaccharides (μg/mg protein) detected by HPAEC-PAD in various SP-Sepharose fractions from FimH-DSG WT and the main peak of FimH-DSG G15A G16A V27A mutant

| Sugar | FimH-DSG WT | | | | | | | | | Total |
|---|---|---|---|---|---|---|---|---|---|---|
| Rhamnose | 0 | 0 | 0 | 0 | 0 | 0 | 0 | 0 | 0 | 0 |
| Nac Gal | 0 | 0 | 0 | 99 | 73 | 0 | 52 | 0 | 177 | 401 |
| Nac Glu | 133 | 190 | 9 | 0 | 0 | 0 | 0 | 44 | 0 | 376 |
| Galactose | 24 | 21 | 6 | 0 | 0 | 0 | 41 | 33 | 35 | 160 |
| Glucose | 8 | 3 | 0 | 19 | 25 | 62 | 34 | 52 | 33 | 236 |
| Mannose | 47 | 35 | 10 | 0 | 0 | 0 | 34 | 59 | 56 | 241 |

| Sugar | FimH-DSG G15A G16A V27A | | | | | | | | | Total |
|---|---|---|---|---|---|---|---|---|---|---|
| Nac-Glucose | 0 | 0 | 20 | 0 | 0 | 0 | 0 | 0 | 0 | 20 |
| Galacose | 0 | 0 | 7 | 0 | 0 | 0 | 0 | 0 | 0 | 7 |
| Mannose | 0 | 0 | 17 | 0 | 0 | 0 | 0 | 0 | 0 | 17 |

Example 20: $FimH_{LD}$ and FimH-DSG G15A G16A V27A Mutants Do Not Bind to E. coli O-Antigens The repeat units of E. coli O-antigens O8 and O9 are composed of polymannose residues. This raised the question of whether FimH might bind O-antigen conjugates in a FimH-O-antigen conjugate combination vaccine. Biolayer interferometry experiments were designed to test whether $FimH_{LD}$ WT could bind to either free O9 polysaccharide or CRM-conjugated O9 polysaccharide, and whether the $FimH_{LD}$ G15A G16A V27A mutant, which in binding assays was shown to have an undetectable affinity for mannoside ligand, could bind. O-antigen binding data is shown in Table 20. At high concentrations of free polysaccharide, a response was observed with $FimH_{LD}$ WT. Higher responses were observed with CRM-conjugated polysaccharide. Detectable binding, however, was eliminated with the mutant protein $FimH_{LD}$ G15A G16A V27A. Similar experiments were set up for FimH-DSG, wherein the ability of FimH-DSG WT or FimH-DSG G15A G16A V27A mutant to bind to free or CRM-conjugated O-antigens of different serotypes (O9, O25b, O1a and O2) was tested Table 21). As expected from their mannoside ligand binding properties, the overall binding affinities of the FimH-DSG WT was significantly lower than the corresponding $FimH_{LD}$ variant. At the highest concentration of CRM conjugate, some titratable binding was observed with FimH-DSG WT with only slightly above background levels of binding seen for the free polysaccharide. As with the $FimH_{LD}$ G15A G16A V27A mutant, the FimH-DSG G15A G16A V27A protein did not bind to any of the free or CRM-conjugated polysaccharides. In conclusion, unlike the parental WT $FimH_{LD}$ or WT FimH-DSG antigens, the derived G15A G16A V27A mutants fail to bind O-antigens, providing a potential path forward for development of a combined FimH and O-antigen vaccine.

TABLE 20

$FimH_{LD}$ G15A G16A V27A mutant does not bind free or CRM-conjugated O-antigen O9 polysaccharide

| | Response (nm) | | | |
|---|---|---|---|---|
| | $FimH_{LD}$ WT | | $FimH_{LD}$ G15A G16A V27A | |
| O-antigen (µg/ml) | Free O9 poly | O9-CRM | Free O9 poly | O9-CRM |
| 200 | 0.765 | 0.988 | 0.019 | 0.017 |
| 100 | 0.349 | 0.466 | −0.007 | 0.020 |
| 50 | 0.162 | 0.253 | 0.023 | 0.018 |
| 25 | 0.074 | 0.131 | 0.024 | 0.022 |
| 12.5 | 0.035 | 0.074 | 0.024 | 0.005 |
| 6.25 | 0.013 | 0.036 | 0.021 | 0.003 |
| 3.13 | 0.004 | 0.02 | 0.027 | 0.013 |

TABLE 21

FimH-DSG G15A G16A V27A mutant does not bind free or CRM-conjugated O-antigen polysaccharides

| | | Response (nm) | | | |
|---|---|---|---|---|---|
| | | FimH-DSG WT | | FimH-DSG G15A G16A V27A | |
| O-antigen serotype | O-antigen (µg/ml) | Free poly | CRM conjugate | Free poly | CRM conjugate |
| O9 | 200 | 0.039 | 0.248 | −0.008 | −0.028 |
| O9 | 100 | 0.037 | 0.134 | −0.002 | −0.028 |
| O9 | 50 | 0.033 | 0.094 | −0.019 | −0.021 |
| O9 | 25 | 0.050 | 0.062 | −0.009 | −0.029 |
| O9 | 12.5 | 0.039 | 0.06 | −0.021 | −0.027 |
| O9 | 6.25 | 0.030 | 0.048 | −0.012 | −0.023 |
| O9 | 3.13 | 0.032 | 0.046 | −0.018 | −0.029 |
| O25b | 200 | −0.009 | 0.179 | −0.051 | −0.043 |
| O25b | 100 | −0.006 | 0.072 | −0.025 | −0.045 |
| O25b | 50 | −0.007 | 0.039 | −0.027 | −0.045 |
| O25b | 25 | −0.004 | 0.026 | −0.029 | −0.043 |
| O25b | 12.5 | −0.002 | 0.019 | −0.028 | −0.046 |
| O25b | 6.25 | 0.000 | 0.013 | −0.028 | −0.045 |
| O25b | 3.13 | −0.006 | 0.011 | −0.03 | −0.048 |
| O1a | 200 | 0.011 | 0.401 | −0.02 | −0.048 |
| O1a | 100 | 0.018 | 0.160 | −0.021 | −0.051 |
| O1a | 50 | 0.009 | 0.072 | −0.025 | −0.042 |
| O1a | 25 | 0.014 | 0.031 | −0.024 | −0.050 |
| O1a | 12.5 | 0.009 | 0.006 | −0.029 | −0.047 |
| O1a | 6.25 | 0.013 | −0.005 | −0.032 | −0.05 |
| O1a | 3.13 | 0.008 | −0.008 | −0.030 | −0.053 |
| O2 | 200 | 0.032 | 0.510 | −0.011 | −0.039 |
| O2 | 100 | 0.029 | 0.240 | −0.046 | −0.051 |
| O2 | 50 | 0.029 | 0.119 | −0.032 | −0.048 |
| O2 | 25 | 0.025 | 0.066 | −0.032 | −0.048 |
| O2 | 12.5 | 0.028 | 0.035 | −0.023 | −0.040 |
| O2 | 6.25 | 0.029 | 0.017 | −0.024 | −0.052 |
| O2 | 3.13 | 0.028 | 0.006 | −0.023 | −0.049 |

Example 21: Non-Human Primates Vaccinated with FimH-DSG G15A G16A V27A Mutant with and without O-Antigens A. Methods 1. FimH IgG dLIA

*E. coli* mutant fimbrial antigen FimH-DSG G15A G16A V27A coupled to spectrally distinct MagPlex-C microspheres (Luminex) were diluted in blocking buffer to the concentration 50,000 beads/mL for 1-2 hours at room temperature while shaking immediately prior to assay primary incubation. The diluted microsphere mixture was added to assay plates containing appropriately diluted non-human primate serum samples, controls and the reference standard, a humanized in-house monoclonal antibody (FimH Y202) that binds the pilin domain of FimH-DSG, for incubation overnight at 2-8° C. while shaking. After washing off non-bound components, a purified R-Phycoerythrin goat anti-human IgG, Fcγ Fragment Specific secondary antibody (Jackson ImmunoResearch Laboratories, 109-116-170) was added to the microsphere mixture and incubated for 90 minutes at room temperature while shaking. The magnitude of the fluorescent PE signal measured by a Luminex FLEX-MAP 3D reader is directly proportional to the amount of anti-FimH-DSG IgG bound to the protein coupled microspheres. The data was analyzed using a custom SAS application, which uses a log/log linear regression model of the standard curve to interpolate antigen-specific antibody concentrations (pg/mL) from median fluorescent intensity. A lower limit of quantitation (LLOQ) of 0.763 µg/mL was calculated from standard curve bias.

2. 4-valent 0-Ag IgG dLIA

*E. coli* long O-antigen polysaccharides of serotypes O25b, O1a, O2 and O6 were covalently conjugated to poly-L-lysine, and the derived conjugates were coupled to spectrally distinct MagPlex-C microspheres (Luminex) with a standard EDC/NHS mediated coupling protocol. Microspheres were incubated with serially diluted non-human primate serum samples, controls and polyclonal standard, for incubation overnight at 2-8° C. while shaking. After washing, bound serotype-specific IgG was detected with a PE-conjugated goat anti-human IgG, Fcγ Fragment Specific secondary antibody (Jackson ImmunoResearch Labortories, 109-115-098) following incubation for 90 minutes at room temperature while shaking. Fluorescence was measured by a Luminex 200 reader for each of the four spectrally distinct regions and expressed as median fluorescent intensities. A standard curve plot of the polyclonal standard titration yielded a linear slope profile with arbitrary assignment from which signals could be interpolated as serotype-specific antibody levels (U/mL).

3. Non-Human Primates (NHPs)

Female Cynomolgus Macaques (*Macaca fasicularis*) were originally obtained from Charles River Laboratories (Houston, TX) before being transferred to Pfizer, Pearl River, NY (age range: 4-5 years, weight range: 3.1-5.9 kg). NHPs were housed in standard quad caging with water and food provided ad libitum. Animals were microchipped subcutaneously to monitor internal temperature. Only NHP free of *E. coli* infection were enrolled based on negative urine qPCR results (see method section 10 below).

4. Vaccination and Blood Collection

Cynomolgus macaques were immunized intramuscularly (0.55 mL) at week 0, 4 and 14 either with vehicle control (PBS, pH 6.2), a monomeric fimbrial antigen FimH-DSG G15A G16A V27A (50 µg/dose), or with a mixture of 4-valent O25b, O1a, O2 and O6 O-antigen polysaccharides conjugates (1 μg/dose) in combination with a monomeric fimbrial antigen FimH-DSG G15A G16A V27A (50 μg/dose). Vaccine antigens were adjuvanted with AS01b (50 μg of MPL and 50 μg of QS-21 per dose).

On week 0, 6 and 16, 10 mL of blood was collected via the femoral vein into 1 serum separator tube (BD Vacutainer), using a 21 g safety needled/vacutainer. Collection tubes were left at room temperature for 30 min and centrifuged at 3000 g for 10 min. Serum in the supernatant was collected, aliquoted and stored at −80° C.

5. E. coli Clinical Isolate

One representative ST131 O25b clinical isolate was selected based on patient's age and origin of sample collection (PFEEC0578, Male, age 38, bladder origin) from UPEC strains collected as part of the Pfizer-sponsored Antimicrobial Testing Leadership and Surveillance (ATLAS) database which is maintained by the International Health Management associates (IHMA) clinical lab. strain carries genes that encode the production of capsular polysaccharides of an unknown type.

6. UPEC Strain Stock Preparation

E. coli stock was prepared by inoculation of 12 mL of LB broth (Teknova, #L8198) followed by an overnight incubation at 37° C. under agitation at 275 rpm. After 18 hrs, the 12 mL culture was diluted into 113 mL of LB broth in a 250 mL flask (Corning, #431407). The culture was incubated for 2 to 3 hrs at 37° C. at ~275 rpm until an $OD_{600}$ between 2.1 and 2.7. Twenty-five mL of glycerol (80%, MP, #3055-044) was mixed to the culture. Aliquots of 5 mL were frozen at −80° C. for long term storage. The concentration of viable bacteria per vial was confirmed by plating serial dilutions of the stock onto TSA plates (BD, BBL Trypticase Soy Agar (Soybean Casein Digest Agar) Catalog #B21283X) and analyzed after 18 hrs incubation at 30° C.

7. Nonhuman Primate Model of Cystitis

NHPs were anesthetized with a Ketamine/Dexdomitor mixture administered intramuscularly. To prevent bladder contamination from urethral catheterization, the anogenital area was wiped down with sterile gauze moistened with sterile saline and/or antiseptic wipes containing Benzalkonium Chloride. A sterile 5 French red rubber catheter, previously coated with Surgi Lube to prevent tissue irritation, was gently introduced through the urethra into the bladder. The bladder was then voided of any urine either via natural flow or by aspiration with a syringe. Through the catheter, a volume of 1 mL containing $10^8$ CFU of UPEC strain PFEEC0578 was administered directly into the bladder.

8. Post Challenge Animal Monitoring

After challenge, animals were monitored twice a day during week 1 and once a day during subsequent weeks. NHPs were monitored up to 30 days post challenge. Monitoring included observation of the appearance of urine output, changes in behavior or appetite, signs of pain/discomfort and body temperature measurement.

9. Urine Collection Via Catheter Placement

To allow collection of clean urine samples, the bladder of anesthetized NHPs were catheterized as described above. After catheter placement, the bladder was voided of urine either via by natural flow or by aspiration with a syringe. When bladders contained no urine, 10 mL of saline was infused and aspiration through the catheter was repeated. All samples collected were immediately stored on ice.

10. DNA Extraction

Extraction of E. coli DNA from up to three replicates of NHP urine samples was performed using Qiagen Minelute DNA Extraction kits (Qiagen, Ref #51306, quantity was sometimes limited by sample volume collected). The manufacturer's Blood and Body Fluid Spin protocol was followed with the following modifications: sample starting volume was increased to 500 μL (if sample volume allowed), Buffer AL volume was increased to 500 μL, Proteinase K volume was increased to 50 μL, 50 μL of Molecular Grade Water (Corning Inc., Ref #46-000-CM) was warmed to 37° C. and used in place of elution buffer EB. Finally, after addition of 37° C. Molecular Grade Water, spin columns were incubated for 5 min at room temperature prior to final spin.

11. Quantitative Real-Time PCR (qPCR)

Quantitative real-time PCR (qPCR) was used to assess bacterial load in NHP urine samples. E. coli O25b serotype specific DNA was amplified with qPCR using the following primers: forward, TTGAAAGTGATGGTTTGGTAAGAAAT (SEQ ID NO: 109); reverse, TGCAGCACGTATGATAACTTCAAAG (SEQ ID NO: 110), and a probe with Fam fluorescent reporter and sequence AGGATATTTTACCCAGCAGTGCCCCGT (SEQ ID NO: 111) was used to quantify replication.

The O25b serotype specific amplicons correspond to portions of the O25b serotype orf10 region. Primers and probe were custom designed, purchased lyophilized from Integrated DNA Technologies, and reconstituted in Buffer TE (Corning Inc., Ref #46-009-CM) to a concentration of 100 nmol/mL.

DNA samples from the DNA extraction procedure described above were assayed in 96 well Applied Biosystems MicroAmp Optical 96 Well Reaction Plates (Applied Biosystems, Ref #N8010560). The qPCR reaction was performed in a total volume of 25 μl using 12.5 μL Applied Biosystems 2X Taqman Fast Advanced Master Mix (Applied Biosystems, Ref #4444554), 0.125 μL of each reconstituted Primer, 0.5 μL Probe, 1.75 μL Molecular Biology Grade Water (Corning Inc., Ref #46-000-CM), and 10 μL of sample per well.

The reaction conditions for amplification of DNA were 50° C. for 2 minutes then 95° C. for 2 min, and 40 cycles of 95° C. for 3 seconds and 60° C. for 30 seconds, run on either an Applied Biosystems 7500 Real Time-PCR System or an Applied Biosystems QuantStudio 6 Real Time-PCR System (Applied Biosystems).

To enable quantitation, a linear standard curve was developed. Aliquots of the same frozen stock of E. coli as used in each challenge experiment (preparation described above) were diluted to 1×109 CFU/mL in Sterile PBS (Corning, 21-040-CM). Subsequent serial dilution was performed to generate solutions containing E. coli at concentrations of $1\times10^8$, $1\times10^7$, $1\times10^6$, $1\times10^6$, $1\times10^5$, $1\times10^4$, 1000, 100, and 10 CFU/mL. Serial dilutions were prepared in sterile PBS (Corning, 21-040-CM) or pooled, twice filtered, NHP urine collected from subjects prior to inoculation. Dilutions in PBS and pooled, twice filtered, NHP urine were later found to be equivalent. The quantity of viable bacteria present at each dilution was confirmed by plating on TSA plates (BD, BBL Trypticase Soy Agar (Soybean Casein Digest Agar) Catalog #B21283X). DNA extraction was performed on each serial dilution using the same methods employed to extract DNA from samples, as described above. These qPCR standards were run on every qPCR assay plate, in duplicate.

Linear Regression analysis was performed using Applied Biosystems QuantStudio software. Statistical analysis determined that the standard curve generated behaved linearly between 100 and $1\times10^8$ bacteria/mL. Consequently, the lower limit of quantitation (LLOQ) was determined to be 100 bacteria/mL. In some instances, samples reached the fluorescence threshold, but at a cycle corresponding to a quantity below the LLOQ, in other instances, the fluorescence threshold was not reached at all (undetermined value). When either of these conditions occurred, the values are reported here as the value of the LLOQ (100 bacteria/mL).

12. Myeloperoxidase (MPO) ELISA

Invitrogen Myeloperoxidase Instant ELISA Kits (Invitrogen, Ref #BMS2038INST) were used to quantify Myeloperoxidase (MPO) in NHP urine. PIPES Buffer was added to neat urine samples to a final concentration of 5% 0.5M PIPES buffer pH 6.8 (Alfa Aesar, Ref #J61786-AK). Samples were vortexed for 15 seconds and then diluted 1:1 with manufacturer supplied Sample Diluent. Samples were assayed in duplicate and manufacturer's instructions were followed for the remainder of the assay. At final endpoint, color intensity at 450 nm was measured on a Spectramax Plus instrument (Molecular Devices). The assay kit's included standards were used to generate a standard curve. For analysis, the assay kit's low standard (156.25 pg/mL) was understood to be the lower limit of detection (LLOD). The Spectramax instrument's companion software (Softmax, Molecular Devices) may extrapolate beyond the value of the low standard. The value of one-half of the LLOD (78.125 pg/mL) was substituted for any values extrapolated below that value or when any assay result fell entirely below the limit of detection.

13. IL-8 Luminex Assay

Interleukin-8 (IL-8) was measured using a Custom Bio-Rad IL-8 Human Cytokine Screening Panel Luminex Assay kit (BioRad Laboratories Inc., REF #17005177). PIPES Buffer was added to neat urine samples to a final concentration of 5% 0.5M PIPES buffer pH 6.8 (Alfa Aesar, Ref #J61786-AK). Samples were vortexed for 15 seconds and then diluted 1:1 with 50% of a modified LXA-4 Buffer (PBS 1x, 0.5% BSA, 0.025% sodium azide). Samples were assayed in duplicate and manufacturer's instructions were followed for the remainder of the assay. Assay plate was read on a BioPlex 200 Luminex instrument (BioRad Laboratories Inc.). The Bio-Plex 200 Luminex instrument's companion software, "BioPlex Manager", and the assay kit's included standards were used to generate a standard curve and to extrapolate sample concentration from fluorescence intensity. The BioPlex Manager software determines the lower limit of quantitation (LLOQ).

14. Total Nucleated Cell Count and Light Microscopy Analysis of Urine Sediments

Within 1 hour of collection, urine samples (500 µl to 1 mL) were fixed with formalin to a final concentration of 1% and sent overnight on ice to Pfizer Groton, CT Upon receipt, total nucleated cells (epithelial cells and polymorphonuclear cells) were counted on a Hemocytometer. Approximately 300 µL total was loaded into the Thermo Scientific Shandon EZ double cyto funnel, 100 µL into one funnel and 200 µL into the other funnel. Samples were cytocentrifuged for 5 min at 750 rpm onto Shandon Double Cytoslide Microscope Coated glass slides using a Thermo Scientific CytoSpin 4 cytocentrifuge. For samples with high cell counts, urine was first diluted 1:10 with 0.9% saline before cytocentrifugation. Using a Sysmex SP-10 instrument, cytoprep slides were then briefly methanol fixed and stained with Giemsa and May-Grunwald stain. For each urine sample, one slide per urine sample was prepared with the two sample volumes listed above.

Cytospin slides containing concentrated and stained urine sediment were evaluated by light microscopy for the presence or absence of increased polymorphonuclear cells (PMN, i.e. granulocytes with segmented or reniform nuclei, generally comprised of neutrophils but also including eosinophils and basophils). The absence of increased PMN cells was determined based on the observation of no PMN or rare PMN. The presence of increased PMN was determined based on the observation of more than rare PMN, relative to the background epithelial cell population.

B. Results

Figure 9:
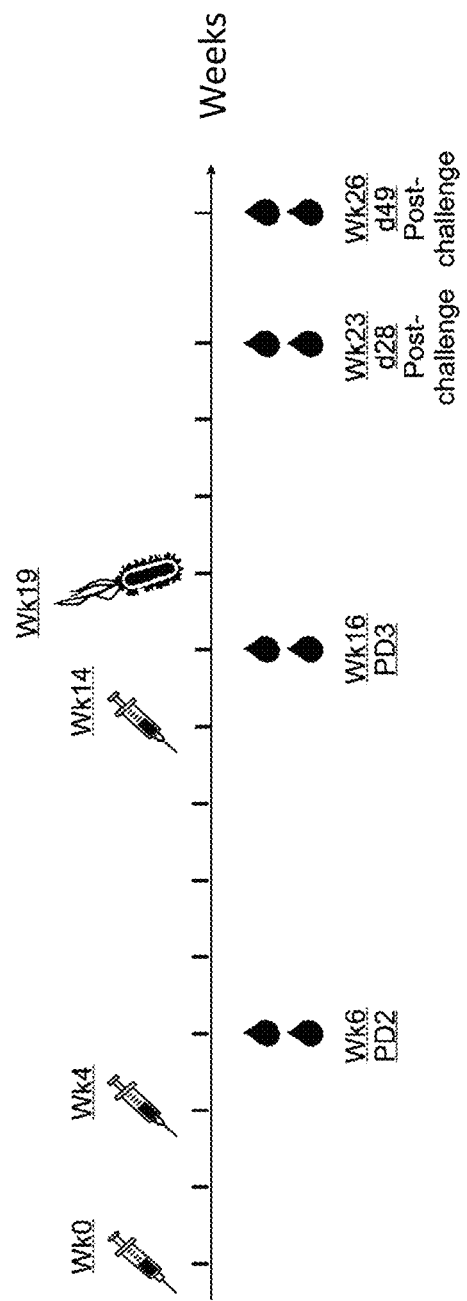
FIG. 9 shows the immunization schedule of non-human primates and subsequent challenge described in Example 21 herein.
Figure 10:
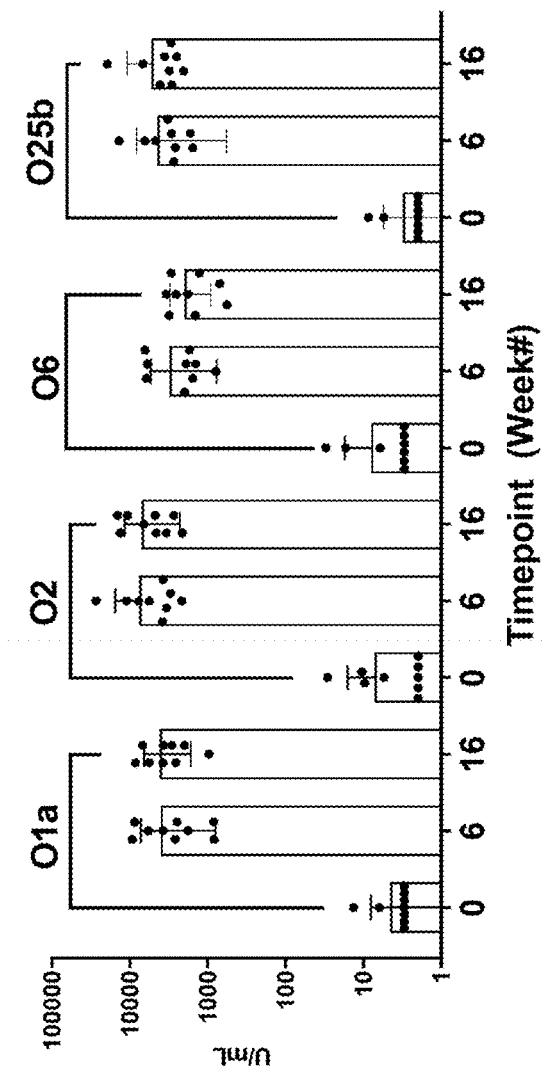
FIG. 10 shows a rise in O-antigen serotype-specific antibodies following vaccination of NHPs with FimH-DSG G15A G16A V27A mutant+4-valent E. coli O-antigens (O1a, O2, O6 and O25b). Legend: Placebo (circle); FimH-DSG G15A G16A V27A (square); FimH-DSG G15A G16A V27A+4-valent O-Antigen (triangle).
Figure 11A:
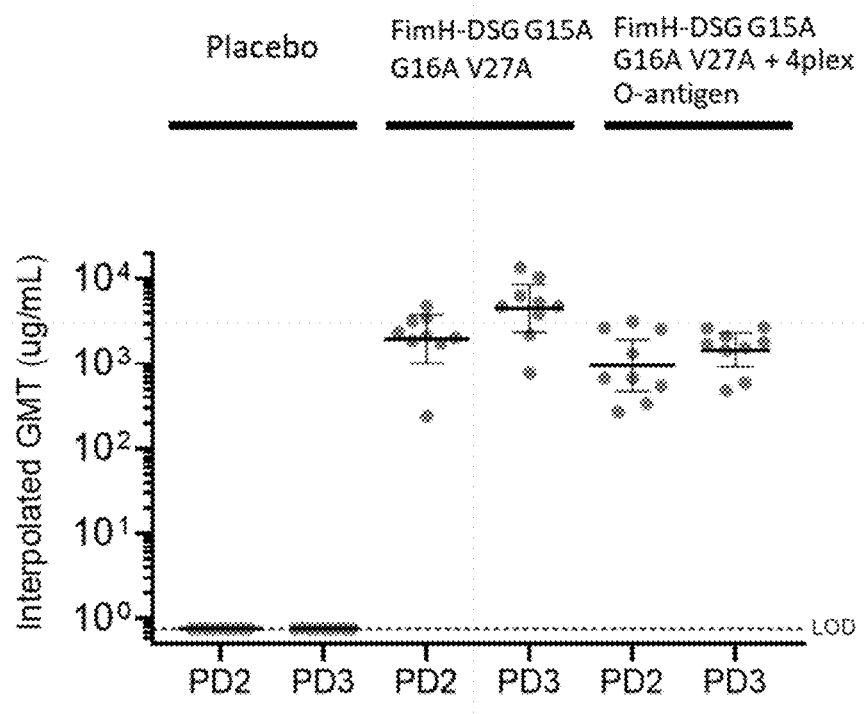
FIG. 11A-11B show that immunization with FimH-DSG G15A G16A V27A+/−4plex O-antigens elicits potent functional anti-FimH antibody responses.

1. Vaccination with FimH-DSG G15A G16A V27A Mutant with and without O-Antigens Elicits Potent Total and Neutralizing Antibodies in Non-Human Primates Non-human primates were vaccinated with FimH-DSG G15A G16A V27A mutant with or without a 4-valent O-antigen conjugate (O25b, O6, O1a, O2) and AS01b adjuvant (FIG. 9). In the FimH-DSG G15A G16A V27A and 4-valent O-antigen vaccinated group, O-antigen serotype-specific antibody titers rose ~400-fold at 6 weeks post vaccination (FIG. 10 and Table 22). Total anti-FimH antibody titers were quantified using a direct Luminex immunoassay (dLIA) (FIG. 11A and Table 23). Animals in the placebo group had titers below the assay limit of quantification. In both vaccinated groups, titers rose after two doses and could be boosted with a third dose. Overall, titers were slightly lower in animals vaccinated with FimH-DSG G15A G16A V27A with O-antigens compared to FimH-DSG G15A G16A V27A alone.

TABLE 22

O-antigen serotype-specific titers in non-human primates vaccinated with FimH-DSG G15A G16A V27A with 4-valent O-antigen

| Serotype | Week | GMT |
|---|---|---|
| O1a | 0 | 3.842 |
|  | 6 | 2903.324 |
|  | 16 | 3446.427 |
| O2 | 0 | 4.318 |
|  | 6 | 5449.571 |
|  | 16 | 5696.599 |
| O6 | 0 | 5.093 |
|  | 6 | 2412.359 |
|  | 16 | 1686.817 |
| O25b | 0 | 2.636 |
|  | 6 | 3483.843 |
|  | 16 | 4028.502 |

TABLE 23

FimH IgG geometric mean titers in non-human primates

| Group Time point | Placebo | | FimH-DSG G15A G16A V27A | | FimH-DSG G15A G16A V27A + 4-4-valent O-antigen | |
|---|---|---|---|---|---|---|
|  | PD2 | PD3 | PD2 | PD3 | PD2 | PD3 |
| GMT | 0.76 | 0.76 | 1965.69 | 4500.47 | 951.61 | 1457.49 |

Figure 11B:
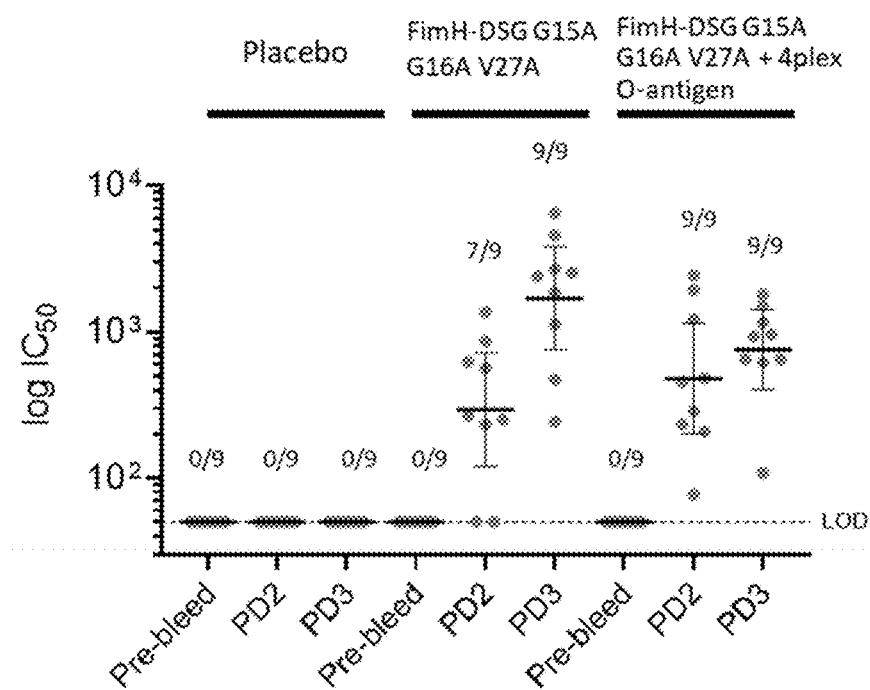

Sera were evaluated in the *E. coli* binding inhibition assay in order to assess ability of anti-FimH antibodies to block binding of *E. coli* to yeast mannan (FIG. 11B and Table 24). The mean $IC_{50}$ of sera from animals vaccinated with FimH-DSG G15A G16A V27A alone rose to 293.65 post dose 2 and 1698.39 post dose 3, while the mean $IC_{50}$ of animals vaccinated with FimH-DSG G15A G16A V27A in combination with O-antigens was 480.12 after dose 2 and 756.45 after dose 3.

TABLE 24

E. coli neutralization assay IC$_{50}$ for non-human primate sera

| Group Time point | Placebo | | | FimH-DSG G15A G16A V27A | | | FimH-DSG G15A G16A V27A + 4-valent O-antigen | | |
|---|---|---|---|---|---|---|---|---|---|
| | Pre-bleed | PD2 | PD3 | Pre-bleed | PD2 | PD3 | Pre-bleed | PD2 | PD3 |
| Geomean IC$_{50}$ | 50 | 50 | 50 | 50 | 293.65 | 1698.39 | 50 | 480.12 | 756.45 |

Together, these data show that FimH-DSG G15A G16A V27A elicits a potent antibody response in non-human primates, and combining with O-antigens results in high titers though slightly lower than with FimH alone.

2. Vaccination with FimH-DSG G15A G16A V27A Mutant with and without O-Antigens Reduces Bacteriuria and Biomarkers of Infection in a Non-Human Primate Model Five weeks after the final boost, vaccinated and placebo treated NHPs were inoculated via intravesical catherization with 108 CFU of UPEC isolate PFEEC0578. Bacteriuria was monitored in catheter collected urine over a period of 28 days. In all placebo treated animals, the instillation of live bacteria led to a high level of bacteriuria on day 2 and 7 post-challenge (geometric mean of approximatively 106 bacteria/mL of urine). Compared to placebo group, animals vaccinated with FimH-DSG G15A G16A V27A or FimH-DSG G15A G16A V27A+4-valent O-antigen exhibited a 300-fold or a 1000-fold reduction in geo mean bacteriuria respectively at day 2 and 7 post-infection.

Figure 12:
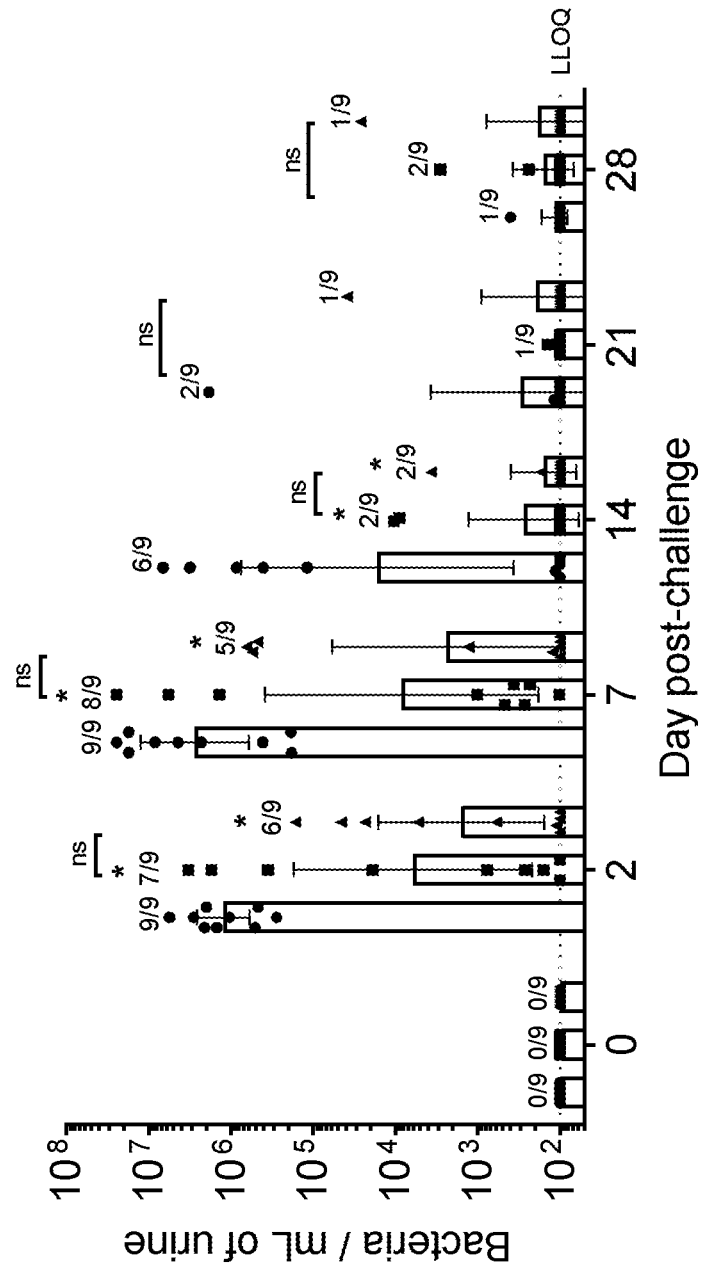
FIG. 12 shows that bacteriuria is reduced in vaccinated nonhuman primates (NHP) after challenge as described in Example 21. Legend: Placebo (circle); FimH-DSG G15A G16A V27A (square); FimH-DSG G15A G16A V27A+4-valent O-Antigen (triangle); *p≤0.007 compared to placebo group.

On day 14, approximately 50% of placebo vaccinated animals still exhibited bacteriuria >105 bacteria/mL of urine. Finally, the majority of placebo NHPs cleared the infection on day 21 and 28. In contrast, most FimH-DSG G15A G16A V27A or FimH-DSG G15A G16A V27A+4-valent O-antigen vaccinated animals cleared the infection by day 14 (FIG. 12).

Figure 13A:
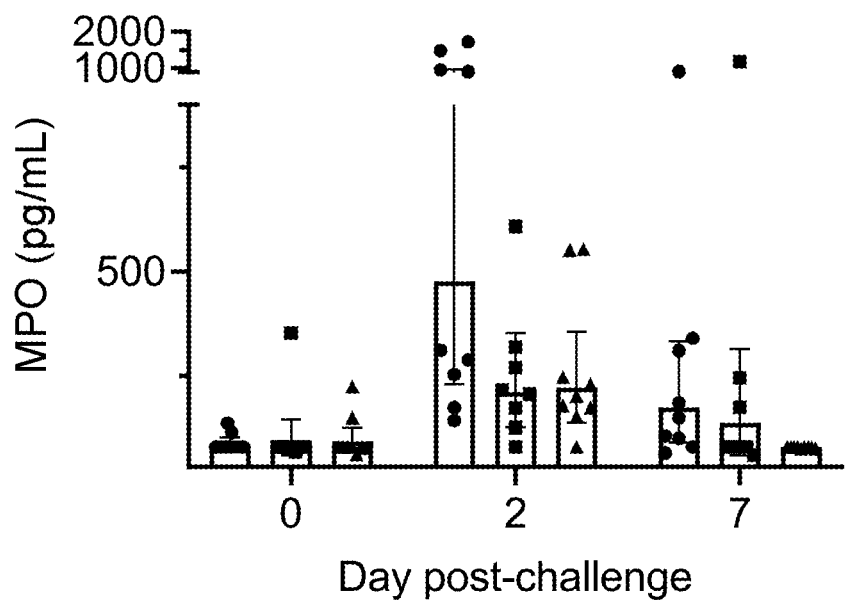
FIG. 13A-13C show that biomarkers of infection are reduced in vaccinated NHP after challenge of the three groups: placebo, FimH-DSG G15A G16A V27A alone and FimH-DSG G15A G16A V27A+4-valent O-antigens, as described in Example 21.
Figure 13B:
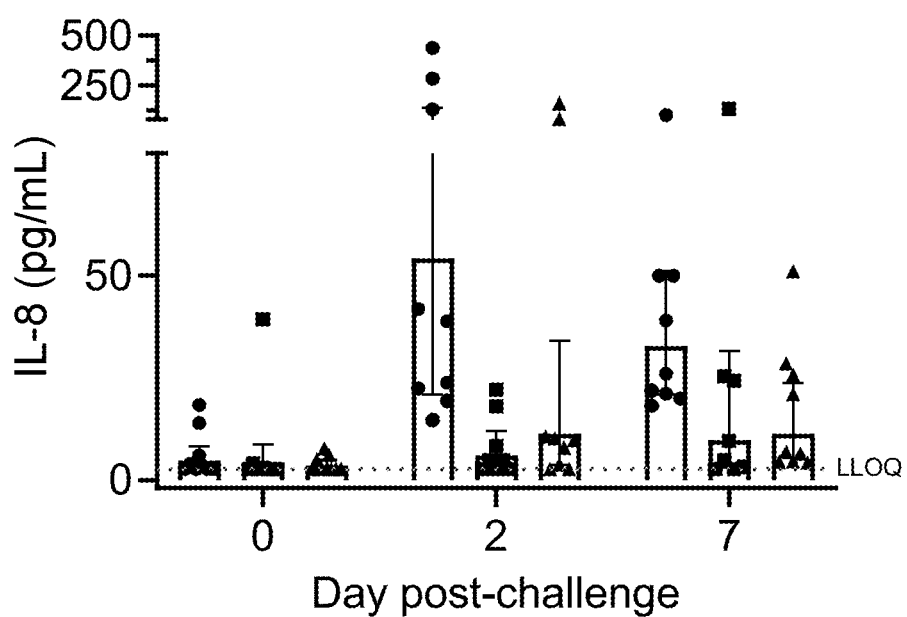
Figure 13C:
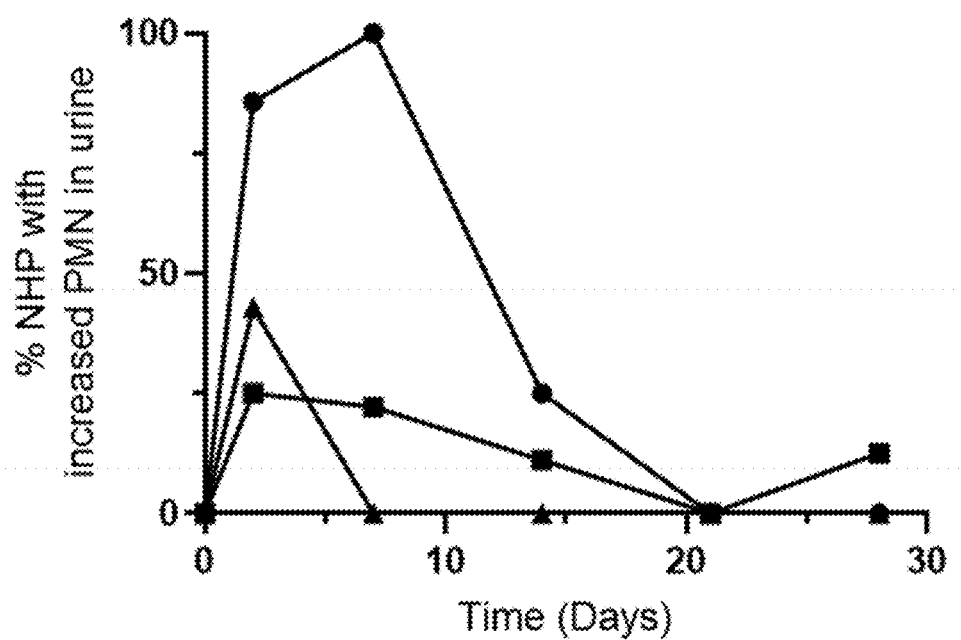

Next, various inflammatory biomarkers were monitored in the urine of challenged NHPs. At day 7 post-challenge, all placebo treated animals exhibited elevated levels of polymorphonuclear (PMN) cells in urine sediment as confirmed by cytology analysis. In contrast, less than 25% of FimH-DSG G15A G16A V27A vaccinated NHPs and no FimH-DSG G15A G16A V27A+4-valent O-antigen immunized animals had increased levels of PMN cells in urine sediment (FIG. 13C). In parallel, we measured levels of myeloperoxidase (MPO) and Interleukin 8 (IL-8) in urine samples over a 7-day period. On day 2 post-challenge, both vaccinated groups exhibited a 2-fold reduction in MPO levels (geometric mean of ~200 pg/mL) compared to placebo group (geometric mean of 470 pg/mL) (FIG. 13A).

In addition, on day 2 and day 7 post-infection, urine concentrations of IL-8 in FimH-DSG G15A G16A V27A vaccinated animals were decreased by approximatively 10- and 5-fold respectively (geometric mean of 5.9 pg/mL and 9.8 pg/mL) compared to levels measured in urine of placebo treated NHPs (geometric mean of 54.2 pg/mL and 32.7 pg/mL). With a similar trend, urine levels of IL-8 on day 2 and day 7 in FimH-DSG G15A G16A V27A in combination with O-antigens immunized NHPs were reduced by approximatively 5- and 3-fold respectively (geometric mean of 11.3 pg/mL) compared to IL-8 concentrations observed in placebo treated animals (FIG. 13B).

C. Conclusions

FimH-DSG G15A G16A V27A mutant induces high anti-FimH IgG titers in NHPs that can be boosted with a 3$^{rd}$ dose. Animals vaccinated with the combination of FimH-DSG G15A G16A V27A mutant and the 4-valent O-antigens showed high O-antigen IgG titers.

FimH-DSG G15A G16A V27A elicits potent neutralizing antibodies in non-human primates. Combination with the 4-valent O-antigens is similarly immunogenic.

FimH-DSG G15A G16A V27A mutant with or without the 4-valent O-antigens reduces bacteriuria and biomarkers of infection in a urinary tract infection model in Cynomolgus macaques.

The Following Clauses Describe Additional Aspects of the Disclosure:

C1. A mutated FimH polypeptide, which comprises at least one amino acid mutation relative to the amino acid sequence of the wild-type FimH polypeptide, wherein the mutation position is selected from the group consisting of: F1, P12, G14, G15, G16, A18, P26, V27, V28, Q32, N33, L34, V35, R60, S62, Y64, G65, L68, F71, T86, L107, Y108, L109, V112, S113, A115, G116, V118, A119, A127, L129, Q133, F144, V154, V155, V156, P157, T158, V163, and V185, wherein the amino acid positions are numbered according to SEQ ID NO:59.

C2. A mutated FimH polypeptide according to clause C1, comprising at least one mutation selected from the group consisting of: F1I; F1L; F1V; F1M; F1Y; F1W; P12C; G14C; G15A; G15P; G16A; G16P; A18C; P26C; V27A; V27C; V28C; Q32C; N33C; L34C; L34N; L34S; L34T; L34D; L34E; L34K; L34R; V35C; R60P; S62C; Y64C; G65A; L68C; F71C; T86C; L107C; Y108C; L109C; V112C; S113C; A115V; G116C; V118C; A119C; A119N; A119S; A119T; A119D; A119E; A119K; A119R; A127C; L129C; Q133K; F144C; V154C; V156C; P157C; T158C; V163I; and V185I, or any combination thereof.

C3. A mutated FimH polypeptide according to clause C2, comprising the mutations G15A and G16A.

C4. A mutated FimH polypeptide according to clause C2, comprising the mutations P12C and A18C.

C5. A mutated FimH polypeptide according to clause C2, comprising the mutations G14C and F144C.

C6. A mutated FimH polypeptide according to clause C2, comprising the mutations P26C and V35C.

C7. A mutated FimH polypeptide according to clause C2, comprising the mutations P26C and V154C.

C8. A mutated FimH polypeptide according to clause C2, comprising the mutations P26C and V156C.

C9. A mutated FimH polypeptide according to clause C2, comprising the mutations V27C and L34C.

C10. A mutated FimH polypeptide according to clause C2, comprising the mutations V28C and N33C.

C11. A mutated FimH polypeptide according to clause C2, comprising the mutations V28C and P157C.

C12. A mutated FimH polypeptide according to clause C2, comprising the mutations Q32C and Y108C.

C13. A mutated FimH polypeptide according to clause C2, comprising the mutations N33C and L109C.

C14. A mutated FimH polypeptide according to clause C2, comprising the mutations N33C and P157C.

C15. A mutated FimH polypeptide according to clause C2, comprising the mutations V35C and L107C.

C16. A mutated FimH polypeptide according to clause C2, comprising the mutations V35C and L109C.

C17. A mutated FimH polypeptide according to clause C2, comprising the mutations S62C and T86C.

C18. A mutated FimH polypeptide according to clause C2, comprising the mutations S62C and L129C.

C19. A mutated FimH polypeptide according to clause C2, comprising the mutations Y64C and L68C.

C20. A mutated FimH polypeptide according to clause C2, comprising the mutations Y64C and A127C.

C21. A mutated FimH polypeptide according to clause C2, comprising the mutations L68C and F71C.

C22. A mutated FimH polypeptide according to clause C2, comprising the mutations V112C and T158C.

C23. A mutated FimH polypeptide according to clause C2, comprising the mutations S113C and G116C.

C24. A mutated FimH polypeptide according to clause C2, comprising the mutations S113C and T158C.

C25. A mutated FimH polypeptide according to clause C2, comprising the mutations V118C and V156C.

C26. A mutated FimH polypeptide according to clause C2, comprising the mutations A119C and V155C.

C27. A mutated FimH polypeptide according to clause C2, comprising the mutations L34N and V27A.

C28. A mutated FimH polypeptide according to clause C2, comprising the mutations L34S and V27A.

C29. A mutated FimH polypeptide according to clause C2, comprising the mutations L34T and V27A.

C30. A mutated FimH polypeptide according to clause C2, comprising the mutations L34D and V27A.

C31. A mutated FimH polypeptide according to clause C2, comprising the mutations L34E and V27A.

C32. A mutated FimH polypeptide according to clause C2, comprising the mutations L34K and V27A.

C33. A mutated FimH polypeptide according to clause C2, comprising the mutations L34R and V27A.

C34. A mutated FimH polypeptide according to clause C2, comprising the mutations A119N and V27A.

C35. A mutated FimH polypeptide according to clause C2, comprising the mutations A119S and V27A.

C36. A mutated FimH polypeptide according to clause C2, comprising the mutations A119T and V27A.

C37. A mutated FimH polypeptide according to clause C2, comprising the mutations A119D and V27A.

C38. A mutated FimH polypeptide according to clause C2, comprising the mutations A119E and V27A.

C39. A mutated FimH polypeptide according to clause C2, comprising the mutations A119K and V27A.

C40. A mutated FimH polypeptide according to clause C2, comprising the mutations A119R and V27A.

C41. A mutated FimH polypeptide according to clause C2, comprising the mutations G15A and V27A.

C42. A mutated FimH polypeptide according to clause C2, comprising the mutations G16A and V27A.

C43. A mutated FimH polypeptide according to clause C2, comprising the mutations G15P and V27A.

C44. A mutated FimH polypeptide according to clause C2, comprising the mutations G16P and V27A.

C45. A mutated FimH polypeptide according to clause C2, comprising the mutations G15A, G16A, and V27A.

C46. A mutated FimH polypeptide according to clause C2, comprising the mutations G65A and V27A.

C47. A mutated FimH polypeptide according to clause C2, comprising the mutations V27A and Q133K.

C48. A mutated FimH polypeptide according to clause C2, comprising the mutations G15A, G16A, V27A, and Q133K.

C49. A mutated FimH polypeptide according to clause C2, comprising the sequence of any one of SEQ ID NOs: 2-58, and 60-64.

C50. A mutated FimH polypeptide according to any of clauses C1-C49, wherein the polypeptide is isolated.

C51. A pharmaceutical composition comprising (i) a mutated FimH polypeptide according to any one of clauses C1-C50 and (ii) a pharmaceutically acceptable carrier.

C52. An immunogenic composition comprising a mutated FimH polypeptide according to any one of clauses C1-C50.

C53. An immunogenic composition according to clause C52, further comprising at least one additional antigen.

C54. An immunogenic composition according to clause C53, wherein the at least one additional antigen is a saccharide, or a polysaccharide, or a glycoconjugate, or a protein.

C55. An immunogenic composition according to clause C52, further comprising at least one adjuvant.

C56. A nucleic acid molecule comprising a nucleotide sequence that encodes an amino acid sequence of a mutated FimH polypeptide according to any one of clauses C1-C49.

C57. A mutated FimH polypeptide according to any of clauses C1-C50, wherein the polypeptide is immunogenic.

C58. A recombinant mammalian cell, comprising a polynucleotide encoding a mutated FimH polypeptide according to any one of clauses C1-C50.

C59. A culture comprising the recombinant cell of clause C58, wherein said culture is at least 5 liters in size.

C60. A method for producing a mutated FimH polypeptide according to any one of clauses C1-C50, comprising culturing a recombinant mammalian cell according to clause C58 under suitable conditions, thereby expressing the polypeptide; and harvesting the polypeptide.

C61. A method for (i) inducing an immune response in a subject against extra-intestinal pathogenic *E. coli*, or (ii) inducing the production of opsonophagocytic and/or neutralizing antibodies in a subject that are specific to extra-intestinal pathogenic *E. coli*, wherein the method comprises administering to the subject an effective amount of a composition according to any one of clauses C51 to C55.

C62. A method according to clause C61, wherein the subject is at risk of developing a urinary tract infection.

C63. A method according to clause C61, wherein the subject is at risk of developing bacteremia.

C64. A method according to clause C61, wherein the subject is at risk of developing sepsis.

C65. A method of eliciting an immune response against *E. coli* in a mammal, comprising administering to the mammal an effective amount of a composition according to any one of clauses C51-C55.

C66. A method according to clause C65, wherein the immune response comprises opsonophagocytic and/or neutralizing antibodies against *E. coli*.

C67. A method according to clause C65, wherein the immune response protects the mammal from an *E. coli* infection.

C68. A method of preventing, treating or ameliorating a bacterial infection, disease or condition in a subject, comprising administering to the subject an immunologically effective amount of a composition according to any one of clauses C51-C55.

C69. An immunogenic composition according to clause C54, wherein the additional antigen is a saccharide comprising a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C70. The immunogenic composition according to clause C69, wherein the saccharide comprises a structure selected from Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, Formula 62D$_1$, Formula O22, Formula O35, Formula O65, Formula O66, Formula O83, Formula O91, Formula O105, Formula O116, Formula O117, Formula O139, Formula O153, Formula O167, and Formula O172, wherein n is an integer from 31 to 100.

C71. The immunogenic composition according to clause C70, wherein the saccharide comprises a structure selected from Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, and Formula 62D$_1$, wherein n is an integer from 31 to 100.

C72. The immunogenic composition according to clause C70, comprising a structure selected from Formula O1 (e.g., Formula O1A, Formula O1B, and Formula O1C), Formula O2, Formula O6 (e.g., Formula O6:K2; K13; K15 and Formula O6:K54), Formula O15, Formula O16, Formula O21, Formula O25 (e.g., Formula O25a and Formula O25b), and Formula O75.

C73. The immunogenic composition according to clause C70, comprising a structure selected from Formula O4, Formula O11, Formula O21, and Formula O75.

C74. The immunogenic composition according to clause C69, wherein the saccharide does not comprise a structure selected from Formula O8, Formula O9a, Formula O9, Formula O20ab, Formula O20ac, Formula O52, Formula O97, and Formula O101.

C75. The immunogenic composition according to clause C69, wherein the saccharide does not comprise a structure selected from Formula O12.

C76. The immunogenic composition according to clause C72, wherein the saccharide is produced by expressing a wzz family protein in a Gram-negative bacterium to generate said saccharide.

C77. The immunogenic composition according to clause C76, wherein the wzz family protein is selected from the group consisting of wzzB, wzz, $wzz_{SF}$, $wzz_{ST}$, fepE, $wzz_{fepE}$, wzz1 and wzz2.

C78. The immunogenic composition according to clause C76, wherein the wzz family protein is wzzB.

C79. The immunogenic composition according to clause C76, wherein the wzz family protein is fepE.

C80. The immunogenic composition according to clause C76, wherein the wzz family protein is wzzB and fepE.

C81. The immunogenic composition according to clause C76, wherein the wzz family protein is derived from *Salmonella enterica*.

C82. The immunogenic composition according to clause C76, wherein the wzz family protein comprises a sequence selected from any one of SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121.

C83. The immunogenic composition according to clause C76, wherein the wzz family protein comprises a sequence having at least 90% sequence identity to any one of 112, SEQ ID NO: 113, SEQ ID NO: 114, SEQ ID NO: 115, and SEQ ID NO: 116.

C84. The immunogenic composition according to clause C76, wherein the wzz family protein comprises a sequence selected from any one of SEQ ID NO: 117, SEQ ID NO: 118, SEQ ID NO: 119, SEQ ID NO: 120, and SEQ ID NO: 121.

C85. The immunogenic composition according to clause C69, wherein the saccharide is synthetically synthesized.

C86. The immunogenic composition according to any one of clauses C69 to C85, wherein the saccharide further comprises an *E. coli* R1 moiety.

C87. The immunogenic composition according to any one of clauses C69 to C85, wherein the saccharide further comprises an *E. coli* R2 moiety.

C88. The immunogenic composition according to any one of clauses C69 to C85, wherein the saccharide further comprises an *E. coli* R3 moiety.

C89. The immunogenic composition according to any one of clauses C69 to C85, wherein the saccharide further comprises an *E. coli* R4 moiety.

C90. The immunogenic composition according to any one of clauses C69 to C85, wherein the saccharide further comprises an *E. coli* K-12 moiety.

C91. The immunogenic composition according to any one of clauses C69 to C90, wherein the saccharide further comprises a 3-deoxy-d-manno-oct-2-ulosonic (KDO) moiety.

C92. The immunogenic composition according to any one of clauses C69 to C85, wherein the saccharide does not further comprise an *E. coli* R1 moiety.

C93. The immunogenic composition according to any one of clauses C69 to C85, wherein the saccharide does not further comprise an *E. coli* R2 moiety.

C94. The immunogenic composition according to any one of clauses C69 to C85, wherein the saccharide does not further comprise an *E. coli* R3 moiety.

C95. The immunogenic composition according to any one of clauses C69 to C85, wherein the saccharide does not further comprise an *E. coli* R4 moiety.

C96. The immunogenic composition according to any one of clauses C69 to C85, wherein the saccharide does not further comprise an *E. coli* K-12 moiety.

C97. The immunogenic composition according to any one of clauses C69 to C90, wherein the saccharide does not further comprise a 3-deoxy-d-manno-oct-2-ulosonic acid (KDO) moiety.

C98. The immunogenic composition according to any one of clauses C69 to C91, wherein the saccharide does not comprise a Lipid A.

C99. The immunogenic composition according to any one of clauses C69 to C98, wherein the polysaccharide has a molecular weight of between 10 kDa and 2,000 kDa, or between 50 kDa and 2,000 kDa.

C100. The immunogenic composition according to any one of clauses C69 to C99, wherein the saccharide has an average molecular weight of 20-40 kDa.

C101. The immunogenic composition according to any one of clauses C69 to C100, wherein the saccharide has an average molecular weight of 40,000 to 60,000 kDa.

C102. The immunogenic composition according to any one of clauses C69 to C101, wherein n is an integer 31 to 90.

C103. An immunogenic composition comprising a mutated FimH polypeptide according to any one of clauses C69 to C50, and a conjugate comprising a saccharide covalently bound a carrier protein, wherein the saccharide is derived from *E. coli*.

C104. An immunogenic composition comprising a mutated FimH polypeptide according to any one of clauses C69 to C50, and a conjugate comprising a saccharide according to any one of clauses C69 to C102, covalently bound to a carrier protein.

C105. An immunogenic composition comprising a mutated FimH polypeptide according to any one of clauses C69 to C50, or fragment thereof; and a conjugate according to any one of clause C69 to clause C102, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C106. The immunogenic composition according to any one of clause C103 to clause C105, wherein the carrier protein is $CRM_{197}$.

C107. The immunogenic composition according to any one of clause C103 to clause C105, wherein the carrier protein is tetanus toxoid (TT).

C108. The immunogenic composition according to any one of clause C103 to clause C105, wherein the carrier protein is poly(L-lysine).

C109. The immunogenic composition according to any one of clause C103 to clause C107, wherein the conjugate is prepared by reductive amination.

C110. The immunogenic composition according to any one of clause C103 to clause C107, wherein the conjugate is prepared by CDAP chemistry.

C111. The immunogenic composition according to any one of clause C103 to clause C107, wherein the conjugate is a single-end linked conjugated saccharide.

C112. The immunogenic composition according to any one of clause C103 to clause C107, wherein the saccharide is conjugated to the carrier protein through a (2-((2-oxoethyl)thio)ethyl)carbamate (eTEC) spacer.

C113. The immunogenic composition according to clause C112, wherein the saccharide is conjugated to the carrier protein through a (2-((2-oxoethyl)thio)ethyl)carbamate (eTEC) spacer, wherein the saccharide is covalently linked to the eTEC spacer through a carbamate linkage, and wherein the carrier protein is covalently linked to the eTEC spacer through an amide linkage.

C114. The immunogenic composition according to any one of clause C112 to clause C113, wherein the $CRM_{197}$ comprises 2 to 20, or 4 to 16, lysine residues covalently linked to the polysaccharide through an eTEC spacer.

C115. The immunogenic composition according to any one of clause C103 to clause C114, wherein the saccharide: carrier protein ratio (w/w) is between 0.2 and 4.

C116. The immunogenic composition according to any one of clause C103 to clause C114, wherein the ratio of saccharide to protein is at least 0.5 and at most 2.

C117. The immunogenic composition according to any one of clause C103 to clause C114, wherein the ratio of saccharide to protein is between 0.4 and 1.7

C118. The immunogenic composition according to any one of clause C111 to clause C117, wherein the saccharide is conjugated to the carrier protein through a 3-deoxy-d-manno-oct-2-ulosonic acid (KDO) residue.

C119. The immunogenic composition according to clause C69, wherein the conjugate comprises a saccharide covalently bound to a carrier protein, wherein the saccharide comprises a structure selected from Formula O8, Formula O9a, Formula O9, Formula O20ab, Formula O20ac, Formula O52, Formula O97, and Formula O101, wherein n is an integer from 1 to 10.

C120. An immunogenic composition comprising a mutated FimH polypeptide, and a saccharide according to any one of clause C69 to clause C102, and a pharmaceutically acceptable diluent.

C121. An immunogenic composition comprising a mutated FimH polypeptide, and a glycoconjugate according to any one of clause C103 to clause C119, and a pharmaceutically acceptable diluent.

C122. The immunogenic composition according to clause C121, comprising at most about 25% free saccharide as compared to the total amount of saccharide in the composition.

C123. The immunogenic composition according to any one of clause C120 to clause C121, further comprising an adjuvant.

C124. The immunogenic composition according to any one of clause C120 to clause C121, further comprising aluminum.

C125. The immunogenic composition according to any one of clause C120 to clause C121, further comprising QS-21.

C126. The immunogenic composition according to any one of clause C120 to clause C121, further comprising a CpG oligonucleotide.

C127. The immunogenic composition according to any one of clause C120 to clause C121, wherein the composition does not include an adjuvant.

C128. An immunogenic composition comprising a mutated FimH polypeptide according to any of clauses C69 to C118, and a saccharide derived from E. coli, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C129. The immunogenic composition according to clause C128, wherein the saccharide is an O-antigen derived from E. coli.

C130. The immunogenic composition according to clause C128, further comprising a pharmaceutically acceptable excipient, carrier or diluent.

C131. The immunogenic composition according to clause C128, wherein the saccharide is an O-antigen derived from E. coli.

C132. An immunogenic composition comprising a mutated FimH polypeptide, and a saccharide according to any one of clause C69 to clause C85, conjugated to a carrier protein through a (2-((2-oxoethyl)thio)ethyl)carbamate (eTEC) spacer, wherein the polysaccharide is covalently linked to the eTEC spacer through a carbamate linkage, and wherein the carrier protein is covalently linked to the eTEC spacer through an amide linkage.

C133. An immunogenic composition comprising a mutated FimH polypeptide, and (i) a conjugate of an E. coli O25B antigen covalently coupled to a carrier protein, (ii) a conjugate of an E. coli O1A antigen covalently coupled to a carrier protein, (iii) a conjugate of an E. coli O2 antigen covalently coupled to a carrier protein, and (iv) a conjugate of an O6 antigen covalently coupled to a carrier protein, wherein the E. coli O25B antigen comprises the structure of Formula O25B, wherein n is an integer greater than 30.

C134. The immunogenic composition of clause C133, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from Pseudomonas aeruginosa; detoxified Exotoxin A of P. aeruginosa (EPA), maltose binding protein (MBP), detoxified hemolysin A of S. aureus, clumping factor A, clumping factor B, Cholera toxin B subunit (CTB), Streptococcus pneumoniae Pneumolysin and detoxified variants thereof, C. jejuni AcrA, C. jejuni natural glycoproteins and Streptococcal C5a peptidase (SCP).

C135. An immunogenic composition comprising a mutated FimH polypeptide according to any one of clauses C69 to C118, and (i) a conjugate of an E. coli O25B antigen covalently coupled to a carrier protein, (ii) a conjugate of an E. coli O4 antigen covalently coupled to a carrier protein, (iii) a conjugate of an E. coli O11 antigen covalently coupled to a carrier protein, and (iv) a conjugate of an O21 antigen covalently coupled to a carrier protein, wherein the E. coli O25B antigen comprises the structure of Formula O75, wherein n is an integer greater than 30.

C136. The immunogenic composition of clause C135, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from Pseudomonas aeruginosa; detoxified Exotoxin A of P. aeruginosa (EPA), maltose binding protein (MBP), detoxified hemolysin A of S. aureus, clumping factor A, clumping factor B, Cholera toxin B subunit (CTB), Streptococcus pneumoniae Pneumolysin and detoxified variants thereof, C. jejuni AcrA, C. jejuni natural glycoproteins and Streptococcal C5a peptidase (SCP).

C137. A method of making an immunogenic composition comprising a mutated FimH polypeptide, and a conjugate comprising a saccharide conjugated to a carrier protein through a (2-((2-oxoethyl)thio)ethyl)carbamate (eTEC) spacer, comprising the steps of a) reacting a saccharide with 1,1'-carbonyl-di-(1,2,4-triazole) (CDT) or 1,1'-carbonyl-diimidazole (CDI), in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues; whereby an eTEC linked glycoconjugate is produced, wherein the saccharide is derived from $E.\ coli$; further comprising expressing a polynucleotide encoding a polypeptide derived from FimH or fragment thereof in a recombinant mammalian cell, and isolating said polypeptide or fragment thereof.

C138. The method according to clause C137, comprising making the immunogenic composition according to any one of clause C69 to clause C102.

C139. The method according to any of one clause C137 to clause C138, wherein the capping step e) comprises reacting the thiolated saccharide-carrier protein conjugate with (i) N-acetyl-L-cysteine as a first capping reagent, and/or (ii) iodoacetamide as a second capping reagent.

C140. The method according to any of one clause C137 to clause C139, further comprising a step of compounding the saccharide by reaction with triazole or imidazole to provide a compounded saccharide, wherein the compounded saccharide is shell frozen, lyophilized and reconstituted in an organic solvent prior to step a).

C141. The method according to any of one clause C137 to clause C140, further comprising purification of the thiolated polysaccharide produced in step c), wherein the purification step comprises diafiltration.

C142. The method according to any of one clause C137 to clause C141, wherein the method further comprises purification of the eTEC linked glycoconjugate by diafiltration.

C143. The method according to any of one clause C137 to clause C142, wherein the organic solvent in step a) is a polar aprotic solvent selected from any one of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2(1H)-pyrimidinone (DMPU) and hexamethylphosphoramide (HMPA), or a mixture thereof.

C144. The method according to any of one clause C137 to clause C142, wherein the medium comprises an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$-$2H_2O$.

C145. The medium according to clause C144, wherein the medium is used for culturing $E.\ coli$.

C146. A method for producing a saccharide according to any one of clause C69 to clause C102, comprising culturing a recombinant $E.\ coli$ in a medium; producing said saccharide by culturing said cell in said medium; whereby said cell produces said saccharide.

C147. The method according to clause C146, wherein the medium comprises an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$-$2H_2O$.

C148. The method according to clause C146, wherein the medium comprises soy hydrolysate.

C149. The method according to clause C146, wherein the medium comprises yeast extract.

C150. The method according to clause C146, wherein the medium does not further comprise soy hydrolysate and yeast extract.

C151. The method according to clause C146, wherein the $E.\ coli$ cell comprises a heterologous wzz family protein selected from any one of wzzB, wzz, $wzz_{SF}$, $wzz_{ST}$, fepE, $wzz_{fepE}$, wzz1 and wzz2.

C152. The method according to clause C146, wherein the $E.\ coli$ cell comprises a $Salmonella\ enterica$ wzz family protein selected from any one of wzzB, wzz, $wzz_{SF}$, $wzz_{ST}$, fepE, $wzz_{fepE}$, wzz1 and wzz2.

C153. The method according to clause C152, wherein the wzz family protein comprises a sequence selected from any one of SEQ ID NO: 112, SEQ ID NO: 113, SEQ ID NO: 114, SEQ ID NO: 115, and SEQ ID NO: 116.

C154. The method according to clause C146, wherein the culturing produces a yield of >120 $OD_{600}$/mL.

C155. The method according to clause C146, further comprising purifying the saccharide.

C156. The method according to clause C146, wherein the purifying step comprises any one of the following: dialysis, concentration operations, diafiltration operations, tangential flow filtration, precipitation, elution, centrifugation, precipitation, ultra-filtration, depth filtration, and column chromatography (ion exchange chromatography, multimodal ion exchange chromatography, DEAE, and hydrophobic interaction chromatography).

C157. A method for inducing an immune response in a subject comprising administering to the subject a composition according to any one of clause C69 to clause C136.

C158. The method according to clause C157, wherein the immune response comprises induction of an anti-$E.\ coli$ O-specific polysaccharide serum antibody.

C159. The method according to clause C157, wherein the immune response comprises induction of an anti-$E.\ coli$ IgG antibody.

C160. The method according to clause C157, wherein the immune response comprises induction of bactericidal activity against $E.\ coli$.

C161. The method according to clause C157, wherein the immune response comprises induction of opsonophagocytic antibodies against $E.\ coli$.

C162. The method according to clause C157, wherein the immune response comprises a geometric mean titer (GMT) level of at least 1,000 to 200,000 after initial dosing.

C163. The method according to clause C157, wherein the composition comprises a saccharide comprising the Formula O25, wherein n is an integer 40 to 100, wherein the immune response comprises a geometric mean titer (GMT) level of at least 1,000 to 200,000 after initial dosing.

C164. The method according to clause C157, wherein the subject is at risk of any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

C165. The method according to clause C157, wherein the subject is a mammal.

C166. A method for (i) inducing an immune response in a subject against extra-intestinal pathogenic *E. coli*, or (ii) inducing the production of opsonophagocytic antibodies in a subject that are specific to extra-intestinal pathogenic *E. coli*, wherein the method comprises administering to the subject an effective amount of the composition according to any one of clause C69 to clause C136.

C167. The method of clause C166, wherein the subject is at risk of developing a urinary tract infection.

C168. The method of clause C166, wherein the subject is at risk of developing bacteremia.

C169. The method of clause C166, wherein the subject is at risk of developing sepsis.

C170. A method for inducing an immune response in a subject comprising administering to the subject a composition according to any one of clauses C69 to clause C136.

C171. The method according to clause C170, wherein the immune response comprises induction of an anti-*E. coli* O-specific polysaccharide serum antibody.

C172. The method according to clause C170, wherein the anti-*E. coli* O-specific polysaccharide serum antibody is an IgG antibody.

C173. The method according to clause C170, wherein the anti-*E. coli* O-specific polysaccharide serum antibody is an IgG antibody has bactericidal activity against *E. coli*.

C174. The immunogenic composition of clause C69, wherein n is greater than the number of repeat units in the corresponding wild-type *E. coli* polysaccharide.

C175. The composition according to clause C174, wherein n is an integer from 31 to 100.

C176. The composition according to clause C174, wherein the saccharide comprises a structure according to any one of Formula O1A, Formula O1B, and Formula O1C, Formula O2, Formula O6, and Formula O25B.

C177. The composition according to clause C174, wherein the saccharide is produced in a recombinant host cell that expresses a wzz family protein having at least 90% sequence identity to any one of SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121.

C178. The composition according to clause C177, wherein the protein comprises any one of SEQ ID NO: 112, SEQ ID NO: 113, SEQ ID NO: 114, SEQ ID NO: 115, and SEQ ID NO: 116.

C179. The saccharide according to clause C174, wherein the saccharide is synthetically synthesized.

C180. An immunogenic composition comprising a mutated FimH polypeptide according to any one of clauses C1 to C55, and (a) a conjugate comprising a carrier protein covalently bound to a saccharide comprising Formula O25b, wherein n is an integer from 31 to 90, (b) a conjugate comprising a carrier protein covalently bound to a saccharide comprising Formula O1A, wherein n is an integer from 31 to 90, (c) a conjugate comprising a carrier protein covalently bound to a saccharide comprising Formula O2, wherein n is an integer from 31 to 90, and (d) a conjugate comprising a carrier protein covalently bound to a saccharide comprising and Formula O6, wherein n is an integer from 31 to 90.

C181. The immunogenic composition according to clause C180, further comprising a conjugate comprising a carrier protein covalently bound to a saccharide comprising a structure selected from any one of the following: Formula O15, Formula O16, Formula O17, Formula O18 and Formula O75, wherein n is an integer from 31 to 90.

C182. The immunogenic composition according to clause C180, comprising at most 25% free saccharide as compared to the total amount of saccharide in the composition.

C183. A method of eliciting an immune response against *E. coli* in a mammal, comprising administering to the mammal an effective amount of the composition according to any one of clauses C180 to C182.

C184. The method according to clause C183, wherein the immune response comprises opsonophagocytic antibodies against *E. coli*.

C185. The method according to clause C183, wherein the immune response protects the mammal from an *E. coli* infection.

C186. A recombinant mammalian cell comprising (a) a first gene of interest encoding a mutated FimH polypeptide of any one of clauses C1 to C55, wherein the gene is integrated between at least two recombination target sites (RTS).

C187. The embodiment of clause C186, wherein the two RTS are chromosomally-integrated within the NL1 locus or the NL2 locus.

C188. The embodiment of clause C186, wherein the first gene of interest further comprises a reporter gene, a gene encoding a difficult to express protein, an ancillary gene or a combination thereof.

C189. The embodiment of clause C186, further comprising a second gene of interest that is integrated within a second chromosomal locus distinct from the locus of (a), wherein the second gene of interest comprises a reporter gene, a gene encoding a difficult to express protein, an ancillary gene or a combination thereof.

C190. The recombinant cell according to C186, wherein the polynucleotide sequence is integrated into the genomic DNA of said mammalian cell.

C191. The recombinant cell according to C186, wherein the polynucleotide sequence is codon optimized for expression in the cell.

C192. The recombinant cell according to C186, wherein the cell is a human embryonic kidney cell.

C193. The recombinant cell according to C192, wherein the human embryonic kidney cell comprises a HEK293 cell.

C194. The recombinant cell according to C193, wherein the HEK293 cell is selected from any one of HEK293T cells, HEK293TS cells, and HEK293E cells.

C195. The recombinant cell according to C186, wherein the cell is a CHO cell.

C196. The recombinant cell according to C195, wherein said CHO cell is a CHO-K1 cell, CHO-DUXB11, CHO-DG44 cell, or CHO-S cell.

C197. The recombinant cell according to C186, wherein the polypeptide is soluble. C198. The recombinant cell according to C186, wherein the polypeptide is secreted from the cell.

C199. A culture comprising the recombinant cell of C186, wherein said culture is at least 5 liter in size.

C200. The culture according to C199, wherein the yield of the polypeptide or fragment thereof is at least 0.05 g/L.

C201. The culture according to C199, wherein the yield of the polypeptide or fragment thereof is at least 0.10 g/L.

C202. A method for producing a polypeptide derived from *E. coli* or a fragment thereof, comprising culturing a recombinant mammalian cell according to C186 under a suitable condition, thereby expressing the polypeptide or fragment thereof; and harvesting the polypeptide or fragment thereof.

C203. The method according to C202, further comprising purifying the polypeptide or fragment thereof.

C204. The immunogenic composition according to Clause C54, further comprising at least one saccharide derived from any one *K. pneumoniae* type selected from the group consisting of O1, O2, O3, and O5.

C205. The immunogenic composition according to Clause C204, further comprising a saccharide derived from *K. pneumoniae* type O1.

C206. The immunogenic composition according to Clause C204, further comprising a saccharide derived from *K. pneumoniae* type O2.

C207. The composition according to Clause C204, further comprising a saccharide derived from *K. pneumoniae* type O3.

C208. The immunogenic composition according to Clause C204, further comprising a saccharide derived from *K. pneumoniae* type O5.

C209. The immunogenic composition according to Clause C204, further comprising a saccharide derived from *K. pneumoniae* type O1 and a saccharide derived from *K. pneumoniae* type O2.

C210. The immunogenic composition according to any one of Clauses C204 to C209, further comprising at least one saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187, wherein n is an integer from 1 to 100, more preferably from 31 to 90.

C211. The immunogenic composition according to Clause C210, wherein the saccharide derived from *K. pneumoniae* is conjugated to a carrier protein; and the saccharide derived from *E. coli* is conjugated to a carrier protein.

C212. A method of eliciting an immune response against *E. coli* in a mammal, comprising administering to the mammal an effective amount of the composition according to any one of Clauses C204-C211.

C213. The method according to Clause C212, wherein the immune response comprises opsonophagocytic antibodies against *E. coli*.

C214. The method according to Clause C212, wherein the immune response protects the mammal from an *E. coli* infection.

C215. A method of eliciting an immune response against *K. pneumoniae* in a mammal, comprising administering to the mammal an effective amount of the composition according to any one of Clauses C204-C211.

C216. The method according to Clause C215, wherein the immune response comprises opsonophagocytic antibodies against *K. pneumoniae*.

C217. The method according to Clause C215, wherein the immune response protects the mammal from a *K. pneumoniae* infection.

C218. The compositions and methods of any of Clauses C204 to C217, wherein the *K. pneumoniae* serotype O1 comprises variant O1V1 or O1V2.

C219. The compositions and methods of any of Clauses C204 to C217, wherein the *K. pneumoniae* serotype O2 comprises variant O2V1 or O2V2.

C220. Use of the compositions set forth in any one of Clauses C1-C219 as set forth herein.

C221. The composition of clause C211, wherein the *K. pneumoniae* O-antigen is selected from the group consisting of a) serotype O1 subtype v1 (O1v1), b) serotype O1 subtype v2 (O1v2), c) serotype O2 subtype v1 (O2v1), and d) serotype O2 subtype v2 (O2v2).

C222. A nucleic acid comprising nucleotides encoding the polypeptides of any one of clauses C1-C221.

C223. The nucleic acid of clause C222, wherein the nucleic acid is RNA.

C224. A nanoparticle comprising the nucleic acid of clause C222 or C223.

C225. The immunogenic composition of this invention, further comprising one or more conjugates having a saccharide selected from the group consisting of Formula O4, Formula O11, Formula O13, Formula O21 and Formula O86, wherein n is an integer from 1 to 100, preferably from 31 to 90.

C226. The immunogenic composition of this invention, further comprising one or more conjugates having a saccharide selected from the group consisting of Formula O1a, Formula O2, Formula O6, and Formula O25b, wherein n is an integer from 1 to 100, preferably from 31 to 90.

The invention claimed is:

1. A mutated FimH polypeptide, which comprises: at least one amino acid substitution relative to the amino acid sequence of the wild-type FimH polypeptide, wherein the substitution is selected from the group consisting of: F1I; F1V; F1M; F1Y; F1W; P12C; G14C; G15A; G15P; G16A; G16P; A18C; P26C; V28C; Q32C; N33C; L34N; L34S; L34T; L34D; L34E; L34K; L34R; V35C; S62C; Y64C; G65A; L68C; F71C; T86C; L107C; Y108C; L109C; V112C; S113C; A115V; G116C; V118C; A119C; A119N; A119S; A119D; A119E; A119K; A119R; A127C; L129C; F144C; V154C; V155C; V156C; T158C; and V185I, and wherein the amino acid positions are numbered according to SEQ ID NO: 59.

2. A mutated FimH polypeptide, which comprises amino acid substitutions relative to the amino acid sequence of the wild-type FimH polypeptide, wherein the amino acid substitutions selected from the group consisting of:
 a) G15A and G16A;
 b) P12C and A18C;
 c) G14C and F144C;
 d) P26C and V35C;
 e) P26C and V154C;
 f) P26C and V156C;
 g) V27A and Q133K;
 h) V28C and N33C;
 i) V28C and P157C;
 j) Q32C and Y108C;
 k) N33C and L109C;
 l) N33C and P157C;
 m) V35C and L107C;
 n) V35C and L109C;
 o) S62C and T86C;
 p) S62C and L129C;
 q) Y64C and L68C;
 r) Y64C and A127C;
 s) L68C and F71C;
 t) V112C and T158C;
 u) S113C and G116C;
 v) S113C and T158C;
 w) V118C and V156C;
 x) A119C and V155C;
 y) L34N and V27A;
 z) L34S and V27A;
 aa) L34T and V27A;
 ab) L34D and V27A;
 ac) L34E and V27A;
 ad) L34K and V27A;
 ae) L34R and V27A;
 af) A119N and V27A;
 ag) A119S and V27A;
 ah) A119T and V27A;
 ai) A119D and V27A;
 aj) A119E and V27A;
 ak) A119K and V27A;
 al) AI119R and V27A;
 am) G15A and V27A;
 an) G16A and V27A;
 ao) G15P and V27A;
 ap) GI6P and V27A;
 aq) G15A, G16A, and V27A;
 ar) G65A and V27A; and
 as) G15A, G16A, V27A, and Q133K, and wherein the amino acid positions are numbered according to SEQ ID NO: 59.

3. A mutated FimH polypeptide comprising a sequence selected from the group consisting of SEQ ID NOs: 2, 3, 5-8, 10-14, 16-21, 23-46, 48-58, and 61-64.

4. The mutated FimH polypeptide according to claim 1, wherein the polypeptide is isolated.

5. A pharmaceutical composition comprising (i) the mutated FimH polypeptide according to claim 1 and (ii) a pharmaceutically acceptable carrier.

6. An immunogenic composition comprising the mutated FimH polypeptide according to claim 1.

7. The immunogenic composition according to claim 6, further comprising an *E. coil* saccharide antigen, wherein the saccharide antigen comprises a structure selected from the group consisting of formula O25b, Formula O1A, Formula O2, and formula O6.

8. The immunogenic composition according to claim 6, further comprising at least one adjuvant.

9. The polypeptide of claim 1, further comprising the amino acid substitution V27A.

10. The polypeptide of claim 2, comprising the amino acid substitutions G15A, G16A, and V27A.

11. The polypeptide of claim 1, wherein the polypeptide is stabilized by a donor-strand peptide of FimG (FimH-DsG).

12. The mutated polypeptide of claim 3, comprising the sequence of SEQ ID NO: 62.

13. A pharmaceutical composition comprising (i) the mutated FimH polypeptide according to claim 2 and (ii) a pharmaceutically acceptable carrier.

14. An immunogenic composition comprising the mutated FimH polypeptide according to claim 2.

15. The immunogenic composition according to claim 14, further comprising an *E. coli* saccharide antigen, wherein the saccharide antigen comprises a structure selected from the group consisting of Formula O25b, Formula O1A, Formula O2, and Formula O6.

16. The immunogenic composition according to claim 14, further comprising at least one adjuvant.

17. A pharmaceutical composition comprising (i) the mutated FimH polypeptide according to claim 3 and (ii) a pharmaceutically acceptable carrier.

18. An immunogenic composition comprising the mutated FimH polypeptide according to claim 3.

19. The immunogenic composition according to claim 18, further comprising an *E. coli* saccharide antigen, wherein the saccharide antigen comprises a structure selected from the group consisting of Formula O25b, Formula O1A, Formula O2, and Formula O6.

20. The immunogenic composition according to claim 18, further comprising at least one adjuvant.

* * * * *

SEQUENCE LISTING

<160> NUMBER OF SEQ ID NOS: 147

<210> SEQ ID NO 1
<211> LENGTH: 160
<212> TYPE: PRT
<213> ORGANISM: Escherichia coli

<400> SEQUENCE: 1

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160
```

<210> SEQ ID NO 2
<211> LENGTH: 160
<212> TYPE: PRT
<213> ORGANISM: Artificial Sequence
<220> FEATURE:
<223> OTHER INFORMATION: Synthetic

<400> SEQUENCE: 2

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Ala Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160
```

<210> SEQ ID NO 3
<211> LENGTH: 160
<212> TYPE: PRT
<213> ORGANISM: Artificial Sequence
<220> FEATURE:
<223> OTHER INFORMATION: Synthetic

<400> SEQUENCE: 3

```
Ile Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Val Pro Thr Gly Gly
145                 150                 155                 160
```

<210> SEQ ID NO 4
<211> LENGTH: 160
<212> TYPE: PRT
<213> ORGANISM: Artificial Sequence
<220> FEATURE:
<223> OTHER INFORMATION: Synthetic

<400> SEQUENCE: 4

```
Leu Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Val Pro Thr Gly Gly
```

<210> SEQ ID NO 5
<211> LENGTH: 160
<212> TYPE: PRT
<213> ORGANISM: Artificial Sequence
<220> FEATURE:
<223> OTHER INFORMATION: Synthetic

<400> SEQUENCE: 5

```
Val Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160
```

<210> SEQ ID NO 6
<211> LENGTH: 160
<212> TYPE: PRT
<213> ORGANISM: Artificial Sequence
<220> FEATURE:
<223> OTHER INFORMATION: Synthetic

<400> SEQUENCE: 6

```
Met Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140
```

```
Val Trp Asn Ile Tyr Ala Asn Asn Asp Val Val Pro Thr Gly Gly
145                 150                 155                 160
```

<210> SEQ ID NO 7
<211> LENGTH: 160
<212> TYPE: PRT
<213> ORGANISM: Artificial Sequence
<220> FEATURE:
<223> OTHER INFORMATION: Synthetic

<400> SEQUENCE: 7

```
Tyr Ala Cys Lys Thr Ala Ser Gly Thr Ala Ile Pro Ile Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160
```

<210> SEQ ID NO 8
<211> LENGTH: 160
<212> TYPE: PRT
<213> ORGANISM: Artificial Sequence
<220> FEATURE:
<223> OTHER INFORMATION: Synthetic

<400> SEQUENCE: 8

```
Trp Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
130                 135                 140
```

Val Trp Asn Ile Tyr Ala Asn Asn Asp Val Val Pro Thr Gly Gly
145                 150                 155                 160

<210> SEQ ID NO 9
<211> LENGTH: 160
<212> TYPE: PRT
<213> ORGANISM: Artificial Sequence
<220> FEATURE:
<223> OTHER INFORMATION: Synthetic

<400> SEQUENCE: 9

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Lys Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

<210> SEQ ID NO 10
<211> LENGTH: 160
<212> TYPE: PRT
<213> ORGANISM: Artificial Sequence
<220> FEATURE:
<223> OTHER INFORMATION: Synthetic

<400> SEQUENCE: 10

Phe Ala Cys Lys Thr Ala Ser Gly Thr Ala Ile Pro Ile Gly Ala Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe

```
                130                 135                 140
Val Trp Asn Ile Tyr Ala Asn Asn Asp Val Val Pro Thr Gly Gly
145                 150                 155                 160

<210> SEQ ID NO 11
<211> LENGTH: 160
<212> TYPE: PRT
<213> ORGANISM: Artificial Sequence
<220> FEATURE:
<223> OTHER INFORMATION: Synthetic

<400> SEQUENCE: 11

Phe Ala Cys Lys Thr Ala Ser Gly Thr Ala Ile Pro Ile Gly Pro Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 12
<211> LENGTH: 160
<212> TYPE: PRT
<213> ORGANISM: Artificial Sequence
<220> FEATURE:
<223> OTHER INFORMATION: Synthetic

<400> SEQUENCE: 12

Phe Ala Cys Lys Thr Ala Ser Gly Thr Ala Ile Pro Ile Gly Gly Ala
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125
```

```
Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160
```

<210> SEQ ID NO 13
<211> LENGTH: 160
<212> TYPE: PRT
<213> ORGANISM: Artificial Sequence
<220> FEATURE:
<223> OTHER INFORMATION: Synthetic

<400> SEQUENCE: 13

```
Phe Ala Cys Lys Thr Ala Ser Gly Thr Ala Ile Pro Ile Gly Gly Pro
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160
```

<210> SEQ ID NO 14
<211> LENGTH: 160
<212> TYPE: PRT
<213> ORGANISM: Artificial Sequence
<220> FEATURE:
<223> OTHER INFORMATION: Synthetic

<400> SEQUENCE: 14

```
Phe Ala Cys Lys Thr Ala Ser Gly Thr Ala Ile Pro Ile Gly Ala Ala
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125
```

```
Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Pro Thr Gly Gly
145                 150                 155                 160
```

<210> SEQ ID NO 15
<211> LENGTH: 160
<212> TYPE: PRT
<213> ORGANISM: Artificial Sequence
<220> FEATURE:
<223> OTHER INFORMATION: Synthetic

<400> SEQUENCE: 15

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Pro Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160
```

<210> SEQ ID NO 16
<211> LENGTH: 160
<212> TYPE: PRT
<213> ORGANISM: Artificial Sequence
<220> FEATURE:
<223> OTHER INFORMATION: Synthetic

<400> SEQUENCE: 16

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Ala Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
```

```
                    115                 120                 125
Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

<210> SEQ ID NO 17
<211> LENGTH: 160
<212> TYPE: PRT
<213> ORGANISM: Artificial Sequence
<220> FEATURE:
<223> OTHER INFORMATION: Synthetic

<400> SEQUENCE: 17

Phe Ala Cys Lys Thr Ala Ser Gly Thr Ala Ile Cys Ile Gly Gly Gly
1               5                   10                  15

Ser Cys Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

<210> SEQ ID NO 18
<211> LENGTH: 160
<212> TYPE: PRT
<213> ORGANISM: Artificial Sequence
<220> FEATURE:
<223> OTHER INFORMATION: Synthetic

<400> SEQUENCE: 18

Phe Ala Cys Lys Thr Ala Ser Gly Thr Ala Ile Pro Ile Cys Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110
```

```
Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Cys
130                 135                 140

Val Trp Asn Ile Tyr Ala Asn Asn Asp Val Val Pro Thr Gly Gly
145                 150                 155                 160

<210> SEQ ID NO 19
<211> LENGTH: 160
<212> TYPE: PRT
<213> ORGANISM: Artificial Sequence
<220> FEATURE:
<223> OTHER INFORMATION: Synthetic

<400> SEQUENCE: 19

Phe Ala Cys Lys Thr Ala Ser Gly Thr Ala Ile Pro Ile Gly Gly Gly
1               5                   10                  15

Ser Ala Asn Val Tyr Val Asn Leu Ala Cys Val Val Asn Val Gly Gln
                20                  25                  30

Asn Leu Cys Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

<210> SEQ ID NO 20
<211> LENGTH: 160
<212> TYPE: PRT
<213> ORGANISM: Artificial Sequence
<220> FEATURE:
<223> OTHER INFORMATION: Synthetic

<400> SEQUENCE: 20

Phe Ala Cys Lys Thr Ala Ser Gly Thr Ala Ile Pro Ile Gly Gly Gly
1               5                   10                  15

Ser Ala Asn Val Tyr Val Asn Leu Ala Cys Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110
```

```
Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Cys Val Val Pro Thr Gly Gly
145                 150                 155                 160

<210> SEQ ID NO 21
<211> LENGTH: 160
<212> TYPE: PRT
<213> ORGANISM: Artificial Sequence
<220> FEATURE:
<223> OTHER INFORMATION: Synthetic

<400> SEQUENCE: 21

Phe Ala Cys Lys Thr Ala Ser Gly Thr Ala Ile Pro Ile Gly Gly Gly
1               5                   10                  15

Ser Ala Asn Val Tyr Val Asn Leu Ala Cys Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Cys Pro Thr Gly Gly
145                 150                 155                 160

<210> SEQ ID NO 22
<211> LENGTH: 160
<212> TYPE: PRT
<213> ORGANISM: Artificial Sequence
<220> FEATURE:
<223> OTHER INFORMATION: Synthetic

<400> SEQUENCE: 22

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Cys Val Asn Val Gly Gln
                20                  25                  30

Asn Cys Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
```

```
                     100                 105                 110
Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 23
<211> LENGTH: 160
<212> TYPE: PRT
<213> ORGANISM: Artificial Sequence
<220> FEATURE:
<223> OTHER INFORMATION: Synthetic

<400> SEQUENCE: 23

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Cys Asn Val Gly Gln
            20                  25                  30

Cys Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 24
<211> LENGTH: 160
<212> TYPE: PRT
<213> ORGANISM: Artificial Sequence
<220> FEATURE:
<223> OTHER INFORMATION: Synthetic

<400> SEQUENCE: 24

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Cys Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95
```

```
Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Cys Thr Gly Gly
145                 150                 155                 160
```

<210> SEQ ID NO 25
<211> LENGTH: 160
<212> TYPE: PRT
<213> ORGANISM: Artificial Sequence
<220> FEATURE:
<223> OTHER INFORMATION: Synthetic

<400> SEQUENCE: 25

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Cys
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Cys Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160
```

<210> SEQ ID NO 26
<211> LENGTH: 160
<212> TYPE: PRT
<213> ORGANISM: Artificial Sequence
<220> FEATURE:
<223> OTHER INFORMATION: Synthetic

<400> SEQUENCE: 26

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Cys Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95
```

```
Ser Arg Thr Asp Lys Pro Trp Pro Val Ala Leu Tyr Cys Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 27
<211> LENGTH: 160
<212> TYPE: PRT
<213> ORGANISM: Artificial Sequence
<220> FEATURE:
<223> OTHER INFORMATION: Synthetic

<400> SEQUENCE: 27

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Cys Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Cys Thr Gly Gly
145                 150                 155                 160

<210> SEQ ID NO 28
<211> LENGTH: 160
<212> TYPE: PRT
<213> ORGANISM: Artificial Sequence
<220> FEATURE:
<223> OTHER INFORMATION: Synthetic

<400> SEQUENCE: 28

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Cys Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
```

```
                    85                  90                  95
Ser Arg Thr Asp Lys Pro Trp Pro Val Ala Cys Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Val Pro Thr Gly Gly
145                 150                 155                 160

<210> SEQ ID NO 29
<211> LENGTH: 160
<212> TYPE: PRT
<213> ORGANISM: Artificial Sequence
<220> FEATURE:
<223> OTHER INFORMATION: Synthetic

<400> SEQUENCE: 29

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Cys Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Cys Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Val Pro Thr Gly Gly
145                 150                 155                 160

<210> SEQ ID NO 30
<211> LENGTH: 160
<212> TYPE: PRT
<213> ORGANISM: Artificial Sequence
<220> FEATURE:
<223> OTHER INFORMATION: Synthetic

<400> SEQUENCE: 30

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Cys Ala Tyr
    50                  55                  60

Gly Gly Val Leu Ser Ser Phe Ser Gly Thr Val Lys Tyr Ser Gly Ser
65                  70                  75                  80
```

Ser Tyr Pro Phe Pro Cys Thr Ser Glu Thr Pro Arg Val Val Tyr Asn
            85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

<210> SEQ ID NO 31
<211> LENGTH: 160
<212> TYPE: PRT
<213> ORGANISM: Artificial Sequence
<220> FEATURE:
<223> OTHER INFORMATION: Synthetic

<400> SEQUENCE: 31

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Cys Ala Tyr
            50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
            85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Cys Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

<210> SEQ ID NO 32
<211> LENGTH: 160
<212> TYPE: PRT
<213> ORGANISM: Artificial Sequence
<220> FEATURE:
<223> OTHER INFORMATION: Synthetic

<400> SEQUENCE: 32

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Cys
            50                  55                  60

Gly Gly Val Cys Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 33
<211> LENGTH: 160
<212> TYPE: PRT
<213> ORGANISM: Artificial Sequence
<220> FEATURE:
<223> OTHER INFORMATION: Synthetic

<400> SEQUENCE: 33

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Cys
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Cys Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 34
<211> LENGTH: 160
<212> TYPE: PRT
<213> ORGANISM: Artificial Sequence
<220> FEATURE:
<223> OTHER INFORMATION: Synthetic

<400> SEQUENCE: 34

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Cys Ser Ser Cys Ser Gly Thr Val Lys Tyr Ser Gly Ser

```
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
                130                 135                 140

Val Trp Asn Ile Tyr Ala Asn Asn Asp Val Val Pro Thr Gly Gly
145                 150                 155                 160

<210> SEQ ID NO 35
<211> LENGTH: 160
<212> TYPE: PRT
<213> ORGANISM: Artificial Sequence
<220> FEATURE:
<223> OTHER INFORMATION: Synthetic

<400> SEQUENCE: 35

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ser Ala Tyr
                50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Cys
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
                130                 135                 140

Val Trp Asn Ile Tyr Ala Asn Asn Asp Val Val Pro Cys Gly Gly
145                 150                 155                 160

<210> SEQ ID NO 36
<211> LENGTH: 160
<212> TYPE: PRT
<213> ORGANISM: Artificial Sequence
<220> FEATURE:
<223> OTHER INFORMATION: Synthetic

<400> SEQUENCE: 36

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ser Ala Tyr
                50                  55                  60
```

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
            85                  90                  95

Ser Arg Thr Asp Lys Pro Trp Pro Val Ala Leu Tyr Leu Thr Pro Val
                100                 105                 110

Cys Ser Ala Cys Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

<210> SEQ ID NO 37
<211> LENGTH: 160
<212> TYPE: PRT
<213> ORGANISM: Artificial Sequence
<220> FEATURE:
<223> OTHER INFORMATION: Synthetic

<400> SEQUENCE: 37

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
            85                  90                  95

Ser Arg Thr Asp Lys Pro Trp Pro Val Ala Leu Tyr Leu Thr Pro Val
                100                 105                 110

Cys Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Val Pro Cys Gly Gly
145                 150                 155                 160

<210> SEQ ID NO 38
<211> LENGTH: 160
<212> TYPE: PRT
<213> ORGANISM: Artificial Sequence
<220> FEATURE:
<223> OTHER INFORMATION: Synthetic

<400> SEQUENCE: 38

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

```
Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Cys Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Cys Pro Thr Gly Gly
145                 150                 155                 160

<210> SEQ ID NO 39
<211> LENGTH: 160
<212> TYPE: PRT
<213> ORGANISM: Artificial Sequence
<220> FEATURE:
<223> OTHER INFORMATION: Synthetic

<400> SEQUENCE: 39

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Cys Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Cys Val Pro Thr Gly Gly
145                 150                 155                 160

<210> SEQ ID NO 40
<211> LENGTH: 160
<212> TYPE: PRT
<213> ORGANISM: Artificial Sequence
<220> FEATURE:
<223> OTHER INFORMATION: Synthetic

<400> SEQUENCE: 40

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Asn Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
```

```
                50                  55                  60
Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
                130                 135                 140

Val Trp Asn Ile Tyr Ala Asn Asn Asp Val Val Val Pro Thr Gly Gly
145                 150                 155                 160

<210> SEQ ID NO 41
<211> LENGTH: 160
<212> TYPE: PRT
<213> ORGANISM: Artificial Sequence
<220> FEATURE:
<223> OTHER INFORMATION: Synthetic

<400> SEQUENCE: 41

Phe Ala Cys Lys Thr Ala Ser Gly Thr Ala Ile Pro Ile Gly Gly Gly
 1               5                  10                  15

Ser Ala Asn Val Tyr Val Asn Leu Ala Pro Ala Val Asn Val Gly Gln
                 20                  25                  30

Asn Ser Val Val Asp Leu Ser Thr Gln Ile Phe Cys His Asn Asp Tyr
                 35                  40                  45

Pro Glu Thr Ile Thr Asp Tyr Val Thr Leu Gln Arg Gly Ser Ala Tyr
                 50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
                130                 135                 140

Val Trp Asn Ile Tyr Ala Asn Asn Asp Val Val Val Pro Thr Gly Gly
145                 150                 155                 160

<210> SEQ ID NO 42
<211> LENGTH: 160
<212> TYPE: PRT
<213> ORGANISM: Artificial Sequence
<220> FEATURE:
<223> OTHER INFORMATION: Synthetic

<400> SEQUENCE: 42

Phe Ala Cys Lys Thr Ala Ser Gly Thr Ala Ile Pro Ile Gly Gly Gly
 1               5                  10                  15

Ser Ala Asn Val Tyr Val Asn Leu Ala Pro Ala Val Asn Val Gly Gln
                 20                  25                  30

Asn Thr Val Val Asp Leu Ser Thr Gln Ile Phe Cys His Asn Asp Tyr
                 35                  40                  45
```

```
Pro Glu Thr Ile Thr Asp Tyr Val Thr Leu Gln Arg Gly Ser Ala Tyr
 50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160

<210> SEQ ID NO 43
<211> LENGTH: 160
<212> TYPE: PRT
<213> ORGANISM: Artificial Sequence
<220> FEATURE:
<223> OTHER INFORMATION: Synthetic

<400> SEQUENCE: 43

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ser Ala Tyr
 50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
                100                 105                 110

Ser Ser Ala Gly Gly Val Asn Ile Lys Ala Gly Ser Leu Ile Ala Val
                115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160

<210> SEQ ID NO 44
<211> LENGTH: 160
<212> TYPE: PRT
<213> ORGANISM: Artificial Sequence
<220> FEATURE:
<223> OTHER INFORMATION: Synthetic

<400> SEQUENCE: 44

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
                35                  40                  45
```

```
Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
 65              70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ser Ile Lys Ala Gly Ser Leu Ile Ala Val
            115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160
```

<210> SEQ ID NO 45
<211> LENGTH: 160
<212> TYPE: PRT
<213> ORGANISM: Artificial Sequence
<220> FEATURE:
<223> OTHER INFORMATION: Synthetic

<400> SEQUENCE: 45

```
Phe Ala Cys Lys Thr Ala Ser Gly Thr Ala Ile Pro Ile Gly Gly Gly
 1               5                  10                  15

Ser Ala Asn Val Tyr Val Asn Leu Ala Pro Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
 65              70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Thr Ile Lys Ala Gly Ser Leu Ile Ala Val
            115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160
```

<210> SEQ ID NO 46
<211> LENGTH: 300
<212> TYPE: PRT
<213> ORGANISM: Artificial Sequence
<220> FEATURE:
<223> OTHER INFORMATION: Synthetic

<400> SEQUENCE: 46

```
Phe Ala Cys Lys Thr Ala Ser Gly Thr Ala Ile Pro Ile Gly Gly Gly
 1               5                  10                  15

Ser Ala Asn Val Tyr Val Asn Leu Ala Pro Val Asn Val Gly Gln
                20                  25                  30

Asn Leu Val Val Asp Leu Ser Thr Gln Ile Phe Cys His Asn Asp Tyr
```

```
            35                  40                  45
Pro Glu Thr Ile Thr Asp Tyr Val Thr Leu Gln Arg Gly Ser Ala Tyr
     50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
                100                 105                 110

Ser Ser Val Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Ala Asp Ala Gly Asn Ser Ile
            195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln Gly Gly Ser Ser Gly Gly Ala Asp
            275                 280                 285

Val Thr Ile Thr Val Asn Gly Lys Val Val Ala Lys
    290                 295                 300

<210> SEQ ID NO 47
<211> LENGTH: 300
<212> TYPE: PRT
<213> ORGANISM: Artificial Sequence
<220> FEATURE:
<223> OTHER INFORMATION: Synthetic

<400> SEQUENCE: 47

Phe Ala Cys Lys Thr Ala Ser Gly Thr Ala Ile Pro Ile Gly Gly Gly
 1               5                  10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
     50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
```

```
            100                 105                 110
Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

Cys Asp Ile Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Ser Gly Gly Ala Asp
        275                 280                 285

Val Thr Ile Thr Val Asn Gly Lys Val Val Ala Lys
    290                 295                 300
```

<210> SEQ ID NO 48
<211> LENGTH: 300
<212> TYPE: PRT
<213> ORGANISM: Artificial Sequence
<220> FEATURE:
<223> OTHER INFORMATION: Synthetic

<400> SEQUENCE: 48

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
```

```
                   165                 170                 175
Gly Ser Val Pro Ile Pro Leu Thr Ile Tyr Cys Ala Lys Ser Gln Asn
                180                 185                 190

Leu Gly Tyr Tyr Leu Ser Gly Thr Ala Asp Ala Gly Asn Ser Ile
            195                 200                 205

Phe Thr Asn Thr Ala Ser Phe Ser Pro Ala Gln Gly Val Gly Val Gln
            210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Ser Gly Gly Ala Asp
            275                 280                 285

Val Thr Ile Thr Val Asn Gly Lys Val Val Ala Lys
            290                 295                 300
```

<210> SEQ ID NO 49
<211> LENGTH: 300
<212> TYPE: PRT
<213> ORGANISM: Artificial Sequence
<220> FEATURE:
<223> OTHER INFORMATION: Synthetic

<400> SEQUENCE: 49

```
Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Ala Asp Ala Gly Asn Ser Ile
            195                 200                 205

Phe Thr Asn Thr Ala Ser Phe Ser Pro Ala Gln Gly Val Gly Val Gln
            210                 215                 220

Leu Thr Arg Gln Gly Thr Ile Ile Pro Ala Asn Asn Thr Val Ser Leu
```

```
                225                 230                 235                 240
Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln Gly Ser Ser Gly Gly Ala Asp
                275                 280                 285

Ile Thr Ile Thr Val Asn Gly Lys Val Val Ala Lys
                290                 295                 300

<210> SEQ ID NO 50
<211> LENGTH: 160
<212> TYPE: PRT
<213> ORGANISM: Artificial Sequence
<220> FEATURE:
<223> OTHER INFORMATION: Synthetic

<400> SEQUENCE: 50

Phe Ala Cys Lys Thr Ala Ser Gly Thr Ala Ile Pro Ile Gly Ala Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Val Pro Thr Gly Gly
145                 150                 155                 160

<210> SEQ ID NO 51
<211> LENGTH: 160
<212> TYPE: PRT
<213> ORGANISM: Artificial Sequence
<220> FEATURE:
<223> OTHER INFORMATION: Synthetic

<400> SEQUENCE: 51

Phe Ala Cys Lys Thr Ala Ser Gly Thr Ala Ile Pro Ile Gly Gly Ala
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80
```

```
Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
           100                 105                 110

Ser Ser Ala Gly Gly Val Ala Ile Lys Ala Gly Ser Leu Ile Ala Val
       115                 120                 125

Leu Ile Leu Arg Gln Thr Asn Asn Tyr Asn Ser Asp Asp Phe Gln Phe
   130                 135                 140

Val Trp Asn Ile Tyr Ala Asn Asn Asp Val Val Pro Thr Gly Gly
145                 150                 155                 160

<210> SEQ ID NO 52
<211> LENGTH: 160
<212> TYPE: PRT
<213> ORGANISM: Artificial Sequence
<220> FEATURE:
<223> OTHER INFORMATION: Synthetic

<400> SEQUENCE: 52

Phe Ala Cys Lys Thr Ala Ser Gly Thr Ala Ile Pro Ile Gly Pro Gly
1               5                   10                  15

Ser Ala Asn Val Tyr Val Asn Leu Ala Pro Ala Val Asn Val Gly Gln
           20                  25                  30

Asn Leu Val Val Asp Leu Ser Thr Gln Ile Phe Cys His Asn Asp Tyr
       35                  40                  45

Pro Glu Thr Ile Thr Asp Tyr Val Thr Leu Gln Arg Gly Ser Ala Tyr
   50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
           100                 105                 110

Ser Ser Ala Gly Gly Val Ala Ile Lys Ala Gly Ser Leu Ile Ala Val
       115                 120                 125

Leu Ile Leu Arg Gln Thr Asn Asn Tyr Asn Ser Asp Asp Phe Gln Phe
   130                 135                 140

Val Trp Asn Ile Tyr Ala Asn Asn Asp Val Val Pro Thr Gly Gly
145                 150                 155                 160

<210> SEQ ID NO 53
<211> LENGTH: 160
<212> TYPE: PRT
<213> ORGANISM: Artificial Sequence
<220> FEATURE:
<223> OTHER INFORMATION: Synthetic

<400> SEQUENCE: 53

Phe Ala Cys Lys Thr Ala Ser Gly Thr Ala Ile Pro Ile Gly Pro Gly
1               5                   10                  15

Ser Ala Asn Val Tyr Val Asn Leu Ala Pro Ala Val Asn Val Gly Gln
           20                  25                  30

Asn Leu Val Val Asp Leu Ser Thr Gln Ile Phe Cys His Asn Asp Tyr
       35                  40                  45

Pro Glu Thr Ile Thr Asp Tyr Val Thr Leu Gln Arg Gly Ser Ala Tyr
   50                  55                  60

Gly Gly Val Leu Ser Ser Phe Ser Gly Thr Val Lys Tyr Ser Gly Ser
65                  70                  75                  80
```

```
Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 54
<211> LENGTH: 160
<212> TYPE: PRT
<213> ORGANISM: Artificial Sequence
<220> FEATURE:
<223> OTHER INFORMATION: Synthetic

<400> SEQUENCE: 54

Phe Ala Cys Lys Thr Ala Ser Gly Thr Ala Ile Pro Ile Gly Ala Ala
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

<210> SEQ ID NO 55
<211> LENGTH: 160
<212> TYPE: PRT
<213> ORGANISM: Artificial Sequence
<220> FEATURE:
<223> OTHER INFORMATION: Synthetic

<400> SEQUENCE: 55

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Pro Gly Ser Ala Tyr
    50                  55                  60

Gly Gly Val Leu Ser Ser Phe Ser Gly Thr Val Lys Tyr Ser Gly Ser
```

```
               65                  70                  75                  80
Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
               100                 105                 110

Ser Ser Ala Gly Gly Val Ala Ile Lys Ala Gly Ser Leu Ile Ala Val
               115                 120                 125

Leu Ile Leu Arg Gln Thr Asn Asn Tyr Asn Ser Asp Asp Phe Gln Phe
       130                 135                 140

Val Trp Asn Ile Tyr Ala Asn Asn Asp Val Val Pro Thr Gly Gly
145                 150                 155                 160
```

<210> SEQ ID NO 56
<211> LENGTH: 160
<212> TYPE: PRT
<213> ORGANISM: Artificial Sequence
<220> FEATURE:
<223> OTHER INFORMATION: Synthetic

<400> SEQUENCE: 56

```
Phe Ala Cys Lys Thr Ala Ser Gly Thr Ala Ile Pro Ile Gly Gly Gly
1               5                  10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Ala Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
               100                 105                 110

Ser Ser Ala Gly Gly Val Ala Ile Lys Ala Gly Ser Leu Ile Ala Val
               115                 120                 125

Leu Ile Leu Arg Gln Thr Asn Asn Tyr Asn Ser Asp Asp Phe Gln Phe
       130                 135                 140

Val Trp Asn Ile Tyr Ala Asn Asn Asp Val Val Pro Thr Gly Gly
145                 150                 155                 160
```

<210> SEQ ID NO 57
<211> LENGTH: 160
<212> TYPE: PRT
<213> ORGANISM: Artificial Sequence
<220> FEATURE:
<223> OTHER INFORMATION: Synthetic

<400> SEQUENCE: 57

```
Phe Ala Cys Lys Thr Ala Ser Gly Thr Ala Ile Pro Ile Gly Gly Gly
1               5                  10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60
```

```
Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Lys Thr Asn Asn Tyr Asn Ser Asp Asp Phe Gln Phe
            130                 135                 140

Val Trp Asn Ile Tyr Ala Asn Asn Asp Val Val Val Pro Thr Gly Gly
145                 150                 155                 160

<210> SEQ ID NO 58
<211> LENGTH: 160
<212> TYPE: PRT
<213> ORGANISM: Artificial Sequence
<220> FEATURE:
<223> OTHER INFORMATION: Synthetic

<400> SEQUENCE: 58

Phe Ala Cys Lys Thr Ala Ser Gly Thr Ala Ile Pro Ile Gly Ala Ala
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Lys Thr Asn Asn Tyr Asn Ser Asp Asp Phe Gln Phe
            130                 135                 140

Val Trp Asn Ile Tyr Ala Asn Asn Asp Val Val Val Pro Thr Gly Gly
145                 150                 155                 160

<210> SEQ ID NO 59
<211> LENGTH: 300
<212> TYPE: PRT
<213> ORGANISM: Artificial Sequence
<220> FEATURE:
<223> OTHER INFORMATION: Synthetic

<400> SEQUENCE: 59

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
50                  55                  60
```

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Ala Asp Ala Gly Asn Ser Ile
    195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln Gly Gly Ser Ser Gly Gly Ala Asp
                275                 280                 285

Val Thr Ile Thr Val Asn Gly Lys Val Val Ala Lys
    290                 295                 300

<210> SEQ ID NO 60
<211> LENGTH: 300
<212> TYPE: PRT
<213> ORGANISM: Artificial Sequence
<220> FEATURE:
<223> OTHER INFORMATION: Synthetic

<400> SEQUENCE: 60

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

```
Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Ser Gly Gly Gly Ala Asp
        275                 280                 285

Val Thr Ile Thr Val Asn Gly Lys Val Val Ala Lys
    290                 295                 300

<210> SEQ ID NO 61
<211> LENGTH: 300
<212> TYPE: PRT
<213> ORGANISM: Artificial Sequence
<220> FEATURE:
<223> OTHER INFORMATION: Synthetic

<400> SEQUENCE: 61

Phe Ala Cys Lys Thr Ala Ser Gly Thr Ala Ile Pro Ile Gly Ala Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190
```

Leu Gly Tyr Tyr Leu Ser Gly Thr Thr Ala Asp Ala Gly Asn Ser Ile
            195                 200                 205

Phe Thr Asn Thr Ala Ser Phe Ser Pro Ala Gln Gly Val Gly Val Gln
            210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Gly Gly Ala Asp
            275                 280                 285

Val Thr Ile Thr Val Asn Gly Lys Val Ala Lys
            290                 295                 300

<210> SEQ ID NO 62
<211> LENGTH: 300
<212> TYPE: PRT
<213> ORGANISM: Artificial Sequence
<220> FEATURE:
<223> OTHER INFORMATION: Synthetic

<400> SEQUENCE: 62

Phe Ala Cys Lys Thr Ala Ser Gly Thr Ala Ile Pro Ile Gly Ala Ala
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
            195                 200                 205

Phe Thr Asn Thr Ala Ser Phe Ser Pro Ala Gln Gly Val Gly Val Gln
            210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Ser Gly Gly Gly Ala Asp
            275                 280                 285

Val Thr Ile Thr Val Asn Gly Lys Val Val Ala Lys
            290                 295                 300

<210> SEQ ID NO 63
<211> LENGTH: 300
<212> TYPE: PRT
<213> ORGANISM: Artificial Sequence
<220> FEATURE:
<223> OTHER INFORMATION: Synthetic

<400> SEQUENCE: 63

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Lys Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Ser Gly Gly Gly Ala Asp
            275                 280                 285

Val Thr Ile Thr Val Asn Gly Lys Val Val Ala Lys
            290                 295                 300

<210> SEQ ID NO 64

```
<211> LENGTH: 300
<212> TYPE: PRT
<213> ORGANISM: Artificial Sequence
<220> FEATURE:
<223> OTHER INFORMATION: Synthetic

<400> SEQUENCE: 64

Phe Ala Cys Lys Thr Ala Ser Gly Thr Ala Ile Pro Ile Gly Ala Ala
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Lys Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Gly Gly Ser Gly Gly Gly Ala Asp
        275                 280                 285

Val Thr Ile Thr Val Asn Gly Lys Val Val Ala Lys
    290                 295                 300

<210> SEQ ID NO 65
<211> LENGTH: 19
<212> TYPE: PRT
<213> ORGANISM: Mus musculus

<400> SEQUENCE: 65

Glu Thr Asp Thr Leu Leu Leu Trp Val Leu Leu Leu Trp Val Pro Gly
1               5                   10                  15

Ser Thr Gly
```

```
<210> SEQ ID NO 66
<211> LENGTH: 207
<212> TYPE: PRT
<213> ORGANISM: Artificial Sequence
<220> FEATURE:
<223> OTHER INFORMATION: Synthetic

<400> SEQUENCE: 66

Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
            20                  25                  30

Val Leu Glu Leu Met Gly Val Gly Ala Leu Glu Ile Thr Leu Arg Thr
        35                  40                  45

Glu Lys Gly Leu Glu Ala Leu Lys Ala Leu Arg Lys Ser Gly Leu Leu
    50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
            100                 105                 110

Thr Pro Thr Glu Val Glu Arg Ala Leu Ala Leu Gly Leu Ser Ala Leu
        115                 120                 125

Lys Phe Phe Pro Ala Glu Pro Phe Gln Gly Val Arg Val Leu Arg Ala
    130                 135                 140

Tyr Ala Glu Val Phe Pro Glu Val Arg Phe Leu Pro Thr Gly Gly Ile
145                 150                 155                 160

Lys Glu Glu His Leu Pro His Tyr Ala Ala Leu Pro Asn Leu Leu Ala
                165                 170                 175

Val Gly Gly Ser Trp Leu Leu Gln Gly Asp Leu Ala Ala Val Met Lys
            180                 185                 190

Lys Val Lys Ala Ala Lys Ala Leu Leu Ser Pro Gln Ala Pro Gly
        195                 200                 205

<210> SEQ ID NO 67
<211> LENGTH: 156
<212> TYPE: PRT
<213> ORGANISM: Artificial Sequence
<220> FEATURE:
<223> OTHER INFORMATION: Synthetic

<400> SEQUENCE: 67

Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Glu Leu Asp
            100                 105                 110
```

```
Ile Leu Ala Leu Val Arg Ala Ile Glu His Ala Ala Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Arg Glu Asp Ala Gly Pro Ala Arg Glu
145                 150                 155

<210> SEQ ID NO 68
<211> LENGTH: 156
<212> TYPE: PRT
<213> ORGANISM: Artificial Sequence
<220> FEATURE:
<223> OTHER INFORMATION: Synthetic

<400> SEQUENCE: 68

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155

<210> SEQ ID NO 69
<211> LENGTH: 209
<212> TYPE: PRT
<213> ORGANISM: Artificial Sequence
<220> FEATURE:
<223> OTHER INFORMATION: Synthetic

<400> SEQUENCE: 69

Met Ser Thr Ile Asn Asn Gln Leu Lys Ala Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Thr Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110
```

```
Asn Pro Ser Thr Val Glu Ala Ala Leu Glu Met Gly Leu Thr Thr Leu
        115                 120                 125

Lys Phe Phe Pro Ala Glu Ala Ser Gly Gly Ile Ser Met Val Lys Ser
130                 135                 140

Leu Val Gly Pro Tyr Gly Asp Ile Arg Leu Met Pro Thr Gly Gly Ile
145                 150                 155                 160

Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
            180                 185                 190

Trp Asp Glu Ile Ala Arg Leu Thr Arg Glu Ile Val Gln Val Asn
        195                 200                 205
Pro

<210> SEQ ID NO 70
<211> LENGTH: 114
<212> TYPE: PRT
<213> ORGANISM: Artificial Sequence
<220> FEATURE:
<223> OTHER INFORMATION: Synthetic

<400> SEQUENCE: 70

Met Pro Ile Phe Thr Leu Asn Thr Asn Ile Lys Ala Thr Asp Val Pro
1               5                   10                  15

Ser Asp Phe Leu Ser Leu Thr Ser Arg Leu Val Gly Leu Ile Leu Ser
                20                  25                  30

Lys Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Ser Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110
Thr Phe

<210> SEQ ID NO 71
<211> LENGTH: 157
<212> TYPE: PRT
<213> ORGANISM: Artificial Sequence
<220> FEATURE:
<223> OTHER INFORMATION: Synthetic

<400> SEQUENCE: 71

Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
            35                  40                  45

Val Phe Asp Val Pro Gly Ala Tyr Glu Ile Pro Leu His Ala Arg Thr
        50                  55                  60

Leu Ala Glu Thr Gly Arg Tyr Gly Ala Val Leu Gly Thr Ala Phe Val
65                  70                  75                  80
```

```
Val Asn Gly Gly Ile Tyr Arg His Glu Phe Val Ala Ser Ala Val Ile
            85                  90                  95

Asp Gly Met Met Asn Val Gln Leu Ser Thr Gly Val Pro Val Leu Ser
        100                 105                 110

Ala Val Leu Thr Pro His Arg Tyr Arg Asp Ser Ala Glu His His Arg
        115                 120                 125

Phe Phe Ala Ala His Phe Ala Val Lys Gly Val Glu Ala Ala Arg Ala
        130                 135                 140

Cys Ile Glu Ile Leu Ala Ala Arg Glu Lys Ile Ala Ala
145                 150                 155
```

<210> SEQ ID NO 72
<211> LENGTH: 205
<212> TYPE: PRT
<213> ORGANISM: Artificial Sequence
<220> FEATURE:
<223> OTHER INFORMATION: Synthetic

<400> SEQUENCE: 72

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205
```

<210> SEQ ID NO 73
<211> LENGTH: 157
<212> TYPE: PRT
<213> ORGANISM: Artificial Sequence
<220> FEATURE:
<223> OTHER INFORMATION: Synthetic

<400> SEQUENCE: 73

```
Met Asn Gln His Ser His Lys Asp Tyr Glu Thr Val Arg Ile Ala Val
1               5                   10                  15

Val Arg Ala Arg Trp His Ala Glu Ile Val Asp Ala Cys Val Ser Ala
            20                  25                  30
```

Phe Glu Ala Ala Met Ala Asp Ile Gly Gly Asp Arg Phe Ala Val Asp
                35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asp Gly Met Met Asn Val Gln Leu Ser Thr Gly Val Pro Val Leu Ser
                100                 105                 110

Ala Val Leu Thr Pro His Arg Tyr Arg Asp Ser Asp Ala His Thr Leu
                115                 120                 125

Leu Phe Leu Ala Leu Phe Ala Val Lys Gly Met Glu Ala Ala Arg Ala
130                 135                 140

Cys Val Glu Ile Leu Ala Ala Arg Glu Lys Ile Ala Ala
145                 150                 155

<210> SEQ ID NO 74
<211> LENGTH: 177
<212> TYPE: PRT
<213> ORGANISM: Artificial Sequence
<220> FEATURE:
<223> OTHER INFORMATION: Synthetic

<400> SEQUENCE: 74

Met Phe Thr Lys Ser Gly Asp Asp Gly Asn Thr Asn Val Ile Asn Lys
  1               5                  10                  15

Arg Val Gly Lys Asp Ser Pro Leu Val Asn Phe Leu Gly Asp Leu Asp
                 20                  25                  30

Glu Leu Asn Ser Phe Ile Gly Phe Ala Ile Ser Lys Ile Pro Trp Glu
                 35                  40                  45

Asp Met Lys Lys Asp Leu Glu Arg Val Gln Val Glu Leu Phe Glu Ile
 50                  55                  60

Gly Glu Asp Leu Ser Thr Gln Ser Ser Lys Lys Ile Asp Glu Ser
 65                  70                  75                  80

Tyr Val Leu Trp Leu Leu Ala Ala Thr Ala Ile Tyr Arg Ile Glu Ser
                 85                  90                  95

Gly Pro Val Lys Leu Phe Val Ile Pro Gly Ser Glu Glu Ala Ser
                100                 105                 110

Val Leu His Val Thr Arg Ser Val Ala Arg Arg Val Glu Arg Asn Ala
                115                 120                 125

Val Lys Tyr Thr Lys Glu Leu Pro Glu Ile Asn Arg Met Ile Ile Val
                130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 75
<211> LENGTH: 157
<212> TYPE: PRT
<213> ORGANISM: Artificial Sequence
<220> FEATURE:
<223> OTHER INFORMATION: Synthetic

<400> SEQUENCE: 75

```
Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
                20                  25                  30

Phe Glu Glu Ala Met Ala Asp Ala Gly Gly Asp Arg Phe Ala Val Asp
            35                  40                  45

Val Phe Asp Val Pro Gly Ala Tyr Glu Ile Pro Leu His Ala Arg Thr
50                      55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Ser Ser Arg Glu His His Glu
            115                 120                 125

Phe Phe Arg Glu His Phe Met Val Lys Gly Val Glu Ala Ala Ala Ala
130                 135                 140

Cys Ile Thr Ile Leu Ala Ala Arg Glu Lys Ile Ala Ala
145                 150                 155

<210> SEQ ID NO 76
<211> LENGTH: 201
<212> TYPE: PRT
<213> ORGANISM: Artificial Sequence
<220> FEATURE:
<223> OTHER INFORMATION: Synthetic

<400> SEQUENCE: 76

Met Gly His Thr Lys Gly Pro Thr Pro Gln Gln His Asp Gly Ser Ala
1               5                   10                  15

Leu Arg Ile Gly Ile Val His Ala Arg Trp Asn Lys Thr Ile Ile Met
                20                  25                  30

Pro Leu Leu Ile Gly Thr Ile Ala Lys Leu Leu Glu Cys Gly Val Lys
            35                  40                  45

Ala Ser Asn Ile Val Val Gln Ser Val Pro Gly Ser Trp Glu Leu Pro
50                  55                  60

Ile Ala Val Gln Arg Leu Tyr Ser Ala Ser Gln Leu Gln Thr Pro Ser
65                  70                  75                  80

Ser Gly Pro Ser Leu Ser Ala Gly Asp Leu Leu Gly Ser Ser Thr Thr
                85                  90                  95

Asp Leu Thr Ala Leu Pro Thr Thr Thr Ala Ser Ser Thr Gly Pro Phe
            100                 105                 110

Asp Ala Leu Ile Ala Ile Gly Val Leu Ile Lys Gly Thr Met Glu His
            115                 120                 125

Phe Glu Tyr Ile Ala Asp Ser Val Ser His Gly Leu Met Arg Val Gln
130                 135                 140

Leu Asp Thr Gly Val Pro Val Ile Phe Gly Val Leu Thr Val Leu Thr
145                 150                 155                 160

Asp Asp Gln Ala Lys Ala Arg Ala Gly Val Ile Glu Gly Ser His Asn
                165                 170                 175

His Gly Glu Asp Trp Gly Leu Ala Ala Val Glu Met Gly Val Arg Arg
            180                 185                 190

Arg Asp Trp Ala Ala Gly Lys Thr Glu
195                 200
```

<210> SEQ ID NO 77
<211> LENGTH: 237
<212> TYPE: PRT
<213> ORGANISM: Artificial Sequence
<220> FEATURE:
<223> OTHER INFORMATION: Synthetic

<400> SEQUENCE: 77

Met Tyr Glu Val Asp His Ala Asp Val Tyr Asp Leu Phe Tyr Leu Gly
1               5                   10                  15

Arg Gly Lys Asp Tyr Ala Ala Glu Ala Ser Asp Ile Ala Asp Leu Val
            20                  25                  30

Arg Ser Arg Thr Pro Glu Ala Ser Ser Leu Leu Asp Val Ala Cys Gly
        35                  40                  45

Thr Gly Thr His Leu Glu His Phe Thr Lys Glu Phe Gly Asp Thr Ala
    50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Gln Leu Gly
                85                  90                  95

Arg Lys Phe Ser Ala Val Val Ser Met Phe Ser Ser Val Gly Tyr Leu
            100                 105                 110

Lys Thr Val Ala Glu Leu Gly Ala Ala Val Ala Ser Phe Ala Glu His
        115                 120                 125

Leu Glu Pro Gly Gly Val Val Val Glu Pro Trp Trp Phe Pro Glu
    130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Arg Glu Tyr
        195                 200                 205

Glu Ala Ala Phe Met Ala Ala Gly Leu Arg Val Glu Tyr Leu Glu Gly
    210                 215                 220

Gly Pro Ser Gly Arg Gly Leu Phe Val Gly Val Pro Ala
225                 230                 235

<210> SEQ ID NO 78
<211> LENGTH: 138
<212> TYPE: PRT
<213> ORGANISM: Artificial Sequence
<220> FEATURE:
<223> OTHER INFORMATION: Synthetic

<400> SEQUENCE: 78

Met Gly Met Lys Glu Lys Phe Val Leu Ile Ile Thr His Gly Asp Phe
1               5                   10                  15

Gly Lys Gly Leu Leu Ser Gly Ala Glu Val Ile Ile Gly Lys Gln Glu
            20                  25                  30

Asn Val His Thr Val Gly Leu Asn Leu Gly Asp Asn Ile Glu Lys Val
        35                  40                  45

Ala Lys Glu Val Met Arg Ile Ile Ile Ala Lys Leu Ala Glu Asp Lys
    50                  55                  60

Glu Ile Ile Ile Val Val Asp Leu Phe Gly Gly Ser Pro Phe Asn Ile

```
                65                  70                  75                  80
Ala Leu Glu Met Met Lys Thr Phe Asp Val Lys Val Ile Thr Gly Ile
                    85                  90                  95

Asn Met Pro Met Leu Val Glu Leu Leu Thr Ser Ile Asn Val Tyr Asp
                100                 105                 110

Thr Thr Glu Leu Leu Glu Asn Ile Ser Lys Ile Gly Lys Asp Gly Ile
                115                 120                 125

Lys Val Ile Glu Lys Ser Ser Leu Lys Met
            130                 135
```

<210> SEQ ID NO 79
<211> LENGTH: 154
<212> TYPE: PRT
<213> ORGANISM: Artificial Sequence
<220> FEATURE:
<223> OTHER INFORMATION: Synthetic

<400> SEQUENCE: 79

```
Met Lys Tyr Asp Gly Ser Lys Leu Arg Ile Gly Ile Leu His Ala Arg
1               5                   10                  15

Trp Asn Leu Glu Ile Ile Ala Ala Leu Val Ala Gly Ala Ile Lys Arg
                20                  25                  30

Leu Gln Glu Phe Gly Val Lys Ala Glu Asn Ile Ile Ile Glu Thr Val
            35                  40                  45

Pro Gly Ser Phe Glu Leu Pro Tyr Gly Ser Lys Leu Phe Val Glu Lys
        50                  55                  60

Gln Lys Arg Leu Gly Lys Pro Leu Asp Ala Ile Ile Pro Ile Gly Val
65                  70                  75                  80

Leu Ile Lys Gly Ser Thr Met His Phe Glu Tyr Ile Cys Asp Ser Thr
                85                  90                  95

Thr His Gln Leu Met Lys Leu Asn Phe Glu Leu Gly Ile Pro Val Ile
                100                 105                 110

Phe Gly Val Leu Thr Cys Leu Thr Asp Glu Gln Ala Glu Ala Arg Ala
            115                 120                 125

Gly Leu Ile Glu Gly Lys Met His Asn His Gly Glu Asp Trp Gly Ala
        130                 135                 140

Ala Ala Val Glu Met Ala Thr Lys Phe Asn
145                 150
```

<210> SEQ ID NO 80
<211> LENGTH: 164
<212> TYPE: PRT
<213> ORGANISM: Artificial Sequence
<220> FEATURE:
<223> OTHER INFORMATION: Synthetic

<400> SEQUENCE: 80

```
Met Ala Val Lys Gly Leu Gly Glu Val Asp Gln Lys Tyr Asp Gly Ser
1               5                   10                  15

Lys Leu Arg Ile Gly Ile Leu His Ala Arg Trp Asn Arg Lys Ile Ile
                20                  25                  30

Leu Ala Leu Val Ala Gly Ala Val Leu Arg Leu Leu Glu Phe Gly Val
            35                  40                  45

Lys Ala Glu Asn Ile Ile Ile Glu Thr Val Pro Gly Ser Phe Glu Leu
        50                  55                  60

Pro Tyr Gly Ser Lys Leu Phe Val Glu Lys Gln Lys Arg Leu Gly Lys
65                  70                  75                  80
```

```
Pro Leu Asp Ala Ile Pro Ile Gly Val Leu Ile Lys Gly Ser Thr
                85                  90                  95

Met His Phe Glu Tyr Ile Cys Asp Ser Thr Thr His Gln Leu Met Lys
                100                 105                 110

Leu Asn Phe Glu Leu Gly Ile Pro Val Ile Phe Gly Val Leu Thr Cys
                115                 120                 125

Leu Thr Asp Glu Gln Ala Glu Ala Arg Ala Gly Leu Ile Glu Gly Lys
                130                 135                 140

Met His Asn His Gly Glu Asp Trp Gly Ala Ala Val Glu Met Ala
145                 150                 155                 160

Thr Lys Phe Asn

<210> SEQ ID NO 81
<211> LENGTH: 175
<212> TYPE: PRT
<213> ORGANISM: Artificial Sequence
<220> FEATURE:
<223> OTHER INFORMATION: Synthetic

<400> SEQUENCE: 81

Met Gly Ala Asn Trp Tyr Leu Asp Asn Glu Ser Ser Arg Leu Ser Phe
1               5                   10                  15

Thr Ser Thr Lys Asn Ala Asp Ile Ala Glu Val His Arg Phe Leu Val
                20                  25                  30

Leu His Gly Lys Val Asp Pro Lys Gly Leu Ala Glu Val Glu Val Glu
                35                  40                  45

Thr Glu Ser Ile Ser Thr Gly Ile Pro Leu Arg Asp Met Leu Leu Arg
50                  55                  60

Val Leu Val Phe Gln Val Ser Lys Phe Pro Val Ala Gln Ile Asn Ala
65                  70                  75                  80

Gln Leu Asp Met Arg Pro Ile Asn Asn Leu Ala Pro Gly Ala Gln Leu
                85                  90                  95

Glu Leu Arg Leu Pro Leu Thr Val Ser Leu Arg Gly Lys Ser His Ser
                100                 105                 110

Tyr Asn Ala Glu Leu Leu Ala Thr Arg Leu Asp Glu Arg Arg Phe Gln
                115                 120                 125

Val Val Thr Leu Glu Pro Leu Val Ile His Ala Gln Asp Phe Asp Met
                130                 135                 140

Val Arg Ala Phe Asn Ala Leu Arg Leu Val Ala Gly Leu Ser Ala Val
145                 150                 155                 160

Ser Leu Ser Val Pro Val Gly Ala Val Leu Ile Phe Thr Ala Arg
                165                 170                 175

<210> SEQ ID NO 82
<211> LENGTH: 208
<212> TYPE: PRT
<213> ORGANISM: Artificial Sequence
<220> FEATURE:
<223> OTHER INFORMATION: Synthetic

<400> SEQUENCE: 82

Met Thr Asp Tyr Ile Arg Asp Gly Ser Ala Ile Lys Ala Leu Ser Phe
1               5                   10                  15

Ala Ile Ile Leu Ala Glu Ala Asp Leu Arg His Ile Pro Gln Asp Leu
                20                  25                  30

Gln Arg Leu Ala Val Arg Val Ile His Ala Cys Gly Met Val Asp Val
                35                  40                  45
```

```
Ala Asn Asp Leu Ala Phe Ser Glu Gly Ala Gly Lys Ala Gly Arg Asn
 50                  55                  60

Ala Leu Leu Ala Gly Ala Pro Ile Leu Cys Asp Ala Arg Met Val Ala
 65                  70                  75                  80

Glu Gly Ile Thr Arg Ser Arg Leu Pro Ala Asp Asn Arg Val Ile Tyr
                 85                  90                  95

Thr Leu Ser Asp Pro Ser Val Pro Glu Leu Ala Lys Lys Ile Gly Asn
                100                 105                 110

Thr Arg Ser Ala Ala Ala Leu Asp Leu Trp Leu Pro His Ile Glu Gly
            115                 120                 125

Ser Ile Val Ala Ile Gly Asn Ala Pro Thr Ala Leu Phe Arg Leu Phe
            130                 135                 140

Glu Leu Leu Asp Ala Gly Ala Pro Lys Pro Ala Leu Ile Ile Gly Met
145                 150                 155                 160

Pro Val Gly Phe Val Gly Ala Ala Glu Ser Lys Asp Glu Leu Ala Ala
                165                 170                 175

Asn Ser Arg Gly Val Pro Tyr Val Ile Val Arg Gly Arg Gly Gly
                180                 185                 190

Ser Ala Met Thr Ala Ala Ala Val Asn Ala Leu Ala Ser Glu Arg Glu
            195                 200                 205
```

<210> SEQ ID NO 83
<211> LENGTH: 128
<212> TYPE: PRT
<213> ORGANISM: Artificial Sequence
<220> FEATURE:
<223> OTHER INFORMATION: Synthetic

<400> SEQUENCE: 83

```
Met Ile Thr Val Phe Gly Leu Lys Ser Lys Leu Ala Pro Arg Arg Glu
 1                5                  10                  15

Lys Leu Ala Glu Val Ile Tyr Ser Ser Leu His Leu Gly Leu Asp Ile
                 20                  25                  30

Pro Lys Gly Lys His Ala Ile Arg Phe Leu Cys Leu Glu Lys Glu Asp
                 35                  40                  45

Phe Tyr Tyr Pro Phe Asp Arg Ser Asp Asp Tyr Thr Val Ile Glu Ile
             50                  55                  60

Asn Leu Met Ala Gly Arg Ser Glu Glu Thr Lys Met Leu Leu Ile Phe
 65                  70                  75                  80

Leu Leu Phe Ile Ala Leu Glu Arg Lys Leu Gly Ile Arg Ala His Asp
                 85                  90                  95

Val Glu Ile Thr Ile Lys Glu Gln Pro Ala His Cys Trp Gly Phe Arg
                100                 105                 110

Gly Arg Thr Gly Asp Ser Ala Arg Asp Leu Asp Tyr Asp Ile Tyr Val
            115                 120                 125
```

<210> SEQ ID NO 84
<211> LENGTH: 235
<212> TYPE: PRT
<213> ORGANISM: Artificial Sequence
<220> FEATURE:
<223> OTHER INFORMATION: Synthetic

<400> SEQUENCE: 84

```
Met Gly Ser Asp Leu Gln Lys Leu Gln Arg Phe Ser Thr Cys Asp Ile
 1                5                  10                  15

Ser Asp Gly Leu Leu Asn Val Tyr Asn Ile Pro Thr Gly Gly Tyr Phe
                 20                  25                  30
```

```
Pro Asn Leu Thr Ala Ile Ser Pro Gln Asn Ser Ser Ile Val Gly
        35                  40                  45

Thr Ala Tyr Thr Val Leu Phe Ala Pro Ile Asp Asp Pro Arg Pro Ala
 50                  55                  60

Val Asn Tyr Ile Asp Ser Val Pro Pro Asn Ser Ile Leu Val Leu Ala
 65                  70                  75                  80

Leu Glu Pro His Leu Gln Ser Gln Phe His Pro Phe Ile Lys Ile Thr
                 85                  90                  95

Gln Ala Met Tyr Gly Gly Leu Met Ser Thr Arg Ala Gln Tyr Leu Lys
                100                 105                 110

Ser Asn Gly Thr Val Val Phe Gly Arg Ile Arg Asp Val Asp Glu His
                115                 120                 125

Arg Thr Leu Asn His Pro Val Phe Ala Tyr Gly Val Gly Ser Cys Ala
        130                 135                 140

Pro Lys Ala Val Val Lys Ala Val Gly Thr Asn Val Gln Leu Lys Ile
145                 150                 155                 160

Leu Thr Ser Asp Gly Val Thr Gln Thr Ile Cys Pro Gly Asp Tyr Ile
                165                 170                 175

Ala Gly Asp Asn Asn Gly Ile Val Arg Ile Pro Val Gln Glu Thr Asp
                180                 185                 190

Ile Ser Lys Leu Val Thr Tyr Ile Glu Lys Ser Ile Glu Val Asp Arg
                195                 200                 205

Leu Val Ser Glu Ala Ile Lys Asn Gly Leu Pro Ala Lys Ala Ala Gln
        210                 215                 220

Thr Ala Arg Arg Met Val Leu Lys Asp Tyr Ile
225                 230                 235

<210> SEQ ID NO 85
<211> LENGTH: 162
<212> TYPE: PRT
<213> ORGANISM: Artificial Sequence
<220> FEATURE:
<223> OTHER INFORMATION: Synthetic

<400> SEQUENCE: 85

Met Ser Gly Met Arg Val Tyr Leu Gly Ala Asp His Ala Gly Tyr Glu
 1               5                  10                  15

Leu Lys Gln Ala Ile Ile Ala Phe Leu Lys Met Thr Gly His Glu Pro
                 20                  25                  30

Ile Asp Cys Gly Ala Leu Arg Tyr Asp Ala Asp Asp Tyr Pro Ala
         35                  40                  45

Phe Cys Ile Ala Ala Ala Thr Arg Thr Val Ala Asp Pro Gly Ser Leu
 50                  55                  60

Gly Ile Val Leu Gly Gly Ser Gly Asn Gly Glu Gln Ile Ala Ala Asn
 65                  70                  75                  80

Lys Val Pro Gly Ala Arg Cys Ala Leu Ala Trp Ser Val Gln Thr Ala
                 85                  90                  95

Ala Leu Ala Arg Glu His Asn Asn Ala Gln Leu Ile Gly Ile Gly Gly
                100                 105                 110

Arg Met His Thr Leu Glu Glu Ala Leu Arg Ile Val Lys Ala Phe Val
                115                 120                 125

Thr Thr Pro Trp Ser Lys Ala Gln Arg His Gln Arg Ile Asp Ile
        130                 135                 140

Leu Ala Glu Tyr Glu Arg Thr His Glu Ala Pro Val Pro Gly Ala
145                 150                 155                 160
```

Pro Ala

<210> SEQ ID NO 86
<211> LENGTH: 157
<212> TYPE: PRT
<213> ORGANISM: Artificial Sequence
<220> FEATURE:
<223> OTHER INFORMATION: Synthetic

<400> SEQUENCE: 86

Met Gly Asp Asp Ala Arg Ile Ala Ala Ile Gly Asp Val Asp Glu Leu
1               5                   10                  15

Asn Ser Gln Ile Gly Val Leu Leu Ala Glu Pro Leu Pro Asp Asp Val
            20                  25                  30

Arg Ala Ala Leu Ser Ala Ile Gln His Asp Leu Phe Asp Leu Gly Gly
        35                  40                  45

Glu Leu Cys Ile Pro Gly His Ala Ala Ile Thr Glu Asp His Leu Leu
    50                  55                  60

Arg Leu Ala Leu Trp Leu Val His Tyr Asn Gly Gln Leu Pro Pro Leu
65                  70                  75                  80

Glu Glu Phe Ile Leu Pro Gly Gly Ala Arg Gly Ala Ala Leu Ala His
                85                  90                  95

Val Cys Arg Thr Val Cys Arg Arg Ala Glu Arg Ser Ile Lys Ala Leu
            100                 105                 110

Gly Ala Ser Glu Pro Leu Asn Ile Ala Pro Ala Ala Tyr Val Asn Leu
        115                 120                 125

Leu Ser Asp Leu Leu Phe Val Leu Ala Arg Val Leu Asn Arg Ala Ala
    130                 135                 140

Gly Gly Ala Asp Val Leu Trp Asp Arg Thr Arg Ala His
145                 150                 155

<210> SEQ ID NO 87
<211> LENGTH: 157
<212> TYPE: PRT
<213> ORGANISM: Artificial Sequence
<220> FEATURE:
<223> OTHER INFORMATION: Synthetic

<400> SEQUENCE: 87

Met Ile Leu Ser Ala Glu Gln Ser Phe Thr Leu Arg His Pro His Gly
1               5                   10                  15

Gln Ala Ala Ala Leu Ala Phe Val Arg Glu Pro Ala Ala Ala Leu Ala
            20                  25                  30

Gly Val Gln Arg Leu Arg Gly Leu Asp Ser Asp Gly Glu Gln Val Trp
        35                  40                  45

Gly Glu Leu Leu Val Arg Val Pro Leu Leu Gly Glu Val Asp Leu Pro
    50                  55                  60

Phe Arg Ser Glu Ile Val Arg Thr Pro Gln Gly Ala Glu Leu Arg Pro
65                  70                  75                  80

Leu Thr Leu Thr Gly Glu Arg Ala Trp Val Ala Val Ser Gly Gln Ala
                85                  90                  95

Thr Ala Ala Glu Gly Gly Glu Met Ala Phe Ala Phe Gln Phe Gln Ala
            100                 105                 110

His Leu Ala Thr Pro Glu Ala Glu Gly Glu Gly Gly Ala Ala Phe Glu
        115                 120                 125

Val Met Val Gln Ala Ala Ala Gly Val Thr Leu Leu Leu Val Ala Met
        130                 135                 140

Ala Leu Pro Gln Gly Leu Ala Ala Gly Leu Pro Pro Ala
145                 150                 155

<210> SEQ ID NO 88
<211> LENGTH: 156
<212> TYPE: PRT
<213> ORGANISM: Artificial Sequence
<220> FEATURE:
<223> OTHER INFORMATION: Synthetic

<400> SEQUENCE: 88

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
        50                  55                  60

Gly Met Pro Gly Lys Lys Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155

<210> SEQ ID NO 89
<211> LENGTH: 209
<212> TYPE: PRT
<213> ORGANISM: Artificial Sequence
<220> FEATURE:
<223> OTHER INFORMATION: Synthetic

<400> SEQUENCE: 89

Met Asp Asp Ile Asn Asn Gln Leu Lys Arg Leu Lys Val Ile Pro Val
1               5                   10                  15

Ile Ala Ile Asp Asn Ala Glu Asp Ile Ile Pro Leu Gly Lys Val Leu
                20                  25                  30

Ala Glu Asn Gly Leu Pro Ala Ala Glu Ile Thr Phe Arg Ser Ser Ala
            35                  40                  45

Ala Val Lys Ala Ile Met Leu Leu Arg Ser Ala Gln Pro Glu Met Leu
        50                  55                  60

Ile Gly Ala Gly Thr Ile Leu Asn Gly Val Gln Ala Leu Ala Ala Lys
65                  70                  75                  80

Glu Ala Gly Ala Asp Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Gln Ala Leu Glu Met Gly Leu Thr Thr Leu
        115                 120                 125

Lys Phe Phe Pro Ala Glu Ala Ser Gly Gly Ile Ser Met Val Lys Ser

```
                130                 135                 140
Leu Val Gly Pro Tyr Gly Asp Ile Arg Leu Met Pro Thr Gly Gly Ile
145                 150                 155                 160

Thr Pro Asp Asn Ile Asp Asn Tyr Leu Ala Ile Pro Gln Val Leu Ala
                165                 170                 175

Cys Gly Gly Thr Trp Met Val Asp Lys Lys Leu Val Arg Asn Gly Glu
                180                 185                 190

Trp Asp Glu Ile Ala Arg Leu Thr Arg Glu Ile Val Glu Gln Val Asn
            195                 200                 205

Pro

<210> SEQ ID NO 90
<211> LENGTH: 114
<212> TYPE: PRT
<213> ORGANISM: Artificial Sequence
<220> FEATURE:
<223> OTHER INFORMATION: Synthetic

<400> SEQUENCE: 90

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
                20                  25                  30

Lys Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Asp Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe

<210> SEQ ID NO 91
<211> LENGTH: 114
<212> TYPE: PRT
<213> ORGANISM: Artificial Sequence
<220> FEATURE:
<223> OTHER INFORMATION: Synthetic

<400> SEQUENCE: 91

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
                20                  25                  30

Glu Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Asp Lys Asn Glu Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asp Leu Asp Gly Asp Asp Val Gly Trp Asn Gly Thr
            100                 105                 110
```

Thr Phe

<210> SEQ ID NO 92
<211> LENGTH: 157
<212> TYPE: PRT
<213> ORGANISM: Artificial Sequence
<220> FEATURE:
<223> OTHER INFORMATION: Synthetic

<400> SEQUENCE: 92

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Glu His His Arg
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

<210> SEQ ID NO 93
<211> LENGTH: 157
<212> TYPE: PRT
<213> ORGANISM: Artificial Sequence
<220> FEATURE:
<223> OTHER INFORMATION: Synthetic

<400> SEQUENCE: 93

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Glu Asp His Glu
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

<210> SEQ ID NO 94
<211> LENGTH: 205
<212> TYPE: PRT
<213> ORGANISM: Artificial Sequence
<220> FEATURE:
<223> OTHER INFORMATION: Synthetic

<400> SEQUENCE: 94

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Glu Val Arg Glu Lys
            180                 185                 190

Ala Lys Lys Phe Val Glu Lys Ile Arg Gly Cys Thr Glu
        195                 200                 205

<210> SEQ ID NO 95
<211> LENGTH: 205
<212> TYPE: PRT
<213> ORGANISM: Artificial Sequence
<220> FEATURE:
<223> OTHER INFORMATION: Synthetic

<400> SEQUENCE: 95

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile

```
                    85                  90                  95
Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Asp Ile Leu
                115                 120                 125

Lys Leu Phe Pro Gly Glu Val Val Gly Pro Glu Phe Val Glu Ala Met
130                 135                 140

Lys Gly Pro Phe Pro Asn Val Lys Phe Val Pro Thr Gly Gly Val Asp
145                 150                 155                 160

Leu Asp Asp Val Cys Glu Trp Phe Asp Ala Gly Val Leu Ala Val Gly
                165                 170                 175

Val Gly Asp Ala Leu Val Glu Gly Asp Pro Asp Val Arg Glu Asp
                180                 185                 190

Ala Lys Glu Phe Val Glu Glu Ile Arg Gly Cys Thr Glu
                195                 200                 205

<210> SEQ ID NO 96
<211> LENGTH: 205
<212> TYPE: PRT
<213> ORGANISM: Artificial Sequence
<220> FEATURE:
<223> OTHER INFORMATION: Synthetic

<400> SEQUENCE: 96

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
                35                  40                  45

Asp Thr Val Ile Lys Ala Leu Ser Val Leu Lys Glu Lys Gly Ala Ile
                50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Asp Ile Leu
                115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Lys Trp Phe Lys Ala Gly Val Leu Ala Val Gly
                165                 170                 175

Val Gly Lys Ala Leu Val Lys Gly Lys Pro Asp Glu Val Arg Glu Lys
                180                 185                 190

Ala Lys Lys Phe Val Lys Lys Ile Arg Gly Cys Thr Glu
                195                 200                 205

<210> SEQ ID NO 97
<211> LENGTH: 157
<212> TYPE: PRT
<213> ORGANISM: Artificial Sequence
<220> FEATURE:
<223> OTHER INFORMATION: Synthetic
```

<400> SEQUENCE: 97

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 98
<211> LENGTH: 157
<212> TYPE: PRT
<213> ORGANISM: Artificial Sequence
<220> FEATURE:
<223> OTHER INFORMATION: Synthetic

<400> SEQUENCE: 98

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Ala Asp Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 99
<211> LENGTH: 157
<212> TYPE: PRT
<213> ORGANISM: Artificial Sequence
<220> FEATURE:

<223> OTHER INFORMATION: Synthetic

<400> SEQUENCE: 99

```
Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155
```

<210> SEQ ID NO 100
<211> LENGTH: 156
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (70)..(70)
<223> OTHER INFORMATION: Xaa is A or K

<400> SEQUENCE: 100

```
Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Glu Gly Cys Asp Ile Val Met Ala Leu
50                  55                  60

Gly Met Pro Gly Lys Xaa Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155
```

```
<210> SEQ ID NO 101
<211> LENGTH: 209
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is S or D
<220> FEATURE:
<221> NAME/KEY: MISC_FEATURE
<222> LOCATION: (3)..(3)
<223> OTHER INFORMATION: Xaa is T or D
<220> FEATURE:
<221> NAME/KEY: MISC_FEATURE
<222> LOCATION: (10)..(10)
<223> OTHER INFORMATION: Xaa is A or R
<220> FEATURE:
<221> NAME/KEY: MISC_FEATURE
<222> LOCATION: (85)..(85)
<223> OTHER INFORMATION: Xaa is T or D
<220> FEATURE:
<221> NAME/KEY: MISC_FEATURE
<222> LOCATION: (119)..(119)
<223> OTHER INFORMATION: Xaa is A or Q
<220> FEATURE:
<221> NAME/KEY: MISC_FEATURE
<222> LOCATION: (163)..(163)
<223> OTHER INFORMATION: Xaa is S or D
<220> FEATURE:
<221> NAME/KEY: MISC_FEATURE
<222> LOCATION: (189)..(189)
<223> OTHER INFORMATION: Xaa is T or R

<400> SEQUENCE: 101

Met Xaa Xaa Ile Asn Asn Gln Leu Lys Xaa Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Xaa Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Xaa Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Xaa Asn Ile Asp Asn Tyr Leu Ala Ile Pro Gln Val Leu Ala
                165                 170                 175

Cys Gly Gly Thr Trp Met Val Asp Lys Lys Leu Val Xaa Asn Gly Glu
            180                 185                 190

Trp Asp Glu Ile Ala Arg Leu Thr Arg Glu Ile Val Glu Gln Val Asn
        195                 200                 205

Pro
```

```
<210> SEQ ID NO 102
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa is T or D
<220> FEATURE:
<221> NAME/KEY: MISC_FEATURE
<222> LOCATION: (33)..(33)
<223> OTHER INFORMATION: Xaa is K or E
<220> FEATURE:
<221> NAME/KEY: MISC_FEATURE
<222> LOCATION: (71)..(71)
<223> OTHER INFORMATION: Xaa is S or D
<220> FEATURE:
<221> NAME/KEY: MISC_FEATURE
<222> LOCATION: (74)..(74)
<223> OTHER INFORMATION: Xaa is R or E
<220> FEATURE:
<221> NAME/KEY: MISC_FEATURE
<222> LOCATION: (101)..(101)
<223> OTHER INFORMATION: Xaa is N or D
<220> FEATURE:
<221> NAME/KEY: MISC_FEATURE
<222> LOCATION: (103)..(103)
<223> OTHER INFORMATION: Xaa is N or D

<400> SEQUENCE: 102

Met Pro Ile Phe Thr Leu Asn Thr Asn Ile Lys Ala Xaa Asp Val Pro
1               5                   10                  15

Ser Asp Phe Leu Ser Leu Thr Ser Arg Leu Val Gly Leu Ile Leu Ser
            20                  25                  30

Xaa Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Xaa Lys Asn Xaa Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Xaa Leu Xaa Gly Asp Asp Val Gly Trp Asn Gly Thr
            100                 105                 110

Thr Phe

<210> SEQ ID NO 103
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (105)..(105)
<223> OTHER INFORMATION: Xaa is S or D
```

```
<220> FEATURE:
<221> NAME/KEY: MISC_FEATURE
<222> LOCATION: (119)..(119)
<223> OTHER INFORMATION: Xaa is R or E
<220> FEATURE:
<221> NAME/KEY: MISC_FEATURE
<222> LOCATION: (121)..(121)
<223> OTHER INFORMATION: Xaa is R or E
<220> FEATURE:
<221> NAME/KEY: MISC_FEATURE
<222> LOCATION: (124)..(124)
<223> OTHER INFORMATION: Xaa is A or D
<220> FEATURE:
<221> NAME/KEY: MISC_FEATURE
<222> LOCATION: (126)..(126)
<223> OTHER INFORMATION: Xaa is H or D
<220> FEATURE:
<221> NAME/KEY: MISC_FEATURE
<222> LOCATION: (128)..(128)
<223> OTHER INFORMATION: Xaa is R or E
<220> FEATURE:
<221> NAME/KEY: MISC_FEATURE
<222> LOCATION: (150)..(150)
<223> OTHER INFORMATION: Xaa is A or N

<400> SEQUENCE: 103

Met Asn Gln His Ser His Lys Asp Xaa Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Asp Gly Met Met Asn Val Gln Leu Xaa Thr Gly Val Pro Val Leu Ser
            100                 105                 110

Ala Val Leu Thr Pro His Xaa Tyr Xaa Asp Ser Xaa Glu Xaa His Xaa
        115                 120                 125

Phe Phe Ala Ala His Phe Ala Val Lys Gly Val Glu Ala Ala Arg Ala
    130                 135                 140

Cys Ile Glu Ile Leu Xaa Ala Arg Glu Lys Ile Ala Ala
145                 150                 155

<210> SEQ ID NO 104
<211> LENGTH: 205
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (126)..(126)
<223> OTHER INFORMATION: Xaa is T or D
<220> FEATURE:
<221> NAME/KEY: MISC_FEATURE
<222> LOCATION: (139)..(139)
<223> OTHER INFORMATION: Xaa is Q or E
<220> FEATURE:
<221> NAME/KEY: MISC_FEATURE
<222> LOCATION: (142)..(142)
<223> OTHER INFORMATION: Xaa is K or E
<220> FEATURE:
<221> NAME/KEY: MISC_FEATURE
<222> LOCATION: (160)..(160)
```

```
<223> OTHER INFORMATION: Xaa is N or D
<220> FEATURE:
<221> NAME/KEY: MISC_FEATURE
<222> LOCATION: (163)..(163)
<223> OTHER INFORMATION: Xaa is N or D
<220> FEATURE:
<221> NAME/KEY: MISC_FEATURE
<222> LOCATION: (166)..(166)
<223> OTHER INFORMATION: Xaa is E or K
<220> FEATURE:
<221> NAME/KEY: MISC_FEATURE
<222> LOCATION: (169)..(169)
<223> OTHER INFORMATION: Xaa is D or K
<220> FEATURE:
<221> NAME/KEY: MISC_FEATURE
<222> LOCATION: (179)..(179)
<223> OTHER INFORMATION: Xaa is S, D or K
<220> FEATURE:
<221> NAME/KEY: MISC_FEATURE
<222> LOCATION: (183)..(183)
<223> OTHER INFORMATION: Xaa is K or E
<220> FEATURE:
<221> NAME/KEY: MISC_FEATURE
<222> LOCATION: (185)..(185)
<223> OTHER INFORMATION: Xaa is T, D, or K
<220> FEATURE:
<221> NAME/KEY: MISC_FEATURE
<222> LOCATION: (192)..(192)
<223> OTHER INFORMATION: Xaa is D or K
<220> FEATURE:
<221> NAME/KEY: MISC_FEATURE
<222> LOCATION: (195)..(195)
<223> OTHER INFORMATION: Xaa is A, E, or K
<220> FEATURE:
<221> NAME/KEY: MISC_FEATURE
<222> LOCATION: (198)..(198)
<223> OTHER INFORMATION: Xaa is E or K
<220> FEATURE:
<221> NAME/KEY: MISC_FEATURE
<222> LOCATION: (199)..(199)
<223> OTHER INFORMATION: Xaa is E or K

<400> SEQUENCE: 104

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Xaa Ile Leu
        115                 120                 125

Lys Leu Phe Pro Gly Glu Val Val Gly Pro Xaa Phe Val Xaa Ala Met
    130                 135                 140

Lys Gly Pro Phe Pro Asn Val Lys Phe Val Pro Thr Gly Gly Val Xaa
145                 150                 155                 160

Leu Asp Xaa Val Cys Xaa Trp Phe Xaa Ala Gly Val Leu Ala Val Gly
                165                 170                 175

Val Gly Xaa Ala Leu Val Xaa Gly Xaa Pro Asp Glu Val Arg Glu Xaa
            180                 185                 190
```

Ala Lys Xaa Phe Val Xaa Xaa Ile Arg Gly Cys Thr Glu
        195             200             205

<210> SEQ ID NO 105
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (38)..(38)
<223> OTHER INFORMATION: Xaa is A or R
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (97)..(97)
<223> OTHER INFORMATION: Xaa is N or D
<220> FEATURE:
<221> NAME/KEY: MISC_FEATURE
<222> LOCATION: (105)..(105)
<223> OTHER INFORMATION: Xaa is S, N, or D
<220> FEATURE:
<221> NAME/KEY: MISC_FEATURE
<222> LOCATION: (119)..(119)
<223> OTHER INFORMATION: Xaa is R, E, or N
<220> FEATURE:
<221> NAME/KEY: MISC_FEATURE
<222> LOCATION: (121)..(121)
<223> OTHER INFORMATION: Xaa is R, E, or D
<220> FEATURE:
<221> NAME/KEY: MISC_FEATURE
<222> LOCATION: (122)..(122)
<223> OTHER INFORMATION: Xaa is K or D
<220> FEATURE:
<221> NAME/KEY: MISC_FEATURE
<222> LOCATION: (124)..(124)
<223> OTHER INFORMATION: Xaa is K or D
<220> FEATURE:
<221> NAME/KEY: MISC_FEATURE
<222> LOCATION: (126)..(126)
<223> OTHER INFORMATION: Xaa is H or D

<400> SEQUENCE: 105

Met Asn Gln His Ser His Lys Asp Xaa Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Xaa Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
            85                  90                  95

Xaa Gly Met Met Asn Val Gln Leu Xaa Thr Gly Val Pro Val Leu Ser
        100                 105                 110

Ala Val Leu Thr Pro His Xaa Tyr Xaa Xaa Ser Xaa Ala Xaa Thr Leu
            115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 106
<211> LENGTH: 142
<212> TYPE: DNA
<213> ORGANISM: Artificial Sequence
<220> FEATURE:
<223> OTHER INFORMATION: Synthetic

<400> SEQUENCE: 106
taatgcttaa gtcgaacaga aagtaatcgt attgtacacg gccgcataat cgaaattaat     60
acgactcact atagggggaat tgtgagcgga taacaattcc ccatcttagt atattagtta  120
agtataagaa ggagatatac tt                                            142

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
taaagaagga gatatcat                                                  18

<210> SEQ ID NO 108
<211> LENGTH: 17
<212> TYPE: DNA
<213> ORGANISM: Artificial Sequence
<220> FEATURE:
<223> OTHER INFORMATION: Synthetic

<400> SEQUENCE: 108
tgagaaggag atatcat                                                   17

<210> SEQ ID NO 109
<211> LENGTH: 26
<212> TYPE: DNA
<213> ORGANISM: Artificial Sequence
<220> FEATURE:
<223> OTHER INFORMATION: Synthetic

<400> SEQUENCE: 109
ttgaaagtga tggtttggta agaaat                                         26

<210> SEQ ID NO 110
<211> LENGTH: 25
<212> TYPE: DNA
<213> ORGANISM: Artificial Sequence
<220> FEATURE:
<223> OTHER INFORMATION: Synthetic

<400> SEQUENCE: 110
tgcagcacgt atgataactt caaag                                          25

<210> SEQ ID NO 111
<211> LENGTH: 27
<212> TYPE: DNA
<213> ORGANISM: Artificial Sequence
<220> FEATURE:

<223> OTHER INFORMATION: Synthetic

<400> SEQUENCE: 111
aggatatttt acccagcagt gccccgt        27

<210> SEQ ID NO 112
<211> LENGTH: 325
<212> TYPE: PRT
<213> ORGANISM: Artificial Sequence
<220> FEATURE:
<223> OTHER INFORMATION: Synthetic

<400> SEQUENCE: 112

```
Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
            20                  25                  30

Thr Ile Ile Ile Ser Val Ile Val Ala Ile Ala Leu Ala Ile Gly Tyr
        35                  40                  45

Leu Ala Val Ala Lys Glu Lys Trp Thr Ser Thr Ala Ile Ile Thr Gln
    50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Glu Glu Pro Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
    130                 135                 140

Gln Met Lys Leu Ala Gln Tyr Ile Gln Gln Val Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Glu Gln Val Thr Lys Pro Gln Val Gln Thr Glu Asp Val Thr
    210                 215                 220

Gln Asp Thr Leu Phe Leu Leu Gly Ser Glu Ala Leu Glu Ser Met Ile
225                 230                 235                 240

Lys His Glu Ala Thr Arg Pro Leu Val Phe Ser Ser Asn Tyr Tyr Gln
                245                 250                 255

Thr Arg Gln Asn Leu Leu Asp Ile Glu Ser Leu Lys Val Asp Asp Leu
            260                 265                 270

Asp Ile His Ala Tyr Arg Tyr Val Met Lys Pro Thr Leu Pro Ile Arg
        275                 280                 285

Arg Asp Ser Pro Lys Lys Ala Ile Thr Leu Ile Leu Ala Val Leu Leu
    290                 295                 300

Gly Gly Met Val Gly Ala Gly Ile Val Leu Gly Arg Asn Ala Leu Arg
305                 310                 315                 320

Asn Tyr Asn Ala Lys
                325
```

<210> SEQ ID NO 113
<211> LENGTH: 326
<212> TYPE: PRT
<213> ORGANISM: Artificial Sequence
<220> FEATURE:
<223> OTHER INFORMATION: Synthetic

<400> SEQUENCE: 113

Met Arg Val Glu Asn Asn Val Ser Gly Gln Asn Asp Pro Glu
1               5                   10                  15

Gln Ile Asp Leu Ile Asp Leu Leu Val Gln Leu Trp Arg Gly Lys Met
        20                  25                  30

Thr Ile Ile Ile Ser Val Ile Val Ala Ile Ala Leu Ala Ile Gly Tyr
            35                  40                  45

Leu Ala Val Ala Lys Glu Lys Trp Thr Ser Thr Ala Ile Ile Thr Gln
    50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Asp Glu Pro Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
    130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Ala Gln Val Thr Lys Pro Gln Ile Gln Gln Thr Gly Glu Asp Ile
    210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
            260                 265                 270

Leu Asp Ile His Ala Tyr Arg Tyr Val Met Lys Pro Thr Leu Pro Ile
        275                 280                 285

Arg Arg Asp Ser Pro Lys Lys Ala Ile Thr Leu Ile Leu Ala Val Leu
    290                 295                 300

Leu Gly Gly Met Val Gly Ala Gly Ile Val Leu Gly Arg Asn Ala Leu
305                 310                 315                 320

Arg Asn Tyr Asn Ala Lys
                325

<210> SEQ ID NO 114
<211> LENGTH: 326
<212> TYPE: PRT
<213> ORGANISM: Artificial Sequence
<220> FEATURE:

<223> OTHER INFORMATION: Synthetic

<400> SEQUENCE: 114

```
Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
            20                  25                  30

Thr Ile Ile Ile Ser Val Val Ala Ile Ala Leu Ala Ile Gly Tyr
                35                  40                  45

Leu Ala Val Ala Lys Glu Lys Trp Thr Ser Thr Ala Ile Ile Thr Gln
    50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Phe Ala Phe Ser Ala Leu Ala Glu Thr Leu Asp Asn
                100                 105                 110

Gln Lys Glu Pro Glu Lys Leu Thr Ile Glu Pro Ser Val Lys Asn Gln
            115                 120                 125

Gln Leu Pro Leu Thr Val Ser Tyr Val Gly Gln Thr Ala Glu Asp Ala
    130                 135                 140

Gln Met Lys Leu Ala Gln Tyr Ile Gln Gln Val Asp Lys Val Asn
145                 150                 155                 160

Gln Glu Leu Glu Lys Asp Leu Lys Asp Asn Leu Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
    195                 200                 205

Gln Ala Gln Val Thr Lys Pro Gln Ile Gln Thr Gly Glu Asp Ile
    210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Asn Leu Lys Val Asp Asp
            260                 265                 270

Leu Asp Ile His Ala Tyr Arg Tyr Val Met Lys Pro Thr Leu Pro Ile
    275                 280                 285

Arg Arg Asp Ser Pro Lys Lys Ala Ile Thr Leu Ile Leu Ala Val Leu
                295                 300

Leu Gly Gly Met Val Gly Ala Gly Ile Val Leu Gly Arg Asn Ala Leu
305                 310                 315                 320

Arg Asn Tyr Asn Ser Lys
                325
```

<210> SEQ ID NO 115
<211> LENGTH: 326
<212> TYPE: PRT
<213> ORGANISM: Artificial Sequence
<220> FEATURE:
<223> OTHER INFORMATION: Synthetic

<400> SEQUENCE: 115

```
Met Arg Val Glu Asn Asn Val Ser Gly Gln Asn His Asp Pro Glu
1               5                   10                  15
```

Gln Ile Asp Leu Ile Asp Leu Leu Val Gln Leu Trp Arg Gly Lys Met
        20                  25                  30

Thr Ile Ile Ile Ser Val Ile Val Ala Ile Ala Leu Ala Ile Gly Tyr
            35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Glu Glu Arg Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Ala Gln Val Thr Lys Pro Gln Ile Gln Gln Thr Gly Glu Asp Ile
210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
            260                 265                 270

Leu Asp Ile His Ala Tyr Arg Tyr Val Met Lys Pro Met Leu Pro Ile
        275                 280                 285

Arg Arg Asp Ser Pro Lys Lys Ala Ile Thr Leu Ile Leu Ala Val Leu
290                 295                 300

Leu Gly Gly Met Val Gly Ala Gly Ile Val Leu Gly Arg Asn Ala Leu
305                 310                 315                 320

Arg Asn Tyr Asn Ala Lys
                325

<210> SEQ ID NO 116
<211> LENGTH: 327
<212> TYPE: PRT
<213> ORGANISM: Artificial Sequence
<220> FEATURE:
<223> OTHER INFORMATION: Synthetic

<400> SEQUENCE: 116

Met Thr Val Asp Ser Asn Thr Ser Ser Gly Arg Gly Asn Asp Pro Glu
1               5                   10                  15

Gln Ile Asp Leu Ile Glu Leu Leu Leu Gln Leu Trp Arg Gly Lys Met
        20                  25                  30

Thr Ile Ile Val Ala Val Ile Ile Ala Ile Leu Leu Ala Val Gly Tyr
            35                  40                  45

```
Leu Met Ile Ala Lys Glu Lys Trp Thr Ser Thr Ala Ile Ile Thr Gln
    50                  55                  60

Pro Asp Ala Ala Gln Val Ala Thr Tyr Thr Asn Ala Leu Asn Val Leu
65                  70                  75                  80

Tyr Gly Gly Asn Ala Pro Lys Ile Ser Glu Val Gln Ala Asn Phe Ile
                85                  90                  95

Ser Arg Phe Ser Ser Ala Phe Ser Ala Leu Ser Glu Val Leu Asp Asn
            100                 105                 110

Gln Lys Glu Arg Glu Lys Leu Thr Ile Glu Gln Ser Val Lys Gly Gln
        115                 120                 125

Ala Leu Pro Leu Ser Val Ser Tyr Val Ser Thr Thr Ala Glu Gly Ala
    130                 135                 140

Gln Arg Arg Leu Ala Glu Tyr Ile Gln Gln Val Asp Glu Glu Val Ala
145                 150                 155                 160

Lys Glu Leu Glu Val Asp Leu Lys Asp Asn Ile Thr Leu Gln Thr Lys
                165                 170                 175

Thr Leu Gln Glu Ser Leu Glu Thr Gln Glu Val Val Ala Gln Glu Gln
            180                 185                 190

Lys Asp Leu Arg Ile Lys Gln Ile Glu Glu Ala Leu Arg Tyr Ala Asp
        195                 200                 205

Glu Ala Lys Ile Thr Gln Pro Gln Ile Gln Gln Thr Gln Asp Val Thr
    210                 215                 220

Gln Asp Thr Met Phe Leu Leu Gly Ser Asp Ala Leu Lys Ser Met Ile
225                 230                 235                 240

Gln Asn Glu Ala Thr Arg Pro Leu Val Phe Ser Pro Ala Tyr Tyr Gln
                245                 250                 255

Thr Lys Gln Thr Leu Leu Asp Ile Lys Asn Leu Lys Val Thr Ala Asp
            260                 265                 270

Thr Val His Val Tyr Arg Tyr Val Met Lys Pro Thr Leu Pro Val Arg
        275                 280                 285

Arg Asp Ser Pro Lys Thr Ala Ile Thr Leu Val Leu Ala Val Leu Leu
    290                 295                 300

Gly Gly Met Ile Gly Ala Gly Ile Val Leu Gly Arg Asn Ala Leu Arg
305                 310                 315                 320

Ser Tyr Lys Pro Lys Ala Leu
                325

<210> SEQ ID NO 117
<211> LENGTH: 377
<212> TYPE: PRT
<213> ORGANISM: Artificial Sequence
<220> FEATURE:
<223> OTHER INFORMATION: Synthetic

<400> SEQUENCE: 117

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
                20                  25                  30

Ile Ser Val Leu Trp Arg Ala Lys Lys Thr Val Met Ala Val Val Phe
            35                  40                  45

Ala Phe Ala Cys Ala Gly Leu Leu Ile Ser Phe Ile Leu Pro Gln Lys
        50                  55                  60

Trp Thr Ser Ala Ala Val Val Thr Pro Pro Glu Pro Val Gln Trp Gln
65                  70                  75                  80
```

```
Glu Leu Glu Lys Ser Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
        115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
        195                 200                 205

Asn Lys Leu Glu Ile Lys Thr Gln Phe Glu Lys Glu Lys Leu Ala Gln
    210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
    290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Gly Val Leu Leu Arg Tyr Ala Met Ala Ser Arg Lys Gln
        355                 360                 365

Asp Ala Met Met Ala Asp His Leu Val
    370                 375

<210> SEQ ID NO 118
<211> LENGTH: 377
<212> TYPE: PRT
<213> ORGANISM: Artificial Sequence
<220> FEATURE:
<223> OTHER INFORMATION: Synthetic

<400> SEQUENCE: 118

Met Ser Ser Leu Asn Ile Lys Gln Gly Ser Glu Ala His Phe Pro Glu
1               5                   10                  15

Tyr Pro Leu Ala Ser Pro Ser Asn Asn Glu Ile Asp Leu Leu Asn Leu
            20                  25                  30

Ile Glu Val Leu Trp Arg Ala Lys Lys Thr Val Met Ala Val Val Phe
        35                  40                  45

Ala Phe Ala Cys Ala Gly Leu Leu Ile Ser Phe Ile Leu Pro Gln Lys
    50                  55                  60
```

Trp Thr Ser Ala Ala Val Val Thr Pro Pro Glu Pro Val Gln Trp Gln
65                  70                  75                  80

Glu Leu Glu Lys Thr Phe Thr Lys Leu Arg Val Leu Asp Leu Asp Ile
            85                  90                  95

Lys Ile Asp Arg Thr Glu Ala Phe Asn Leu Phe Ile Lys Lys Phe Gln
                100                 105                 110

Ser Val Ser Leu Leu Glu Glu Tyr Leu Arg Ser Ser Pro Tyr Val Met
        115                 120                 125

Asp Gln Leu Lys Glu Ala Lys Ile Asp Pro Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Ser Ala Leu Tyr Thr Ser Trp Thr Leu Ser Phe
                165                 170                 175

Thr Ala Pro Thr Ser Glu Glu Ala Gln Lys Val Leu Ala Gly Tyr Ile
            180                 185                 190

Asp Tyr Ile Ser Ala Leu Val Val Lys Glu Ser Ile Glu Asn Val Arg
        195                 200                 205

Asn Lys Leu Glu Ile Lys Thr Gln Phe Glu Lys Glu Lys Leu Ala Gln
    210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
    290                 295                 300

Val Glu Gln Leu Thr Lys Thr Asn Ile Asn Asp Val Asn Phe Thr Pro
305                 310                 315                 320

Phe Lys Tyr Gln Leu Arg Pro Ser Leu Pro Val Lys Lys Asp Gly Gln
                325                 330                 335

Gly Lys Ala Ile Ile Val Ile Leu Ser Ala Leu Val Gly Met Val
            340                 345                 350

Ala Cys Gly Gly Val Leu Leu Arg His Ala Met Ala Ser Arg Lys Gln
        355                 360                 365

Asp Ala Met Met Ala Asp His Leu Val
    370                 375

<210> SEQ ID NO 119
<211> LENGTH: 377
<212> TYPE: PRT
<213> ORGANISM: Artificial Sequence
<220> FEATURE:
<223> OTHER INFORMATION: Synthetic

<400> SEQUENCE: 119

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
            20                  25                  30

Ile Ser Val Leu Trp Arg Ala Lys Lys Thr Val Met Ala Val Val Phe
        35                  40                  45

```
Ala Phe Ala Cys Ala Gly Leu Leu Ile Ser Phe Ile Leu Pro Gln Lys
         50                  55                  60

Trp Thr Ser Ala Ala Val Val Thr Pro Pro Glu Pro Val Gln Trp Gln
 65                  70                  75                  80

Glu Leu Glu Lys Ser Phe Thr Lys Leu Arg Val Leu Asp Leu Asp Ile
                 85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
        115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
        195                 200                 205

Asn Lys Leu Glu Ile Lys Thr Gln Phe Glu Lys Glu Lys Leu Ala Gln
    210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
    290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Gly Val Leu Leu Arg Tyr Ala Met Ala Ser Arg Lys Gln
        355                 360                 365

Asp Ala Met Met Ala Asp His Leu Val
    370                 375

<210> SEQ ID NO 120
<211> LENGTH: 377
<212> TYPE: PRT
<213> ORGANISM: Artificial Sequence
<220> FEATURE:
<223> OTHER INFORMATION: Synthetic

<400> SEQUENCE: 120

Met Ser Ser Leu Asn Ile Lys Gln Gly Ser Asp Ala His Phe Pro Asp
1               5                  10                  15

Tyr Pro Leu Ala Ser Pro Ser Asn Asn Glu Ile Asp Leu Leu Asn Leu
            20                  25                  30
```

Ile Ser Val Leu Trp Arg Ala Lys Lys Thr Val Met Ala Val Val Phe
        35                  40                  45

Ala Phe Ala Cys Ala Gly Leu Leu Ile Ser Phe Ile Leu Pro Gln Lys
    50                  55                  60

Trp Thr Ser Ala Ala Val Val Thr Pro Pro Glu Pro Val Gln Trp Gln
65                  70                  75                  80

Glu Leu Glu Lys Thr Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
            115                 120                 125

Asp Gln Leu Lys Glu Ala Lys Ile Asp Glu Leu Asp Leu His Arg Ala
        130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Ala Leu Val Val Lys Glu Ser Ile Glu Asn Val Arg
        195                 200                 205

Asn Lys Leu Glu Ile Lys Thr Gln Phe Glu Lys Glu Lys Leu Ala Gln
        210                 215                 220

Asp Arg Ile Lys Met Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
        290                 295                 300

Val Glu Gln Leu Thr Lys Ala Asn Ile Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Ser Val Leu Leu Arg Tyr Ala Met Ala Ser Arg Lys Gln
        355                 360                 365

Asp Ala Met Met Ala Asp His Leu Val
    370                 375

<210> SEQ ID NO 121
<211> LENGTH: 378
<212> TYPE: PRT
<213> ORGANISM: Artificial Sequence
<220> FEATURE:
<223> OTHER INFORMATION: Synthetic

<400> SEQUENCE: 121

Met Pro Ser Leu Asn Val Lys Gln Glu Lys Asn Gln Ser Phe Ala Gly
1               5                   10                  15

Tyr Ser Leu Pro Pro Ala Asn Ser His Glu Ile Asp Leu Phe Ser Leu
            20                  25                  30

Ile Glu Val Leu Trp Gln Ala Lys Arg Arg Ile Leu Ala Thr Val Phe
        35                  40                  45

Ala Phe Ala Cys Val Gly Leu Leu Leu Ser Phe Leu Leu Pro Gln Lys
    50                  55                  60

Trp Thr Ser Gln Ala Ile Val Thr Pro Ala Glu Ser Val Gln Trp Gln
65                  70                  75                  80

Gly Leu Glu Arg Thr Leu Thr Ala Leu Arg Val Leu Asp Met Glu Val
                85                  90                  95

Ser Val Asp Arg Gly Ser Val Phe Asn Leu Phe Ile Lys Lys Phe Ser
            100                 105                 110

Ser Pro Ser Leu Leu Glu Glu Tyr Leu Arg Ser Ser Pro Tyr Val Met
        115                 120                 125

Asp Gln Leu Lys Gly Ala Gln Ile Asp Glu Gln Asp Leu His Arg Ala
130                 135                 140

Ile Val Leu Leu Ser Glu Lys Met Lys Ala Val Asp Ser Asn Val Gly
145                 150                 155                 160

Lys Lys Asn Glu Thr Ser Leu Phe Thr Ser Trp Thr Leu Ser Phe Thr
                165                 170                 175

Ala Pro Thr Arg Glu Glu Ala Gln Lys Val Leu Ala Gly Tyr Ile Gln
            180                 185                 190

Tyr Ile Ser Asp Ile Val Val Lys Glu Thr Leu Glu Asn Ile Arg Asn
        195                 200                 205

Gln Leu Glu Ile Lys Thr Arg Tyr Glu Gln Glu Lys Leu Ala Met Asp
210                 215                 220

Arg Val Arg Leu Lys Asn Gln Leu Asp Ala Asn Ile Gln Arg Leu His
225                 230                 235                 240

Tyr Ser Leu Glu Ile Ala Asn Ala Ala Gly Ile Lys Arg Pro Val Tyr
                245                 250                 255

Ser Asn Gly Gln Ala Val Lys Asp Asp Pro Asp Phe Ser Ile Ser Leu
            260                 265                 270

Gly Ala Asp Gly Ile Ser Arg Lys Leu Glu Ile Glu Lys Gly Val Thr
        275                 280                 285

Asp Val Ala Glu Ile Asp Gly Asp Leu Arg Asn Arg Gln Tyr His Val
290                 295                 300

Glu Gln Leu Ala Ala Met Asn Val Ser Asp Val Lys Phe Thr Pro Phe
305                 310                 315                 320

Lys Tyr Gln Leu Ser Pro Ser Leu Pro Val Lys Lys Asp Gly Pro Gly
                325                 330                 335

Lys Ala Ile Ile Ile Ile Leu Ala Ala Leu Ile Gly Gly Met Met Ala
            340                 345                 350

Cys Gly Gly Val Leu Leu Arg His Ala Met Val Ser Arg Lys Met Glu
        355                 360                 365

Asn Ala Leu Ala Ile Asp Glu Arg Leu Val
    370                 375

<210> SEQ ID NO 122
<211> LENGTH: 22
<212> TYPE: DNA
<213> ORGANISM: Artificial Sequence
<220> FEATURE:
<223> OTHER INFORMATION: Synthetic

<400> SEQUENCE: 122
gaagcaaacc gtacgcgtaa ag                                              22

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
cgaccagctc ttacacggcg                                                 20

<210> SEQ ID NO 124
<211> LENGTH: 36
<212> TYPE: DNA
<213> ORGANISM: Artificial Sequence
<220> FEATURE:
<223> OTHER INFORMATION: Synthetic

<400> SEQUENCE: 124
gaaataggac cactaataaa tacacaaatt aataac                               36

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
ataattgacg atccggttgc c                                               21

<210> SEQ ID NO 126
<211> LENGTH: 27
<212> TYPE: DNA
<213> ORGANISM: Artificial Sequence
<220> FEATURE:
<223> OTHER INFORMATION: Synthetic

<400> SEQUENCE: 126
gctatttacg ccctgattgt cttttgt                                         27

<210> SEQ ID NO 127
<211> LENGTH: 22
<212> TYPE: DNA
<213> ORGANISM: Artificial Sequence
<220> FEATURE:
<223> OTHER INFORMATION: Synthetic

<400> SEQUENCE: 127
attgagaacc tgcgtaaacg gc                                              22

<210> SEQ ID NO 128
<211> LENGTH: 24
<212> TYPE: DNA
<213> ORGANISM: Artificial Sequence
<220> FEATURE:
<223> OTHER INFORMATION: Synthetic

<400> SEQUENCE: 128
tgaagagcgg ttcagataac ttcc                                            24

<210> SEQ ID NO 129
<211> LENGTH: 21
<212> TYPE: DNA

<213> ORGANISM: Artificial Sequence
<220> FEATURE:
<223> OTHER INFORMATION: Synthetic

<400> SEQUENCE: 129
cgatccggaa acctcctaca c                                    21

<210> SEQ ID NO 130
<211> LENGTH: 26
<212> TYPE: DNA
<213> ORGANISM: Artificial Sequence
<220> FEATURE:
<223> OTHER INFORMATION: Synthetic

<400> SEQUENCE: 130
gattattcgc gcaacgctaa acagat                               26

<210> SEQ ID NO 131
<211> LENGTH: 23
<212> TYPE: DNA
<213> ORGANISM: Artificial Sequence
<220> FEATURE:
<223> OTHER INFORMATION: Synthetic

<400> SEQUENCE: 131
tgatcattga cgatccggta gcc                                  23

<210> SEQ ID NO 132
<211> LENGTH: 70
<212> TYPE: DNA
<213> ORGANISM: Artificial Sequence
<220> FEATURE:
<223> OTHER INFORMATION: Synthetic

<400> SEQUENCE: 132
cggtagctgt aaagccaggg gcggtagcgt ggtttaaacc caagcaacag atcggcgtcg    60
tcggtatgga                                                          70

<210> SEQ ID NO 133
<211> LENGTH: 78
<212> TYPE: DNA
<213> ORGANISM: Artificial Sequence
<220> FEATURE:
<223> OTHER INFORMATION: Synthetic

<400> SEQUENCE: 133
agcttccata ccgacgacgc cgatctgttg cttgggttta aaccacgcta ccgcccctgg    60
ctttacagct accgagct                                                 78

<210> SEQ ID NO 134
<211> LENGTH: 30
<212> TYPE: DNA
<213> ORGANISM: Artificial Sequence
<220> FEATURE:
<223> OTHER INFORMATION: Synthetic

<400> SEQUENCE: 134
ggtagctgta aagccagggg cggtagcgtg                           30

<210> SEQ ID NO 135
<211> LENGTH: 30
<212> TYPE: DNA
<213> ORGANISM: Artificial Sequence
<220> FEATURE:
<223> OTHER INFORMATION: Synthetic -continued

<400> SEQUENCE: 135
ccataccgac gacgccgatc tgttgcttgg                                              30

<210> SEQ ID NO 136
<211> LENGTH: 23
<212> TYPE: PRT
<213> ORGANISM: Homo sapiens

<400> SEQUENCE: 136

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 137
<211> LENGTH: 18
<212> TYPE: PRT
<213> ORGANISM: Homo sapiens

<400> SEQUENCE: 137

Met His Ser Ser Ala Leu Leu Cys Cys Leu Val Leu Leu Thr Gly Val
1               5                   10                  15

Arg Ala

<210> SEQ ID NO 138
<211> LENGTH: 25
<212> TYPE: PRT
<213> ORGANISM: Human respiratory syncytial virus A (strain A2)

<400> SEQUENCE: 138

Met Glu Leu Leu Ile Leu Lys Ala Asn Ala Ile Thr Thr Ile Leu Thr
1 5 10 15

Ala Val Thr Phe Cys Phe Ala Ser Gly
20 25

<210> SEQ ID NO 139
<211> LENGTH: 15
<212> TYPE: PRT
<213> ORGANISM: Human respiratory syncytial virus A (strain A2)

<400> SEQUENCE: 139

Met Ala Ile Ile Tyr Leu Ile Leu Leu Phe Thr Ala Val Arg Gly
1 5 10 15

<210> SEQ ID NO 140
<211> LENGTH: 365
<212> TYPE: PRT
<213> ORGANISM: Homo sapiens

<400> SEQUENCE: 140

Met Gly Val Pro Arg Pro Gln Pro Trp Ala Leu Gly Leu Leu Leu Phe
1 5 10 15

Leu Leu Pro Gly Ser Leu Gly Ala Glu Ser His Leu Ser Leu Leu Tyr
20 25 30

His Leu Thr Ala Val Ser Ser Pro Ala Pro Gly Thr Pro Ala Phe Trp
35 40 45

Val Ser Gly Trp Leu Gly Pro Gln Gln Tyr Leu Ser Tyr Asn Ser Leu
50 55 60

Arg Gly Glu Ala Glu Pro Cys Gly Ala Trp Val Trp Glu Asn Gln Val
65 70 75 80

```
Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 141
<211> LENGTH: 62
<212> TYPE: PRT
<213> ORGANISM: Homo sapiens

<400> SEQUENCE: 141

Met Gly Val Pro Arg Pro Gln Pro Trp Ala Leu Gly Leu Leu Leu Phe
1               5                   10                  15

Leu Leu Pro Gly Ser Leu Gly Phe Ala Cys Lys Thr Ala Asn Gly Thr
            20                  25                  30

Ala Ile Pro Ile Gly Gly Gly Ser Ala Asn Val Tyr Val Asn Leu Ala
        35                  40                  45

Pro Val Val Asn Val Gly Gln Asn Leu Val Val Asp Leu Ser
    50                  55                  60

<210> SEQ ID NO 142
<211> LENGTH: 574
<212> TYPE: PRT
```

<213> ORGANISM: Human respiratory syncytial virus A (strain A2)

<400> SEQUENCE: 142

```
Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Pro Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Ile Asn Leu Cys Asn Val
    370                 375                 380
Asp Ile Phe Asn Pro Lys Tyr Asp Cys Lys Ile Met Thr Ser Lys Thr
385                 390                 395                 400
```

```
Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 143
<211> LENGTH: 64
<212> TYPE: PRT
<213> ORGANISM: Human respiratory syncytial virus A (strain A2)

<400> SEQUENCE: 143

Met Glu Leu Leu Ile Leu Lys Ala Asn Ala Ile Thr Thr Ile Leu Thr
1               5                   10                  15

Ala Val Thr Phe Cys Phe Ala Ser Gly Phe Ala Cys Lys Thr Ala Asn
            20                  25                  30

Gly Thr Ala Ile Pro Ile Gly Gly Ser Ala Asn Val Tyr Val Asn
        35                  40                  45

Leu Ala Pro Val Val Asn Val Gly Gln Asn Leu Val Val Asp Leu Ser
    50                  55                  60

<210> SEQ ID NO 144
<211> LENGTH: 178
<212> TYPE: PRT
<213> ORGANISM: Homo sapiens

<400> SEQUENCE: 144

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95
```

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 145
<211> LENGTH: 57
<212> TYPE: PRT
<213> ORGANISM: Homo sapiens

<400> SEQUENCE: 145

Met His Ser Ser Ala Leu Leu Cys Cys Leu Val Leu Leu Thr Gly Val
1               5                   10                  15

Arg Ala Phe Ala Cys Lys Thr Ala Asn Gly Thr Ala Ile Pro Ile Gly
            20                  25                  30

Gly Gly Ser Ala Asn Val Tyr Val Asn Leu Ala Pro Val Val Asn Val
        35                  40                  45

Gly Gln Asn Leu Val Val Asp Leu Ser
        50                  55

<210> SEQ ID NO 146
<211> LENGTH: 562
<212> TYPE: PRT
<213> ORGANISM: Influenza A virus (strain A/Japan/305/1957 H2N2)

<400> SEQUENCE: 146

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
20 25 30

Thr Asn Leu Glu Arg Asn Val Thr Val Thr His Ala Lys Asp Ile Leu
35 40 45

Glu Lys Thr His Asn Gly Lys Leu Cys Lys Leu Asn Gly Ile Pro Pro
50 55 60

Leu Glu Leu Gly Asp Cys Ser Ile Ala Gly Trp Leu Leu Gly Asn Pro
65 70 75 80

Glu Cys Asp Arg Leu Leu Ser Val Pro Glu Trp Ser Tyr Ile Met Glu
85 90 95

Lys Glu Asn Pro Arg Asp Gly Leu Cys Tyr Pro Gly Ser Phe Asn Asp
100 105 110

Tyr Glu Glu Leu Lys His Leu Leu Ser Ser Val Lys His Phe Glu Lys
115 120 125

Val Lys Ile Leu Pro Lys Asp Arg Trp Thr Gln His Thr Thr Thr Gly
130 135 140

Gly Ser Arg Ala Cys Ala Val Ser Gly Asn Pro Ser Phe Phe Arg Asn
145 150 155 160

Met Val Trp Leu Thr Lys Glu Gly Ser Asp Tyr Pro Val Ala Lys Gly
165 170 175

Ser Tyr Asn Asn Thr Ser Gly Glu Gln Met Leu Ile Ile Trp Gly Val

```
                180             185             190
His His Pro Ile Asp Glu Thr Glu Gln Arg Thr Leu Tyr Gln Asn Val
            195             200             205

Gly Thr Tyr Val Ser Val Gly Thr Ser Thr Leu Asn Lys Arg Ser Thr
210             215             220

Pro Glu Ile Ala Thr Arg Pro Lys Val Asn Gly Gln Gly Gly Arg Met
225             230             235             240

Glu Phe Ser Trp Thr Leu Leu Asp Met Trp Asp Thr Ile Asn Phe Glu
            245             250             255

Ser Thr Gly Asn Leu Ile Ala Pro Glu Tyr Gly Phe Lys Ile Ser Lys
            260             265             270

Arg Gly Ser Ser Gly Ile Met Lys Thr Glu Gly Thr Leu Glu Asn Cys
        275             280             285

Glu Thr Lys Cys Gln Thr Pro Leu Gly Ala Ile Asn Thr Thr Leu Pro
            290             295             300

Phe His Asn Val His Pro Leu Thr Ile Gly Glu Cys Pro Lys Tyr Val
305             310             315             320

Lys Ser Glu Lys Leu Val Leu Ala Thr Gly Leu Arg Asn Val Pro Gln
                325             330             335

Ile Glu Ser Arg Gly Leu Phe Gly Ala Ile Ala Gly Phe Ile Glu Gly
                340             345             350

Gly Trp Gln Gly Met Val Asp Gly Trp Tyr Gly Tyr His His Ser Asn
        355             360             365

Asp Gln Gly Ser Gly Tyr Ala Ala Asp Lys Glu Ser Thr Gln Lys Ala
    370             375             380

Phe Asp Gly Ile Thr Asn Lys Val Asn Ser Val Ile Glu Lys Met Asn
385             390             395             400

Thr Gln Phe Glu Ala Val Gly Lys Glu Phe Gly Asn Leu Glu Arg Arg
                405             410             415

Leu Glu Asn Leu Asn Lys Arg Met Glu Asp Gly Phe Leu Asp Val Trp
                420             425             430

Thr Tyr Asn Ala Glu Leu Leu Val Leu Met Glu Asn Glu Arg Thr Leu
            435             440             445

Asp Phe His Asp Ser Asn Val Lys Asn Leu Tyr Asp Lys Val Arg Met
    450             455             460

Gln Leu Arg Asp Asn Val Lys Glu Leu Gly Asn Gly Cys Phe Glu Phe
465             470             475             480

Tyr His Lys Cys Asp Asp Glu Cys Met Asn Ser Val Lys Asn Gly Thr
                485             490             495

Tyr Asp Tyr Pro Lys Tyr Glu Glu Glu Ser Lys Leu Asn Arg Asn Glu
            500             505             510

Ile Lys Gly Val Lys Leu Ser Ser Met Gly Val Tyr Gln Ile Leu Ala
            515             520             525

Ile Tyr Ala Thr Val Ala Gly Ser Leu Ser Leu Ala Ile Met Met Ala
            530             535             540

Gly Ile Ser Phe Trp Met Cys Ser Asn Gly Ser Leu Gln Cys Arg Ile
545             550             555             560

Cys Ile
```

<210> SEQ ID NO 147
<211> LENGTH: 54
<212> TYPE: PRT
<213> ORGANISM: Influenza A virus (strain A/Japan/305/1957 H2N2)

```
<400> SEQUENCE: 147

Met Ala Ile Ile Tyr Leu Ile Leu Leu Phe Thr Ala Val Arg Gly Phe
1               5                   10                  15

Ala Cys Lys Thr Ala Asn Gly Thr Ala Ile Pro Ile Gly Gly Gly Ser
            20                  25                  30

Ala Asn Val Tyr Val Asn Leu Ala Pro Val Val Asn Val Gly Gln Asn
            35                  40                  45

Leu Val Val Asp Leu Ser
        50
```